United States Patent
Stolle et al.

(10) Patent No.: US 6,787,651 B2
(45) Date of Patent: Sep. 7, 2004

(54) SUBSTITUTED INDOLES, PHARMACEUTICAL COMPOUNDS CONTAINING SUCH INDOLES AND THEIR USE AS PPAR-γ BINDING AGENTS

(75) Inventors: Andreas Stolle, Leverkusen (DE); Jacques P. Dumas, Bethany, CT (US); William Carley, La Jolla, CA (US); Philip D. G. Coish, New Haven, CT (US); Steven R. Magnuson, Hamden, CT (US); Yamin Wang, Sandy Hook, CT (US); Dhanapalan Nagarathnam, Bethany, CT (US); Derek B. Lowe, Hamden, CT (US); Ning Su, Hamden, CT (US); William H. Bullock, Easton, CT (US); Ann-Marie Campbell, Monroe, CT (US); Ning Qi, Hamden, CT (US); Jeremy L. Baryza, Mountain View, CA (US); James H. Cook, East Hampton, CT (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/974,319

(22) Filed: Oct. 9, 2001

(65) Prior Publication Data

US 2003/0087902 A1 May 8, 2003

Related U.S. Application Data

(60) Provisional application No. 60/243,665, filed on Oct. 27, 2000, and provisional application No. 60/239,195, filed on Oct. 10, 2000.

(51) Int. Cl.[7] .................... C07D 209/34; C07D 405/02; C07D 407/04; C07D 413/06; C07D 491/056
(52) U.S. Cl. ...................... 544/143; 544/373; 546/176; 548/159; 548/181; 548/222; 548/425; 548/430; 548/464; 548/466; 548/467; 548/492
(58) Field of Search .......................... 546/176; 548/425, 548/467

(56) References Cited

U.S. PATENT DOCUMENTS

| | | | |
|---|---|---|---|
| 3,723,464 A | 3/1973 | Yamamoto et al. | 260/326.15 |
| 3,781,299 A | 12/1973 | Yamamoto et al. | 260/326.15 |
| 3,828,027 A | 8/1974 | Yamamoto et al. | 260/239.3 |
| 3,922,264 A | 11/1975 | Yamamoto et al. | 260/239.3 |
| 4,697,018 A | 9/1987 | Schmidt et al. | 546/94 |
| 5,296,499 A | 3/1994 | Sohda et al. | 514/419 |
| 5,464,863 A | 11/1995 | Nagamine et al. | 514/443 |
| 5,563,157 A | 10/1996 | Harrison et al. | 514/339 |
| 5,684,032 A | 11/1997 | Elliott et al. | 514/414 |
| 5,686,481 A | 11/1997 | Elliott et al. | 514/414 |
| 5,869,519 A | 2/1999 | Karanewsky et al. | 514/415 |
| 5,877,197 A | 3/1999 | Karanewsky et al. | 514/397 |
| 5,891,902 A | 4/1999 | Machii et al. | 514/415 |
| 5,902,726 A | 5/1999 | Kliever et al. | 435/7.1 |
| 5,994,554 A | 11/1999 | Kliever et al. | 548/183 |
| 6,090,839 A | 7/2000 | Adams et al. | |
| 6,121,271 A | 9/2000 | Dollings et al. | 514/269 |

FOREIGN PATENT DOCUMENTS

| | | |
|---|---|---|
| CH | 561702 | 5/1975 |
| EP | 0 449 196 | 10/1991 |
| EP | 0 782 989 | 7/1997 |
| FR | 2648459 | 12/1990 |
| JP | 47-3615 | 2/1972 |
| JP | 47-27192 | 10/1972 |
| JP | 5-43544 | 2/1993 |
| JP | 6-145150 | 5/1994 |
| JP | 9-100278 | 4/1997 |
| JP | 10-195048 | 7/1998 |
| WO | 9414434 | 7/1994 |
| WO | 9513266 | 5/1995 |
| WO | 9618393 | 6/1996 |
| WO | 9719077 | 5/1997 |
| WO | 9907351 | 2/1999 |
| WO | 9947511 | 9/1999 |
| WO | 00/23425 | 4/2000 |
| WO | 0027832 | 5/2000 |
| WO | 0044743 | 8/2000 |
| WO | 0046195 | 8/2000 |
| WO | 0046196 | 8/2000 |
| WO | 0046197 | 8/2000 |
| WO | 0046198 | 8/2000 |
| WO | 0046199 | 8/2000 |

OTHER PUBLICATIONS

Bunker et al., Chemical Abstracts, 125:58266, 1996.*

Rami, H. K., Smith, S. A., "Synthetic Ligands for PRARγ–Review of Patent Literature 1994–1999", Exp. Opin. Ther. Patents, 10(5): 623–634 (2000).

Nichols, J.S., Parks, D. J., Consler, T. G., and Blanchard, S. G., "Development of a Scintillation Proximity Assay for Peroxisome Proliferator–Activated Receptor γ Ligand Binding Domain", Analytical Biochemistry, 257 112–119 (1998).

Henke, B. R., Adkison, K. K., Blanchard, S. G., Leesnitzer, L. M., Mook, R. A., Plunker, K. kD., Ray, J. A., Roberson, C. Unwalla, R., and Willson, T. M., "Synthesis and Biological Activity of a Novel Series of Indole–Derived PRARγ Agonists", Bioorganic & Medicinal Chemistry Letters, 9: 3329–3334 (1999).

Ali, M. I., Abdel–Fattah, A. M., Hussain, S. M., El–Reedy, A. M., "Reaction of 2–Carboxyl–1–Methylindole–3–Acetic Acetic Anhydride with Amines and with S–Methylisothiosemicarbazide", J. Heterocyclic Chem., 19: 993–996 (1982).

(List continued on next page.)

*Primary Examiner*—Fiona T. Powers
(74) *Attorney, Agent, or Firm*—Robert H. Brink

(57) ABSTRACT

Disclosed are substituted indoles, pharmaceutical compositions containing such indoles, and their use in treating or preventing PPAR-γ mediated diseases or conditions, such as osteopenia, osteoporosis, cancer, diabetes and atherosclerosis.

14 Claims, No Drawings

OTHER PUBLICATIONS

Achab, S., Guyot, M., Potier, P., "An Expeditious Synthesis of Structural Analogs of the Marine Cytotoxic Agents Grossularines–1 and –2", Tetrahedron Letters, 36(15): 2615–2618 (1995).

Micheli, F., DiFabio, R., Baraldi, D., Conti, N., Cugola, A., Gastaldi, P., Giacobbe, S., Marchioro, C., Mugnaini, M., Rossi, L., Pecunioso, A., and Pentassuglia, G., "Substituted Indole–2–Carboxylates as Potent Antagonists of the Glycine Binding Site Associated with the NMDA Receptor", Arch. Pharm. Pharm. Med. Chem., 332: 271–278 (1999).

Kogan, N. A., "3–Indolylphenylacetonitriles", Translation from Khimiya Geterotsiklicheskikh Soedinenii, No. 11, pp. 1482–1486, Nov. 1978, Plenum Publishing Corporation 1997.

Terent'ev, P. B., Stanoeva, R. R., Khaimova, M. A., Kosimov, A. K., Kost, A. N., "Mass Spectra of Steroisomeric cis– and trans–2–Alkyl–3–Aryl(Hetaryl)–4–(Methoxycarbonyl)–3, 4–Dihydro–1H–Isoquinol–1–ones and 1,2,3,4–Tetrahydroisoquinolines", Translation from Khimiya Geterotsiklicheskikh Soedinenii, No. 10, pp. 1395–1397, Oct. 1980, Plenum Publishing Corporation 1981.

Kogan, N. A., Vekshina, L. I., "Reaction of 3– and 4–Pyridinealdehydes with Indole–2–Carboxylic Acid", Translation from Khimiko–Garmatsevticeskii Zhurnal, vol. 12, No. 5, pp. 62–66, May 1978, Plenum Publishing Corporation 1979.

Murakami, Y., Tani, M., Suzuki, M., Sudoh, K., Uesato, M., Tanaka, K., Yokoyama, Y., "Synthetic Studies on Indoles and Related Compounds. XII. A Simple General Method for the C–3 Acylation of Ethyl Indole–2–Carboxylates", Chem. Pharm. Bull., 33(11): 4707–4716 (1985).

Yokoyama, Y., Ikeda, M., Saito, M., Yoda, T., Suzuki, H., Murakami, Y., "Palladium–Catalyzed Reaction of 3–Bromoindole Derivative with Allyl Esters in the Presence of Hexa–n–Butyldistannane", Heterocycles, 31(8): 1505–1511 (1990).

Nagarathman, D., Johnson, M. E., "A Novel Dimerization of Ethyl 3–Cyanomethyl–2–Indolecarboxylate", Tetrahedron Letters, 34(20): 3215–3218 (1993).

Sakamoto, T., Nagano, R., Kondo, Y., Yamanaka, H., "Palladium–Catalyzed Coupling Reaction of3–Iodoindoles and 3–Iodobenzo[h]thiphene with Terminal Acetylenes", Chem. Pharm. Bull., 36(6): 2248–2252 (1988).

Yamamoto, H., Saito, C., Inaba, S., Awata, H., Yamamoto, M., Sakai, Y., Komatsu, T., "Novel Quinazoline Derivatives. II. A new anti–inflammatory agent, SL–512", Arzneim.–Forsch. (Drug Res.), 23(9): 1266–1271 (1973).

Saleha, S., Siddiqui, A.A., Khan, N.H., "A Convenient Synthesis of New Indole Derivatives", Indian J. Chem., 19B: 81–82 (1980).

Basanagoudar, L. D., Mahaganshetti, C. S., Dambal, S. B., "Synthesis of 7–phenyl–5,6–dihydro–indolo[1,2–a]quinoxalines", Indian J. Chem., 30B: 883–885 (1991).

Jones, C. D., "The Preparation of 2–Substituted Indole Sulfonamides and Subsequent Conversion to Indole–2–carboxylic Acids, Indole–2–carbonitriles, and 2–Acylindoles", J. Org., Chem., 37(23): 3624–3625 (1972).

Malapel–Andrieu, B., Jean–Yves, M., "Synthesis and Reactivity of Substituted 3–([Trifuluoromethyl)sulfonyl] oxy)–1H–indole–2–carboxylate in Palladium–Catalyzed Reactions", Tetrahedron, 54: 11079–11094 (1998).

Collot, V., Schmitt, M., Marwah, A. K., Norberg, B., Bourguignon, J.–J., "Synthesis of 3–Phenylindoline– 2–carboxamides as Semi–Rigid Phenylalanine Mimetics", Tetrahedron Letters, 38(46): 8033–8036 (1997).

Mederski, W. W. K. R., Lefort, M., Germann, M., Kux, D., "N–Aryl Heterocycles via Coupling Reactions with Arylboronic Acids", Tetrahedron, 55: 12757–12770 (1999).

Schuster, H. F., Coppola, G. M., "Fused Lactones as a Route to Functionalized 1–Substituted Indoles", J. Heterocyclic Chem., 31: 1381–1384 (1994).

Collot, V., Schmitt, M., Marwah, P., Bourguignon, J.–J., "Regiospecific Functionalization of Indole–2–Carboxylates and Diastereoselective Prpearation of the Corresponding Indolines", Heterocycles, 51(12): 2823–2847 (1999).

Sakamoto, T., Kondo, Y., Takazawa, N., Yamanaka, H., "Preparation and palladium–catalysed arylation of indolylzine halides", J. Chem. Soc., Perkin Trans. 1, pp. 1927–1934 (1996).

Sakamoto, T., Kondo, Y., Takazawa, N., Yamanaka, H., "Indolylzinc Iodides by Oxidative Addition of Active Zinc to Iodoindoles", Tetrahedron Letters, 34(37): 5955–5956 (1993).

Ishii, H., Sugiura, T., Akiyama, Y., Ichikawa, Y., Watanabe, T., Murakami, Y., "Fischer Indolization and its Related Compounds. XXIII. Fischer Indolization of Ethyl Pyruvate 2–(2,6–Dimethoxyphenyl)phenylhydrazone", Chem. Pharm. Bull., 38(8): 2118–2126 (1990).

Medvedeva, T. M., Bezborodov, A. M., Zheludkova, M. D., Zhdanova, N. F., Kudnin, A. N., "Synthesis and Pharmacological Activity of Fusaric Acid and its Derivatives", Translation from Khimiko–Garmatsevticeskii Zhurnal, vol. 12, No. 5, pp. 66–69, May 1978, Plenum Publishing Corporation 1979.

Brown, P. J., Smith–Oliver, T. A., Charifson, P. S., Tomkinson, N., Fivush, A. M., Sternbach, D. D., Wade, L. E., Orband–Miller, L., Parks, D. J., Blanchard, S. G., Kliewer, S. A., Lehmann, J. M., and Willson, T. M., "Identification of peroxisome proliferator–activated receptor ligands from a biased chemical library", Chemistry & Biology, 4(12): 909–917 (1997).

Achab, Saied, et al., "An expeditious synthesis of structural analogs of the marine cytotoxic agents grossularines–1 and–2," Tetrahedron Lett., (1995), 36(15), pp. 2615–2618.

Gabrielyan, G. E. et al., "Indole derivatives. XXXVII. Synthesis of indole compounds containing a furan ring," Arm. Khim. ZH., (1973), 26(9), pp. 768–774.

Mederski, W.W.K.R. et al., "2, Endothelin Antagonists: Evaluation of 2,1,3–Benzothiadiazole as a Methylendioxyphenyl Bioisoster," Bioorganic & Medicinal Chemistry Letters, Oxford, G.B., vol. 8, No. 1, 1998, pp. 17–22.

* cited by examiner

SUBSTITUTED INDOLES, PHARMACEUTICAL COMPOUNDS CONTAINING SUCH INDOLES AND THEIR USE AS PPAR-γ BINDING AGENTS

FIELD OF THE INVENTION

The invention relates to substituted indoles, pharmaceutical compositions containing such indoles, and their use in treating or preventing diseases or conditions mediated by the Peroxisome Proliferator Activated Receptor-γ (PPAR-γ).

BACKGROUND

Peroxisome Proliferator Activated Receptors (PPARs) belong to the steroid/retinoid receptor superfamily of ligand-activated transcription factors. Willson, et al., *Curr. Opin. Chem. Biol.*, (1997), Vol. 1, pp 235–241. To date, three mammalian PPARs have been identified, namely PPAR-α, PPAR-γ, and PPAR-δ.

PPARs regulate expression of target genes by binding to DNA response elements as heterodimers with the retinoid X receptor. These DNA response elements have been identified in the regulatory regions of a number of genes encoding proteins involved in lipid metabolism and energy balance. The biological role of the PPARs in the regulation of lipid metabolism and storage has been recently reviewed. Spiegelman, *Diabetes*, (1998), Vol. 47, pp. 507–514; Schoonjans, et al., *Curr. Opin. Lipidol.*, (1997), Vol. 8, pp 159–166; Brun, et al., *Curr. Opin. Lipidol.*, (1997), Vol. 8, pp 212–218.

Molecules that interact with PPAR-γ may be useful in modulating PPAR-γ mediated processes for the treatment or prevention of various diseases and conditions. For example, essential dietary fatty acids and certain of their eicosanoid metabolites are naturally occurring hormonal ligands for the PPAR-γ receptor, which can promote adipogenesis through activation of the PPAR-γ receptor. Kliewer, et al., *Proc. Natl. Acad. Sci. USA*, (1997), Vol. 94, pp 4318–4323; Kliewer, et al., *Cell*, (1995), Vol. 83, pp 813–819. Therefore, molecules that inhibit the adipogenic effects of endogenous PPAR-γ hormones may be useful in the treatment of diseases caused by increased fat accumulation or lipid storage, such as osteoporosis, obesity and acne. Tontonoz, et al., *Curr. Opin. Genet. Dev.*, (1995), Vol. 5, pp 571–576. For example, it has been noted that the thiazolidinedione (TZD) class of PPAR-γ ligands promotes adipogenesis in bone marrow and inhibits expression of markers of the osteoblast phenotype, such as alkaline phosphatase. Paulik, et al., *Cell Tissue Res.*, (1997), Vol. 290, pp 79–87. These effects may lead to low bone mineral density and osteoporosis. Similarly, it is known that TZDs can promote lipid accumulation in sebocytes. Rosenfield, et al., *N. Dermatology*, (1998), Vol. 196, pp 43–46. These effects may lead to sebocyte differentiation and acne formation. Thus, molecules that block adipogenesis in adipocytes, pre-adipocytes, bone marrow, or sebocytes may have beneficial effects in the treatment of obesity, osteoporosis, or acne.

The PPAR-γ receptor has been found in tissues other than adipose, and it is believed that synthetic PPAR-γ ligands and natural PPAR-γ hormones (natural ligands) may have beneficial effects in many other diseases including cardiovascular disease, inflammation, and cancer. Schoonjans, supra; Ricote, et al., *Nature*, (1998), Vol. 391, pp 79–82; Mueller, et al., *Mol. Cell*, (1998), Vol. 1, pp 465–470.

TZD PPAR-γ ligands enhance the actions of insulin in man and reduce circulating glucose levels in rodent models of diabetes. The PPAR-γ receptor is expressed in adipose tissue and plays a pivotal role in the regulation of adipocyte differentiation in vitro. TZD such as rosiglitazone induce adipocyte differentiation in vitro through activation of the PPAR-γ receptor.

Although there are clearly therapeutic uses for PPAR-γ ligands in the treatment of diseases of lipid metabolism and energy balance, it is possible that there will be side effects of these drugs. For example, PPAR-γ ligands that promote adipocyte differentiation in vivo could lead to increased fat accumulation and weight gain. This side effect might offset the beneficial effects of a PPAR-γ ligand in the treatment of diabetes or other diseases where obesity is a risk factor. Spiegelman, supra; Brun, supra.

There is precedent among other member of the steroid/retinoid receptor superfamily that synthetic ligands can be identified which mimic many of the beneficial effects but inhibit some of the detrimental side effects of the natural hormones. McDonnell, *Biochem. Soc. Trans.*, (1998), Vol. 26, pp 54–60. These synthetic ligands have been given various labels, including antagonists, anti-hormones, partial agonists, selective receptor modulators, tissue selective ligands, and others. Katzenellenbogen, et al., *Mol. Endocinol.*, (1996), Vol. 10, pp 119–131. Compounds are needed that will modulate PPAR-γ mediated processes for the treatment or prevention of diseases such as osteoporosis, cancer, etc. without the concomitant side-effects of natural hormones.

SUMMARY OF THE INVENTION

The invention provides compounds that modulate PPAR-γ mediated processes, particularly substituted indole compounds, which can act as agonists or antagonists of PPAR-γ and thereby modulate PPAR-γ mediated processes. The invention further provides pharmaceutical compositions containing such compounds. Finally, the invention provides for methods of treating or preventing a PPAR-γ mediated diseases or condition in a mammal by administering a compound of the invention.

The invention relates to compounds of the Formula I:

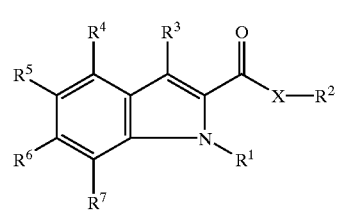

wherein $R^1$ is $R^8$—$R^9$;

$R^8$ is selected from alkyl of 1–7 carbon atoms, alkenyl of 2–8 carbon atoms, alkynyl of 2–8 carbon atoms, $(CH_2)_tS(=O)_2$, and $(CH_2)_nC(=O)$;

t is 1–7;

n is 0–8;

$R^9$ is selected from phenyl, cycloalkyl of 3–8 carbon atoms, heterocycloalkyl of 3–8 carbon atoms and 1–2 heteroatoms selected from N, S and O, cycloalkenyl of 5–9 carbon atoms, and heterocycloalkenyl of 3–8 carbon atoms and 1–2 heteroatoms selected from N, S and O, wherein $R^9$ may be substituted with alkoxy of 1–8 carbon atoms, haloalkoxy of 1–8 carbon atoms and a number of halogen atoms up to the perhalo level, halogen, alkyl of 1–8 carbon atoms, haloalkyl of 1–8 carbon atoms and a number of halogen atoms up to the perhalo level, or $Q\text{—}(CH_2)_n R^{10}$;

Q is selected from $NR^{33}$, NH, S and O;

$R^{10}$ is selected from cycloalkyl of 3–9 carbon atoms, heterocycloalkyl of 3–8 carbon atoms and 1–2 heteroatoms selected from N, S and O, cycloalkenyl of 5–9 carbon atoms, and heterocycloalkenyl of 3–8 carbon atoms and 1–2 heteroatoms selected from N, S and O;

$R^{33}$ is selected from alkyl of 1–8 carbon atoms, alkenyl of 1–8 carbon atoms and alkynyl of 1–8 carbon atoms;

X is selected from $NR^{33}$, NH, O, and S;

$R^2$ is selected from hydrogen, alkyl of 1–8 carbon atoms, haloalkyl of 1–8 carbon atoms and a number of halogen atoms up to the perhalo level, and $(CH_2)_n S(=O)_2 R^{11}$;

$R^{11}$ is selected from aryl of 5–14 carbon atoms and heteroaryl of 3–11 carbon atoms and 1–2 heteroatoms selected from N, S and O, with the proviso that $R^{11}$ is not isoxazole, wherein $R^{11}$ may be substituted with alkyl of 1–8 carbon atoms, alkenyl of 2–8 carbon atoms, alkynyl of 2–8 carbon atoms, alkoxy of 1–8 carbon atoms, haloalkyl of 1–8 carbon atoms and a number of halogen atoms up to the perhalo level, haloalkoxy of 1–8 carbon atoms and a number of halogen atoms up to the perhalo level, or halogen;

$R^3$ is selected from:

(a) $R^{12}\text{—}R^{13}$, wherein $R^{12}$ is selected from alkyl of 1–7 carbon atoms, alkenyl of 2–7 carbon atoms, alkynyl of 2–7 carbon atoms, and $C(=O)$, and $R^{13}$ is selected from cycloalkyl of 3–7 carbon atoms, cycloalkenyl of 5–9 carbon atoms, heterocycloalkyl of 3–8 carbon atoms and 1–2 heteroatoms selected from N, S and O, and heterocycloalkenyl of 3–8 carbon atoms and 1–2 hetero atoms selected from N, S and O, wherein $R^{13}$ may be substituted with alkyl of 1–8 carbon atoms, alkenyl of 2–8 carbon atoms, alkynyl of 2–8 carbon atoms, alkoxy of 1–8 carbon atoms, haloalkyl of 1–8 carbon atoms and a number of halogen atoms up to the perhalo level, haloalkoxy of 1–8 carbon atoms and a number of halogen atoms up to the perhalo level, or halogen; or (b) cycloalkyl of 3–9 carbon atoms, heterocycloalkyl of 3–8 carbon atoms and 1–2 heteroatoms selected from N, S and O, cycloalkenyl of 3–8 carbon atoms and 1–2 heteroatoms selected from N, S and O, and heterocycloalkenyl of 3–8 carbon atoms and 1–2 heteroatoms selected from N, S and O, all of which may be substituted with alkyl of 1–8 carbon atoms, alkenyl of 2–8 carbon atoms, alkynyl of 2–8 carbon atoms, cycloalkyl of 3–9 carbon atoms, heterocycloalkyl of 3–8 carbon atoms and 1–2 heteroatoms selected from N, S and O, cycloalkenyl of 3–8 carbon atoms and 1–2 heteroatoms selected from N, S and O, heterocycloalkenyl of 3–8 carbon atoms and 1–2 heteroatoms selected from N, S and O, aryl of 5–14 carbon atoms and heteroaryl of 4–8 carbon atoms and 1–2 heteroatoms selected from N, S and O, or may be spiro fused with cycloalkyl of 3–9 carbon atoms, heterocycloalkyl of 3–8 carbon atoms and 1–2 heteroatoms selected from N, S and O, cycloalkenyl of 3–8 carbon atoms and 1–2 heteroatoms selected from N, S and O, heterocycloalkenyl of 3–8 carbon atoms and 1–2 heteroatoms selected from N, S and O, aryl of 5–14 carbon atoms and heteroaryl of 4–8 carbon atoms and 1–2 heteroatoms selected from N, S and O; or (c) aryl of 5–14 carbon atoms or heteroaryl of 3–11 carbon atoms and 1–2 heteroatoms selected from N, S and O, which are substituted with 1–3 of the following:

(i) $Si(CH_3)_3$;

(ii) cycloalkyl of 3–9 carbon atoms, heterocycloalkyl of 3–8 carbon atoms and 1–2 heteroatoms selected from N, S and O, cycloalkenyl of 5–9 carbon atoms, and heterocycloalkenyl of 3–8 carbon atoms and 1–2 heteroatoms selected from N, S and O;

(iii) $S(=O)_2 R^{14}$ wherein $R^{14}$ is selected from cycloalkyl of 3–7 carbon atoms, heterocycloalkyl of 3–8 carbon atoms and 1–2 heteroatoms selected from N, S and O, cycloalkenyl of 5–9 carbon atoms, heterocycloalkenyl of 3–8 carbon atoms and 1–2 heteroatoms selected from N, S and O, aryl of 5–14 carbon atoms and heteroaryl of 4–11 carbon atoms and 1–2 heteroatoms selected from N, S and O;

(iv) $R^{15}$, which combines with $R^5$ to form a radical of the formula $\text{—Y—}(CH_2)_t\text{—}$ Y—, wherein Y is selected from $NR^{33}$, NH, S and O;

(v) $C(=O)R^{16}$, wherein $R^{16}$ is selected from alkyl of 1–8 carbon atoms, cycloalkyl of 3–9 carbon atoms, heterocycloalkyl of 3–8 carbon atoms and 1–2 heteroatoms selected from N, S and O, cycloalkenyl of 5–9 carbon atoms, heterocycloalkenyl of 3–8 carbon atoms and 1–2 heteroatoms selected from N, S and O, and $Z\text{—}R^{17}$ wherein Z is selected from $(CH_2)_n$, NH, $NR^{33}$, O and S, wherein $R^{17}$ is selected from cycloalkyl of 3–9 carbon atoms, heterocycloalkyl of 3–8 carbon atoms and 1–2 heteroatoms selected from N, S and O, cycloalkenyl of 5–9 carbon atoms, heterocycloalkenyl of 3–8 carbon atoms and 1–2 heteroatoms selected from N, S and O, aryl of 5–14 carbon atoms and heteroaryl of 3–11 carbon atoms and 1–2 heteroatoms selected from N, S and O;

(vi) $Z\text{—}R^{18}\text{—}R^{19}$, wherein:

$R^{18}$ is selected from alkyl of 1–8 carbon atoms, cycloalkyl of 3–9 carbon atoms, heterocycloalkyl of 3–8 carbon atoms and 1–2 heteroatoms selected from N, S and O, cycloalkenyl of 5–9 carbon atoms, heterocycloalkenyl of 3–8 carbon atoms and 1–2 heteroatoms selected from N, S and O, aryl of 5–14 carbon atoms, heteroaryl of 3–11 carbon atoms and 1–2 heteroatoms selected from N, S and O, and $(CH_2)_nC(=O)$, and $R^{19}$ is selected from hydrogen, halogen, haloalkyl of 1–8 carbon atoms and a number of halogen atoms up to the perhalo level, alkyl of 1–8 carbon atoms, alkenyl of 2–8 carbon atoms, alkynyl of 2–8 carbon atoms, cycloalkyl of 3–9 carbon atoms, heterocycloalkyl of 3–8 carbon atoms and 1–2 heteroatoms selected from N, S and O, cycloalkenyl of 5–9 carbon atoms, heterocycloalkenyl of 3–8 carbon atoms and 1–2 hetero atoms selected from N, S and O, $R^{20}$—$R^{21}$ and Z—$R^{21}$, and Z is as defined above, and $R^{20}$ is selected from aryl of 5–14 carbon atoms and heteroaryl of 3–11 carbon atoms and 1–2 heteroatoms selected from N, S and O, and $R^{21}$ is selected from hydrogen, cycloalkyl of 3–9 carbon atoms, heterocycloalkyl of 3–8 carbon atoms and 1–2 heteroatoms selected from N, S and O, cycloalkenyl of 5–9 carbon atoms, heterocycloalkenyl of 3–8 carbon atoms and 1–2 hetero atoms selected from N, S and O, aryl of 5–14 carbon atoms and heteroaryl of 3–11 carbon atoms and 1–2 heteroatoms selected from N, S and O;

with the proviso that when $R^3$ is furyl, benzofuranyl, benzothienyl, benzoxazolidinyl, benzoxazolyl, benzothiazolydinyl, benzothiazolyl, benzoisothiazolyl, benzopyrazolyl, benzoimidazolyl, benzoimidazolidinyl, benzoisooxazolyl, or benzoxadiazolyl $R^3$ may be unsubstituted, and with the further proviso that, (1) when $R^3$ is aryl or heteroaryl, Z is O or $(CH_2)_n$, $R^{18}$ is $(CH_2)_nC(=O)$, alkyl, aryl or heteroaryl, and $R^{19}$ is hydrogen, halogen, haloalkyl or alkyl, or (2) when $R^3$ is phenyl or napthyl and $R^{16}$ is alkyl, one of the following applies:

$R^5$ is other than hydrogen and $R^{23}$ is other than alkyl or alkenyl,

X is NH and $R^2$ is $(CH_2)_nS(=O)_2R^{11}$, $R^8$ is $(CH_2)_nC(=O)$, $(CH_2)_nS(=O)_2$, alkenyl or alkynyl, $R^9$ is substituted with $Q(CH_2)_nR^{10}$, $R^7$ is other than hydrogen, or $R^4$ is other than hydrogen; and (d) furyl, benzofuranyl, benzothienyl, benzoxazolidinyl, benzoxazolyl, benzothiazolydinyl, benzothiazolyl, benzoisothiazolyl, benzopyrazolyl, benzoimidazolyl, benzoimidazolidinyl, benzoisooxazolyl, or benzoxadiazolyl, which may be substituted with alkyl of 1–8 carbon atoms, alkenyl of 2–8 carbon atoms, alkynyl of 2–8 carbon atoms, alkoxy of 1–8 carbon atoms, haloalkyl of 1–8 carbon atoms and a number of halogen atoms up to the perhalo level, haloalkoxy of 1–8 carbon atoms and a number of halogen atoms up to the perhalo level, or halogen; or $R^4$ is selected from hydrogen and E—$R^{34}$—$R^{35}$, wherein E is selected from $NR^{33}$, NH, S and O;

$R^{34}$ is selected from alkyl of 1–8 carbon atoms, cycloalkyl of 3–9 carbon atoms, heterocycloalkyl of 3–8 carbon atoms and 1–2 heteroatoms selected from N, S and O, cycloalkenyl of 5–9 carbon atoms, and heterocycloalkenyl of 3–8 carbon atoms and 1–2 heteroatoms selected from N, S and O;

$R^{35}$ is selected from hydrogen, halogen, haloalkyl of 1–8 carbon atoms and a number of halogen atoms up to the perhalo level, alkyl of 1–8 carbon atoms, alkenyl of 2–8 carbon atoms, alkynyl of 2–8 carbon atoms, cycloalkyl of 3–9 carbon atoms, heterocycloalkyl of 3–8 carbon atoms and 1–2 heteroatoms selected from N, S and O, cycloalkenyl of 5–9 carbon atoms, and heterocycloalkenyl of 3–8 carbon atoms and 1–2 heteroatoms selected from N, S and O; and $R^{33}$ has the meaning given above;

$R^5$ (1) is selected from:

(a) hydrogen;

(b) $(CH_2)_qCOOH$
where q is 1–4

(c) $C(=O)R^{22}$, wherein $R^{22}$ is selected from alkyl of 1–8 carbon atoms, cycloalkyl of 3–9 carbon atoms, heterocycloalkyl of 3–8 carbon atoms and 1–2 heteroatoms selected from N, S and O, cycloalkenyl of 5–9 carbon atoms, heterocycloalkenyl of 3–8 carbon atoms and 1–2 heteroatoms selected from N, S and O, aryl of 5–14 carbon atoms and heteroaryl of 3–11 carbon atoms and 1–2 heteroatoms selected from N, S and O;

(d) cycloalkyl of 3–9 carbon atoms, heterocycloalkyl of 3–8 carbon atoms and 1–2 heteroatoms selected from N, S and 0, cycloalkenyl of 5–9 carbon atoms, and heterocycloalkenyl of 3–8 carbon atoms and 1–2 heteroatoms selected from N, S and O;

(e) —$(CH_2)_n$—D—$R^{23}$, wherein:

(i) D is selected from $NR^{33}$, NH, S and O, and (ii) $R^{23}$ is selected from alkyl of 1–8 carbon atoms, alkenyl of 2–8 carbon atoms, alkynyl of 2–8 carbon atoms, $C(=O)R^{24}$, and $(CH_2)_mR^{24}$, wherein m is 0–4, with the proviso that when $R^3$ is phenyl or napthyl, Z is O, $R^{18}$ is alkyl and $R^{19}$ is hydrogen, halogen, haloalkyl or alkyl, m is 1–4, $R^{24}$ is selected from cycloalkyl of 3–9 carbon atoms, heterocycloalkyl of 3–8 carbon atoms and 1–2 heteroatoms selected from N, S and O, cycloalkenyl of 5–9 carbon atoms, heterocycloalkenyl of 3–8 carbon atoms and 1–2 heteroatoms selected from N, S and O, $C(=O)$OH, $NHR^{27}$—$R^{28}$, $NR^{27}$—$R^{28}$, $(CH_2)_nOR^{27}$—$R^{28}$, NH—$R^{29}$—$R^{30}$ and $R^{29}$—$R^{30}$, $R^{27}$ is alkyl of 1–8 carbon atoms, $R^{28}$ is selected from hydrogen, cycloalkyl of 3–9 carbon atoms, heterocycloalkyl of 3–8 carbon atoms and 1–2 heteroatoms selected from N, S and O, cycloalkenyl of 5–9 carbon atoms, heterocycloalkenyl of 3–8 carbon atoms and 1–2 heteroatoms selected from N, S and O, aryl of 5–14 carbon atoms and heteroaryl of 4–11 carbon atoms and 1–2 heteroatoms selected from N, S and O, $R^{29}$ is selected from cycloalkyl of 3–9 carbon atoms, heterocycloalkyl of 3–8 carbon atoms and 1–2 heteroatoms selected from N, S and O, cycloalkenyl of 5–9 carbon atoms, heterocycloalkyl of 3–8 carbon atoms and 1–2 heteroatoms selected from N, S and O, aryl of 5–14 carbon atoms, and heteroaryl of 4–11 carbon atoms and 1–2 heteroatoms selected from N, S and O, and R$^{30}$ is selected from hydrogen, halogen, haloalkyl of 1–8 carbon atoms and a number of halogen atoms up to the perhalo level, alkyl of 1–8 carbon atoms, alkenyl of 2–8 carbon atoms, alkynyl of 2–8 carbon atoms, alkoxy of 1–8 carbon atoms, aryl of 5–14 carbon atoms, heteroaryl of 4–11 carbon atoms and 1–2 heteroatoms selected from N, S and O, and C(=O)OH, or (2) R$^5$ combines with R$^6$ to form a radical of formula —Y—(CH$_2$)$_t$—Y—, wherein Y is as defined above;

R$^6$ is selected from hydrogen, OH, and T—R$^{18}$—R$^{19}$,
wherein T is selected from NR$^{33}$, NH, S and O and R$^{18}$, R$^{19}$ and R$^{33}$ are as defined above;

R$^7$ is selected from hydrogen, C(=O)R$^{22}$, (CH$_2$)$_n$—D—R$^{23}$, and R$^{31}$—R$^{32}$,
wherein D, R$^{22}$ and R$^{23}$ are as defined above, and R$^{31}$ is selected from alkyl of 1–7 carbon atoms, alkenyl of 2–8 carbon atoms, alkynyl of 2–8 carbon atoms, and C(=O), and R$^{32}$ is selected from aryl of 5–14 carbon atoms, heteroaryl of 3–11 carbon atoms and 1–2 heteroatoms selected from N, S and O, cycloalkyl of 3–9 carbon atoms, cycloalkenyl of 5–9 carbon atoms, heterocycloalkyl of 3–8 carbon atoms and 1–2 heteroatoms selected from N, S and O, and heterocycloalkenyl of 3–8 carbon atoms and 1–2 heteroatoms selected from N, S and O,
wherein R$^{32}$ may be substituted with alkyl of 1–7 carbon atoms, alkenyl of 2–8 carbon atoms, alkynyl of 2–8 carbon atoms, alkoxy of 1–8 carbon atoms, haloalkyl of 1–8 carbon atoms and a number of halogen atoms up to the perhalo level, haloalkoxy of 1–8 carbon atoms and a number of halogen atoms up to the perhalo level, or halogen;

and pharmaceutically acceptable salts thereof.

The invention further relates to pharmaceutical compositions containing any of the above-described compounds of Formula I and a pharmaceutically acceptable carrier.

The invention also provides methods for treating or preventing a PPAR-γ mediated disease or condition in a mammal. The PPAR-γ mediated disease or condition may be osteopororsis, osteopenia, PPAR-γ mediated cancer, including breast, prostate, colon and lung cancer, inflammation, including atherosclerosis, inflammatory bowel disease, Alzheimer's disease and rheumatoid arthritis, hypertension, hyperglycemia, type 1 diabetes, type 2 diabetes, syndrome X, insulin resistance, obesity, dyslipidemia, hypertriglyceridemia, diabetic dyslipidemia, hyperlipidemia, hypercholesteremia, and skin disorders, such as acne, psoriasis, dermatitis, eczema, keratosis and inflammatory skin conditions caused by lupus erythematosus. The methods of the invention provide for the administration of a compound of Formula I or a compound of Formula IIa:

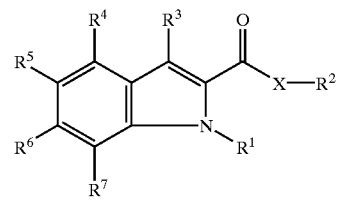

(IIa)

wherein

R$^1$
(1) is selected from hydrogen and R$^8$—R$^9$, or
(2) combines with R$^7$ to form a radical of the formula

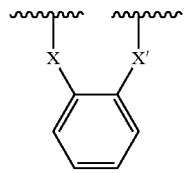

R$^8$ is selected from alkyl of 1–8 carbon atoms, alkenyl of 2–8 carbon atoms, alkynyl of 2–8 carbon atoms, (CH$_2$)$_n$S(=O)$_2$ and (CH$_2$)$_n$C(=O);

R$^9$ is selected from aryl of 5–14 carbon atoms, heteroaryl of 4–11 carbon atoms and 1–2 heteroatoms selected from N, S and O, cycloalkyl of 3–9 carbon atoms, heterocycloalkyl of 3–8 carbon atoms and 1–2 heteroatoms selected from N, S and O, cycloalkenyl of 5–9 carbon atoms, and heterocycloalkenyl of 3–8 carbon atoms and 1–2 heteroatoms selected from N, S and O;
wherein R$^9$ may be substitituted with alkoxy of 1–8 carbon atoms, haloalkoxy of 1–8 carbon atoms and a number of halogen atoms up to the perhalo level, halogen, alkyl of 1–8 carbon atoms, haloalkyl of 1–8 carbon atoms and a number of halogen atoms up to the perhalo level, or X—(CH$_2$)$_n$CH$_3$R$^{10}$, R$^{10}$ is selected from cycloalkyl of 3–9 carbon atoms, heterocycloalkyl of 3–8 carbon atoms and 1–2 heteroatoms selected from N, S and O, cycloalkenyl of 5–9 carbon atoms, heterocycloalkenyl of 3–8 carbon atoms and 1–2 heteroatoms selected from N, S and O;

X and X' are each independently selected from NH, NR$^{33}$, (CH$_2$)$_n$, O and S;

n is a number from 0–8;

R$^{33}$ is selected from alkyl of 1–8 carbon atoms, alkenyl of 2–8 carbon atoms and alkynyl of 2–8 carbon atoms;

R$^2$ is selected from hydrogen, alkyl of 1–8 carbon atoms, haloalkyl of 1–8 carbon atoms and a number of halogen atoms up to the perhalo level, NHS(=O)$_2$R$^{11}$, and (CH$_2$)$_n$S(=O)$_2$R$^{11}$;

R$^{11}$ is selected from aryl of 5–14 carbon atoms and heteroaryl of 4–11 carbon atoms and 1–2 heteroatoms selected from N, S and O,
wherein R$^{11}$ may be substituted with alkyl of 1–8 carbon atoms, alkenyl of 2–8 carbon atoms, alkynyl of 2–8 carbon atoms, alkoxy of 1–8 carbon atoms, haloalkyl of 1–8 carbon atoms and a number of halogen atoms up to the perhalo level, alkoxy of 1–8 carbon atoms, haloalkoxy of 1–8 carbon atoms and a number of halogen atoms up to the perhalo level, or halogen;

$R^3$ is selected from:
(a) hydrogen,
(b) $R^{12}$—$R^{13}$, wherein
  $R^{12}$ is selected from alkyl of 1–8 carbon atoms, alkenyl of 2–8 carbon atoms, alkynyl of 2–8 carbon atoms, and $(CH_2)_n C(=O)$,
  $R^{13}$ is selected from aryl of 5–14 carbon atoms, heteroaryl of 4–11 carbon atoms and 1–2 heteroatoms selected from N, S and O, cycloalkyl of 3–9 carbon atoms, cycloalkenyl of 5–9 carbon atoms, heterocycloalkyl of 3–8 carbon atoms and 1–2 heteroatoms selected from N, S and O, and heterocycloalkenyl of 3–8 carbon atoms and 1–2 heteroatoms selected from N, S and O,
    wherein $R^{13}$ may be substituted with alkyl of 1–8 carbon atoms, alkenyl of 2–8 carbon atoms, alkynyl of 2–8 carbon atoms, haloalkyl of 1–8 carbon atoms and a number of halogen atoms up to the perhalo level, alkoxy of 1–8 carbon atoms, haloalkoxy of 1–8 carbon atoms and a number of halogen atoms up to the perhalo level, or halogen;
(c) cycloalkyl of 3–9 carbon atoms, cycloalkenyl of 5–9 carbon atoms, heterocycloalkyl of 3–8 carbon atoms and 1–2 heteroatoms selected from N, S and O, heterocycloalkenyl of 3–8 carbon atoms and 1–2 heteroatoms selected from N, S and O, all of which may be:
  (i) substituted with aryl of 5–14 carbon atoms, heteroaryl of 4–11 carbon atoms and 1–2 heteroatoms selected from N, S and O, cycloalkyl of 3–9 carbon atoms, cycloalkenyl of 5–9 carbon atoms, heterocycloalkyl of 3–8 carbon atoms and 1–2 heteroatoms selected from N, S and O, heterocycloalkenyl of 3–8 carbon atoms and 1–2 heteroatoms selected from N, S and O, and $C(=O)(CH_2)_n CH_3$, or
  (ii) fused with a spiro ring of 1–6 carbon atoms, or
  (iii) fused with an aryl of 5–14 carbon atoms or a heteroaryl of 4–11 carbon atoms and 1–2 heteroatoms selected from N, S and O, either of which may be substituted with alkyl of 1–8 carbon atoms, alkenyl of 2–8 carbon atoms, alkynyl of 2–8 carbon atoms, haloalkyl of 1–8 carbon atoms and a number of halogen atoms up to the perhalo level, alkoxy of 1–8 carbon atoms, haloalkoxy of 1–8 carbon atoms and a number of halogen atoms up to the perhalo level, or halogen;
(d) aryl of 5–14 carbon atoms or heteroaryl of 4–11 carbon atoms and 1–2 heteroatoms selected from N, S and O, either of which may be substituted with:
  (i) —$Si(CH_3)_3$;
  (ii) $S(=O)_2 R^{14}$, wherein $R^{14}$ is selected from aryl of 5–14 carbon atoms, heteroaryl of 4–11 carbon atoms and 1–2 heteroatoms selected from N, S and O, cycloalkyl of 3–9 carbon atoms, cycloalkenyl of 5–9 carbon atoms, heterocycloalkyl of 3–8 carbon atoms and 1–2 heteroatoms selected from N, S and O, and heterocycloalkenyl of 3–8 carbon atoms and 1–2 heteroatoms selected from N, S and O,
  (iii) $R^{15}$, which combines with $R^5$ to form a radical of the formula —Y—$(CH_2)_n$—Y—, wherein Y and n are as defined above;
  (iv) $C(=O)R^{16}$,
    wherein $R^{16}$ is selected from alkyl of 1–8 carbon atoms and X—$R^{17}$ wherein $R^{17}$ is selected from aryl of 5–14 carbon atoms, heteroaryl of 4–11 carbon atoms and 1–2 heteroatoms selected from N, S and O, cycloalkyl of 3–9 carbon atoms, cycloalkenyl of 5–9 carbon atoms, heterocycloalkyl of 3–8 carbon atoms and 1–2 heteroatoms selected from N, S and O, and heterocycloalkenyl of 3–8 carbon atoms and 1–2 heteroatoms selected from N, S and O, and
    wherein X is as defined above;
  (v) X—$R^{18}$—$R^{19}$
    $R^{18}$ is selected from alkyl of 1–8 carbon atoms, aryl of 5–14 carbon atoms, heteroaryl of 4–11 carbon atoms and 1–2 heteroatoms selected from N, S and O, cycloalkyl of 3–9 carbon atoms, cycloalkenyl of 5–9 carbon atoms, heterocycloalkyl of 3–8 carbon atoms and 1–2 heteroatoms selected from N, S and O, and heterocycloalkenyl of 3–8 carbon atoms and 1–2 heteroatoms selected from N, S and O,
    $R^{19}$ is selected from hydrogen, halogen, haloalkyl of 1–8 carbon atoms and a number of halogen atoms up to the perhalo level, alkyl of 1–8 carbon atoms, alkenyl of 2–8 carbon atoms, alkynyl of 2–8 carbon atoms, aryl of 5–14 carbon atoms, heteroaryl of 4–11 carbon atoms and 1–2 heteroatoms selected from N, S and O, cycloalkyl of 3–9 carbon atoms, cycloalkenyl of 5–9 carbon atoms, heterocycloalkyl of 3–8 carbon atoms and 1–2 heteroatoms selected from N, S and O, and heterocycloalkenyl of 3–8 carbon atoms and 1–2 heteroatoms selected from N, S and O, $R^{20}$—$R^{21}$ and X—$R^{21}$,
    X is as defined above,
    $R^{20}$ is aryl of 5–14 carbon atoms or heteroaryl of 4–11 carbon atoms and 1–2 heteroatoms selected from N, S and O, and
    $R^{21}$ is selected from aryl of 5–14 carbon atoms, heteroaryl of 4–11 carbon atoms and 1–2 heteroatoms selected from N, S and O, cycloalkyl of 3–9 carbon atoms, cycloalkenyl of 5–9 carbon atoms, heterocycloalkyl of 3–8 carbon atoms and 1–2 heteroatoms selected from N, S and O, and heterocycloalkenyl of 3–8 carbon atoms and 1–2 heteroatoms selected from N, S and O,
$R^4$ is selected from hydrogen and X—$R^{18}$—$R^{19}$,
  wherein X, $R^{18}$ and $R^{19}$ have the meanings given above;
$R^5$ (1) is selected from:
(a) hydrogen;
(b) $R^{12}$—$R^{13}$
  wherein $R^{12}$ and $R^{13}$ are as defined above,
(c) $C(=O)R^{22}$, wherein
  $R^{22}$ is selected from alkyl of 1–8 carbon atoms, aryl of 5–14 carbon atoms, heteroaryl of 4–11 carbon atoms and 1–2 heteroatoms selected from N, S and O, cycloalkyl of 3–9 carbon atoms, cycloalkenyl of 5–9 carbon atoms, heterocycloalkyl of 3–8 carbon atoms and 1–2 heteroatoms selected from N, S and O, and heterocycloalkenyl of 3–8 carbon atoms and 1–2 heteroatoms selected from N, S and O,
(d) alkyl of 1–8 carbon atoms, alkenyl of 2–8 carbon atoms, alkynyl of 2–8 carbon atoms, aryl of 5–14 carbon atoms, heteroaryl of 4–11 carbon atoms and 1–2 heteroatoms selected from N, S and O, cycloalkyl of 3–9 carbon atoms, cycloalkenyl of 5–9 carbon atoms, heterocycloalkyl of 3–8 carbon atoms and 1–2 heteroatoms selected from N, S and O, and heterocycloalkenyl of 3–8 carbon atoms and 1–2 heteroatoms selected from N, S and O, (e) —$(CH_2)_n$—Y—$R^{23}$, wherein:
  (i) Y and n are as defined above,
  (ii) $R^{23}$ is selected from alkyl of 1–8 carbon atoms, alkenyl of 2–8 carbon atoms, alkynyl of 2–8 carbon atoms, C(=O)$R^{24}$, $(CH_2)_n R^{24}$, and $R^{25}$—$R^{26}$, wherein
    $R^{25}$ is alkyl of 1–8 carbon atoms,
    $R^{26}$ is selected from aryl of 5–14 carbon atoms, heteroaryl of 4–11 carbon atoms and 1–2 heteroatoms selected from N, S and O, cycloalkyl of 3–9 carbon atoms, cycloalkenyl of 5–9 carbon atoms, heterocycloalkyl of 3–8 carbon atoms and 1–2 heteroatoms selected from N, S and O, and heterocycloalkenyl of 3–8 carbon atoms and 1–2 heteroatoms selected from N, S and O,
    $R^{24}$ is selected from cycloalkyl of 3–9 carbon atoms, cycloalkenyl of 5–9 carbon atoms, heterocycloalkyl of 3–8 carbon atoms and 1–2 heteroatoms selected from N, S and O, heterocycloalkenyl of 3–8 carbon atoms and 1–2 heteroatoms selected from N, S and O, C(=O)OH, NHR$^{27}$—$R^{28}$, NR$^{27}$—$R^{28}$, NR$^{33}$R$^{27}$—R$^{28}$, $(CH_2)_n R^{27}$—$R^{28}$, and $R^{29}$—$R^{30}$,
    $R^{27}$ is alkyl of 1–8 carbon atoms,
    $R^{28}$ is selected from hydrogen, aryl of 5–14 carbon atoms, heteroaryl of 4–11 carbon atoms and 1–2 heteroatoms selected from N, S and O, cycloalkyl of 3–9 carbon atoms, cycloalkenyl of 5–9 carbon atoms, heterocycloalkyl of 3–8 carbon atoms and 1–2 heteroatoms selected from N, S and O, and heterocycloalkenyl of 3–8 carbon atoms and 1–2 heteroatoms selected from N, S and O, all of which, with the exception of hydrogen, may be fused with aryl of 5–14 carbon atoms or heteroaryl of 4–11 carbon atoms and 1–2 heteroatoms selected N, S and O,
    $R^{29}$ is selected from aryl of 5–14 carbon atoms, heteroaryl of 4–11 carbon atoms and 1–2 heteroatoms selected from N, S and O, cycloalkyl of 3–9 carbon atoms, cycloalkenyl of 5–9 carbon atoms, heterocycloalkyl of 3–8 carbon atoms and 1–2 heteroatoms selected from N, S and O, and heterocycloalkenyl of 3–8 carbon atoms and 1–2 heteroatoms selected from N, S and O, and
    $R^{30}$ is selected from hydrogen, halogen, haloalkyl of 1–8 carbon atoms and a number of halogen atoms up to the perhalo level, alkyl of 1–8 carbon atoms, alkenyl of 2–8 carbon atoms, alkynyl of 2–8 carbon atoms, alkoxy of 1–8 carbon atoms, haloalkoxy of 1–8 carbon atoms and a number of halogen atoms up to the perhalo level, aryl of 5–14 carbon atoms and heteroaryl of 4–11 carbon atoms and 1–2 heteroatoms selected from N, S and O;
  (2) combines with $R^6$ to form a radical of the formula —Y—$(CH_2)_n$—Y—, wherein Y and n have the meanings given above;

$R^6$ is selected from hydrogen, OH and X—$R^{18}$—$R^{19}$, wherein X, $R^{18}$ and $R^{19}$ have the meanings give above $R^7$ is selected from hydrogen, C(=O)$R^{22}$, $(CH_2)_n$—Y—$R^{23}$, and $R^{12}$—$R^{13}$, wherein $R^{22}$, $R^{23}$, $R^{12}$, $R^{13}$, Y and n have the meanings give above; and pharmaceutically acceptable salts thereof.

The present invention therefore provides compounds, pharmaceutical compositions containing such compounds, and methods for the treatment or prevention of PPAR-γ mediated diseases and conditions. Compounds, compositions and methods of the present invention therefore are useful in treatment of PPAR-γ mediated diseases and conditions without the concomitant undesired side-effects of natural hormones. These and other aspects of the invention will be more apparent from the following description and claims.

DETAILED DESCRIPTION OF THE INVENTION

The invention provides novel, substituted indoles of Formula I, pharmaceutical compositions containing such indoles, and their use in the treatment or prevention of PPAR-γ mediated diseases or conditions in a mammal. The invention further provides methods of treating or preventing PPAR-γ mediated diseases or conditions in a mammal, such as a human, by administration of a compound of Formula IIa. The compounds of Formula I and Formula IIa have both been broadly described above.

In one embodiment of the compounds of Formula I:

$R^8$ is alkyl $R^9$ is phenyl, which may or may not be substituted;

X is O;

$R^2$ is hydrogen; and $R^3$ is aryl, particularly phenyl, or heteroaryl, either of which may or may not be substituted.

As used herein, the term "aryl" includes aromatic ring structures that are substituents on another atom. These aryls may also be substituted with substituents, such as halogen, haloalkyl, alkoxy, haloalkoxy, etc. Non-limiting examples of aryls include phenyl, napthyl, etc. Likewise, the term "heteroaryl" as used herein includes aromatic ring structures containing between one and two heteroatoms, such as O, N and S, that are substituents on another atom. These heteroaryls may also be substituted with substituents, such as alkyl, alkenyl, alkoxy, haloalkoxy, halogen, haloalkyl, etc. Non-limiting examples of heteroaryls include pyridyl, furyl, quinolyl, etc.

As used herein the term "alkyl" includes straight-chain or branched alkyls of between 1 and 8 carbon atoms. The term "alkenyl" includes straight-chain or branched alkenyls of between 2 and 8 carbon atoms. As used herein the term "alkynyl" includes straight-chain or branched alkynyls of between 2 and 8 carbon atoms. Such alkyls, alkenyls and alkynyls may be terminal or may be linkers between other portions of a molecule.

Examples of compounds of the invention where $R^3$ is a heteroaryl include, but are not limited to:

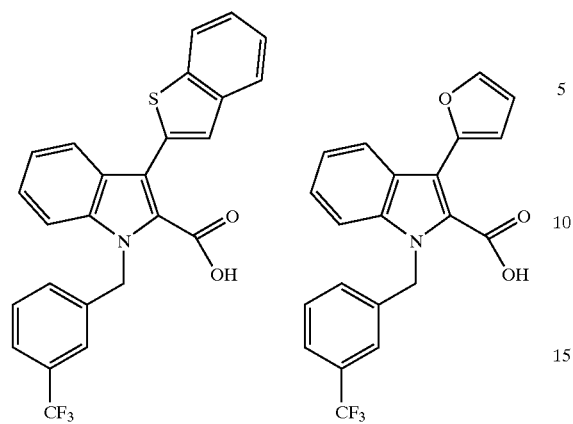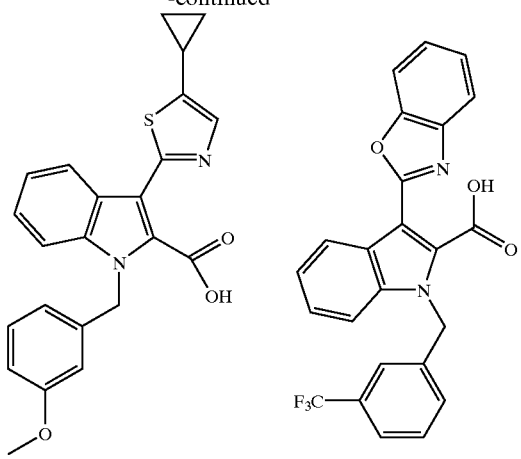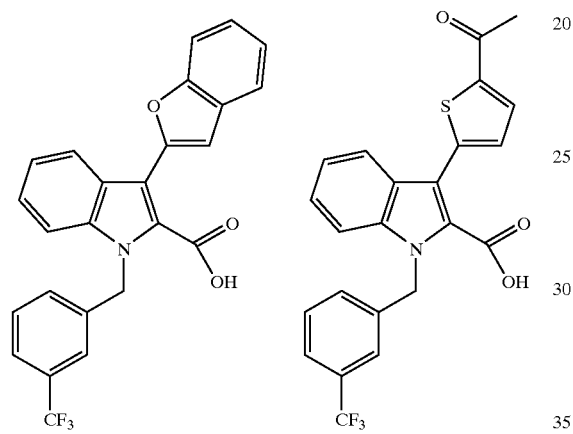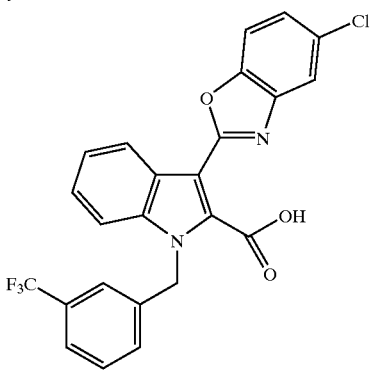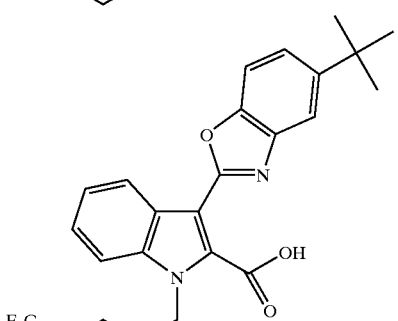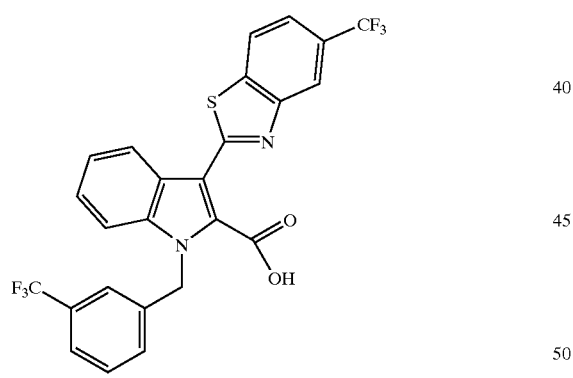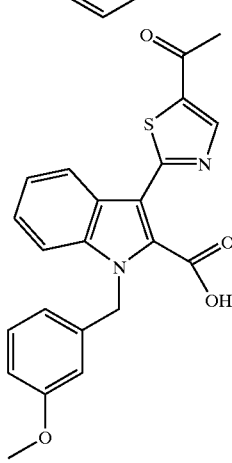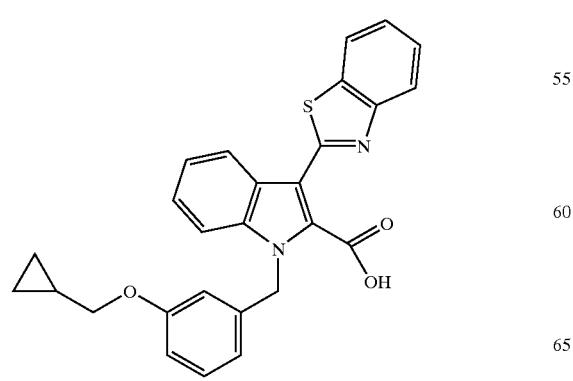
Examples of compounds of the invention where $R^3$ is phenyl include, but are not limited to:

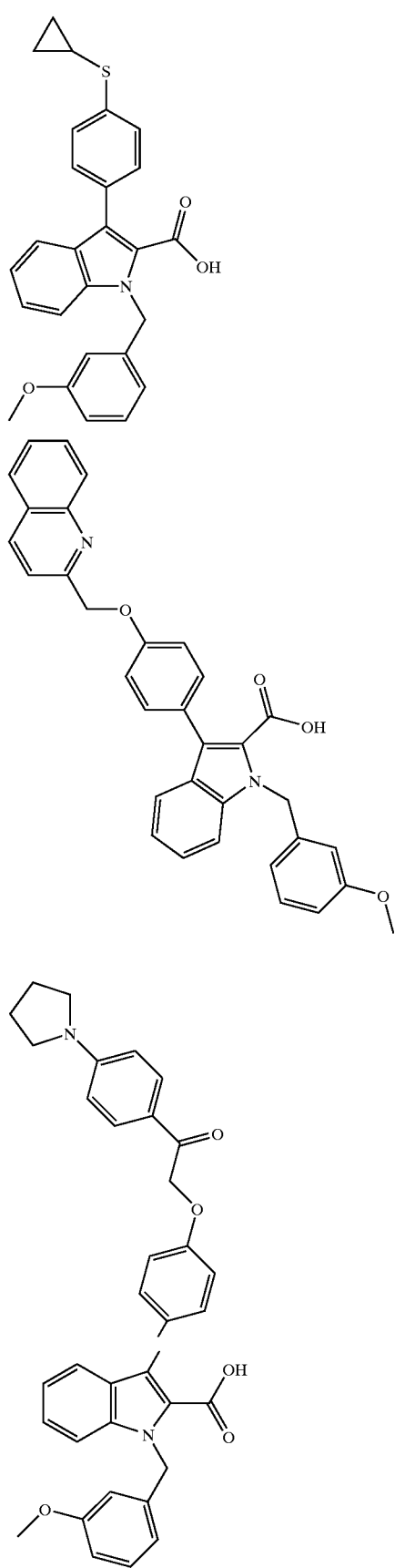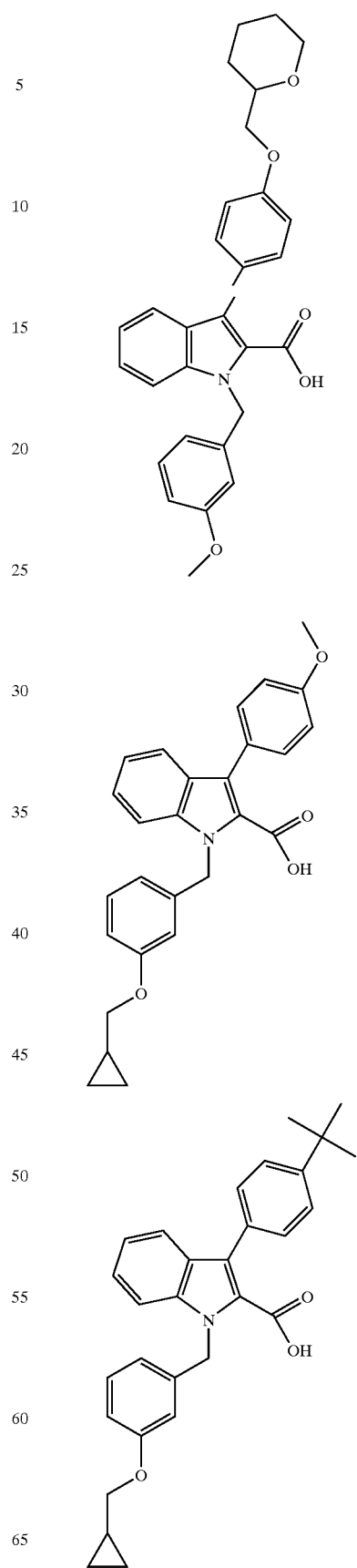

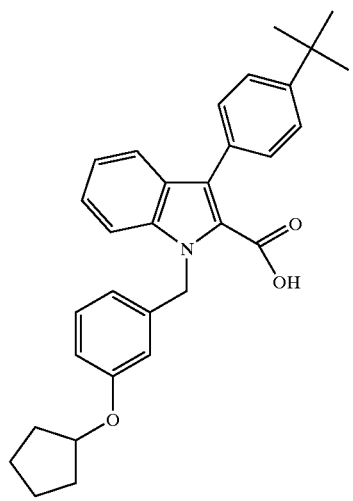
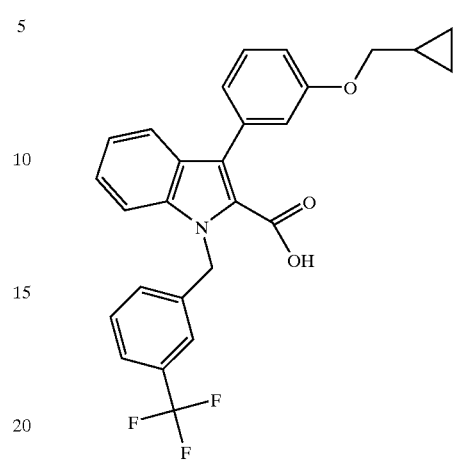
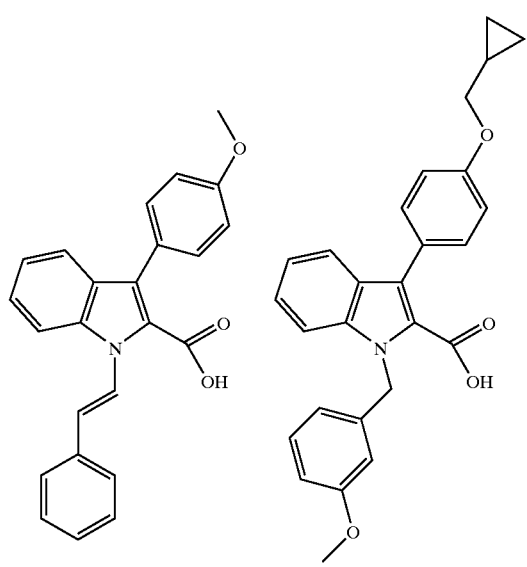
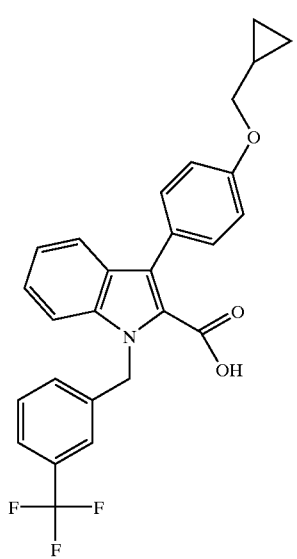

-continued
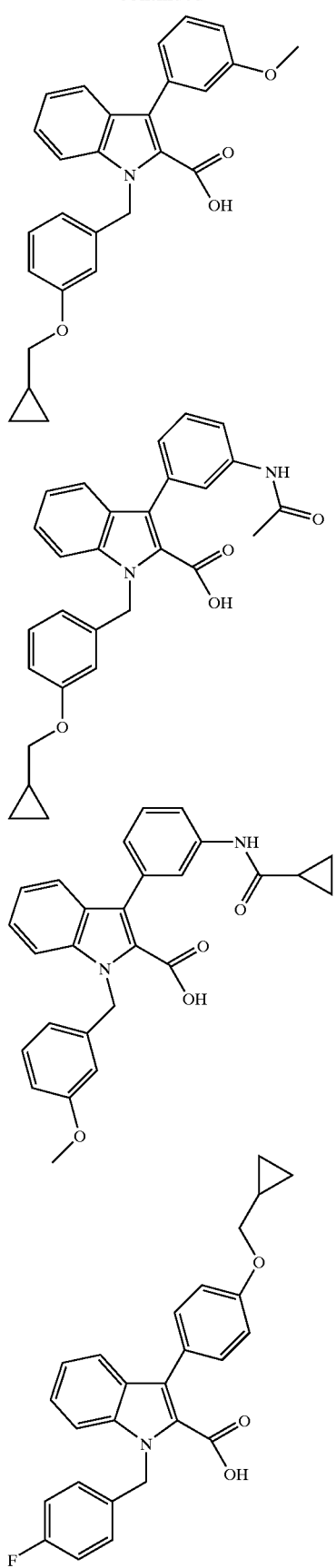
-continued
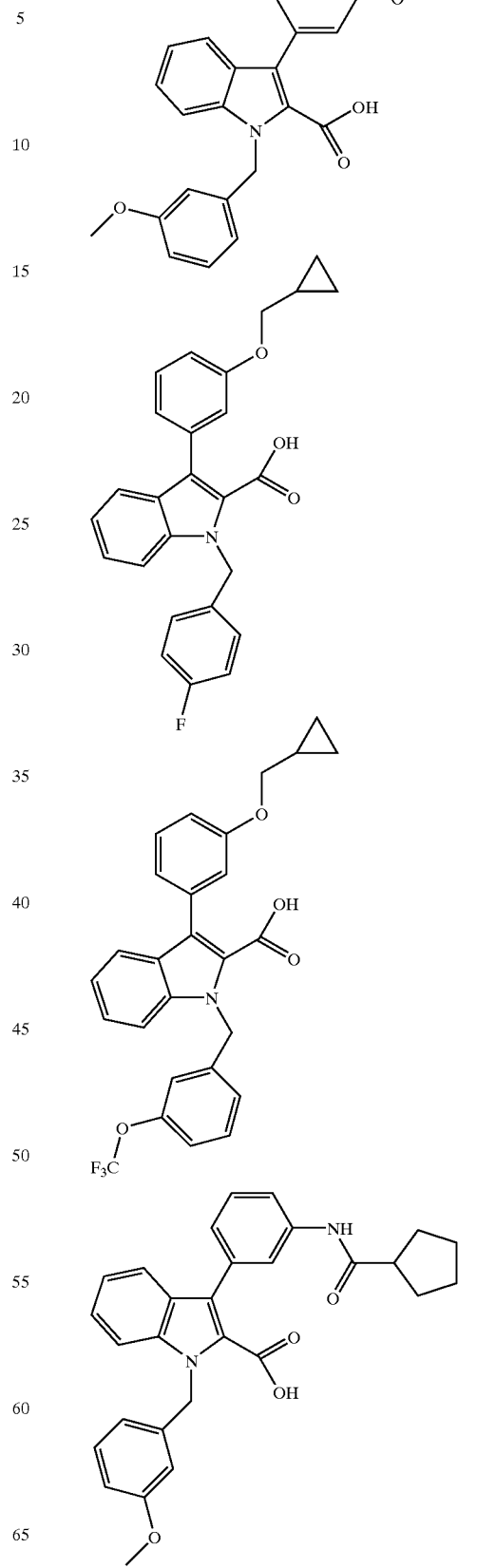

-continued

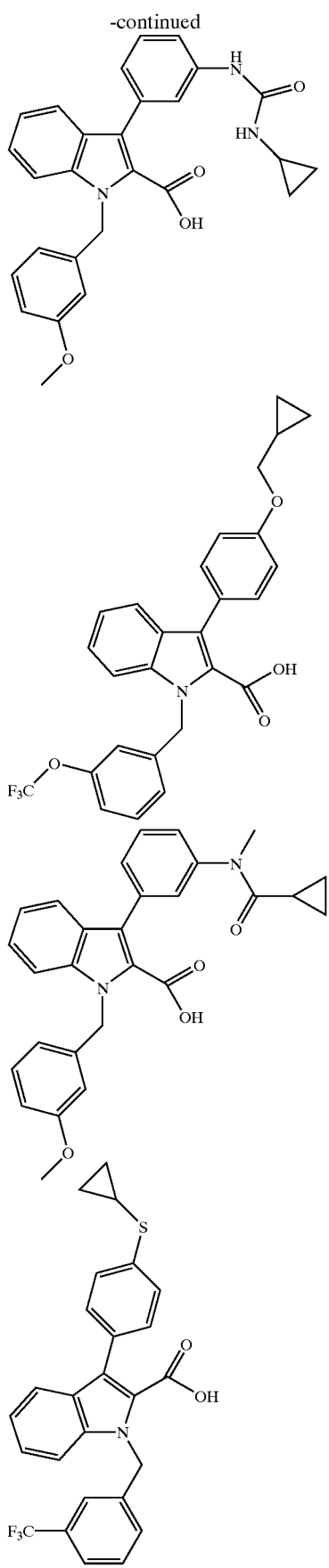

In another embodiment of the invention, $R^3$ is $R^{12}$—$R^{13}$, where $R^{13}$ is cycloalkyl, heterocycloalkyl, cycloalkenyl or heterocycloalkenyl. Examples of compounds of the invention where $R^3$ is $R^{12}$—$R^{13}$ include, but are not limited to:

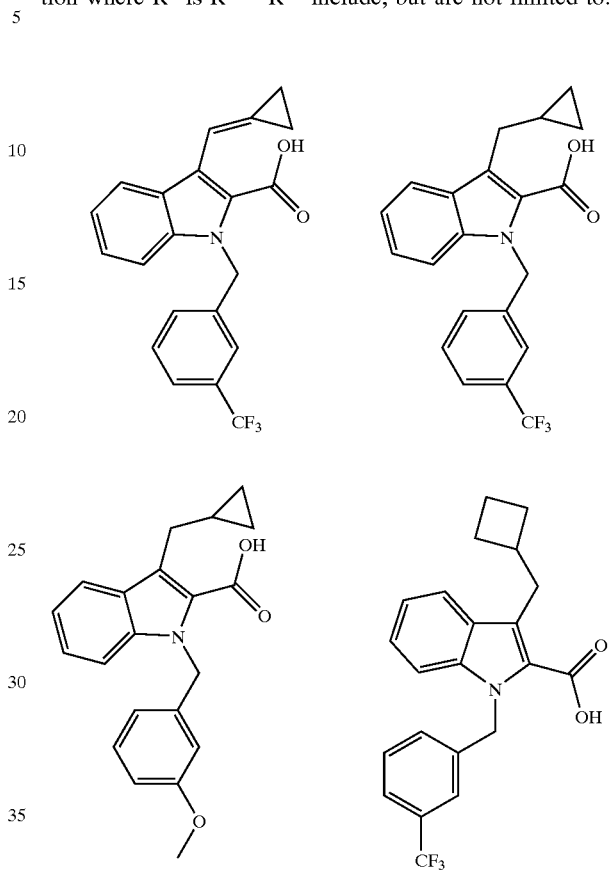

In other embodiments of the invention, $R^3$ is a cycloalkyl, heterocylcoalkyl, cycloalkenyl or heterocycloalkenyl, which may be substituted or may be fused with a spiro ring of 3–9 carbon atoms. Examples of compounds of the invention where $R^3$ is a cycloalkyl, heterocylcoalkyl, cycloalkenyl or heterocycloalkenyl include, but are not limited to:

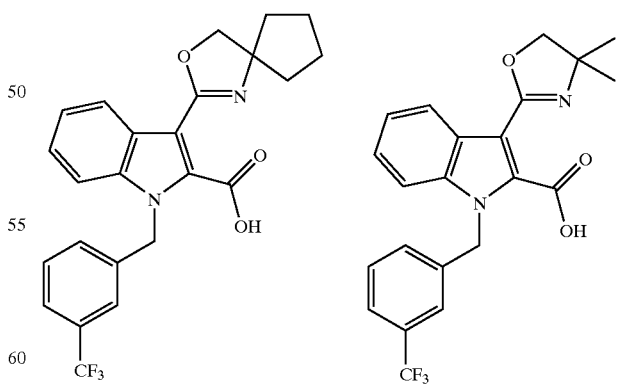

In still other embodiments of the invention, $R^4$, $R^5$, $R^6$ and/or $R^7$ may be other than hydrogen. Examples of compounds of the invention where $R^4$, $R^5$, $R^6$ and/or $R^7$ are other than hydrogen include, but are not limited to:

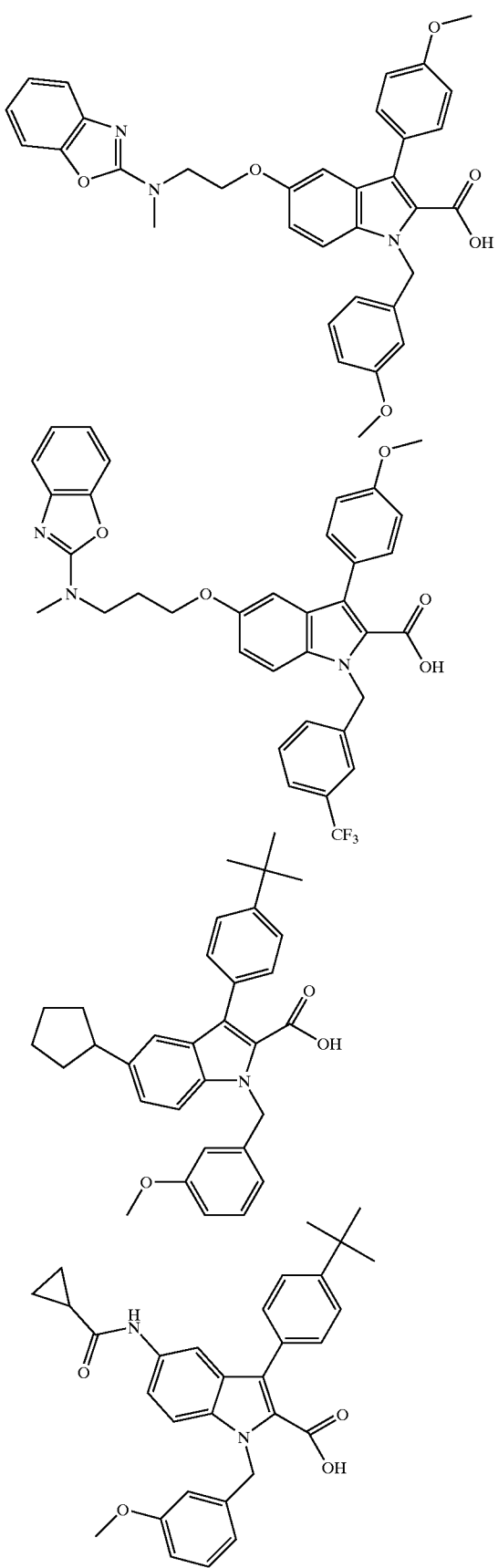
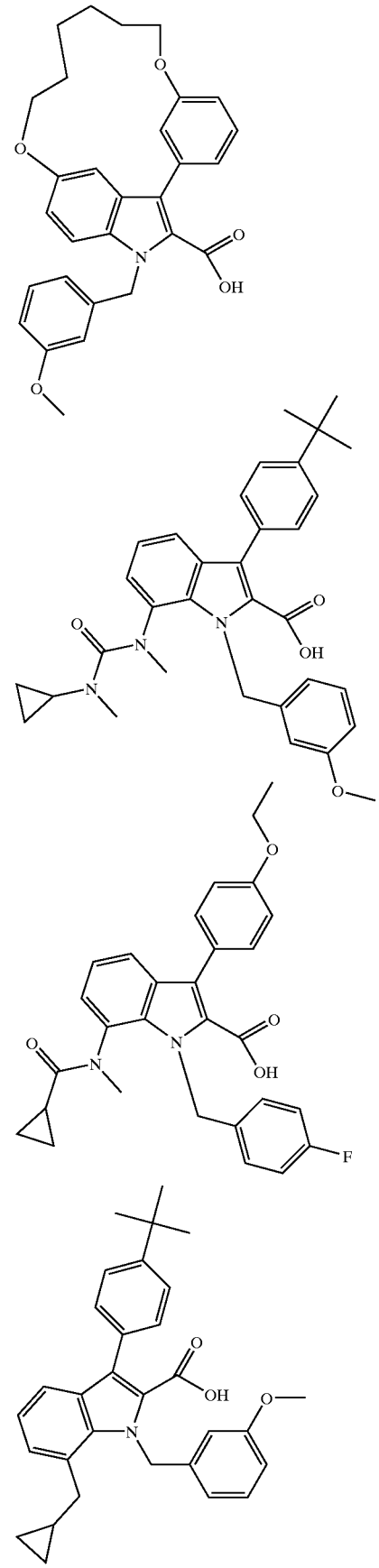

25
-continued
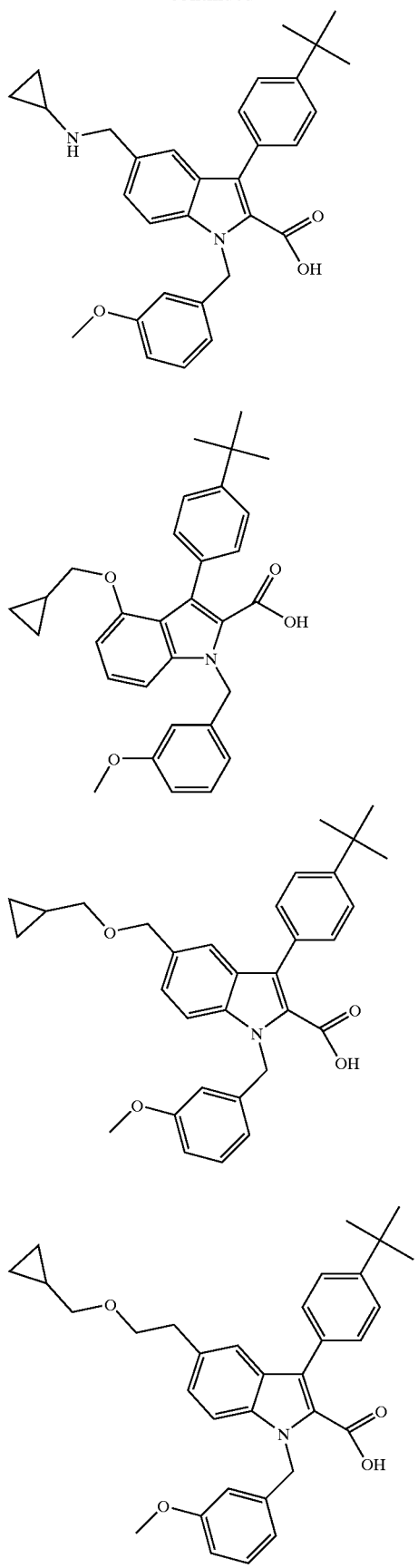
26
-continued
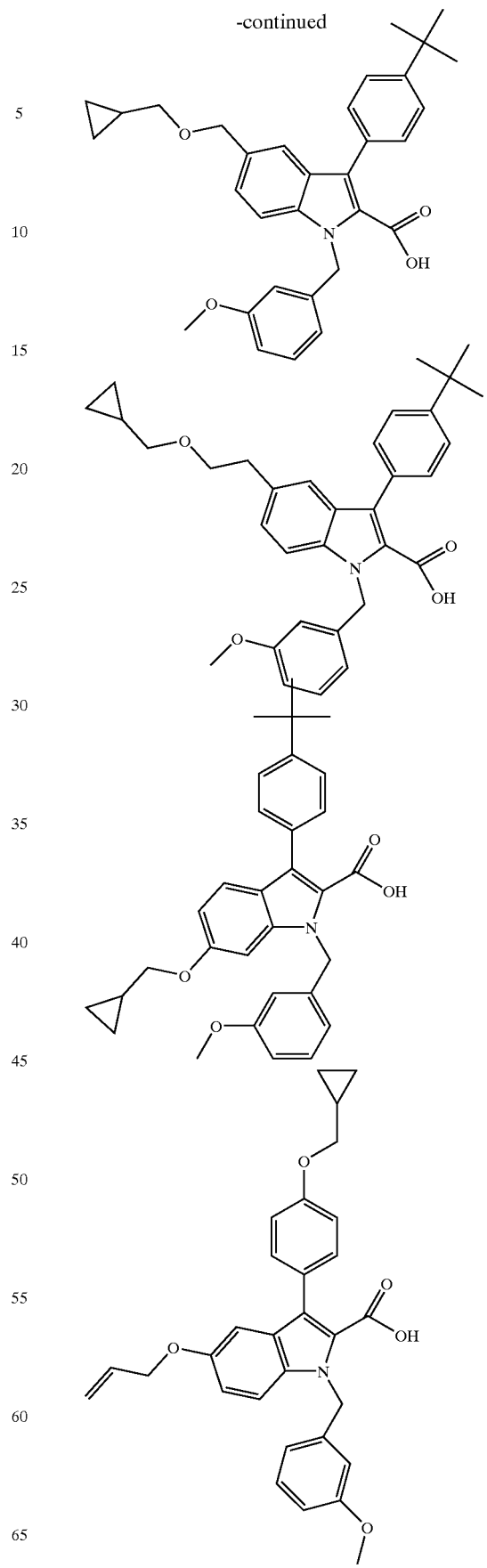

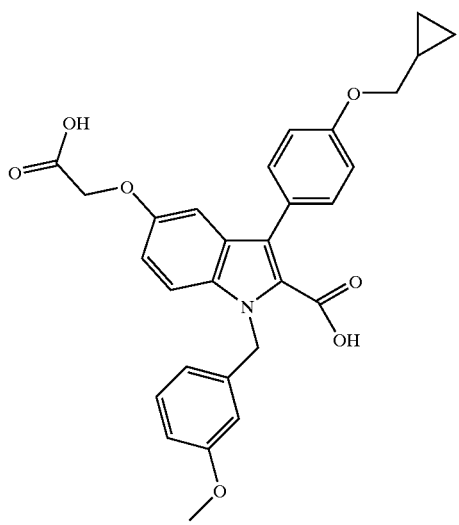

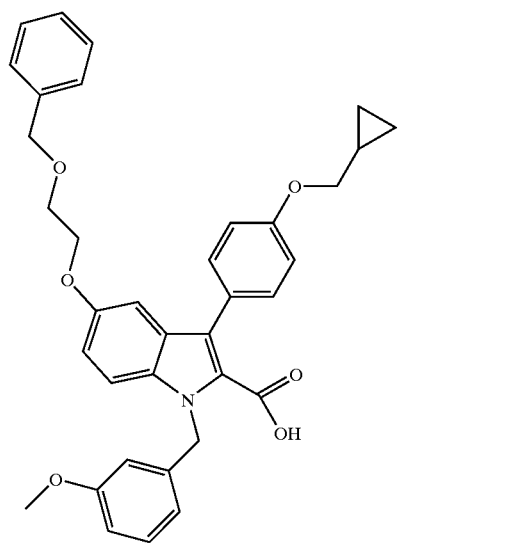

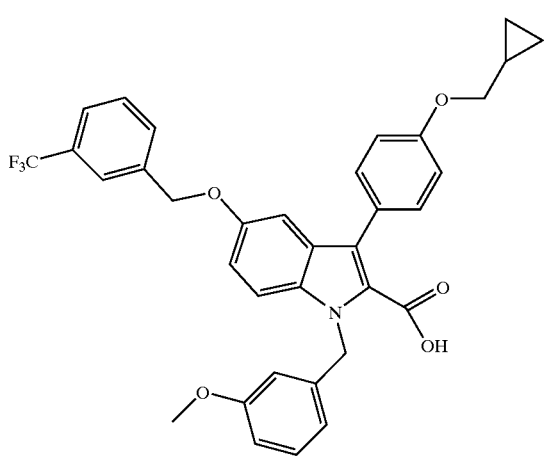

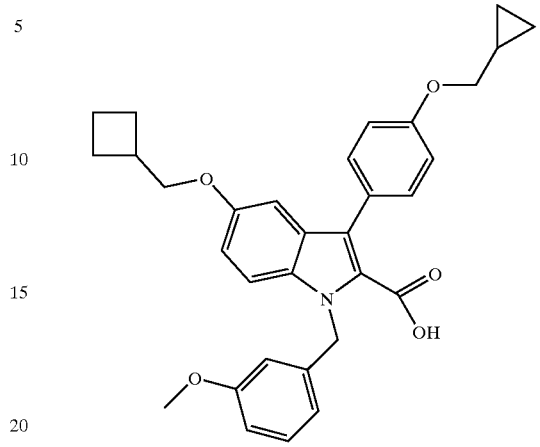

Compounds of Formulas I and IIa may be useful in the treatment or prevention of PPAR-γ mediated diseases or conditions. An agent which binds to PPAR-γ may be employed for a wide variety of indications, including, but not limited to:

(1) osteoporosis and osteopenia, see, Nuttall, et al., *Bone* 27 (2), (2000), 177–184; Gimble, et al., *Bone* 19 (5), (1996), 421–428;

(2) cancer, particularly PPAR-γ mediated cancers, such as breast and prostate cancers (see, Gelman, et al., *Cell. and Mol. Life Sci.*, 55 (6–7), (1999), 935–943; Kersten, et al., *Nature*, 405 (6785), May 25, 2000, 421–424), colon cancer (see, Saez, et al., *Nat. Med.*, 4 (9) Sept. 1998, 1058–1061; Lefebvre, et al., *Nat. Med.*, 4 (9), Sept. 1998, 1053–1057; Demetri, et al., *Proc. Nat'l. Acad. Sci. USA*, 96 (7), Mar. 30, 1999, 3951–3956) liposarcoma (Demetri, et al., *Proc. Nat'l. Acad. Sci USA*, 96 (7), Mar. 30, 1999, 3951–3956) and lung cancer (see, Chang, et al., *Cancer Res.*, 60, 2000, 1129–1138);

(3) hyperglycemia, type 1 diabetes, type 2 diabetes, syndrome X, and insulin resistance, (see Lehmann, et al., *J. Bio. Chem.*, 270 (22) (1995), 12953–12956; Spiegelman, *Diabetes*, 47 (4), (1998), 507–514);

(4) obesity, (see Zhou, et al., *Proc. Nat'l. Ac. Sci. USA*, 96 (5), (1999), 2391–2395; U.S. Pat. No. 6,033,656);

(5) inflammation, particularly inflammatory bowel disease (see *Cell. and Mol. Life Sci.*, 55 (6–7), (1999), 935–943), Alzheimer's disease (see, Combs, et al, *J. Neurosci.* 20 (2), 2000, 558–567), rheumatoid arthritis (see, Jiang, et al., *Nature* 391 (6662), 1998, 82–86), and atherosclerosis (see Pasceri, et al., *Circulation*, 101 (3), 2000, 235–238);

(6) cardiovascular disease, particularly hypertension, (see *Cell. and Mol. Life Sci.*, 55 (6–7), (1999), 935–943 review);

(7) dyslipidemia, hypertriglyceridemia, diabetic dyslipidemia, hyperlipidemia and hypercholesteremia (see Hulin, et al., *Curr. Pharm. Design,* 2 (1996), 85–102); and (8) skin disorders, particularly inflammatory skin disorders caused by lupus erythematosus, and acne, psoriasis, dermatitis, eczema and keratosis (see, WO 99/34783; U.S. Pat. No. 5,981,586).

Compounds of Formulas I and IIa are preferably used in the treatment or prevention of osteopenia, osteoporosis, and PPAR-γ mediated cancers, including breast, prostate and colon cancer.

The present invention also includes pharmaceutically acceptable salts of the compounds of Formulas I and IIa. Suitable pharmaceutically acceptable salts are well known to those skilled in the art and include basic salts of inorganic and organic acids, such as hydrochloric acid, hydrobromic acid, sulphuric acid, phosphoric acid, methanesulphonic acid, trifluoromethanesulfonic acid, sulphonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid. In addition, pharmaceutically acceptable salts include acid salts of inorganic bases, such as salts containing alkaline cations (e.g., $Li^+$ $Na^+$ or $K^+$), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations such as those arising from protonation or peralkylation of triethylamine, N,N-diethylamine, N,N-dicyclohexylamine, pyridine, N,N-dimethylaminopyridine (DMAP), 1,4-diazabicyclo[2.2.2] octane (DABCO), 1,5-diazabicyclo[4.3.0]non-5-ene (DBN) and 1,8-diazabicyclo[5.4.0]undec-7-ene (DBU).

A number of the compounds of Formulas I and IIa possess asymmetric carbons and can therefore exist in racemic and optically active forms. Methods of separation of enantiomeric and diastereomeric mixtures are well known to the skilled in the art. The present invention encompasses any racemic or optically active forms of compounds described in Formula I or Formula IIa which possess PPAR-γ modulating activity or the use of any racemic or optically active forms of the compounds described in Formulas I and IIa for the treatment or prevention of PPAR-γ mediated diseases or conditions.

The therapeutic agents of the invention may be employed alone or concurrently with other therapies. For example, when employed as a treatment for osteoporosis or osteopenia, the compounds of the invention may be used in combination with a calcium source, vitamin D or analogues of vitamin D, and/or antiresorptive therapies such as estrogen replacement therapy, treatment with a fluoride source, treatment with calcitonin or a calcitonin analogue, or treatment with a bisphosphonate such as alendronate. The method of the invention is intended to be employed for treatment of PPAR-γ mediated diseases or conditions in both humans and other mammals.

The compounds may be administered orally, dermally, parenterally, by injection, by inhalation or spray, or sublingually, rectally or vaginally in dosage unit formulations. The term "administered by injection" includes intravenous, intraarticular, intramuscular, subcutaneous and parenteral injections, as well as use of infusion techniques. Dermal administration may include topical application or transdermal administration. One or more compounds may be present in association with one or more non-toxic pharmaceutically acceptable carriers and, if desired, other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations.

Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oil phase may be a vegetable oil, for example olive oil or arachis oil, or a mineral oil, for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

Compounds of the invention may also be administered transdermally using methods known to those skilled in the art (see, e.g., Chien; "Transdermal Controlled Systemic Medications"; Marcel Dekker, Inc.; 1987. Lipp et al. WO 94/04157 Mar. 3, 1994). For example, a solution or suspension of a compound of Formula I or IIa in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I or Ia may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures one or more materials selected from lower alcohols, lower ketones, lower carboxylic acid esters, polar ethers, lower hydrocarbons, halogenated hydrocarbons.

Suitable penetration enhancing materials for transdermal delivery systems are known to those skilled in the art, and include, for example, monohydroxy or polyhydroxy alcohols such as ethanol, propylene glycol or benzyl alcohol, saturated or unsaturated $C_8$–$C_{18}$ fatty alcohols such as lauryl alcohol or cetyl alcohol, saturated or unsaturated $C_8$–$C_{18}$ fatty acids such as stearic acid, saturated or unsaturated fatty esters with up to 24 carbons such as methyl, ethyl, propyl, isopropyl, n-butyl, sec-butyl isobutyl tert-butyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures one or more materials selected from monohydroxy or polyhydroxy alcohols, saturated or unsaturated $C_8$–$C_{18}$ fatty alcohols, saturated or unsaturated $C_8$–$C_{18}$ fatty acids, saturated or unsaturated fatty esters with up to 24 carbons, diesters of saturated or unsaturated dicarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrene-butadiene coploymers, and natural and synthetic rubbers. Cellulose ethers, derivatized polyethylenes, and silicates may also be used as matrix components. Additional additives, such as viscous resins or oils may be added to increase the viscosity of the matrix.

For all regimens of use disclosed herein for compounds of Formulas I and IIa, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.1 to 200 mg administered between one to four times daily. The transdermal concentration will preferably be that required to maintain a daily dose of from 0.01 to 200 mg/Kg. The daily inhalation dosage regimen will preferably be from 0.01 to 10 mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, but not limited to the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of a compound of Formula I or IIa or a pharmaceutically acceptable salt thereof given for a defined number of days, can be ascertained by those skilled in the art using conventional treatment tests.

The compounds of Formulas I and IIa may be prepared by use of known chemical reactions and procedures, from known compounds (or from starting materials which, in turn, are producible from known compounds) through the preparative methods shown below, as well as by other reactions and procedures known to the skilled in the art. Such reactions and procedures include, but are not limited to, esterification, hydrolysis, alkylation, acylation neutralization, coupling, oxidation, reduction, condensation, elimination and substitution reactions. Nevertheless, the following general preparative methods are presented to aid practitioners in synthesizing the compounds of the invention, with more detailed particular examples being presented in the experimental section. The examples are for illustrative purposes only and are not intended, nor should they be construed, to limit the invention in any way.

Within the scope of each method, optional substituents may appear on reagents or intermediates which may act as protecting groups or other non-participating groups. Utilizing methods well known to those skilled in the art, such groups are introduced and/or removed during the course of the synthetic schemes to provide the compounds of the present invention. All variable groups not defined below are as described hereinabove.

In general, compounds of Formula I or IIa may be prepared from the appropriately substituted indoles, by esterification, hydrolysis, sulfonylation or neutralization reactions as shown in Flow Diagram I:

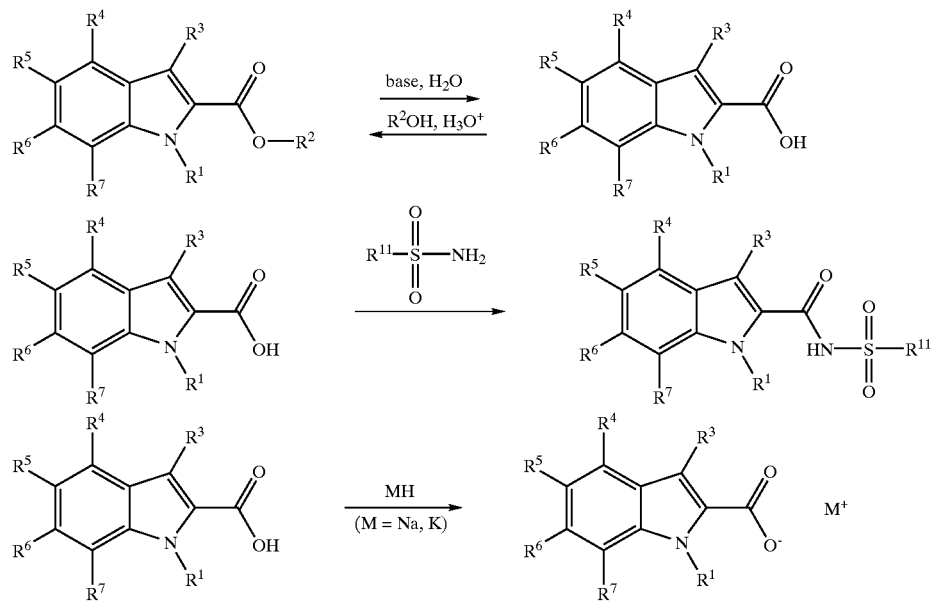

Flow Diagram I

Preparation of certain Formula I compounds with a variety of $R^3$ substituents may be prepared by a sequence involving conversion of VI to a boronic acid intermediate, followed by a palladium-facilitated coupling reaction with an organohalide and base, such as triethylamine, potassium carbonate or Huenig's base, as shown in Flow Diagram II. Alternatively, either a boronic acid or organotin intermediate may be coupled with VI under similar conditions.

Other compounds with heterocycloakenyl or heteroaryl substituents at the $R^3$ position may prepared by condensation of 3-carboxy-substituted indoles with 2-aminoethanols, 2-aminophenols or 2-aminothiols as illustrated in Flow Diagram III.

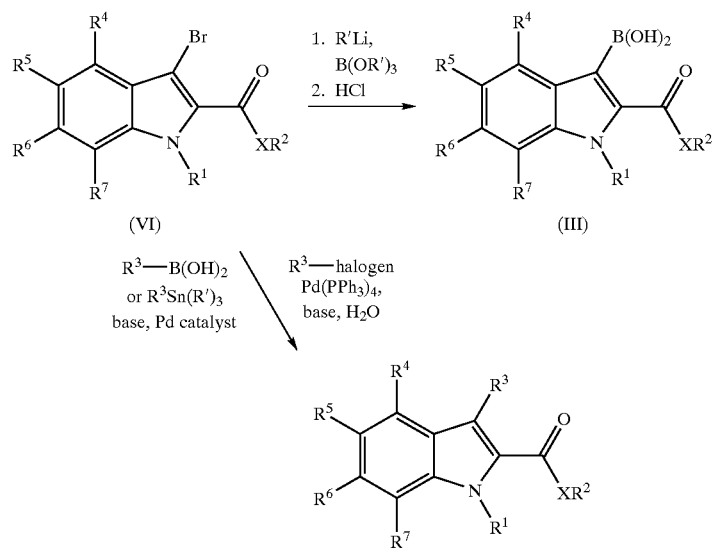

Flow Diagram II $R'$ = lower alkyl;
halogen = Br, Cl, I

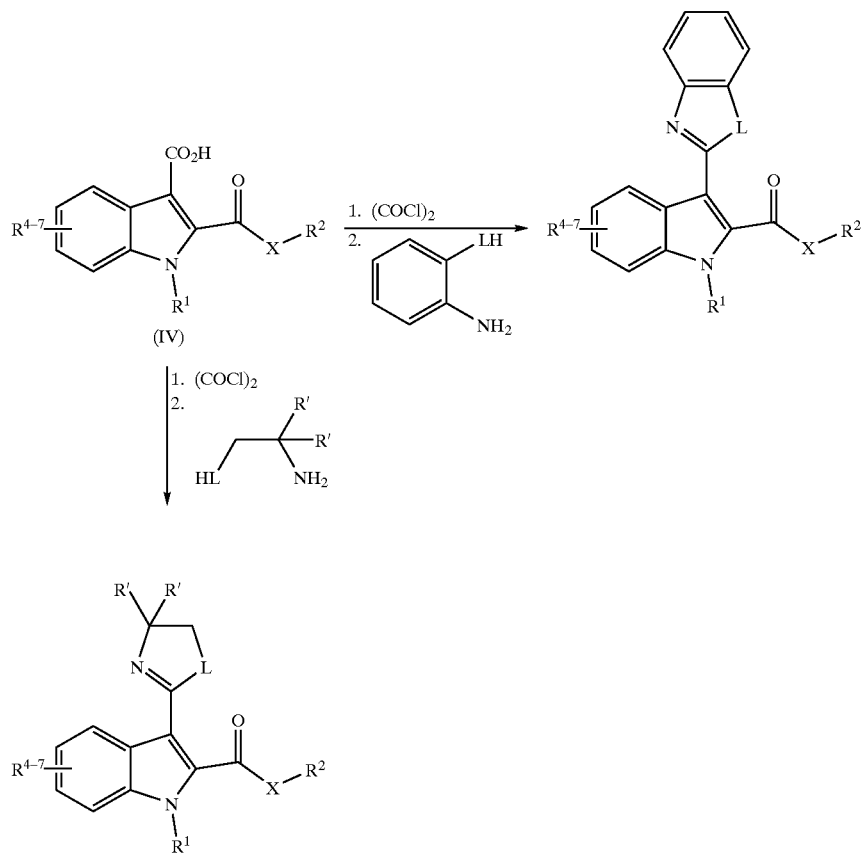
L = O, S, N—Me
R' = lower alkyl
Certain aryl substituents on the $R^3$ aryl ring may be further transformed to other substituents by standard means. An illustration of this is shown in Flow Diagram IV, in which a nitro group is reduced and acylated to provide amido substituents.
Flow Diagram IV
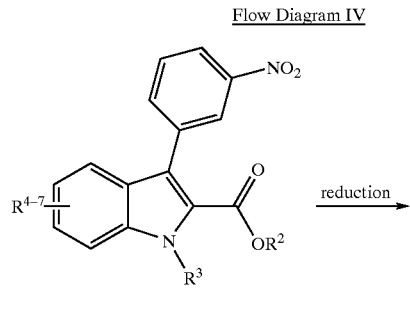
-continued
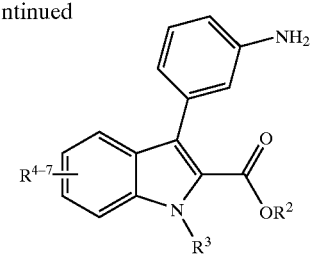
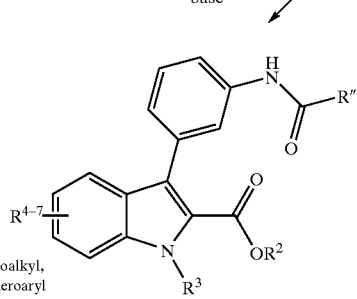
$R''$ = alkyl, cycloalkyl, aryl, or heteroaryl Compounds of Formula I which bear certain $R^3$ substituents may be prepared by Friedel-Crafts acylation of the corresponding unsubstituted indole, followed by reduction of the carbonyl group to a methylene, as shown in Flow Diagram V.

Flow Diagram V

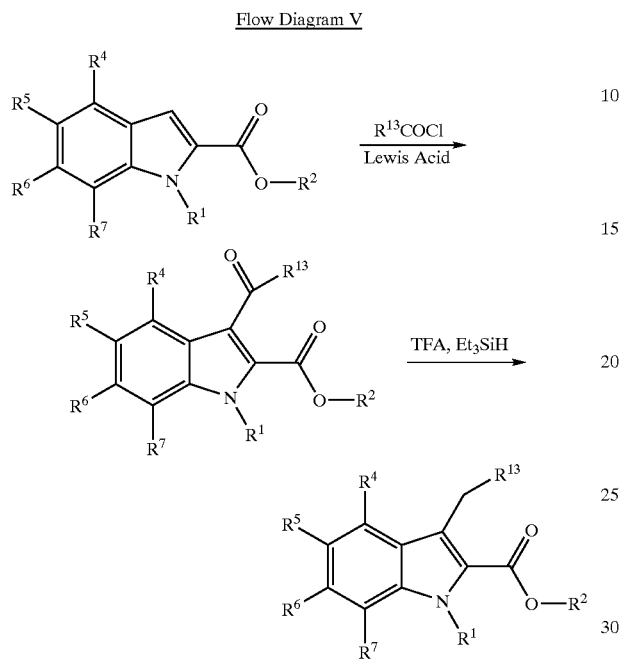

Compounds of Formula I with similar substituents at either $R^5$ or $R^7$ may be likewise prepared, either individually (Flow Diagram VI) or as mixtures (Flow Diagram VII) by an analogous sequence of acylation and reduction reactions. In the latter scheme, where $R^5$ and $R^7$ are hydrogen in the starting materials, individual compounds may be obtained by chromatographic separation of products (Ig and Ii) after the initial step.

Flow Diagram VI

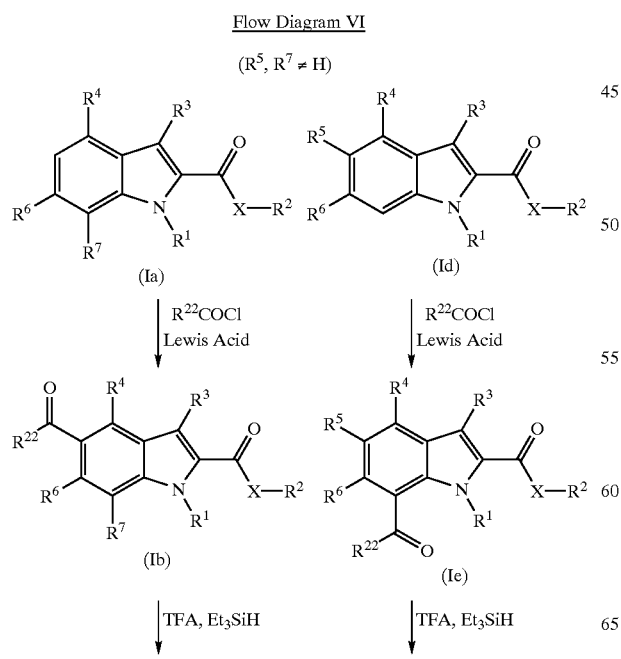

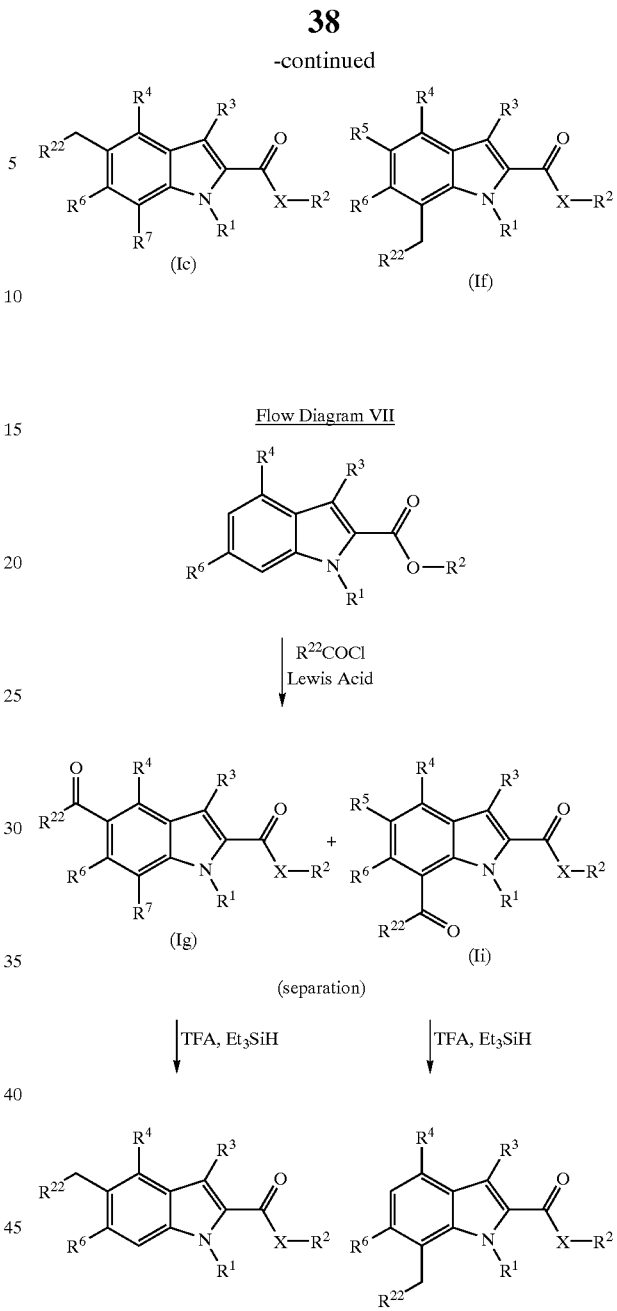

O-Alkylation reactions may be utilized to prepare Formula I compounds bearing substituents on $R^4$, $R^5$, $R^6$ or $R^7$ positions. For example, alkylation of the corresponding hydroxy intermediates provides ethers containing an $R^{18}$ or $R^{23}$ group, depending upon position, as shown in Flow Diagram VIII.

Flow Diagram VIII

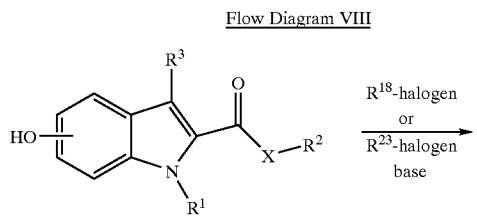

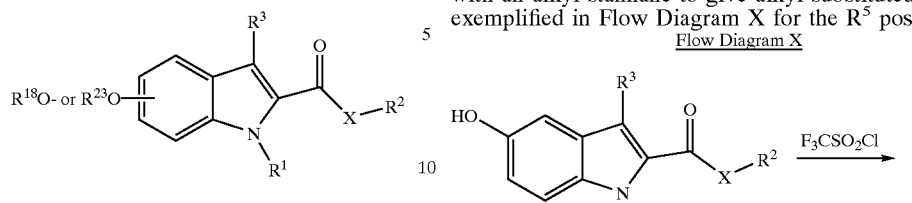

A more detailed example of this process is shown for compounds bearing R⁵ the group in Flow Diagram IX.

Other compounds of Formula I may also be obtained from a hydroxy intermediate. For example, the hydroxy group may be converted to a trifluoromethylsulfonate which reacts with an alkyl stannane to give alkyl-substituted indoles, as exemplified in Flow Diagram X for the R⁵ position.

Flow Diagram X

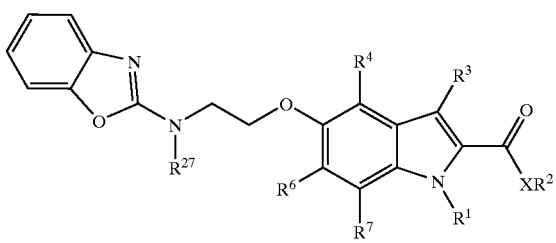

Flow Diagram IX

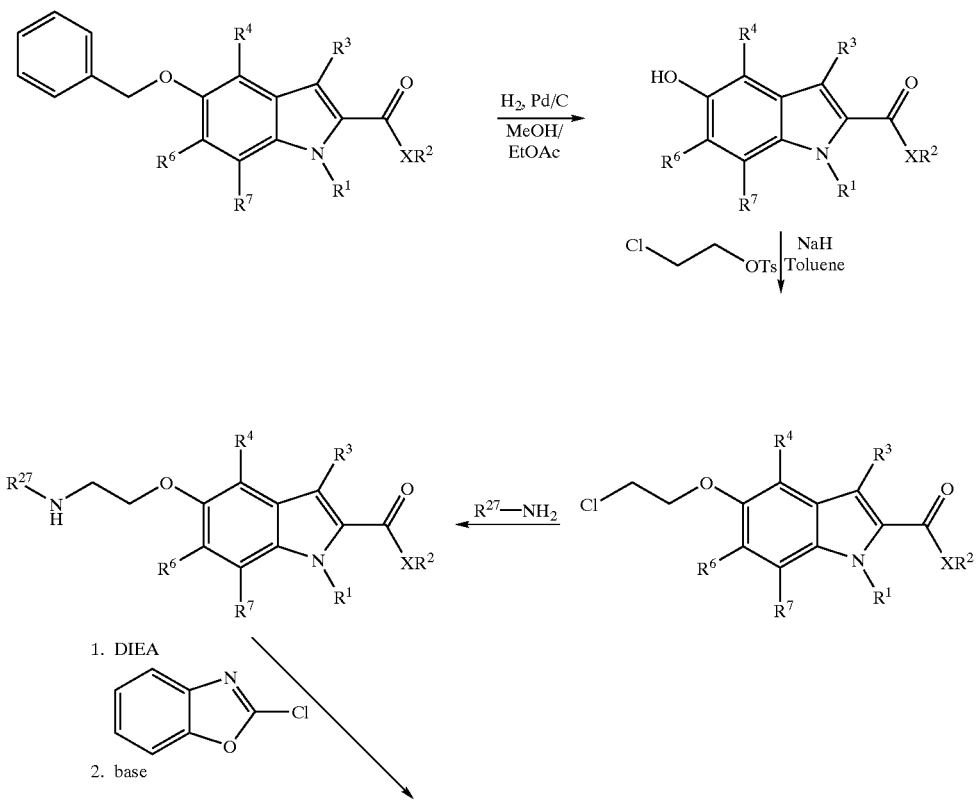

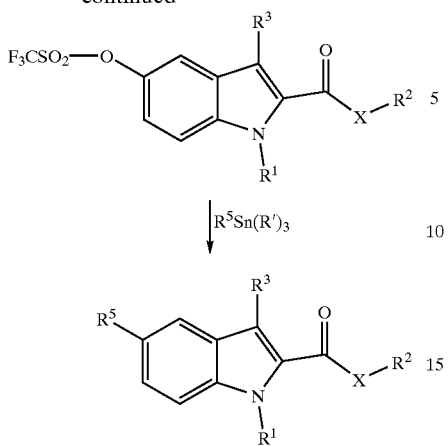

Nitration of indoles that are unsubstituted at positions 5 and/or 7 provides nitro-substituted intermediates which may be reduced and either acylated or alkylated to give a variety of Formula I compounds as shown in Flow Diagram XI.

Indole intermediates which are useful in the preparation of compounds in the present invention are either commercially available or may be prepared by standard methods. These transformations are summarized in Flow Diagram XII for intermediates of Formula VI, IV and V. For example, an appropriately substituted 2-bromonitrobenzene may be converted to a 2-nitrocinnamic acid derivative which cyclizes to an indole upon reduction. The resulting indole intermediate may then be brominated at the 3 position, and the desired $R^1$ substituent introduced by N-alkylation giving the intermediate compounds of Formula VI. Compounds of Formula IV may be prepared from VI in a stepwise sequence involving halogen-metal exchange, addition to formaldehyde, and oxidation of the resulting carbinol to a 3-carboxylic acid. It is understood that the presence of certain $R^4$—$R^7$ substituents may require additional steps of protection and deprotection during this process in order to avoid undesired side reactions.

Flow Diagram XI

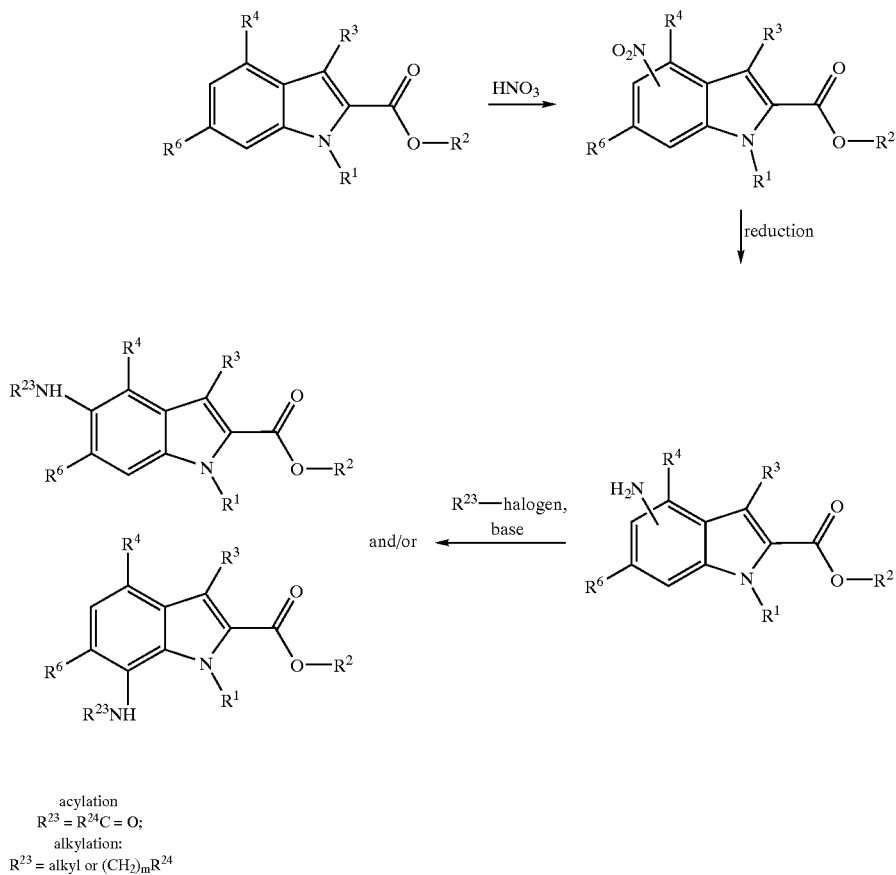

acylation
$R^{23} = R^{24}C = O$;
alkylation:
$R^{23} = $ alkyl or $(CH_2)_m R^{24}$ Flow Diagram XII

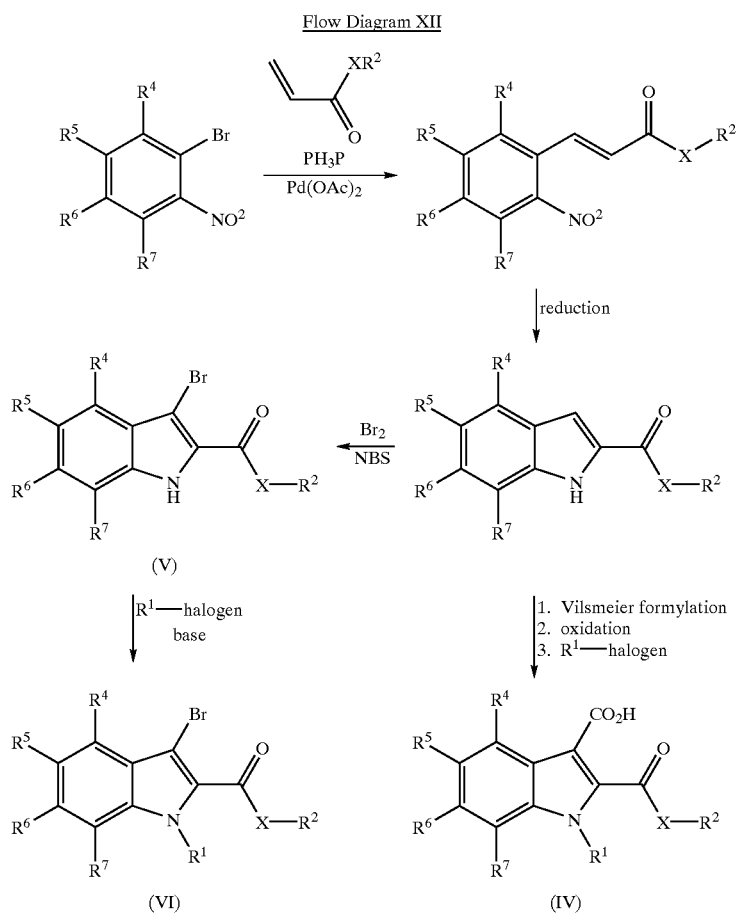

The introduction of the carboxyl functionality at position 2 of other indole compounds may be accomplished by a sequence shown in Flow Diagram XIII. The nitrogen of the unsubstituted indole is first protected as a sulfonamide, then subjected to acylation conditions catalyzed by Lewis acid. Protection may be then be removed and the desired $R^1$ attached as described above.

Flow Diagram XIII

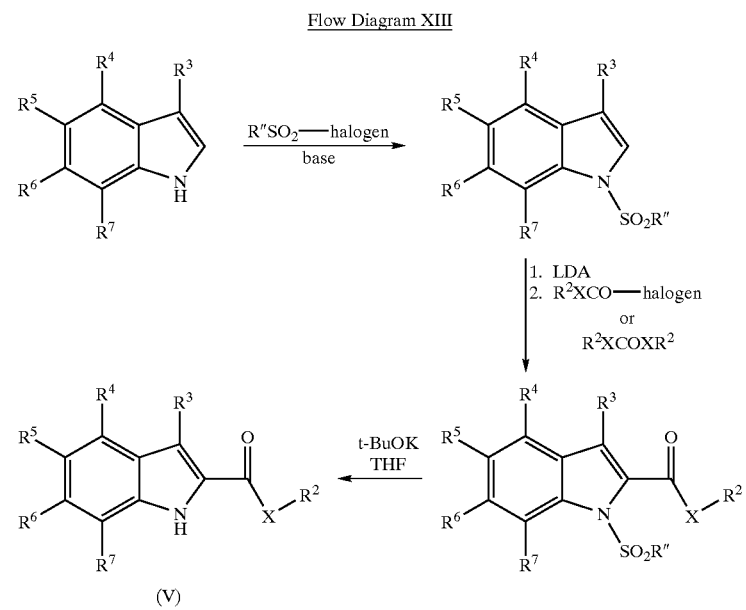

Preparative Examples

Examples of preparations of both intermediates and compounds of the invention are provided in the following detailed synthetic procedures. In the tables of compounds to follow, the synthesis of each compound is referenced back to these exemplary preparative steps. All temperatures are reported uncorrected in degrees Celsius (° C.). Unless otherwise indicated, all parts and percentages are by volume.

All reactions were performed under a positive pressure of dry argon, and were stirred magnetically unless otherwise indicated. Sensitive liquids and solutions were transferred via syringe or cannula, and introduced into reaction vessels through rubber septa. Commercial grade reagents and solvents were used without further purification. Thin-layer chromatography (TLC) was performed on Whatman® pre-coated, glass-backed silica gel 60A F-254 250 µm plates. Column chromatography (flash chromatography) was performed using 230–400 mesh EM Science® silica gel. Melting points (mp) were determined using a Thomas-Hoover melting point apparatus, an Electrothermal melting point apparatus, or a Mettler FP66 automated melting point apparatus and are uncorrected.

$^1$H-NMR spectra were recorded with a Varian Mercury (300 MHz,) or a Bruker Avance 500 (500 MHz) spectrometer with either Me$_4$Si (δ 0.00) or residual protonated solvent (CDCl$_3$ δ 7.26; CD$_3$OD δ 3.30; DMSO-D$_6$ δ 2.49; Acetone-D$_6$ δ 2.04; or CD$_3$CN δ 1.94).

HPLC—electrospray mass spectra (HPLC ES-MS) were obtained using a Hewlett-Packard 1100 HPLC equipped with a quaternary pump, a variable wavelength detector, a YMC Pro C18 2.0 mm×23 mm column, and a Finnigan LCQ ion trap mass spectrometer with electrospray ionization. Gradient elution from 90% A to 95% B over 4 minutes was used on the HPLC. Buffer A was 98% water, 2% Acetonitrile and 0.02% TFA. Buffer B was 98% Acetonitrile, 2% water and 0.018% TFA. Spectra were scanned from 140–1200 amu using a variable ion time according to the number of ions in the source.

Fourier transform infrared spectra were obtained using a Mattson 4020 Galaxy Series spectrophotometer.

Elemental analyses were conducted by Robertson Microlit Labs, Madison N.J. NMR mass and infrared spectra, and elemental analyses of the compounds were consistent with the assigned structures.

List of Abbreviations and Acronyms

As employed herein, the following terms have the indicated meanings.

| | |
|---|---|
| Ac$_2$O | acetic anhydride |
| AIBN | 2,2'-azobisisobutyronitrile |
| anh | anhydrous |
| aq | aqueous |
| BOC | tert-butoxycarbonyl |
| BuLi | n-butyllithium |
| calc'd | calculated |
| Celite ® | diatomaceous earth |
| conc. | concentrated |
| mCPBA | 3-chloroperoxybenzoic acid |
| dec. | decomposition |
| DAST | (diethylamino)sulfur trifluoride |
| DIAD | diisopropyl azodicarboxylate |
| DMAP | 4-dimethylaminopyridine |
| DME | dimethoxyethane |
| DMF | N,N-dimethylformamide |
| DMPU | 1,3-dimethyl-3,4,5,6-tetrahydro-2(1H)-pyrimidinone |
| DMSO | dimethylsulfoxide |
| DPPF | bis(diphenylphosphino)ferrocene |
| EDCIHCl | 1-(3-dimethylaminopropyl)-3-ethylcarbodiimide hydrochloride |
| EtOAc | ethyl acetate |
| EtOH | ethanol (100%) |
| Et$_2$O | diethyl ether |
| Et$_3$N | triethylamine |
| KN(SiMe$_3$)$_2$ | potassium bis(trimethylsilyl)amide |
| KOtBu | potassium tert-butoxide |
| LiAlH$_4$ | lithium aluminum hydride |
| LiBH$_4$ | lithium borohydride |
| LiN(SiMe$_3$)$_2$ | lithium bis(trimethylsilyl)amide |
| MeOH | methanol |
| NMM | 4-methylmorpholine |
| obs'd | observed |
| Oxone ® | potassium peroxymonosulfate |
| PCC | pyridinium chlorochromate |
| Ph$_3$P | triphenylphosphine |
| PdCl$_2$(dppf) | [1,1'-bis(diphenylphosphino)ferrocene]dichloro paladium(II) |
| Pd(PPh$_3$)$_4$ | tetrakis(triphenylphosphine)palladium(0) |
| PivCl | trimethylacetyl chloride |
| rt | room temperature |
| TBAF | tetrabutylammonium fluoride |
| TBDMSCl | tert-butyldimethylsilyl chloride |
| TBDMSOTf | tert-butyldimethylsilyl triflate |
| THF | tetrahydrofuran |
| TFA | trifluoroacetic acid |
| TRIBAL | triisobutylaluminum |

EXAMPLE 1

4-(Cyclopropylmethoxy)iodobenzene

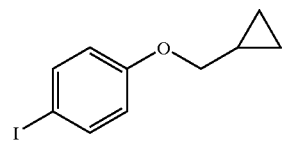

A solution of 4-iodophenol (11.0 g, 50.0 mmol) in tetrahydrofuran (30 mL+10 mL rinse) was added to a cooled (0° C.) and stirred suspension of sodium hydride (1.44 g, 60.0 mmol) in tetrahydrofuran (30 mL). The cold bath was removed and the reaction was stirred for 1 h. A solution of (bromomethyl)cyclopropane (16.2 g, 120.0 mmol) in tetrahydrofuran (20 mL) and then HMPA (5 mL) were added successively and the reaction was heated (55° C.) for 18 h. After cooling, the reaction was quenched with cold water (500 mL) and then extracted with ethyl acetate (3×200 mL). The combined organic extracts were washed with brine, dried over anhydrous magnesium sulfate, and concentrated in vacuo. Flash chromatography of the residue over silica gel using 10% dichloromethane/hexane afforded 12.6 g (92%) of the desired Example 1. The product had: $^1$H NMR (300 MHz, CDCl$_3$) δ 7.54 (d, 2 H), 6.68 (d, 2 H), 3.76 (d, 2 H), 1.20–1.35 (m, 1 H), 0.60–0.70 (m, 2 H), 0.31–0.39 (m, 2 H); mass spectroscopy gave M$^+$ of 274.0 (calc'd exact mass for C$_{10}$H$_{11}$IO=273.99).

EXAMPLE 2

3-(Cyclopropylmethoxy)iodobenzene

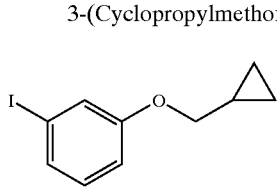

3-Iodophenol (11.0 g, 50.0 mmol) was converted to 12.4 g (90%) of the desired product using the method described for Example 1. The product had: $^1$H NMR (300 MHz, CDCl$_3$) δ 7.23–7.31 (m, 2 H), 6.99 (dd, 1 H), 6.84–6.90 (m, 1 H), 3.77 (d, 2 H), 1.25–1.35 (m, 1 H), 0.60–0.70 (m, 2 H), 0.32–0.39 (m, 2 H); mass spectroscopy gave MH$^+$ of 275.0 (calc'd exact mass for C$_{10}$H$_{11}$IO=273.99).

EXAMPLE 3

4-Bromo-1-cyclopropylthiobenezene

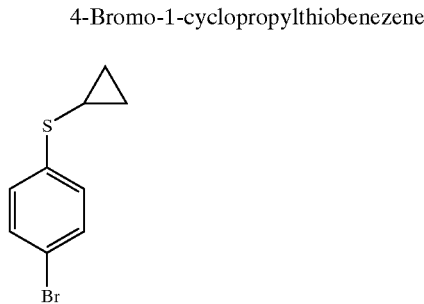

To a solution of cyclopropylphenyl sulfide (5 g, 34.2 mmol) in 342 mL chloroform, a solution of bromine (1.94 g, 37.6 mmol) in 113 mL chloroform was added dropwise. The reaction mixture was stirred at rt overnight and then quenched with aq. NaHCO$_3$ and sat. Na$_2$S$_2$O$_5$. The reaction was extracted with dichloromethane and the organic phase was washed with water and brine, dried over anhydrous sodium sulfate, and concentrated in vacuo. An oil (6.19 g, 79% yield) was given after distillation. $^1$H NMR (DMSO, δ=2.48): 7.45–7.49 (m, 2H), 7.25–7.30 (m, 2H), 2.22–2.28 (m, 1H), 1.04–1.10 (m, 2H), and 0.53–0.58 (m, 2H). MS [M+H]=229 (HPLC/MS).

EXAMPLE 4

2,5-Dibromo-1,3-thiozole

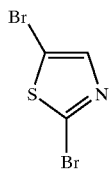

(Caution: Blast shield recommended). Nitric acid (65%, 11.6 mL) was added slowly to a 0° C. solution of commercially available 2-amino-5-bromothiazole monohydrobromide (10 g, 38.4 mmol) in phosphoric acid (85%, 30 mL). The mixture was cooled to −5° C. and an aq. solution of sodium nitrite (3.44 g, 50 mmol) was added slowly, while maintaining the bath temperature below 0° C. The mixture was stirred for 2 h. A solution of copper sulfate (8.0 gm) and sodium bromide (10.3 g) in water (30 mL) was added slowly at 0° C. and the resulting mixture was stirred for 4 h. The mixture was adjusted to pH 7 and extracted with ether. The combined extracts were dried and concentrated under reduced pressure. Purification of the remaining oil by flash chromatography (silica gel, 10:1 hexane:ethyl acetate) afforded 4.3 g (46%) of Example 4. Rf=0.91 (10/1 hexane/ethyl acetate); GCMS (CI) obs'd: 242, 244, 246; calc'd 241.

EXAMPLE 5

4-(Cyclopropylmethoxy)phenylboronic acid

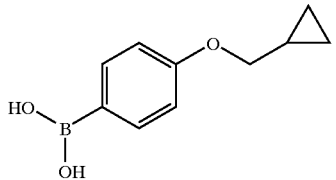

Butyl lithium (2.5 M in hexane, 14.4 mL, 36 mmol) was added dropwise (5 min) to a cooled (−78° C.) and stirred solution of 4-(cyclopropylmethoxy)iodobenzene 1 (9.00 g, 32.8 mmol) in tetrahydrofuran (100 mL). After 20 min, trimethyl borate (11.3 mL, 10.4 g, 100 mmol) was added dropwise (10 mL). The reaction was stirred for an additional 20 min, and was then allowed to warm to rt. The reaction was quenched with 1 M hydrochloric acid (300 mL) and stirring was continued for 30 min. The product was extracted with diethyl ether (4×100 mL) and then the combined organic extracts were dried over anhydrous magnesium sulfate and concentrated in vacuo. The residue was dissolved in toluene and then concentrated. This operation was repeated (5×) until the distillate was colorless and left 5.67 g (90%) of crude product. This material was used without purification or analysis.

The following compounds were prepared according to the method of Example 5:

| Ex. No. | Structure | Yield [%] | MS [M + H⁺] | Rf | mp [° C.] |
|---|---|---|---|---|---|
| 6 | (3-(cyclopropylmethoxy)phenyl)boronic acid | 93 | | | |
| 7 | (4-(cyclopropylthio)phenyl)boronic acid | 75 | | | |
| 8 | (4-cyclopropylphenyl)boronic acid | 85 | | | |

EXAMPLE 9

1-(Bromomethyl)-3-(cyclopropylmethoxy)benzene

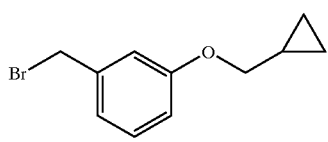

Pyridine (3.20 mL, 3.13 g, 39.6 mmol) and a solution of dibromophenylphosphorane (13.9 g, 32.9 mmol) in acetonitrile (50 mL) were added successively to a cooled (0 ° C.) and stirred solution of 1-(hydroxymethyl)-3-(cyclopropylmethoxy)benzene, (Example 10, 4.40 g, 24.7 mmol) in acetonitrile (100 mL). The mixture was allowed to warm to rt and stirring was continued for 16 h. The reaction was quenched with saturated aqueous sodium thiosulfate (300 mL) and extracted with ethyl acetate (3×200 mL). The combined organic extracts were washed with 1 M hydrochloric acid and brine, dried over anhydrous magnesium sulfate, and concentrated in vacuo. Flash chromatography of the residue over silica gel using 20% ethyl acetate/hexane gave 3.80 g (64%) of the Example 9. The product had: $^1$H NMR (300 MHz, acetone-$D_6$) d 7.22 (t, 1 H), 7.01 (m, 2 H), 6.82–6.88 (m, 1 H), 4.56 (s, 2 H), 3.83 (d, 2 H), 1.16–1.29 (m, 1 H), 0.52–0.62 (m, 2 H), 0.31–0.41 (m, 2 H).

EXAMPLE 10

1-(Hydroxymethyl)-3-(cyclopropylmethoxy)benzene

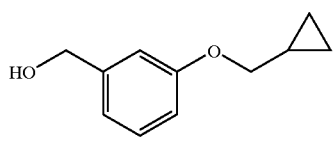

Sodium borohydride (0.75 g, 20 mmol) was added in portions to a stirred solution of 3-(cyclopropylmethoxy) benzaldehyde (Lit: *Chem. Pharm. Bull.* 1975, 23, 2878) (3.5 g, 20 mmol) in methanol (80 mL). The mixture was stirred for 2 h and then quenched with water (300 mL). The product was extracted with ethyl acetate (3×150 mL) and then the combined organic extracts were dried over magnesium sulfate, filtered, and concentrated in vacuo to leave 3.2 g (89%) of crude product. This material was used in the next reaction without further purification or analysis.

EXAMPLE 11

Ethyl 5-(tert-butyldimethylsiloxy)-1H-indole-2-carboxylate

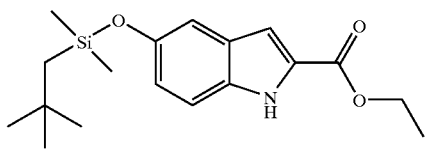

Imidazole (2.30 g, 33.2 mmol) and tert-butyldimethylsilyl chloride (2.50 g, 16.6 mmol) were added successively to a stirred solution of ethyl 5-hydroxy-1H-indole-2-carboxylate (1.70 g, 8.29 mmol) in dichloromethane (100 mL). The reaction was stirred for 16 h and then diluted with dichloromethane (300 mL). The solution was washed with water and brine, dried over anhydrous magnesium sulfate, and concentrated in vacuo to leave 2.65 g (100%) of Example 11. The product had: $^1$H NMR (300 MHz, acetone-$D_6$) d 10.73–10.88 (br s, 1 H), 7.39 (d, 1 H), 7.11 (d, 1 H), 7.05 (s, 1 H), 6.86 (dd, 1 H, 4.34 (q, 2 H), 1.36 (t, 3 H), 1.09 (s, 9 H), 0.20 (s, 6 H).

EXAMPLE 12

Ethyl 3-[(4-methoxyphenyl)methyl]indole-2-carboxylate

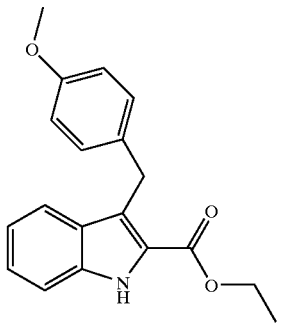

To a solution of ethyl 1-[(4-methoxyphenyl)methyl] indole-2-carboxylate (Example 38) (950 mg, 3.07 mmol) in dichloromethane (15 mL) was added trifluoroacetic acid (1.2 mL). The resulting pink solution was stirred for 18 h at RT. The reaction was quenched with 1.0 N aqueous sodium hydroxide and the organic layer was collected. The aqueous layer was extracted with ethyl acetate, and the combined organic layers were dried over anhydrous magnesium sulfate, concentrated to an oil, and purified by flash chromatography on silica in 8:1 hexane: ethyl acetate (v/v) to yield 468 mg (49%) of Example 12 of a white solid. $^1$H NMR (300 MHz, DMSO-$d_6$) δ 11.56 (s, 1H), 7.64–7.58 (m, 1H), 7.42–7.38 (m, 1H), 7.26–7.14 (m, 3H), 7.02–6.97 (m, 1H), 6.80–6.7 (m, 2H), 4.35 (s, 2H), 4.34 (q, J=7.1 Hz, 2H), 3.65 (s, 3H), 1.33 (t, J=7.1 Hz, 3H); TLF $R_f$=0.44 (4:1 Hexane: ethyl acetate (v/v)).

EXAMPLE 13

Ethyl 5-(benzyloxy)-3-bromo-1H-indole-2-carboxylate

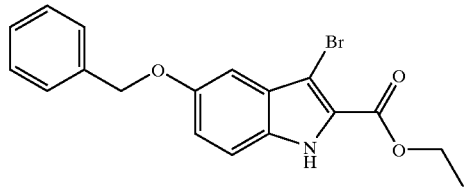

A solution of N-bromosuccinimide (7.83 g, 44.0 mmol) in N,N-dimethylformamide (30 mL) was added dropwise (40 min) to a cooled (0 ° C.) and stirred solution of ethyl 5-(benzyloxy)-1H-indole-2-carboxylate (10.0 g, 39.2 mmol) in N,N-dimethylformamide (20 mL). The cold bath was removed and stirring was continued for an additional 1.5 h. The reaction was poured over ice water (600 mL) and the resulting precipitate was collected by vacuum filtration. The precipitate was washed with water and dried to give 12.9 g (98%) of crude product. This material was used in the next reaction without further purification or analysis.

EXAMPLE 14 tert-Butyl 3-Bromoindole-2-carboxylate

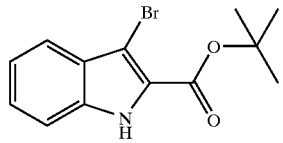

Indole-2-carboxylic acid was converted to 3-bromoindole-2-carboxylic acid using the method described for Example 13. N,N-dimethylformamide di-tert-butyl acetal (35 mL) was added dropwise to a stirring mixture of indole-3-bromo-2-carboxylic acid (14.9 g, 62 mmol) suspended in toluene (100 mL). After the addition was complete, the reaction was heated at 90° C. for 8 h. The reaction mixture was then cooled to room temperature and washed with cold water (2×100 mL). The organic layer was dried over anhydrous magnesium sulfate and concentrated under reduced pressure to yield the crude tert-butyl 3-bromoindole-2-carboxylate, assume quantitative yield. The crude product was used in the next step without purification.

The following compounds were prepared according to the methods of Examples 13 and 14:
| Ex. No. | Structure | Yield [%] | MS [M + H+] | Rf | mp [° C.] |
|---|---|---|---|---|---|
| 15 | 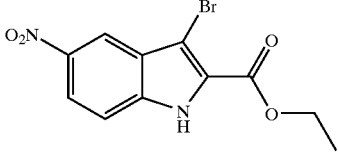 | 96 | | 0.58 (Hexane/ ethyl acetate 2:1) | |
| 16 | 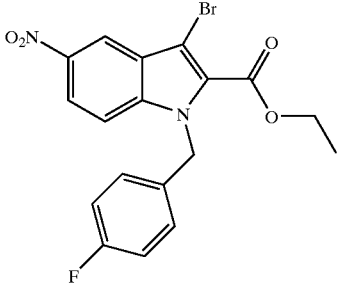 | 58 | | 0.70 (Hexane/ ethyl acetate 2:1) | |
| 17 | 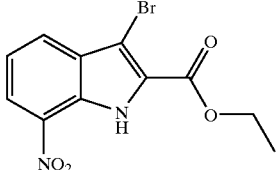 | 100 | 312.5 | | |
| 18 | 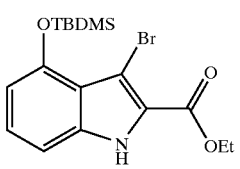 | 73 | 398 | | |
| 19 | 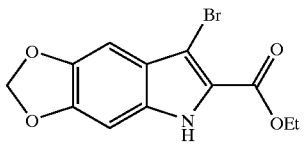 | 87 | | 0.4 (Hexane/ ethyl acetate 8:2) | |
| 20 | 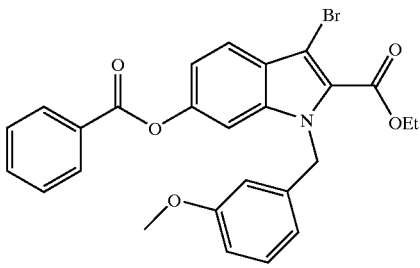 | 92 | 508.1 | 0.27 (Hexane/ ethyl acetate 8:2) | |
| 21 | 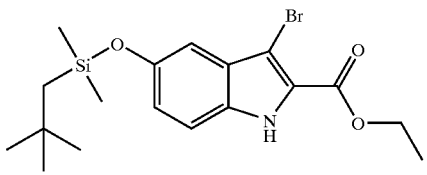 | 89 | | | |

EXAMPLE 22

Ethyl 5-(benzyloxy)-3-bromo-1-(3-methoxybenzyl)-
1H-indole-2-carboxylate

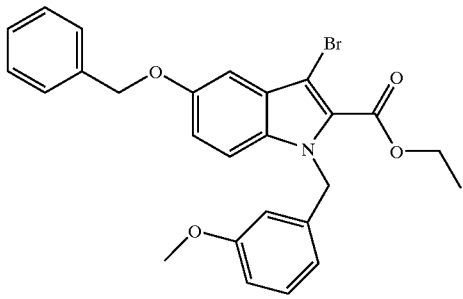

Powdered potassium carbonate (2.79 g, 20.2 mmol) and 3-methoxybenzyl bromide (2.03 g, 10.1 mmol) were added successively to a stirred solution of ethyl 5-(benzyloxy)-3-bromo-1H-indole-2-carboxylate, Lit. WO96/18393 (3.63 g, 9.70 mmol) in N,N-dimethylformamide (20 mL). The reaction was stirred for 23 h and then diluted with water (250 mL). The product was extracted with ethyl acetate (3×100 mL) and then the combined organic extracts were washed with brine, dried over anhydrous magnesium sulfate, and concentrated in vacuo. Recrystalization of the residue using methanol afforded 4.03 g (84%) of the desired product. The product had: $^1$H NMR (300 MHz, CDCl$_3$) δ 7.05–7.91 (m, 9 H), 6.74 (dd, 1 H), 6.53–6.63 (m, 2 H), 5.37 (s, 2 H), 4.37 (q, 2 H), 3.71 (s, 3 H), 1.39 (t, 3 H); mass spectroscopy gave MH$^+$=494.1 (calc'd exact mass for $C_{26}H_{24}BrNO_4$=493.09).

EXAMPLE 23

Ethyl 5-(benzyloxy)-3-bromo-1-(4-fluorobenzyl)-
1H-indole-2-carboxylate

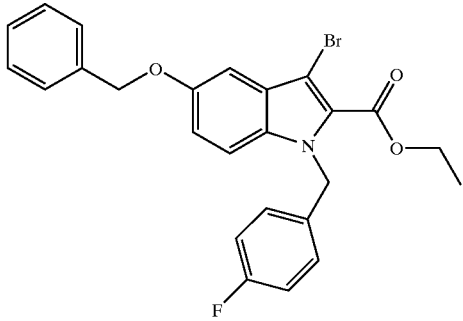

A solution of ethyl 5-(benzyloxy)-3-bromo-1H-indole-2-carboxylate, Ref. WO96/18393 (6.77 g, 20.3 mmol, Ref. 96/18393) in N,N-dimethylformamide (10+5 mL rinse) was added slowly (10 min) to a cooled (0° C.) and stirred suspension of sodium hydride (0.72 g, 30 mmol) in N,N-dimethylformamide (30 mL). The reaction was stirred for 1 h and then 4-fluorobenzylbromide (3.7 mL, 5.7 g, 30 mmol) was added. The cold bath was removed and the mixture was stirred for 18 h. The reaction was quenched by pouring over ice water (400 mL) and then the product was extracted with ethyl acetate (3×100 mL). The combined organic extracts were washed with brine, dried over anhydrous magnesium sulfate and concentrated in vacuo. Flash chromatography of the residue over silica gel using 50% dichloromethane/hexane gave 6.80 g (75%) of the desired product containing trace impurities. The product had: $^1$H NMR (300 MHz, CDCl$_3$) δ 6.84–7.53 (m, 12 H), 5.72 (s, 2 H), 5.13 (s, 2 H), 4.38 (q, 2 H), 1.40 (t, 3 H).

EXAMPLE 24

Ethyl 5-[2-(5-methyl-2-phenyl-1,3-thiazol-4-yl)
ethoxy]-1-(tetrahydro-2-furanylmethyl)-1H-indole-
2-carboxylate

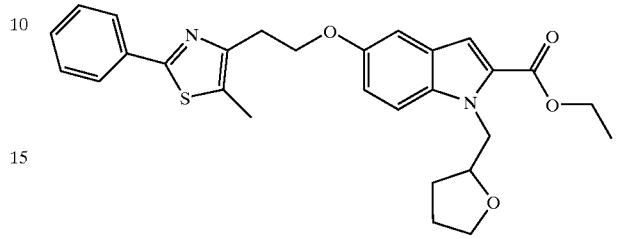

A solution of ethyl 5-[2-(5-methyl-2-phenyl-1,3-thiazol-4-yl)ethoxy]-1H-indole-2-carboxylate 220 (40.7 mg, 0.100 mmol) in N,N-dimethylformamide (0.9 mL) was added to a stirred mixture of cesium carbonate (325 mg, 1.00 mmol) and 2-(bromomethyl)tetrahydrofuran (19.8 mg, 0.120 mmol) in N,N-dimethylformamide (2.4 mL). The reaction was stirred for 16 h and then the mixture was filtered though a plug (500 mg) of silica gel using ethyl acetate to rinse. The filtrate was concentrated in vacuo and then reverse phase preparative HPLC chromatography gave 19.8 mg of product (retention time=2.4 min.). This material was taken to the next reaction without further purification or analysis.

EXAMPLE 25

Ethyl 3-formyl-1-(3-methoxybenzyl)-1H-indole-2-
carboxylate

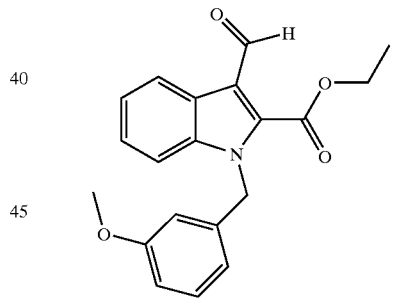

Sodium hydride (60% dispersion in mineral oil, 2.40 g, 60.0 mmol) was cooled to 0° C., and anhydrous methyl sulfoxide (75.0 mL, 1.06 mol) was added. The mixture was stirred at 0° C. for 15 minutes before a solution of ethyl 3-formyl-1H-indole-2-carboxylate (10.9 g, 50.2 mmol, Lit. J. Heterocyclic Chem. 1997, 34, 1431.) in 75 mL of methyl sulfoxide was added over a 20 minute period. The resulting solution was warmed to room temperature and stirred for 1 hour. 3-Methoxybenzylbromide (9.8 mL, 70.0 mmol) was added, and the solution was heated at 60° C. for 16 hours. The solution was cooled and poured into water (500 mL). The aqueous solution was extracted with ethyl acetate (3×), and the combined organic extracts were washed with 1 N hydrochloric acid (2×), water, and brine. The solution was dried over anhydrous magnesium sulfate and concentrated in vacuo. Trituration of the residue with 33% hexane/Et$_2$O provided the title compound as a solid (13.8 g, 81%). The product had: $^1$H NMR (300 MHz, acetone-d$_6$) δ 10.61 (s, 1

H), 8.43 (d, 1 H), 7.61 (d, 1 H), 7.30–7.45 (m, 2 H), 7.19 (dd, 1 H), 6.80 (dd, 1 H), 6.63–6.74 (m, 2 H), 5.88 (s, 2 H), 4.48 (dq, 2 H), 3.70 (s, 3 H), 1.37 (t, 3 H); mass spectroscopy gave MH$^+$=338.1 (calc'd exact mass for $C_{20}H_{19}NO_4$= 337.13).

EXAMPLE 26

Ethyl 3-(4-methoxybenzoyl)-1-(3-methoxybenzyl)-1H-indole-2-carboxylate

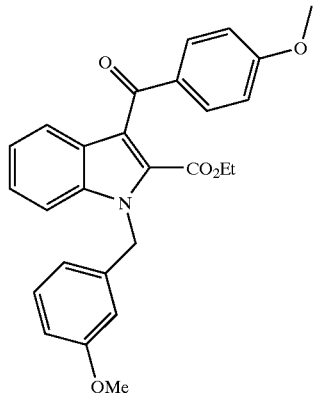

Indole 203 (244 mg, 0.76 mmol) was added to a suspension of sodium hydride (36 mg, 0.91 mmol) in N,N-dimethylformamide (3 mL). After 10 min., sodium iodide (20 mg, 0.133 mmol) and 3-methoxybenzyl chloride (0.13 mL, 0.91 mmol) was added and the resulting mixture was stirred at rt. for ~15 h. Purification (silica gel chromatography 25:75 ethyl acetate:hexane) afforded 236 mg (70%) of Example 26. Rf=0.33 (75/25 hexane/ethyl acetate); LRMS (+esi) obs'd: 444.1; calc'd 443.17.

EXAMPLE 27
tert-Butyl 3-(4-Methoxyphenyl)-1-{[3-(trifluoromethyl)phenyl]sulfonyl}indole-2-carboxylate

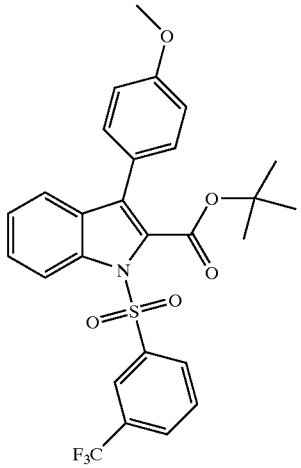

To a stirring solution of tert-butyl-3-(4-methoxyphenyl) indole-2-carboxylate (Example 105, 75 mg, 0.23 mmol) in tetrahydrofuran (0.4 mL) was added potassium tert-butoxide (1 M in tetrahydrofuran, 0.4 mL) in one aliquot. After 10 minutes chloro[3-(trifluoromethyl)phenyl]sulfone (113 mg, 0.46 mmol) was added. The reaction mixture was stirred at room temperature overnight. The resulting mixture was diluted with ethyl acetate (4 mL) and quenched with water (2 mL). The organic phase was extracted with ethyl acetate (3×4 mL). The combined organic layers were dried over anhydrous magnesium sulfate and concentrated under reduced pressure. The crude product was filtered through a plug of silica gel (30% ethyl acetate/hexane) to provide tert-butyl 3-(4-methoxyphenyl)-1-{[3-(trifluoromethyl)phenyl]sulfonyl}indole-2-carboxylate (45 mg, 37%), which was used in the next step without further purification.

The following compounds were prepared according to the methods of Examples 22–27:

| Ex. No. | Structure | Yield [%] | MS [M + H$^+$] | Rf | mp [° C.] |
|---|---|---|---|---|---|
| 28 | 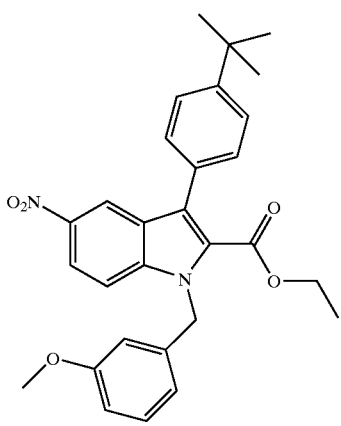 | 50 | | | |

-continued

| Ex. No. | Structure | Yield [%] | MS [M + H⁺] | Rf | mp [° C.] |
|---|---|---|---|---|---|
| 29 | 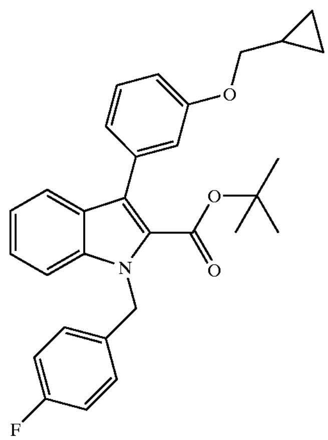 | 44 | | | |
| 30 | 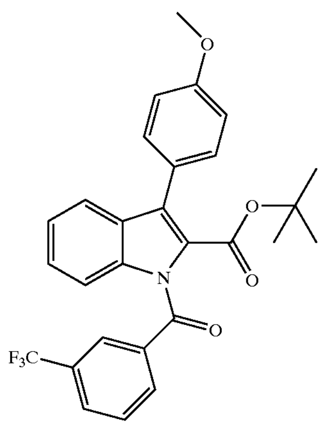 | 27 | | | |
| 31 | 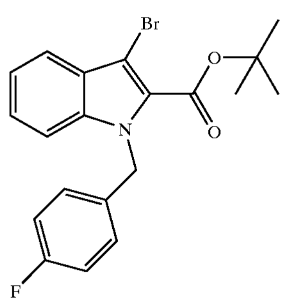 | 54 | | | |
| 32 | 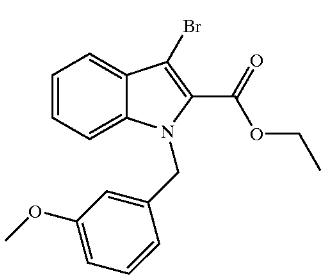 | 73 | 390 | | |

| Ex. No. | Structure | Yield [%] | MS [M + H⁺] | Rf | mp [° C.] |
|---|---|---|---|---|---|
| 33 | ethyl 3-bromo-1-(3-trifluoromethylbenzyl)-1H-indole-2-carboxylate | 88 | 426 | 0.50 (hexane/ethyl acetate 9:1) | |
| 34 | tert-butyl 3-bromo-1-(4-trifluoromethoxybenzyl)-1H-indole-2-carboxylate | 39 | | | |
| 35 | tert-butyl 3-bromo-1-(3-trifluoromethylbenzyl)-1H-indole-2-carboxylate | crude | | | |
| 36 | tert-butyl 3-bromo-1-(3-methoxybenzyl)-1H-indole-2-carboxylate | 98 | 360.0 | 0.59 (Hexane/ethyl acetate 7:1) | |
| 37 | ethyl 3-(4-methoxybenzoyl)-1-(3-trifluoromethylbenzyl)-1H-indole-2-carboxylate | 96 | 482.1 | 0.38 (Hexane/ethyl acetate 3:1) | |

-continued

| Ex. No. | Structure | Yield [%] | MS [M + H⁺] | Rf | mp [° C.] |
|---|---|---|---|---|---|
| 38 | 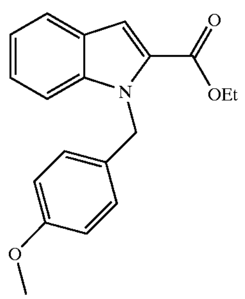 | 58 | 562.2 | 0.72 (Hexane/ethyl acetate 4:1) | |
| 40 | 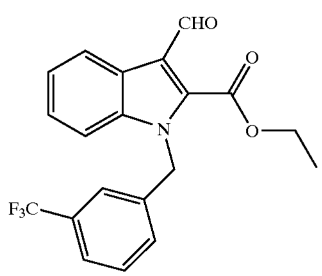 | 80 | 376.1 | 0.31 (Hexane/ethyl acetate 2:1) | |
| 41 | 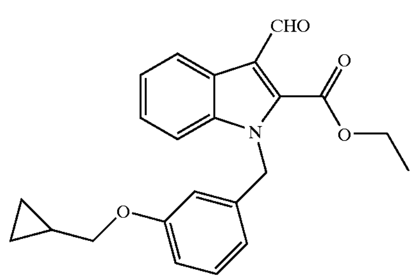 | crude | | | |
| 42 | 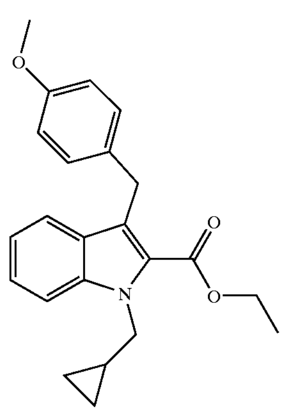 | 77 | | 0.56 (Hexane/ethyl acetate 4:1) | |

| Ex. No. | Structure | Yield [%] | MS [M + H+] | Rf | mp [° C.] |
|---|---|---|---|---|---|
| 43 | 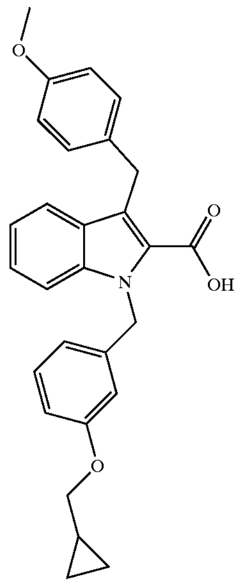 | 76 | 598.2 | 0.48 (Hexane/ethyl acetate 4:1) | |
| 44 | 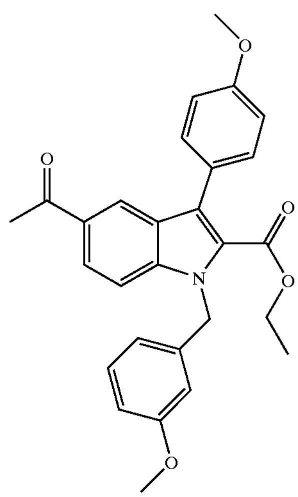 | 64 | | 0.39 (Hexane/ethyl acetate 4:1) | |
| 45 | 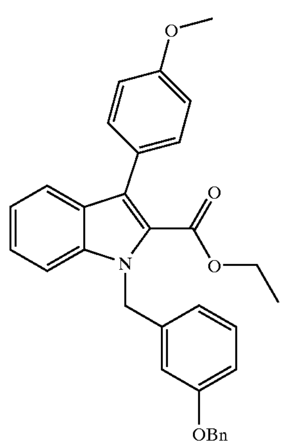 | 100 crude | | | |

| Ex. No. | Structure | Yield [%] | MS [M + H+] | Rf | mp [° C.] |
|---|---|---|---|---|---|
| 46 | 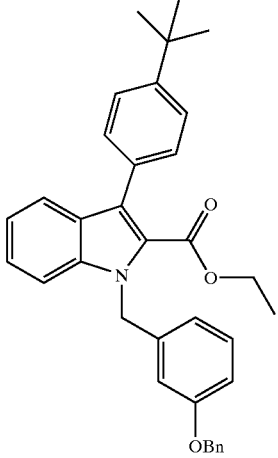 | 100 crude | | | |
| 47 | 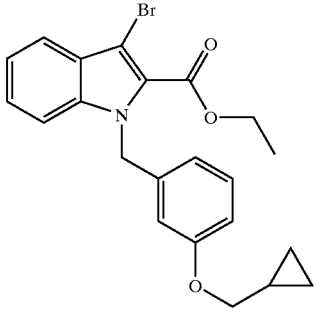 | 51 | 428 | | |
| 48 | 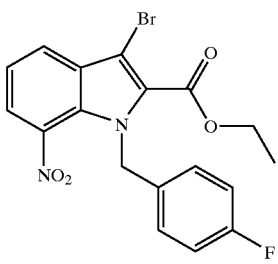 | 78 | 421 | | |
| 49 | 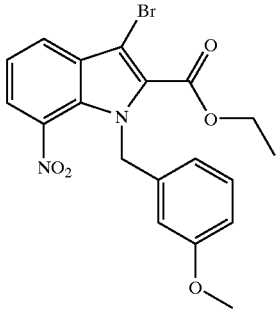 | 58 | 433 | | |

-continued

| Ex. No. | Structure | Yield [%] | MS [M + H+] | Rf | mp [° C.] |
|---|---|---|---|---|---|
| 50 | 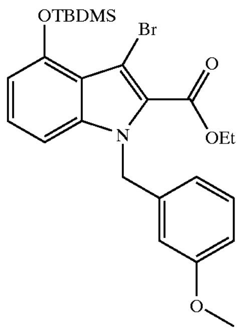 | 40 | | 0.65 (Hexane/ethyl acetate 3:1) | |
| 51 | 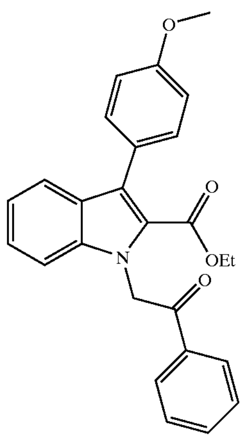 | 100 crude | | | |
| 52 | 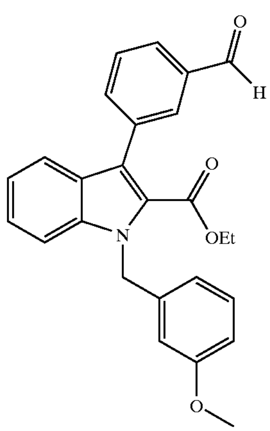 | 32 | | | |

-continued

| Ex. No. | Structure | Yield [%] | MS [M + H+] | Rf | mp [° C.] |
|---|---|---|---|---|---|
| 53 | 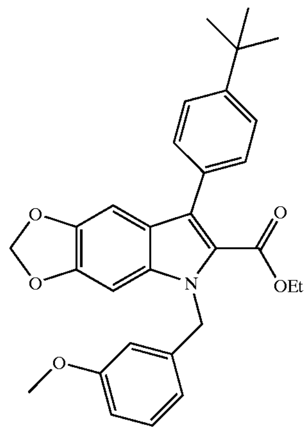 | 55 | | 0.53 (Hexane/ethyl acetate 4:1) | |
| 54 | 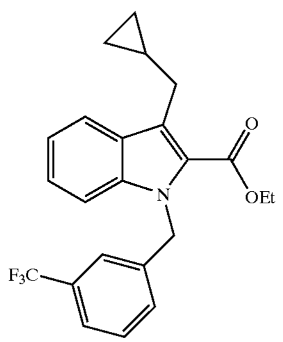 | 72 | 416.4 | 0.58 (Hexane/ethyl acetate 9:1) | |
| 55 | 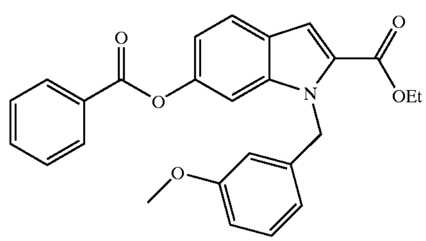 | 34 | 432.4 | 0.60 (Hexane/ethyl acetate 4:1) | |
| 56 | 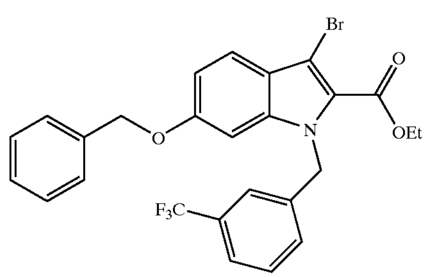 | 90 | 454.3 | 0.75 (Hexane/ethyl acetate 7:3) | |
| 57 | 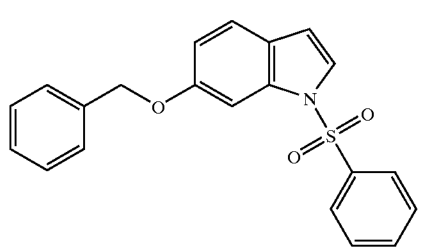 | 88 | | 0.55 (Hexane/ethyl acetate 4:1) | |

| Ex. No. | Structure | Yield [%] | MS [M + H+] | Rf | mp [° C.] |
|---|---|---|---|---|---|
| 58 | 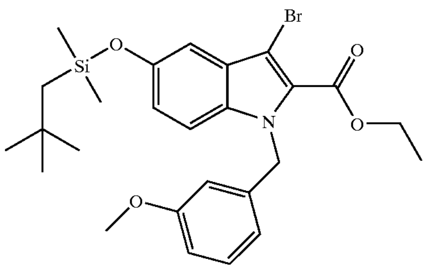 | 87 | | | |
| 59 | 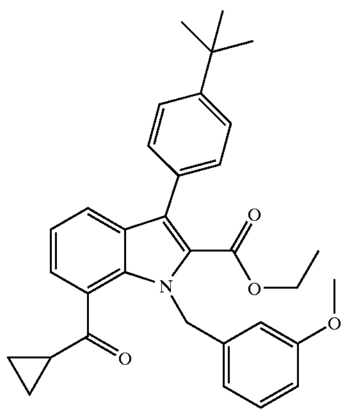 | 71 | | | |
| 60 | 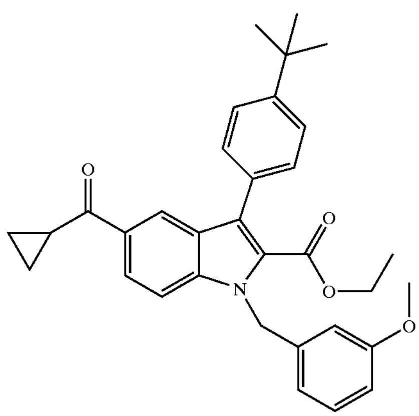 | 40 | | | |
| 227 | 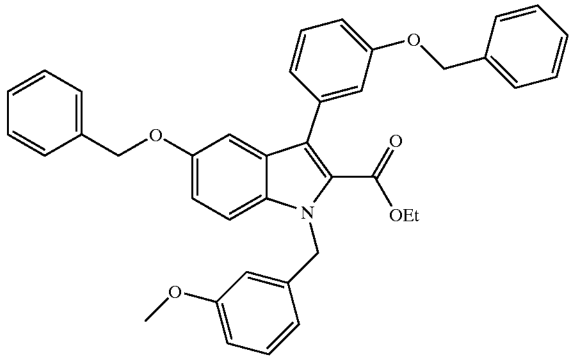 | 75 | 598.2 | | |

| Ex. No. | Structure | Yield [%] | MS [M + H⁺] | Rf | mp [° C.] |
|---|---|---|---|---|---|
| 228 | 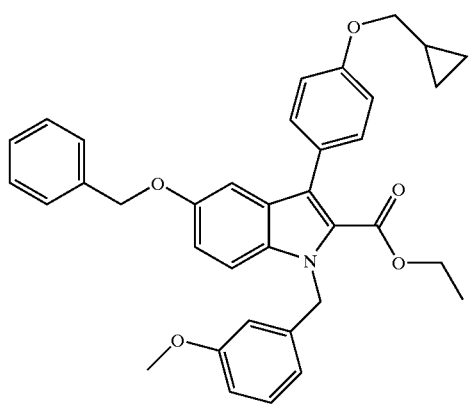 | 27 crude | | | |

EXAMPLE 61

Ethyl 5-(benzyloxy)-3-[4-(cyclopropylmethoxy)phenyl]-1-(3-methoxybenzyl)-1H-indole-2-carboxylate Example 5 (2.30 g, 12.0 mmol) and 2 M aqueous sodium carbonate (20 mL) were added to a stirred solution of ethyl 5-(benzyloxy)-3-bromo-1-(3-methoxybenzyl)-1H-indole-2-carboxylate (4.03 g, 8.15 mmol) in EtOH (30 mL) and toluene (30 mL). Argon was bubbled through the mixture for 15 min and then tetrakis(triphenylphosphine)palladium(0) (1.15 g, 1.00 mmol) was added. The reaction was heated (85° C.) for 16 h and then cooled. The mixture was diluted with 1 M hydrochloric acid (200 mL) and then extracted with ethyl acetate (3×100 mL). The combined organic extracts were washed with water and brine, dried over anhydrous magnesium sulfate, and concentrated in vacuo. Flash chromatography of the residue over silica gel using 60% dichloromethane/hexane gave 3.41 g (75%) of Example 61. The product had: $^1$H NMR (300 MHz, CDCl$_3$) δ 6.95–7.48 (m, 13 H), 6.65–6.77 (m, 3 H), 5.76 (m, 2 H), 5.01 (s, 2 H), 4.13 (q, 2 H), 3.90 (d, 2 H), 3.74 (s, 3 H), 1.30–1.41 (s, 1 H), 1.05 (t, 3 H), 0.65–0.75 (m, 2 H), 0.38–0.45 (m, 2 H); mass spectroscopy gave MH⁺=562.2 (calc'd exact mass for $C_{36}H_{35}NO_5$=561.25).

EXAMPLE 62

Ethyl 3-(benzothiozole)-1-(3-trifluoromethylbenzyl)-indole-2-carboxylate

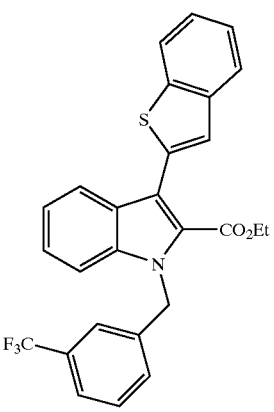

A mixture of Example 33 (300 mg, 0.70 mmol), benzothiophene-2-boronic acid (195 mg, 1.1 mmol), 2N Na$_2$CO$_3$ (0.7 mL) and N,N-dimethylformamide (7 mL) was flushed with argon. Pd(OAc)$_2$ (16 mg, 0.07 mmol) and P(o-tolyl)$_3$ (43 mg, 0.14 mmol) were added and the mixture was heated at 100° C. for ~15 h. The mixture was cooled and filtered through a short column of silica gel and sodium bicarbonate (elution with ethyl acetate). The filtrate was concentrated and the remaining oil was purified by flash chromatography (silica gel, 7:1 hexane:ethyl acetate) to afford 178 mg (53%) of Example 62 as a white solid. Rf=0.51 (7/1 hexane/ethyl acetate); LRMS (+esi) obs'd: 480.0; calc'd 479.1.

EXAMPLE 63

Ethyl 3-(2-furyl)-1-(3-trifluoromethylbenzyl)-indole-2-carboxylate

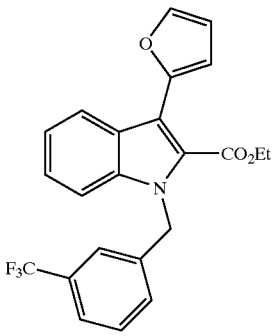

A mixture of Example 33 (300 mg, 0.70 mmol), 2-(tributylstannyl)furan (0.22 mL, 0.7 mmol), lithium chloride (30 mg, 0.7 mmol) and N,N-dimethylformamide (7 mL) was flushed with argon. Tetrakis(triphenylphosphine) palladium (80 mg, 0.07 mmol) was added and the mixture was heated at 100° C. for ~15 h. The mixture was cooled and filtered through a short column of silica gel (elution with ethyl acetate). The filtrate was washed with water and brine, concentrated and the remaining oil was purified by flash chromatography (silica gel, 7:1 hexane:ethyl acetate) to afford 160 mg (55%) of Example 63 as a white solid. Rf=0.45 (7/1 hexane/ethyl acetate); LRMS (+esi) obs'd: 414.1; calc'd 413.1.

EXAMPLE 64

Ethyl 3-(2-phenylethynyl)-1-(3-trifluoromethylbenzyl)-1H-indole-2-carboxylate

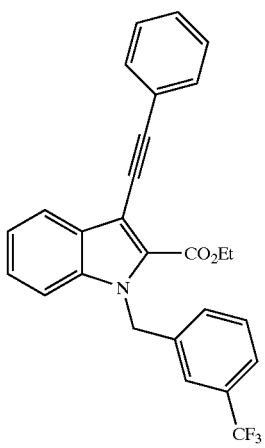

A suspension/solution of Example 33 (500 mg, 1.17 mmol), phenyl acetylene (600 mg, 5.86 mmol), triethylamine (5.5 mL) in dry N,N-dimethylformamide (12 mL) was flushed with argon. Copper iodide (73 mg, 0.38 mmol) and Pd(dppf)$_2$Cl$_2$-dichloromethane (96 mg, 0.12 mmol) was added and again the system was flushed with Ar. The mixture was then heated at 79° C. for 70 min. The suspension was filtered through Celite® (elution with ether) and the filtrate was washed water (3×20 mL) and brine (20 mL). The ether layer was again filtered through silica to remove precipitates (elution with ether). The filtrate was concentrated and the remaining oil was purified by radial chromatography (4 mm silica gel plate, 95/5 hexane/ethyl acetate) to afford 23 mg (4%) of Example 64 as a brown solid. Rf=0.23 (95/5 hexane/ethyl acetate).

EXAMPLE 65

Ethyl 7-(4-tert-butylphenyl)-5H-[1,3]dioxolo[4,5]-f]indole-6-carboxylate

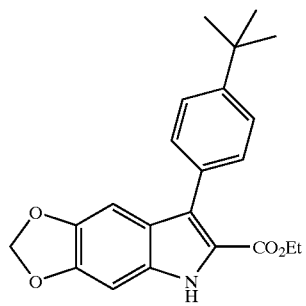

To a dry 100 mL round bottom flask and stir bar, purged with argon gas, was charged with 0.14 g of Pd$_2$(dba)$_3$ and 0.14 g trifurylphosphine followed by addition of 5 ml of toluene. The contents were stirred until homogeneous at which time a of ethyl 7-bromo-5H-[1,3]dioxolo[4,5-f]-indole-6-carboxylate (Example 19, 1.92 g, 6.13 mmol) in toluene (5 mL) was added to the catalyst solution via cannula. After approximately 10–15 minutes of stirring a 10 mL ethanol solution of 4-tert-butyl-phenyl boronic acid (1.64g, 9.2 mmol) to a stirring solution via cannula. This was followed by addition of 15 mL of 2M sodium carbonate dropwise to the pot. The contents were heated to reflux overnight. The reaction was then quenched with 3 N hydrochloric acid and extracted with 3 times with 30 mL of ethyl acetate. The organic layer was then dried over anhydrous sodium sulfate and then concentrated in vacuo. The crude material was purified via column chromatography yielding 1.24 g (55%) of a white solid (Rf-0.38 20% ethyl acetate/hexane). The product had: $^1$H NMR (300 MHz, acetone-D$_6$) 7.46 Hz (d, 1 H), 7.02 Hz (d, 1H) 6.97 Hz (d, 2H), 6.87 Hz (d, 2H), 5.99 Hz (d, 2H), 4.18 Hz (q, 2H), 1.35 Hz (s, 9H), 1.32 Hz (t, 3H).

EXAMPLE 66

Ethyl 3-[4-(cyclopropylmethoxy)phenyl]-5-hydroxy-1-(3-methoxybenzyl)-1H-indole-2-carboxylate

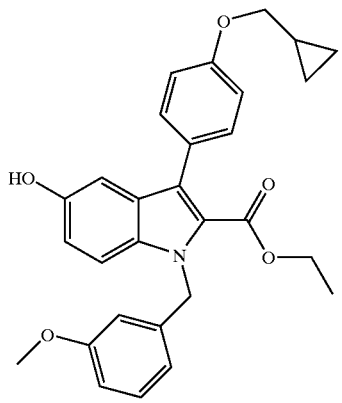

1-Bromo-4-cyclopropylmethoxy)benzene (2.30 g, 12.0 mmol) and 2 M aqueous sodium carbonate (20 mL) were added to a stirred solution of ethyl 5-(TBDMSO)-3-bromo-1-(3-methoxybenzyl)-1H-indole-2-carboxylate (Example 58, 4.03 g, 8.15 mmol) in ethanol (30 mL) and toluene (30 mL). Argon was bubbled through the mixture for 15 min and then tetrakis(triphenylphosphine)palladium(0) (1.15 g, 1.00 mmol) was added. The reaction was stirred with heating (85° C.) for 16 h and then cooled. The mixture was diluted with 1 M hydrochloric acid (200 mL) and then extracted with ethyl acetate (3×100 mL). The combined organic extracts were washed with water and brine, dried over anhydrous magnesium sulfate, and concentrated in vacuo. The residue was dissolved in tetrahydrofuran (100 mL) and tetrabutylammonium fluoride (1.0 M in tetrahydrofuran, 20 mL, 20 mmol) was added. The reaction was stirred for 1 h and then diluted with ethyl acetate (300 mL). The solution was washed with water and brine, dried over anhydrous magnesium sulfate, and concentrated in vacuo. Flash chromatography of the residue over silica gel using 20% ethyl acetate/hexane afforded 1.10 g (65%) of the desired product. The product had: $^1$H NMR (300 MHz, acetone-$D_6$) δ 7.85 (s, 1 H), 7.28–7.37 (m, 3 H), 7.12 (dd, 1 H), 6.84–7.00 (m, 4 H), 6.61–6.74 (m, 3 H), 5.73 (s, 2 H), 4.09 (q, 2 H), 3.86 (d, 2 H), 3.67 (s, 3 H), 1.20–1.32 (m, 1 H), 0.84 (t, 3 H), 0.52–0.63 (m, 2 H), 0.31–0.41 (m, 2 H).

The following compounds were prepared according to the methods of Example 61–66:

| Ex. No. | Structure | Yield [%] | MS [M + H⁺] | Rf | mp [° C.] |
|---|---|---|---|---|---|
| 67 | 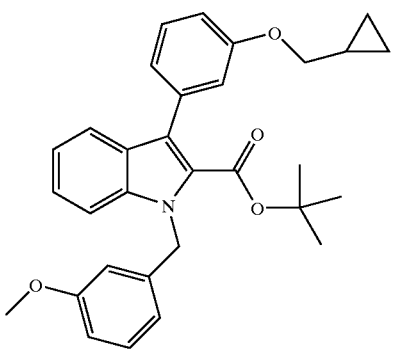 | 33 | 484.3 | | |
| 68 | 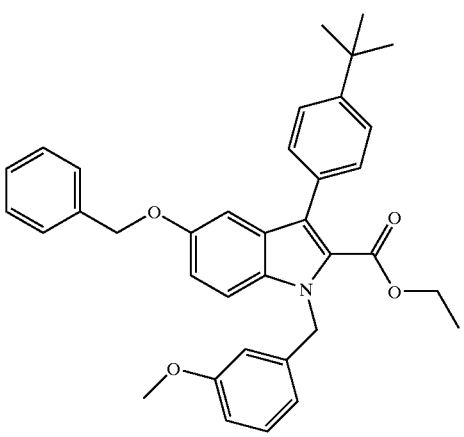 | 86 | 548.2 | 0.82 (Hexane/ethyl acetate 2:1) | |

-continued

| Ex. No. | Structure | Yield [%] | MS [M + H⁺] | Rf | mp [° C.] |
|---|---|---|---|---|---|
| 69 | 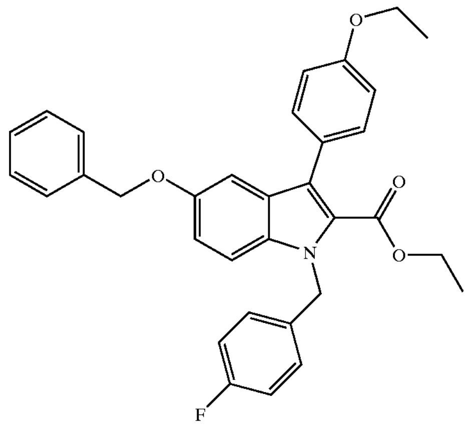 | 68 | 428.2 | 0.8 (Hexane/ethyl acetate 2:1) | |
| 70 | 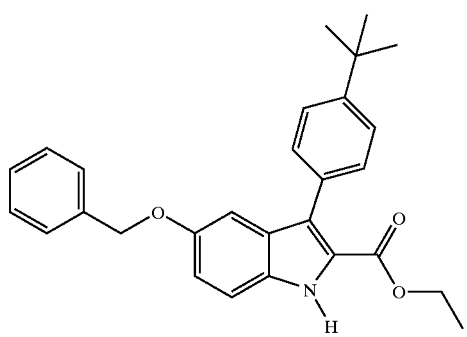 | 68 | 428.2 | 0.80 (Hexane/ethyl acetate 2:1) | |
| 71 | 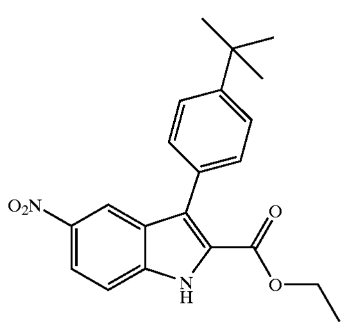 | 66 | | 0.62 (Hexane/ethyl acetate 2:1) | |

-continued
| Ex. No. | Structure | Yield [%] | MS [M + H⁺] | Rf | mp [° C.] |
|---|---|---|---|---|---|
| 72 | 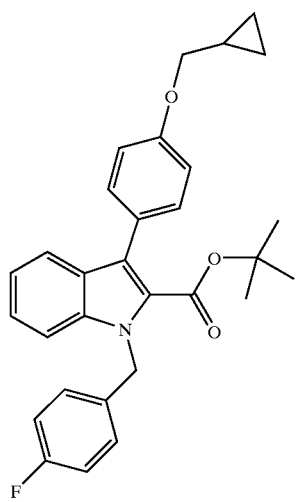 | 55 | | | |
| 73 | 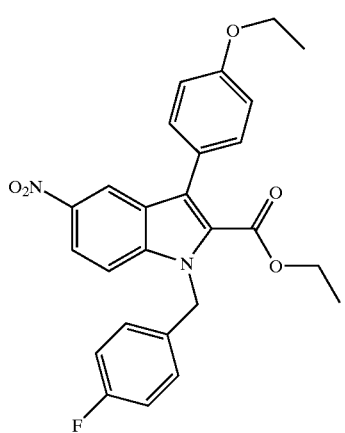 | 73 | | 0.71 (Hexane/ethyl acetate 2:1) | |
| 74 | 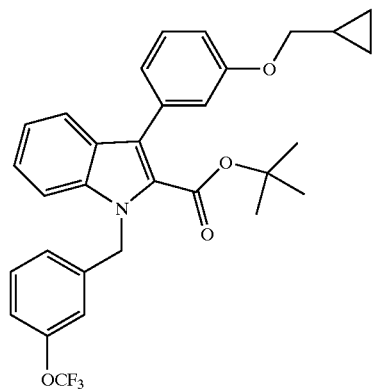 | 43 | | | |

-continued
| Ex. No. | Structure | Yield [%] | MS [M + H+] | Rf | mp [° C.] |
|---|---|---|---|---|---|
| 75 | 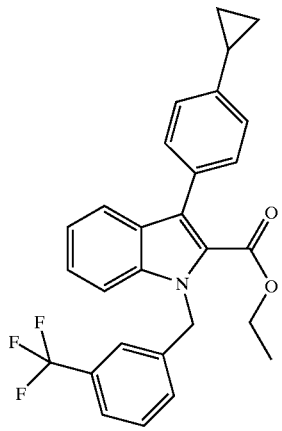 | 50 | 464 | | |
| 76 | 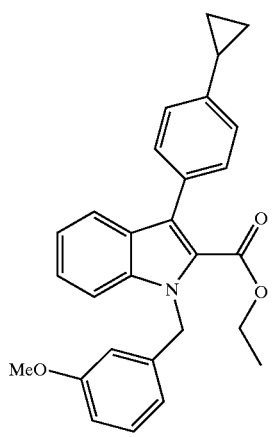 | 56 | 426 | | |
| 77 | 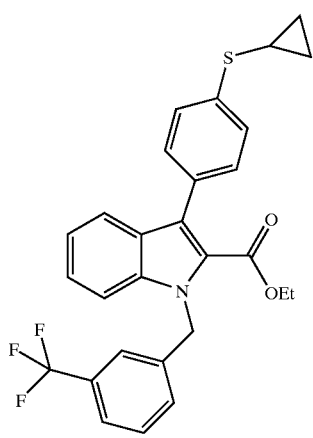 | 71 | 496 | | |

-continued
| Ex. No. | Structure | Yield [%] | MS [M + H+] | Rf | mp [° C.] |
|---|---|---|---|---|---|
| 78 | 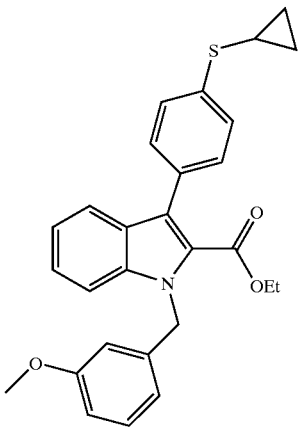 | 67 | 458 | | |
| 79 | 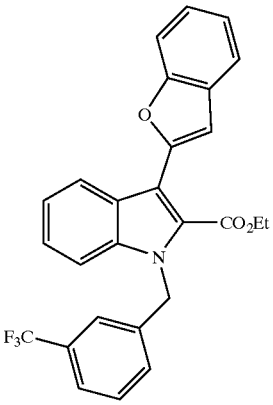 | 25 | | 0.53 (Hexane/ethyl acetate 7:1) | |
| 80 | 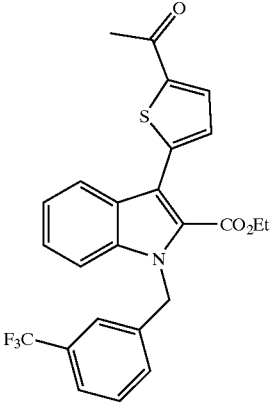 | 62 | 472.2 | 0.3 (Hexane/ethyl acetate 7:1) | |

-continued

| Ex. No. | Structure | Yield [%] | MS [M + H+] | Rf | mp [° C.] |
|---|---|---|---|---|---|
| 81 | 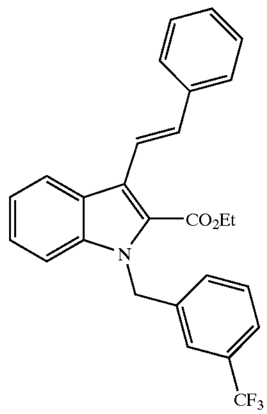 | crude | 450.1 | 0.26 (Hexane/ethyl acetate 95:5) | |
| 82 | 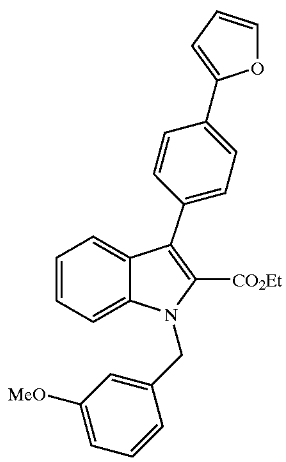 | 88 | 452.2 | 0.49 (hexane/ether 8:2) | |
| 83 | 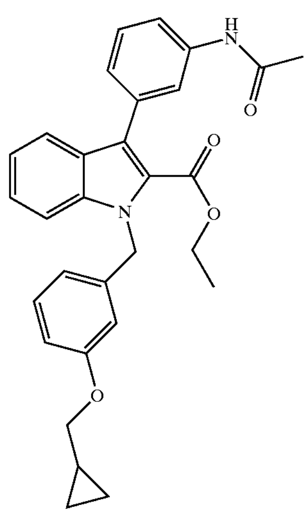 | 61 | 483.1 | 0.31 (Hexane/ethyl acetate 1:1) | |

-continued

| Ex. No. | Structure | Yield [%] | MS [M + H⁺] | Rf | mp [° C.] |
|---|---|---|---|---|---|
| 84 | 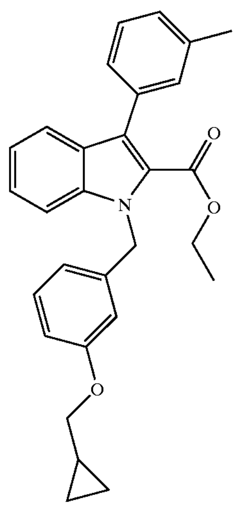 | crude | 440.2 | 0.45 (Hexane/ethyl acetate 9:1) | |
| 85 | 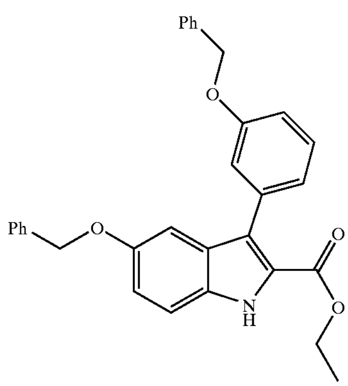 | 67 | 478.1 | 0.32 (Hexane/ethyl acetate 4:1) | |
| 86 | 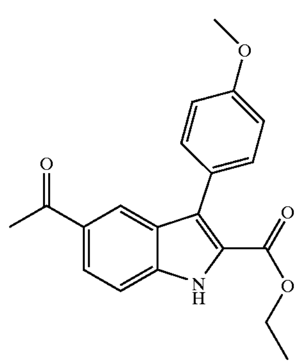 | 45 | | 0.24 (Hexane/ethyl acetate 4:1) | |

-continued

| Ex. No. | Structure | Yield [%] | MS [M + H+] | Rf | mp [° C.] |
|---|---|---|---|---|---|
| 87 | 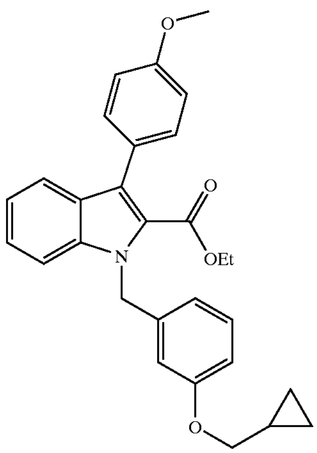 | 74 | | | |
| 88 | 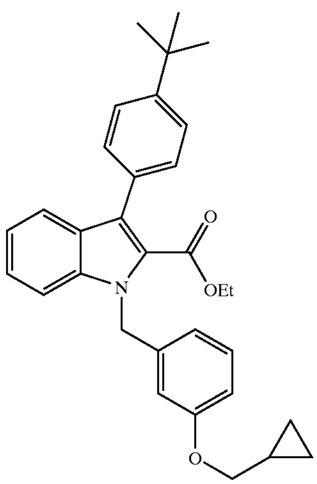 | 68 | | | |
| 89 | 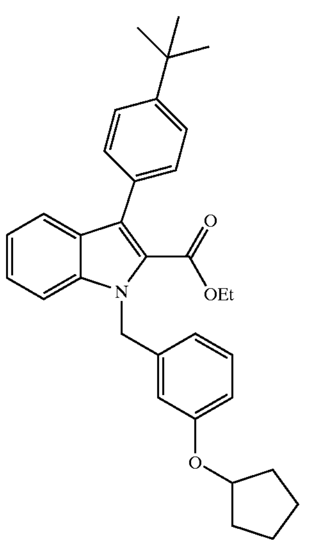 | 80 | | | |

-continued
| Ex. No. | Structure | Yield [%] | MS [M + H+] | Rf | mp [° C.] |
|---|---|---|---|---|---|
| 90 | 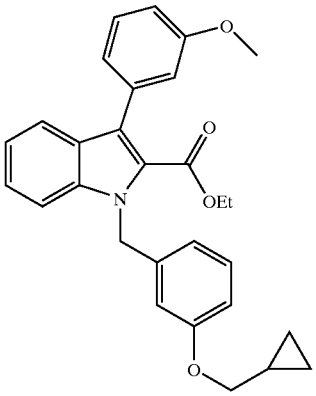 | 100 | | 0.56 (Hexane/ethyl acetate 4:1) | |
| 91 | 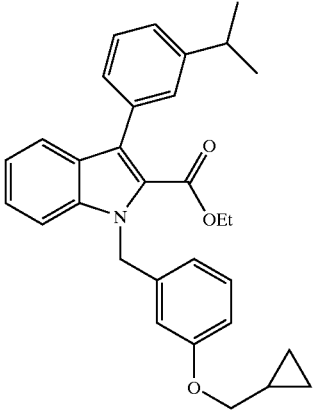 | 100 | | 0.71 (Hexane/ethyl acetate 4:1) | |
| 92 | 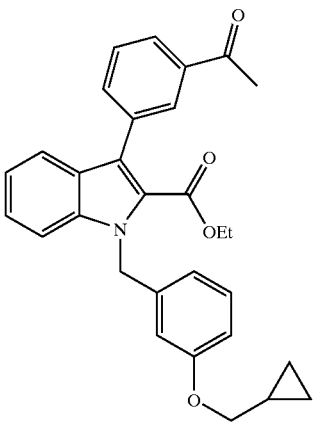 | 57 | 468 | 0.50 (Hexane/ethyl acetate 3:1) | |

-continued

| Ex. No. | Structure | Yield [%] | MS [M + H+] | Rf | mp [° C.] |
|---|---|---|---|---|---|
| 93 | 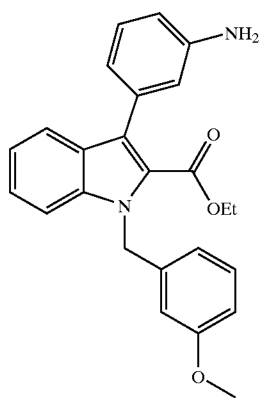 | 62 | | 0.50 (Hexane/ethyl acetate 2:1) | |
| 94 | 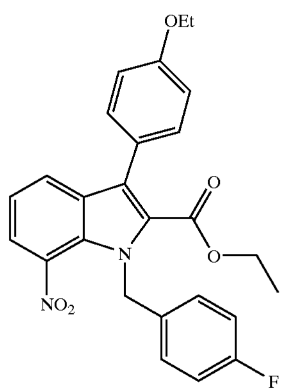 | 75 | 463 | | |
| 95 | 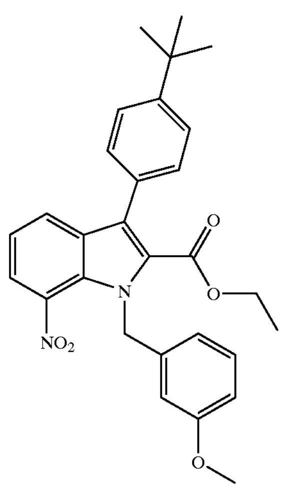 | 79 | | | |

-continued

| Ex. No. | Structure | Yield [%] | MS [M + H⁺] | Rf | mp [° C.] |
|---|---|---|---|---|---|
| 96 | 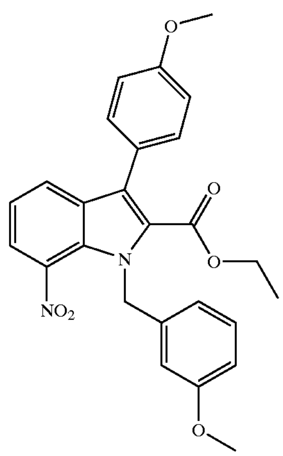 | 100 | 461 | | |
| 97 | 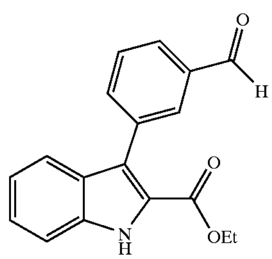 | 73 | 294 (M⁺) GC-MS | | |
| 98 | 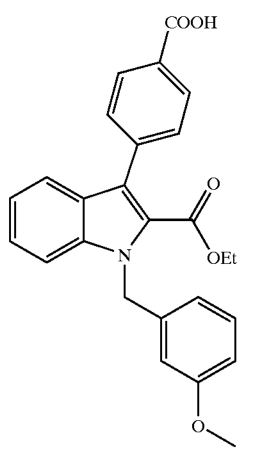 | 64 | | | |

-continued

| Ex. No. | Structure | Yield [%] | MS [M + H+] | Rf | mp [° C.] |
|---|---|---|---|---|---|
| 99 | 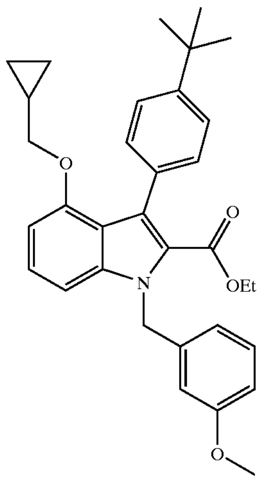 | 50 | | | |
| 100 | 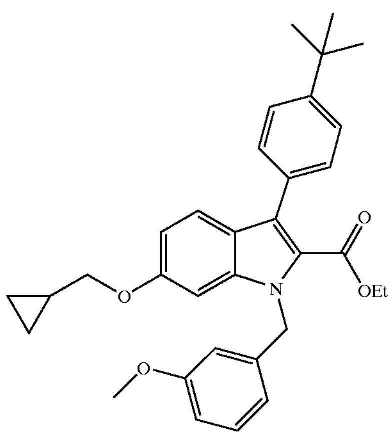 | 27 | 512.7 | 0.7 (Hexane/ethyl acetate 4:1) | |
| 101 | 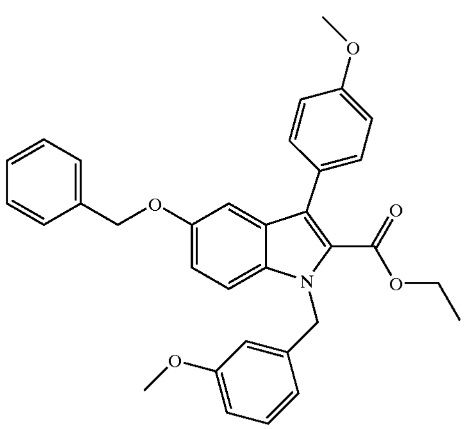 | 69 | 522.8 | | |

-continued

| Ex. No. | Structure | Yield [%] | MS [M + H⁺] | Rf | mp [° C.] |
|---|---|---|---|---|---|
| 102 | 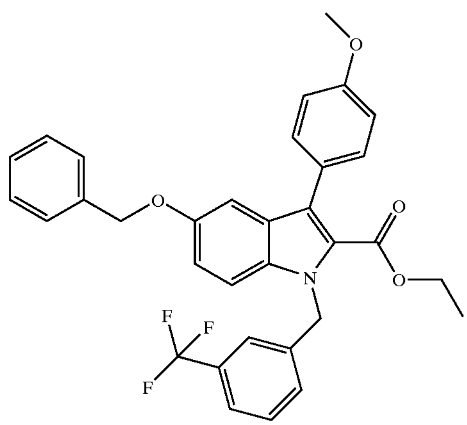 | 74 | 560.1 | 0.36 (Hexane/ethyl acetate 6:1) | |
| 121 | 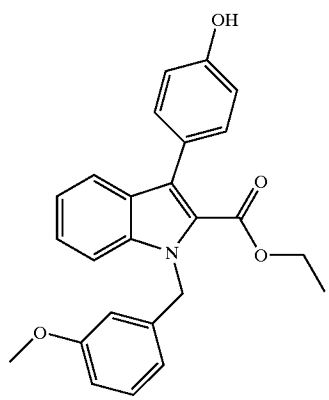 | 77 | 402 | | |
| 225 | 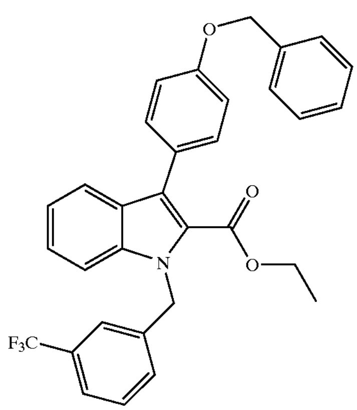 | 77 | | | |

-continued

| Ex. No. | Structure | Yield [%] | MS [M + H+] | Rf | mp [° C.] |
|---|---|---|---|---|---|
| 226 | 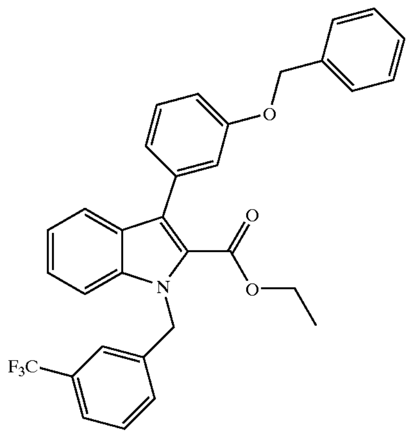 | 72 | | | |
| 103 | 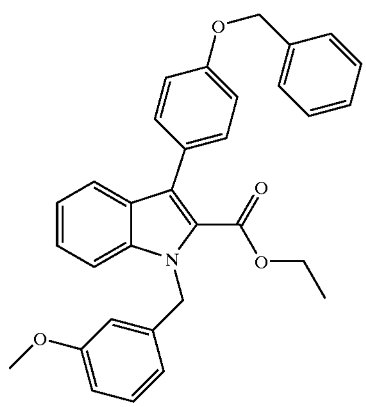 | 86 | 492 | | |
| 105 | 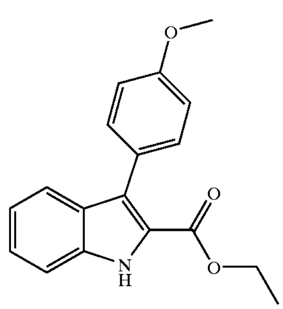 | 53 | | | |
| 224 | 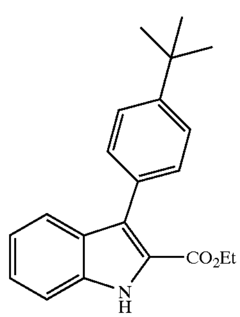 | 93 | | 0.50 (Hexane/ethyl acetate 4:1) | |

EXAMPLE 106

2-tert-Butoxycarbonyl) 1-[3-(trifluoromethyl)benzyl]-indole-3-yl boronic acid

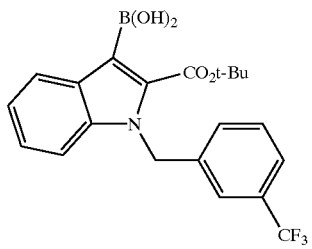

A solution of butyllithium in hexane (7.10 mL, 1.6 M) was added to a −78° C. solution of Example 35 (4.95 gm, 10.9 mmol) in tetrahydrofuran (30 mL). After 5 min., trimethyl borate (3.72 mL, 32.7 mmol) was added and the mixture was allowed to warm to rt. over 2 h. 2N hydrochloric acid (30 mL) was added and the mixture was vigorously stirred for 30 min. Ethyl acetate was added and the layers were separated. The organic layer was dried and concentrated. Trituration of the remaining oil with ether followed by drying under reduced pressure afforded 2.3 g (50%) of Example 106 as a white solid. Rf=0.29 (4/1 hexane/ethyl acetate).

The following compounds were prepared according to the methods of Example 106:

EXAMPLE 109 tert-Butyl 3-(5-bromo-1,3-thiazol-2-yl)-1-[3-(trifluoromethyl)benzyl]-indole-2-carboxylate

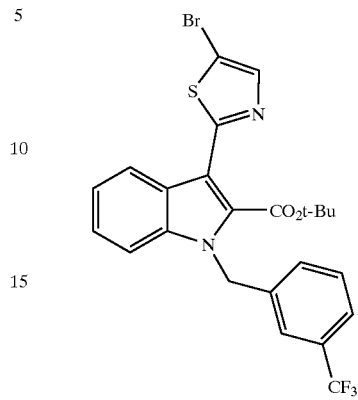

To a solution of Example 106 (150 mg, 0.36 mmol) and Example 4 (68 mg, 0.28 mmol) in toluene (0.7 mL) and ethanol (0.7 mL) was added aq. $Na_2CO_3$ (0.36 mL, 2N). The reaction vessel was flushed with Ar for 10 min. Tetrakis (triphenylphosphine)-palladium (34 mg, 0.029 mmol) was added and the mixture was heated at 85° C. until the disappearance of the boronic acid. The mixture was cooled and filtered. The filtrate was concentrated and the remaining oil was purified by flash chromatography (silica gel, 7:1 hexane:ethyl acetate) to afford 100 mg (66%) of Example 109 as a yellow solid. Rf=0.61 (7/1 hexane/ethyl acetate); LRMS (+esi) obs'd: 536.8; calc'd 536.0.

The following compounds were prepared according to the method of Example 109:

| Ex. No. | Structure | Yield [%] | MS [M + H⁺] | Rf | mp [° C.] |
|---|---|---|---|---|---|
| 108 | 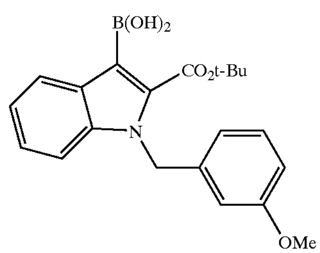 | 44 | | 0.28 (Hexane/ethyl acetate 4:1) | |

| Ex. No. | Structure | Yield [%] | MS [M + H⁺] | Rf | mp [° C.] |
|---|---|---|---|---|---|
| 110 | 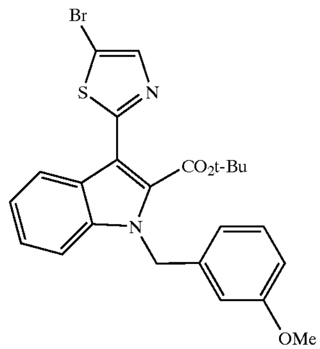 | 43 | 498.9 | 0.72 (Hexane/ethyl acetate 4:1) | |

EXAMPLE 111 tert-Butyl 3-(5-acetyl-1,3-thiazol-2-yl)-1-[3-(trifluoromethyl)benzyl]-indole-2-carboxylate

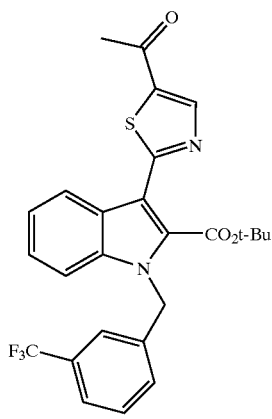

A mixture of Example 108 (300 mg, 0.56 mmol), Pd(PPh$_3$)$_4$ (70 mg, 0.06 mmol) and lithium chloride (80 mg, 1.68 mmol) in tetrahydrofuran (2 mL) and toluene (2 mL) was flushed with argon. 1-Ethoxyvinyl tri-n-butylstannane (224 mg, 0.62 mmol) was added and the mixture was heated at 90° C. for 4 h. A second portion of stannane (107 mg, 0.30 mmol) was added and heating was continued for 1 h. The mixture was cooled to rt. and 10% hydrochloric acid (2 mL) was added. The mixture was stirred for 1 h. The mixture was washed with water, dried and concentrated. The oil thus obtained was purified by flash chromatography (silica gel, 5:1 hexane:ethyl acetate) to afford 280 mg of slightly impure Example 111 which was used without further purification. LRMS (+esi) obs'd: 500.9; calc'd 500.1.

The following compounds were prepared according to the method of Example 111:

| Ex. No. | Structure | Yield [%] | MS [M + H⁺] | Rf | mp [° C.] |
|---|---|---|---|---|---|
| 111A | 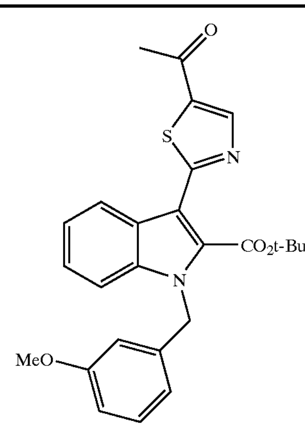 | crude | 463.0 | 0.32 (Hexane/ethyl acetate 5:1) | |

EXAMPLE 112 tert-Butyl 3-(5-cyclopropyl-1,3-thiazol-2-yl)-1-(3-methoxybenzyl)-indole-2-carboxylate

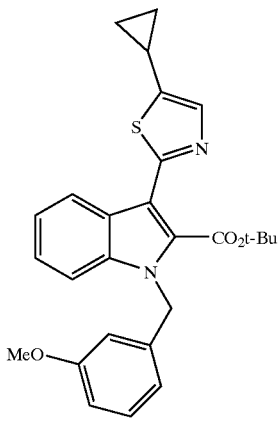

Cyclopropyl boronic acid: A solution of t-butyllithium in hexane (17.0 mL, 25.4 mmol) was added to a −78° C. solution of cyclopropyl bromide (1.51 gm, 12.4 mmol) in dry tetrahydrofuran (20 mL). After stirring for 15 min., trimethoxy borate (1.23 gm, 11.8 mmol) was added and the resulting mixture was warmed to rt. over 1 h. 2N HCl (15 mL) was added and the aq. phase was extracted with ethyl acetate. The extracts were dried over anhydrous sodium sulfate and concentrated to give the cyclopropyl boronic which was used in the coupling step without further purification.

A mixture of cyclopropyl boronic acid (75 mg, 0.84 mmol), Example 110 (200 mg, 0.42 mmol), $Na_2CO_3$ (2N, 0.9 mL), and N,N-dimethylformamide (3.5 mL) was flushed with argon. Palladium(II) acetate (18 mg, 0.08 mmol) and P(o-tolyl)$_3$ (50 mg, 0.16 mmol) were added and the mixture was heated at 100° C. for 1 h. The mixture was cooled, diluted with ethyl acetate, and washed with water. The organic layer was dried over anhydrous sodium sulfate and concentrated. Purification of the remaining oil by flash chromatography gave slightly impure Example 112 which was used without further purification. LRMS (+esi) obs'd: 461.0; calc'd 460.2.

EXAMPLE 113

Ethyl 3-(4-ethoxyphenyl)-1-(4-fluorobenzyl)-5-hydroxy-1H-indole-2-carboxylate

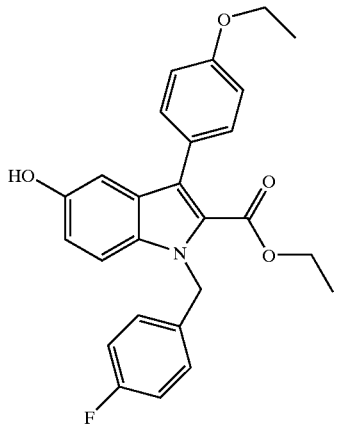

A solution of ethyl 5-(benzyloxy)-3-(4-ethoxyphenyl)-1-(4-fluorobenzyl)-1H-indole-2-carboxylate (Example 69, 4.7 g, 9.0 mmol) in ethyl acetate (15 mL) was added to a suspension of 10% palladium on charcoal (2.0 g) in ethyl acetate (10 mL). The mixture was placed under an atmosphere of hydrogen (1 atm) and stirred for 16 h. The reaction was filtered through a pad of Celite using ethyl acetate to rinse. Evaporation of the filtrate left 3.5 g (90%) of the desired product. The product had: $^1$H NMR (300 MHz, acetone-D$_6$) δ 7.98 (s, 1 H), 6.89–7.42 (m, 11 H), 5.81 (s, 2 H), 4.03–4.19 (m, 4 H), 1.41 (t, 3 H), 1.04 (t, 3 H).

EXAMPLE 114

Ethyl-1-[(3-hydroxyphenyl)methyl]-3-(4-methoxyphenyl)indole-2-carboxylate

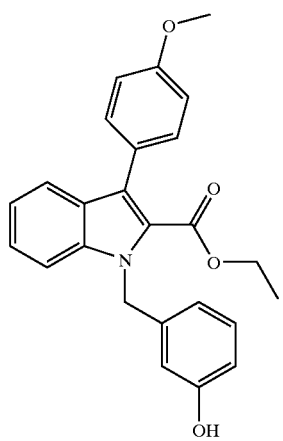

To a Parr shaker bottle purged with Argon was added palladium on carbon (Degussa type) (500 mg), ethyl acetate (10 mL), ethyl 3-(4-methoxyphenyl)-1-{[3-(phenylmethoxy)phenyl]methyl}indole-2-carboxylate (Example 45, 5 g crude material, 7.0 mmol, in 120 mL methanol and 40 mL ethyl acetate). The mixture was hydrogenated at 55 psi for 48 h. The mixture was then filtered through Celite and the filtrate was concentrated in vacuo. The residue was purified with silica gel flash chromatography using hexane/ethyl acetate (3/1 to 2/1) to give ethyl 1-[(3-hydroxyphenyl)methyl]-3-(4-methoxyphenyl)indole-2-carboxylate as a light yellow oil (2.5 g, 89%): MS (M$^+$) calcd for $C_{25}H_{23}NO_4$ 401.1, found 401.0; $^1$H NMR (CDCl$_3$) δ 7.60 (dd, J=8.1 Hz, 1H), 7.30–7.45 (m, 4H), 7.13–7.21 (m, 2H), 6.98 (d, J=8.1 Hz, 2H), 6.64–6.78 (m, 2H), 6.52 (s, 1H), 5.77 (s, 2H), 4.14 (q, J=7.0 Hz, 2H), 1.04 (t, J=7.0 Hz, 3H).

The following compounds were prepared according to the method of Example 114:

| Ex. No. | Structure | Yield [%] | MS [M + H$^+$] | Rf | mp [° C.] |
|---|---|---|---|---|---|
| 115 | 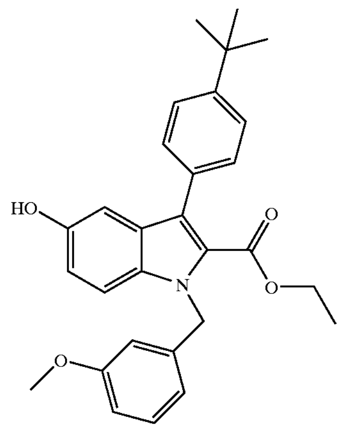 | 93 | 458.2 | 0.67 (Hexane/ethyl acetate 2:1) | |
| 116 | 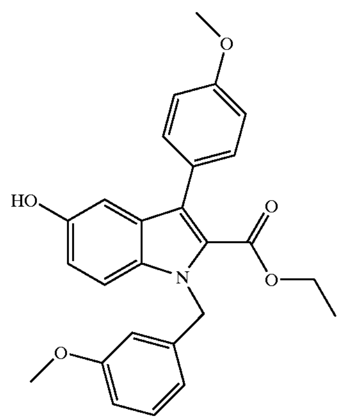 | 97 | 432.1 | 0.35 (Hexane/ethyl acetate 2:1) | |
| 117 | 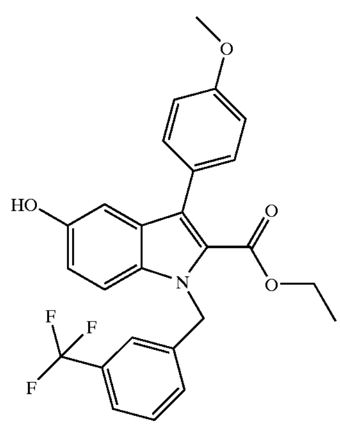 | 92 | 470.1 | 0.41 (Hexane/ethyl acetate 2:1) | |

-continued
| Ex. No. | Structure | Yield [%] | MS [M + H+] | Rf | mp [° C.] |
|---|---|---|---|---|---|
| 118 | 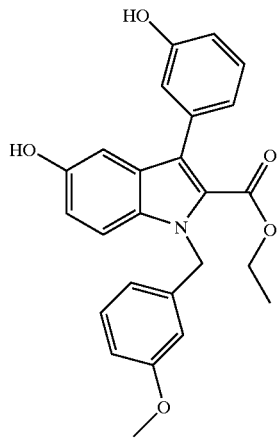 | 100 | 417.2 | 0.22 (Hexane/ethyl acetate 2:1) | |
| 119 | 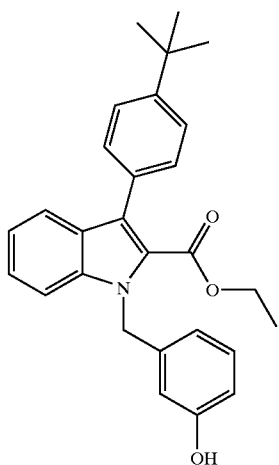 | 56 | | | |
| 120 | 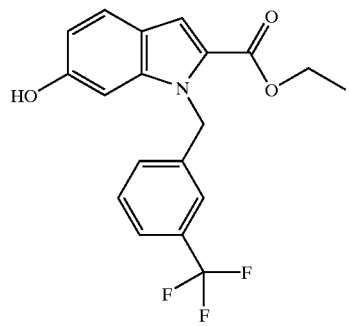 | 63 | | | |

| Ex. No. | Structure | Yield [%] | MS [M + H+] | Rf | mp [° C.] |
|---|---|---|---|---|---|
| 122 | 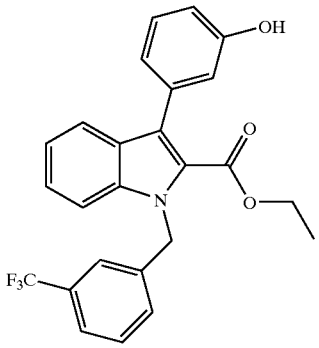 | 86 | | | |
| 123 | 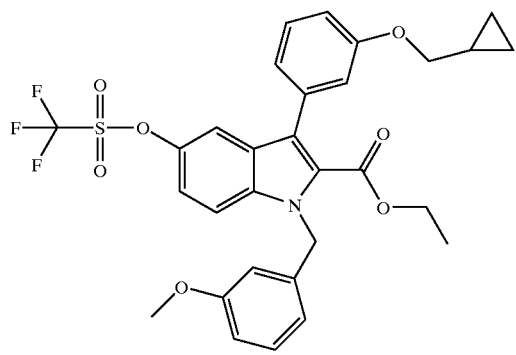 | 96 | | 0.19 (Hexane/ethyl acetate 4:1) | |

EXAMPLE 124

Ethyl 3-[3-(cyclopropylmethoxy)phenyl]-1-(3-methoxybenzyl)-5-{[(trifluoromethyl)sulfonyl]oxy}-1H-indole-2-carboxylate Triflic anhydride (0.84 mL, 1.4 g, 5.0 mmol) and dimethylaminopyridine (25 mg, 0.20 mmol) were added to a cooled (0° C.) and stirred solution of ethyl 3-[3-(cyclopropylmethoxy)phenyl]-5-hydroxy-1-(3-methoxybenzyl)-1H-indole-2-carboxylate (Example 66, 1.00 g, 2.12 mmol) in dichloromethane (10 mL) and pyridine (2 mL). The reaction was warmed to rt and then stirred an additional 2 h. The solution was diluted with ethyl acetate (100 mL), washed with water and brine, dried over anhydrous magnesium sulfate, and concentrated in vacuo. Flash chromatography of the residue over silica gel using 15% ethyl acetate/hexane afforded 1.14 g (89%) of desired product. The product had: $^1$H NMR (300 MHz, acetone-D$_6$) δ 7.73 (d, 1 H), 7.54 (d, 1 H), 7.35–7.42 (m, 3 H), 7.20 (dd, 1 H), 7.00–7.07 (m, 2 H), 6.68–6.83 (m, 3 H), 5.88 (s, 2 H), 4.16 (q, 2 H), 3.91 (d, 2 H), 3.72 (s, 3 H), 1.25–1.35 (m, 1 H), 10.5 (t, 3 H), 0.55–0.65 (m, 2 H), 0.32–0.42 (m, 2 H); mass spectroscopy gave M$^+$=603.1 (exact mass calc'd for C$_{20}$H$_{28}$F$_3$NO$_7$S=603.15).

The following compounds were prepared according to the method of Example 124:

| Ex. No. | Structure | Yield [%] | MS [M + H+] | Rf | mp [° C.] |
|---|---|---|---|---|---|
| 125 | 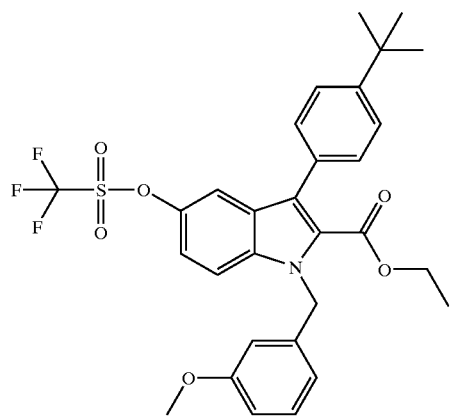 | 96 | | | |
| 126 | 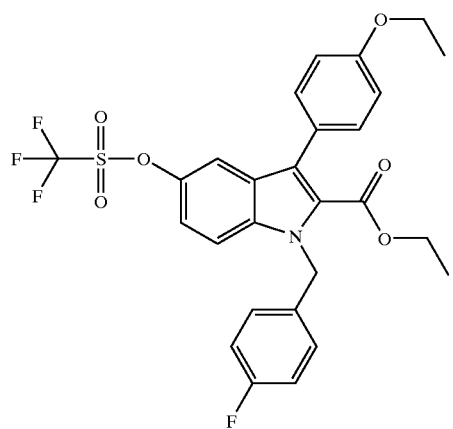 | 52 | | | |
| 127 | 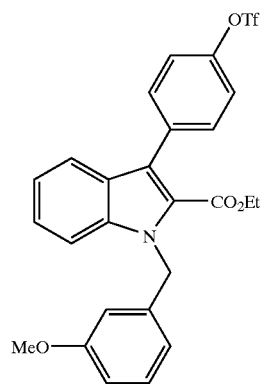 | 48 | 533.9 | | |

EXAMPLE 128

Ethyl 3-(4-tert-butylphenyl)-5-(2-cyclopenten-1-yl)-1-(3-methoxybenzyl)-1H-indole-2-carboxylate

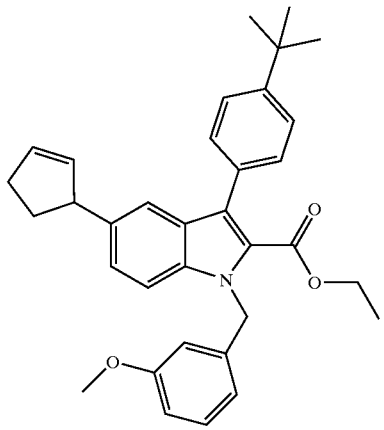

Cyclopentene (0.44 mL, 341 mg, 5.0 mmol), palladium acetate (22 mg, 0.10 mmol), tetrabutylammonium bromide (322 mg, 1.0 mmol) and potassium acetate (295 mg, 1.0 mmol) were added to a stirred solution of ethyl 3-(4-tert-butylphenyl)-1-(3-methoxybenzyl)-5-{[(trifluoromethyl)sulfonyl]oxy}-1H-indole-2-carboxylate (Example 125, 570 mg, 1.0 mmol) in N,N-dimethylformamide (5 mL). The reaction was stirred for 48 h and then diluted with ethyl acetate (100 mL). The solution was washed with brine, dried over anhydrous magnesium sulfate, and concentrated in vacuo. Flash chromatography of the residue over silica gel using 6:1 ethyl acetate/hexane gave 230 mg, (45%) of the desired product. The product had: $^1$H NMR (300 MHz, acetone-D$_6$) δ 7.49–7.56 (m, 3 H), 7.37–7.43 (m, 3 H), 7.17–7.23 (m, 2 H), 6.68–6.92 (m, 3 H), 4.09 (q, 3 H), 3.92–4.01 (m, 1 H), 3.75 (s, 3 H), 2.31–2.50 (m, 3 H), 1.62–1.77 (m, 1 H), 1.39 (s, 9 H), 0.98 (t, 3 H).

EXAMPLE 129

Ethyl 3-(4-tert-butylphenyl-(3-methoxybenzyl)-5-vinyl-1H-indole-2-carboxylate

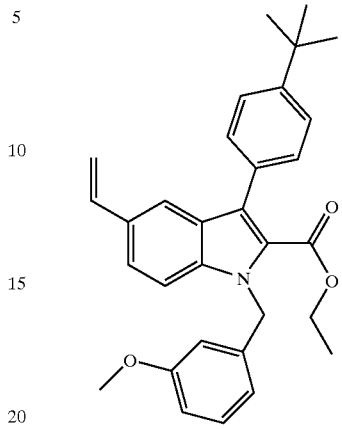

Lithium chloride (297 mg, 7.0 mmol) and tributylvinyl tin (0.43 mL, 467 mg, 1.5 mmol) were added to a stirred solution of ethyl 3-(4-tert-butylphenyl)-1-(3-methoxybenzyl)-5-{[(trifluoromethyl)sulfonyl]oxy}-1H-indole-2-carboxylate (Example 125, 570 mg, 0.995 mmol) in tetrahydrofuran (10 mL). Argon was bubbled through the mixture for 10 min and then tetrakis(triphenylphospine) palladium (115 mg, 0.10 mmol) was added. The reaction was heated (67° C. for 18 h and then cooled to rt. The mixture was diluted with ethyl acetate (100 mL) and then washed successively with water, 10% aqueous ammonium hydroxide, water and brine. The organic solution was dried over anhydrous magnesium sulfate and concentrated in vacuo. Flash chromatography of the residue over silica gel using 10% ethyl acetate/hexane gave 334 mg (72%) of the desired product. The product had: $^1$H NMR (300 MHz, CDCl$_3$) δ 7.14–7.58 (m, 8 H), 6.64–6.82 (m, 4 H), 5.77 (s, 2 H), 5.65 (dd, 1 H), 5.13 (dd, 1 H), 4.10 (q, 2 H), 3.73 (s, 3 H), 1.40 (s, 9 H), 0.95 (t, 3 H); mass spectroscopy gave MH$^+$=468.2 (calc'd exact mass for C$_{31}$H$_{33}$NO$_3$=467.25).

The following compounds were prepared according to the method of Examples 128–129:

| Ex. No. | Structure | Yield [%] | MS [M + H$^+$] | Rf | mp [° C.] |
|---|---|---|---|---|---|
| 130 | 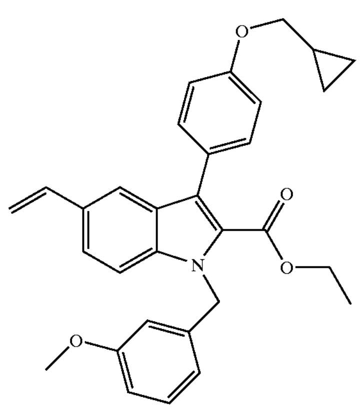 | 3 | 482.1 | 0.48 (Hexane/ethyl acetate 4:1) | |

| Ex. No. | Structure | Yield [%] | MS [M + H⁺] | Rf | mp [° C.] |
|---|---|---|---|---|---|
| 131 | 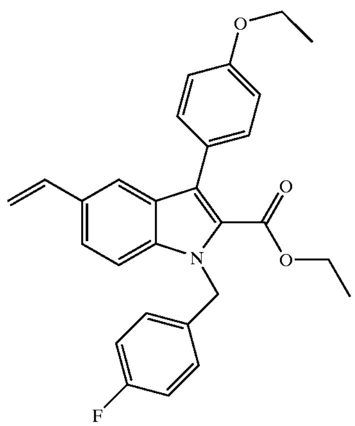 | 69 | | 0.41 (Hexane/ethyl acetate 5:1) | |
| 132 | 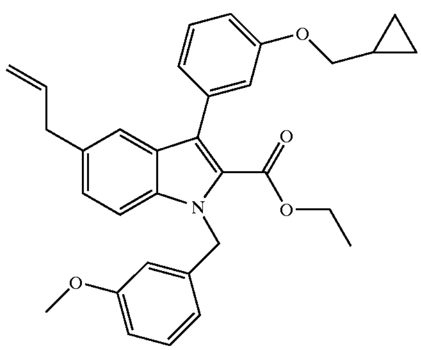 | 82 | 496.2 | | |

EXAMPLE 133

Ethyl 3-(4-tert-butylphenyl)-5-(2-hydroxyethyl)-1-(3-methoxybenzyl)-1H-indole-2-carboxylate

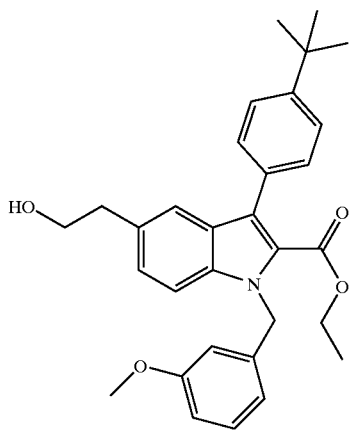

Acetic acid (63 μL, 66 mg, 1.1 mmol) was added slowly to a cooled (0° C.) and stirred slurry of sodium borohydride (41.6 mg, 1.10 mmol) in tetrahydrofuran (2 mL). The mixture was stirred for 1 h and then a solution of ethyl 3-(4-tert-butylphenyl)-1-(3-methoxybenzyl)-5-vinyl-1H-indole-2-carboxylate (Example 129, 430 mg, 0.920 mmol) in tetrahydrofuran (5+2 mL rinse) was added. The reaction was stirred overnight and then cooled (0° C.). The reaction was quenched by successive addition of EtOH (6 mL), 6 M aqueous sodium acetate (5 mL) and 27% aqueous hydrogen peroxide (5 mL). The mixture was heated (50° C.) for 1 h and then cooled. The reaction was diluted with water (100 mL) and then extracted with ethyl acetate (3×50 mL). The combined organic extracts were washed with brine, dried over anhydrous magnesium sulfate, and concentrated in vacuo. Flash chromatography of the residue over silica gel using 30% ethyl acetate/hexane afforded 325 mg (75%) of desired product. The product had: ¹H NMR (300 MHz, CDCl₃) δ 7.28–7.48 (m, 6 H), 7.15–7.22 (m, 2 H), 6.75 (dd, 1 H), 6.64–6.72 (m, 2 H), 7.76(s, 2 H), 4.08 (q, 2 H), 3.78–4.00 (m, 3 H), 3.73 (s, 3 H), 2.91 (t, 2 H), 1.39 (s, 9 H), 0.95 (t, 3 H).

The following compounds were prepared according to the method of Example 133

| Ex. No. | Structure | Yield [%] | MS [M + H+] | Rf | mp [° C.] |
|---|---|---|---|---|---|
| 134 | 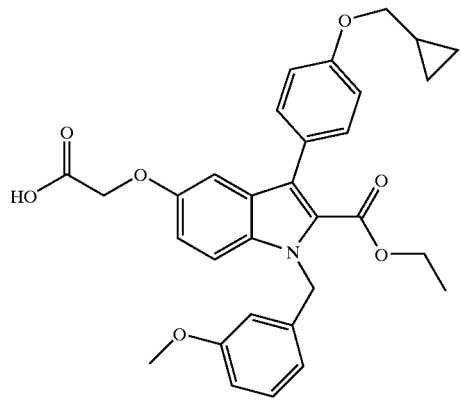 | 56 | 462.2 | | |

EXAMPLE 135

{[3-[4-(Cyclopropylmethoxy)phenyl]-2-(ethoxycarbonyl)-1-(3-methoxybenzyl)-1H-indol-5-yl]oxy}acetic acid

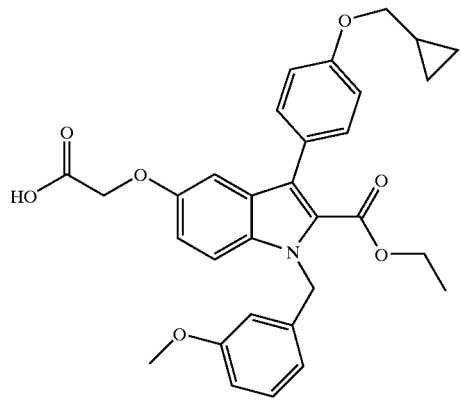

Formic acid (1 mL) was added to a stirred solution of ethyl 5-(2-tert-butoxy-2-oxoethoxy)-3-[4-(cyclopropylmethoxy)phenyl]-1-(3-methoxybenzyl)-1H-indole-2-carboxylate (Example 150, 20 mg, 0.035 mmol) in dichloromethane (1 mL). The reaction was stirred for 1 h and then concentrated in vacuo. Flash chromatography of the residue over silica gel using (1:1 ethyl acetate/hexane) gave 10 mg (53% of the desired product. The product had: $^1$H NMR (300 MHz, CD$_3$OD) δ 7.30–7.48 (m, 3 H), 6.92–7.19 (m, 4 H), 6.77 (dd, 1 H), 6.54–6.68 (m, 3 H), 5.79 (s, 2 H), 4.61 (s, 2 H), 4.13 (q, 2 H), 3.95 (d, 2 H), 3.74 (s, 3 H), 1.29–1.41 (m, 1 H), 1.25 (t, 3 H), 0.61–0.71 (m, 2 H), 0.39–0.49 (m, 2 H); mass spectroscopy gave MH+ of 530.2 (calc'd exact mass for C$_{31}$H$_{31}$NO$_7$=529.21).

EXAMPLE 136

Ethyl 3-[3-(cyclopropylmethoxy)phenyl]-1-(3-methoxybenzyl)-5-(2-oxoethoxy)-1H-indole-2-carboxylate

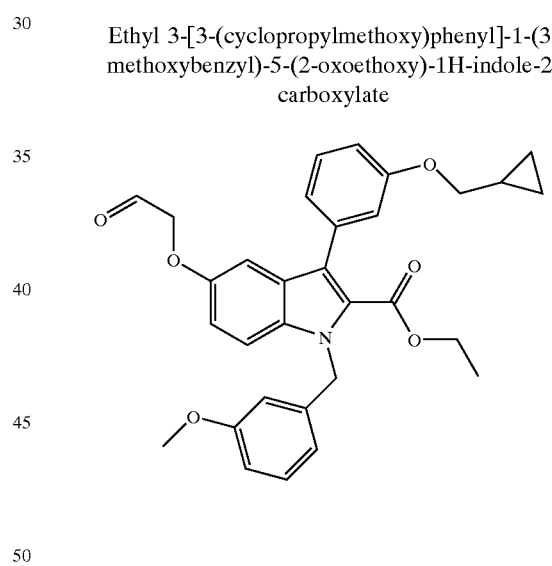

Sodium periodate (812 mg, 3.80 mmol) and osmium tetroxide (2.5 wt % solution in tert-butanol, 1.2 mL, 0.10 mmol) were added to a stirred solution of ethyl 3-[4-(cyclopropyl-methoxy)phenyl]-1-(3methoxy-benzyl)-5-allyloxy-1H-indole-2-carboxylate (Example 149, 640 mg, 1.25 mmol) in tetrahydrofuran (15 mL) and water (1.5 mL). The reaction was stirred for 16 h and then diluted with water (100 mL). The product was extracted with ethyl acetate (3×50 mL) and then the combined organic extracts were washed with water, dried over anhydrous magnesium sulfate, and concentrated in vacuo. Flash chromatography of the residue over silica gel using 8:1 hexane/ethyl acetate gave 395 mg (62%) of product containing impurities. The material was used in the next reaction without further purification or analysis.

EXAMPLE 137

Ethyl 3-[3-(cyclopropylmethoxy)phenyl]-5-(2-hydroxyethoxy)-1-(3-methoxybenzyl)-1H-indole-2-carboxylate

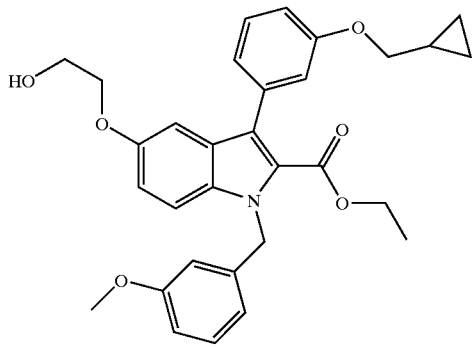

Sodium borohydride (38 mg, 1.0 mmol) was added to a stirred solution of ethyl 3-[3-(cyclopropylmethoxy)phenyl]-1-(3-methoxybenzyl)-5-(2-oxoethoxy)-1H-indole-2-carboxylate (Example 136, 380 mg, 0.74 mmol) in methanol (10 mL). The reaction was stirred for 2 h and then the reaction was quenched with water (100 mL). The product was extracted with ethyl acetate (3×40 mL) and then the combined organic extracts were washed with brine, dried over anhydrous magnesium sulfate and concentrated in vacuo to leave 363 mg (95%) of product containing some impurities. The material was used in the next reaction without further purification. The product had: $^1$H NMR (300 MHz, acetone-$D_6$) δ 7.34–7.46 (m, 3 H), 7.16 (dd, 1 H), 6.93–7.02 (m, 4 H), 6.65–6.81 (m, 3 H), 5.78 (s, 2 H), 3.82–4.23 (m, 9 H), 3.69 (s, 3 H), 1.24–1.34 (m, 1 H), 1.02 (t, 3 H), 0.60–0.70 (m, 2 H), 0.34–0.44 (m, 2 H).

EXAMPLE 138

Ethyl 3-[3-(cyclopropylmethoxy)phenyl]-1-(3-methoxybenzyl)-5-(2-oxoethyl)-1H-indole-2-carboxylate

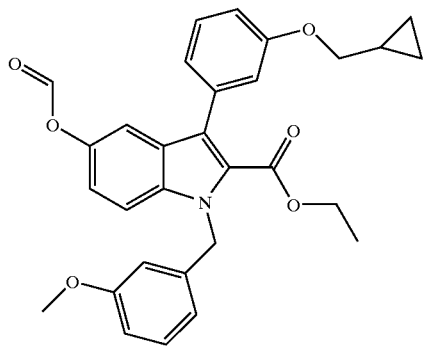

Sodium periodate (430 mg, 2.0 mmol) and osmium tetroxide (2.5 wt % solution in tert-butanol, 0.50 mL, 0.05 mmol) were added to a stirred solution of ethyl 5-allyl-3-[3-(cyclopropylmethoxy)phenyl]-1-(3-methoxybenzyl)-1H-indole-2-carboxylate (Example 132, 385 mg, 0.777 mmol) in tetrahydrofuran (10 mL) and water (1 mL). The reaction was stirred for 18 h and then diluted with water (100 mL). The product was extracted with ethyl acetate (3×50 mL) and then the combined organic extracts were washed with water, dried over anhydrous magnesium sulfate, and concentrated in vacuo. Flash chromatography of the residue over silica gel using 15% ethyl acetate/hexane gave 183 mg (47%) of product containing impurities. The material was used in the next reaction without further purification. Mass spectroscopy gave MH$^+$=498.1 (exact mass calc'd for $C_{31}H_{31}NO_5$= 497.22).

EXAMPLE 139

[3[3-(Cyclopropylmethoxy)phenyl]-2-(ethoxycarbonyl)-1-(3-methoxybenzyl)-1H-indol-5-yl]acetic acid

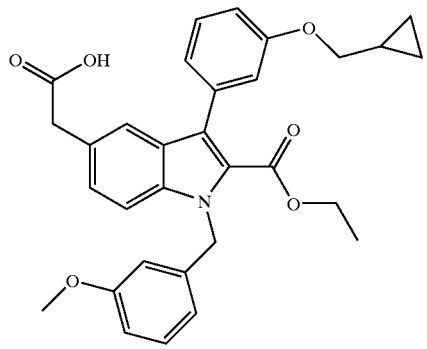

2-Methyl-2-butene (2 mL), sodium phosphate monobasic (307 mg, 2.6 mmol) and sodium perchlorate (307 mg, 3.4 mmol) were added to a stirred solution of ethyl 3-[3-(cyclopropylmethoxy)phenyl]-1-(3-methoxybenzyl)-5-(2-oxoethyl)-1H-indole-2-carboxylate (Example 138, 169 mg, 0.34 mmol) in tert-butanol (8 mL) and water (3 mL). The reaction was stirred for 24 h and then diluted with ethyl acetate (100 mL). The solution was washed with brine, dried over anhydrous magnesium sulfate and concentrated in vacuo. Flash chromatography of the residue over silica gel using 60% ethyl acetate/hexane afforded 35 mg (20%) of the product. The product had: $^1$H NMR (300 MHz, acetone-$D_6$) δ 6.96–7.57 (m, 8 H), 6.58–6.80 (m, 3 H), 5.83 (s, 2 H), 4.11 (q, 2 H), 3.90 (d, 2 H), 3.70 (s, 3 H), 3.67 (s, 2 H), 1.24–1.40 (m, 1 H), 1.03 (t, 3 H), 0.55–0.65 (m, 2 H), 0.35–0.46 (m, 2 H); mass spectroscopy gave M–H$^+$=512.5 (calc'd exact mass for $C_{31}H_{31}NO_6$=513.22).

EXAMPLE 140

Ethyl 3-(4-tert-butylphenyl)-5-formyl-1-(3-methoxybenzyl)-1H-indole-2-carboxylate

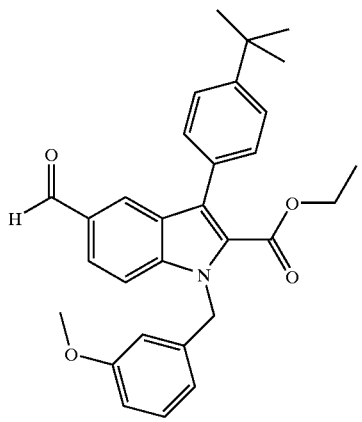

Ethyl 3-(4-tert-butylphenyl)-1-(3-methoxybenzyl)-5-vinyl-1H-indole-2-carboxylate (Example 129, 2.28 g, 4.9 mmol) was dissolved in anhydrous tetrahydrofuran (25 mL), and osmium tetroxide (2.5 weight % solution in 2-methyl-2-propanol, 1.5 mL, 0.15 mmol) was added. After ten minutes, the reaction mixture was cooled with an ice bath. Sodium periodate (2.10 g, 9.8 mmol) was added followed by a minimum volume of water to dissolve the solids. The reaction was allowed to return to room temperature, and after 30 minutes, the reaction was partitioned between water and diethyl ether. The organic layer was separated, dried over anhydrous magnesium sulfate, and concentrated. The resulting crude oil was passed through a pad of silica gel with 20% ethyl acetate/hexane. The filtrate was concentrated in vacuo without heat to provide the title compound as a brown oil (1.70 g, 75%). The product had: $^1$H NMR (300 MHz, acetone-d$_6$) 10.01 (s, 1 H), 8.15 (d, 1 H), 7.88 (d, 1 H), 7.75 (d, 1 H), 7.54 (d, 2 H), 7.44 (d, 2 H), 7.21–7.19 (m, 1 H), 6.81–6.79 (m, 1 H), 6.72–6.69 (m, 2 H), 5.92 (s, 2 H), 4.12 (q, 2 H), 3.71 (s, 3 H), 1.39 (s, 9 H), 0.78 (t, 3 H).

EXAMPLE 141

Ethyl 3-(4-tert-butylphenyl)-5-(hydroxymethyl)-1-(3-methoxybenzyl)-1H-indole-2-carboxylate

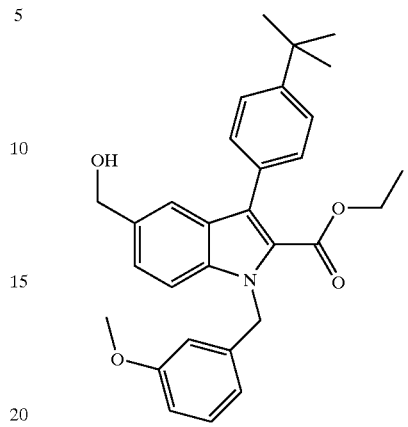

Ethyl 3-(4-tert-butylphenyl)-5-formyl-1-(3-methoxybenzyl)-1H-indole-2-carboxylate (Example 140, 700 mg, 1.493 mmol) was dissolved in ethanol (15 mL) and cooled to 0° C. Sodium borohydride (57 mg, 1.50 mmol) was added, and the solution was stirred for 1 hour. Water (27 μL, 1.5 mmol) was added, and the mixture was allowed to warm to room temperature. The mixture was concentrated via rotary evaporation, and the residue was partitioned between ethyl acetate and water. The organic layer was separated, washed with brine, dried over anhydrous magnesium sulfate, and concentrated. The resulting crude oil was purified by flash chromatography on silica gel eluted with hexane then 20% ethyl acetate/hexane. The title compound was collected as a foam (530 mg, 75%). The product had: $^1$H NMR (300 MHz, acetone-d$_6$) δ 7.56–7.55 (m, 1 H), 7.53–7.51 (m, 1 H), 7.50–7.47 (m, 2 H), 7.41–7.39 (m, 1 H), 7.37–7.34 (m, 2 H), 7.18–7.16 (m, 1 H), 6.77–6.75 (m, 1 H), 6.68–6.70 (m, 2 H), 5.85 (s, 2 H), 4.65 (d, 2 H), 4.09 (q, 2 H), 4.06–4.04 (m, 1 H), 3.70 (s, 3 H), 1.38 (s, 9 H), 0.96 (t, 3 H); mass spectroscopy gave MH$^+$=472.2 (calc'd exact mass for C$_{30}$H$_{33}$NO$_4$=471.24).

The following compounds were prepared according to the method of Example 141:

| Ex. No. | Structure | Yield [%] | MS [M + H$^+$] | Rf | mp [° C.] |
|---|---|---|---|---|---|
| 142 | 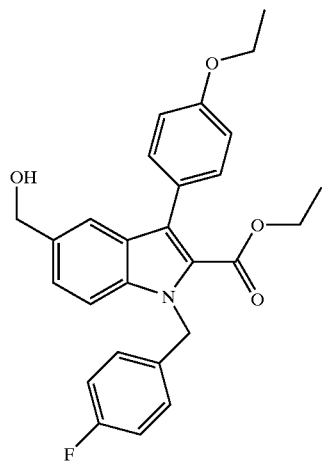 | 97 | 448.1 | | |

| Ex. No. | Structure | Yield [%] | MS [M + H⁺] | Rf | mp [° C.] |
|---|---|---|---|---|---|
| 143 | 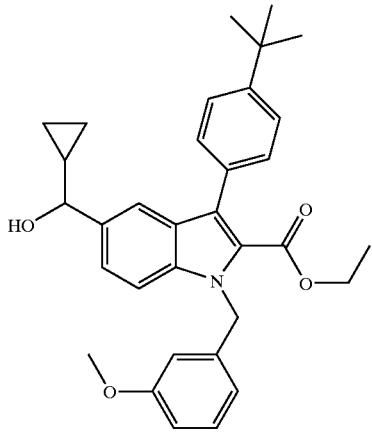 | | | | crude |

EXAMPLE 144

Ethyl 3-[4-(cyclopropylmethoxy)phenyl]-5-ethoxy-1-(3-methoxybenzyl)-1H-indole-2-carboxylate

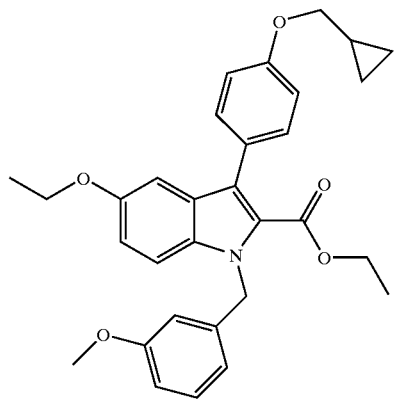

Iodoethane (468 mg, 3.0 mmol) and powdered potassium carbonate (138 mg, 1.0 mmol) was added to a solution of ethyl 3-[4-(cyclopropylmethoxy)phenyl]-5-hydroxy-1-(3-methoxybenzyl)-1H-indole-2-carboxylate (Example 66, 120 mg, 0.25 mmol) in DMF (5 mL). The mixture was heated (50° C.) for 16 h and then cooled. The resulting mixture was diluted with ethyl acetate (50 mL), washed with water and brine, dried over anhydrous magnesium sulfate, and concentrated in vacuo. The residue was purified by preparative TLC using 4:1 ethyl acetate/hexane as the eluant, to afford 52 mg (42%) of the desired product. The product had: $^1$H NMR (300 MHz, acetone-D$_6$) δ 7.42 (d, 1 H), 7.37 (d, 2 H), 7.19 (t, 1 H), 6.92–7.01 (m 4 H), 6.74–6.77 (m, 1 H), 6.64–6.68 (m, 2 H), 5.80 (s, 2 H), 4.13 (q, 2 H), 3.88–3.98 (m, 4 H), 3.69 (s, 3 H), 1.34–1.45 (m, 4 H), 1.04 (t, 3 H), 0.56–0.66 (m, 2 H), 0.34–0.44 (m, 2 H).

EXAMPLE 145

Ethyl 3-[3-(cyclopropylmethoxy)phenyl]-5-(2-ethoxyethoxy)-1-(3-methoxybenzyl)-1H-indole-2-carboxylate

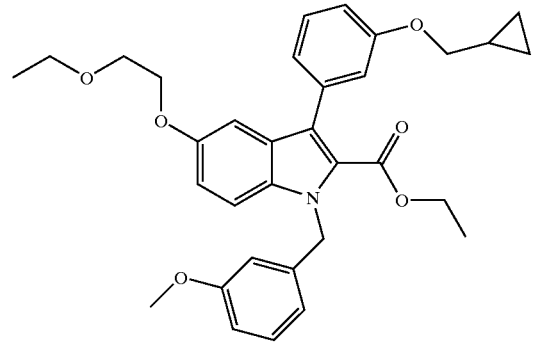

A solution of ethyl 3-[3-(cyclopropylmethoxy)phenyl]-5-(2-hydroxyethoxy)-1-(3-methoxybenzyl)-1-H-indole-2-carboxylate (Example 223, 110 mg, 0.23 mmol) was added to a cooled (0° C.) and stirred suspension of sodium hydride (12 mg, 0.50 mmol) in N,N-dimethylformamide (5 mL). The cold bath was removed and the reaction was stirred for 1 h. Ethyl iodide (80 µL, 156 mg, 1.0 mmol) was added and the reaction was stirred for an additional hour. The reaction was quenched with methanol (1 mL) and then diluted with water (50 mL). The product was extracted with ethyl acetate (3×30 mL) and then the combined organic extracts were washed with brine, dried over anhydrous magnesium sulfate, and concentrated in vacuo. Flash chromatography of the residue over silica gel using 4:1 hexane/ethyl acetate gave 62 mg (50%) of product. The product had: $^1$H NMR (300 MHz, acetone-D$_6$) δ 7.42 (d, 1 H), 7.29–7.36 (m, 2 H), 7.14 (dd, 1 H), 6.94–7.02 (m, 4 H), 6.63–6.79 (m, 3 H), 5.78 (s, 2 H), 3.99–4.12 (m, 4 H), 3.86 (d, 2 H), 3.64–3.71 (m, 5 H), 3.48 (q, 2 H), 1.24–1.34 (m, 1 H), 1.11 (t, 3 H), 0.98 (t, 3 H), 0.54–0.64 (m, 2 H), 0.32–0.42 (m, 2 H).

The following compounds were prepared according to the methods of Examples 144–145:

| Ex. No. | Structure | Yield [%] | MS [M + H+] | Rf | mp [° C.] |
|---|---|---|---|---|---|
| 146 | 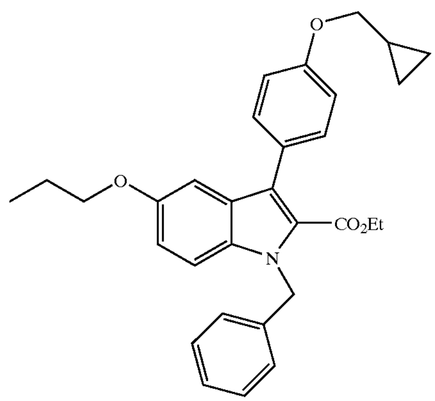 | 53 | | 0.85 (Hexane/ ethyl acetate 5:1) | |
| 147 | 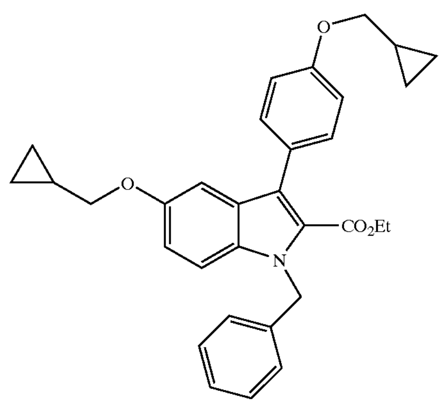 | 49 | | 0.85 (Hexane/ ethyl acetate 5:1) | |
| 148 | 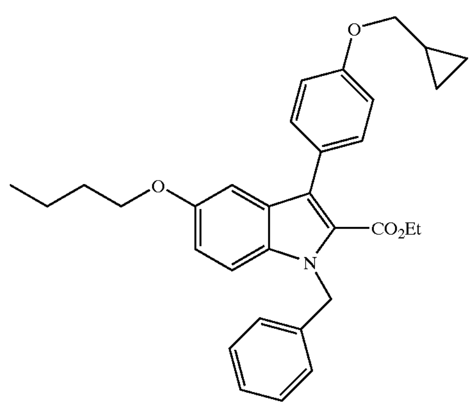 | 57 | | 0.85 (Hexane/ ethyl acetate 5:1) | |

-continued

| Ex. No. | Structure | Yield [%] | MS [M + H⁺] | Rf | mp [° C.] |
|---|---|---|---|---|---|
| 149 | 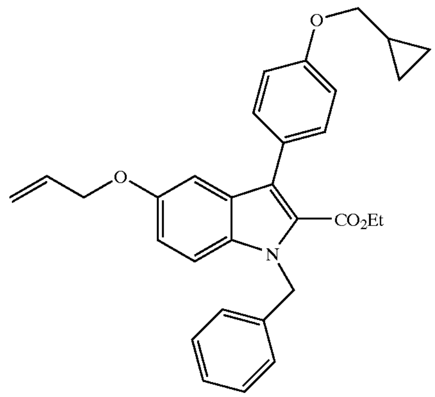 | 55 | | 0.85 (Hexane/ ethyl acetate 5:1) | |
| 150 | 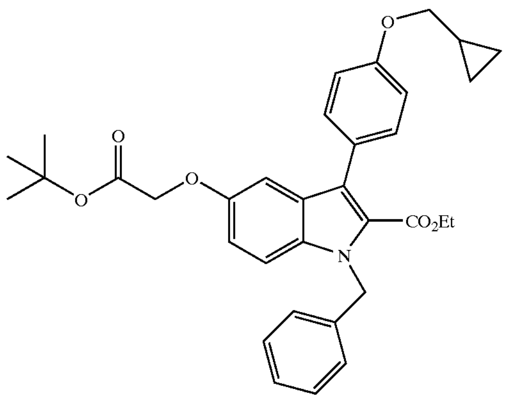 | 80 | | 0.85 (Hexane/ ethyl acetate 5:1) | |
| 151 | 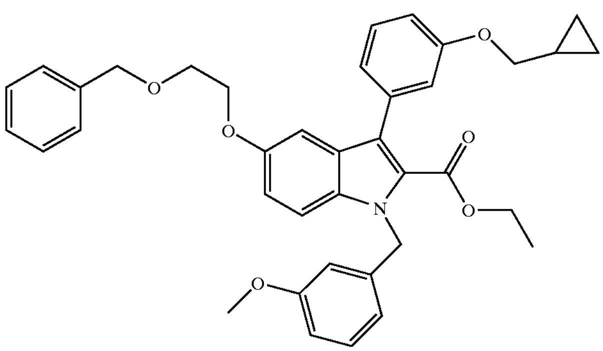 | 65 | | | |
| 152 | 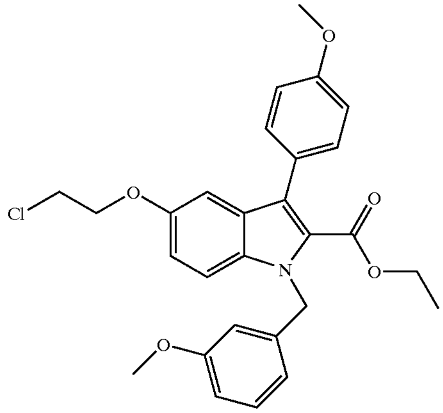 | 80 | 494.1 | 0.27 (Hexane/ ethyl acetate 6:1) | |

-continued

| Ex. No. | Structure | Yield [%] | MS [M + H+] | Rf | mp [° C.] |
|---|---|---|---|---|---|
| 153 | 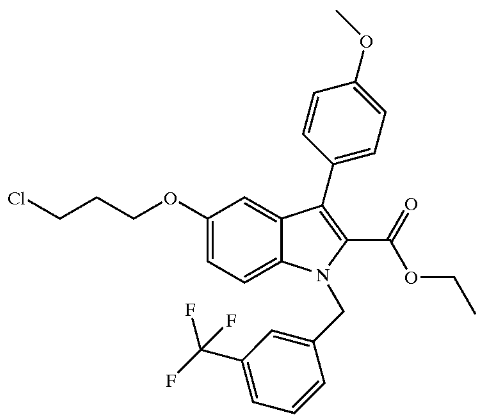 | 99 | 546.0 | 0.50 (Hexane/ ethyl acetate 2:1) | |
| 154 | 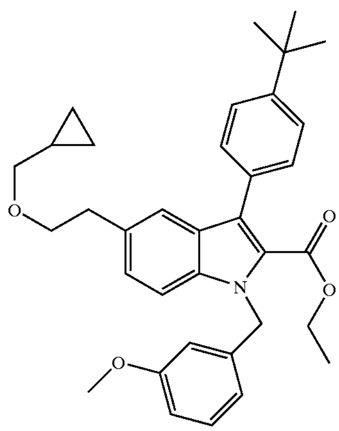 | 38 | | | |
| 155 | 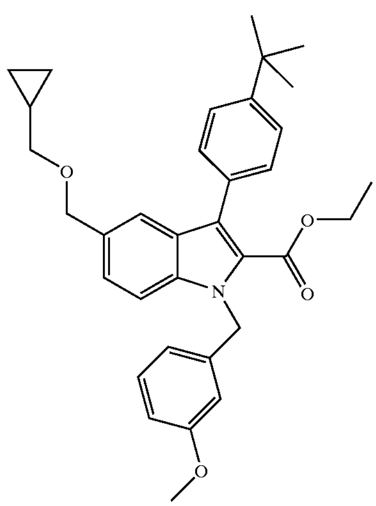 | 41 | 562.2 | | |

EXAMPLE 156

Ethyl 1-(3-methoxybenzyl)-3-(4-methoxyphenyl)-5-[2-(methylamino)ethoxy]-1H-indole-2-carboxylate

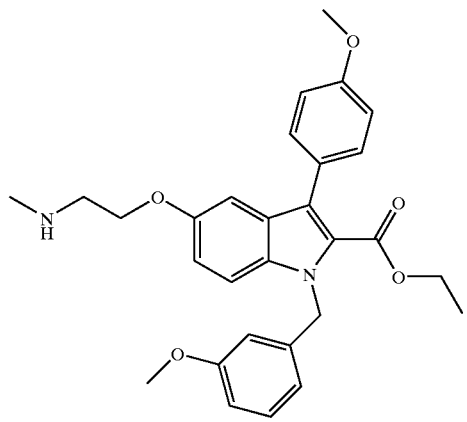

A reaction mixture of ethyl 5-(2-chloroethoxy)-1-(3-methoxybenzyl)-3-(4-methoxyphenyl)-1H-indole-2-carboxylate (Example 152, 290 mg, 0.588 mmol) and methylamine in tetrahydrofuran (2 M, 40 ml) was sealed in a stainless steel vessel (100 ml, bomb) at 0° C. Then it was heated and stirred at 120° C. for 3 days in a oil bath. Oil bath was removed and the bomb was allowed to cooled to room temperature before opened. The reaction solution was transferred to an round-bottomed flask and solvent was concentrated in vacuo. The residue was dissolved in ethyl acetate and washed with 1N NaOH. The organic phase was dried over anhydrous sodium sulfate, concentrated and purified by flash column (silica gel, hexane: ethyl acetate=1:1 to ethyl acetate:2M NH3/ methanol =9:1). 214 mg desired product was obtained as a light yellow oil in 75%. MS (M+H)= 489.2, Rf=0.28 (ethyl acetate:2M NH3/methanol=4:1).

The following compounds were prepared according to the method of Example 156:

EXAMPLE 158

Ethyl 5-{2-[1,3-benzoxazol-2-yl(methyl)amino]ethoxy}-1-(3-methoxybenzyl)-3-(4-methoxyphenyl)-1H-indole-2-carboxylate

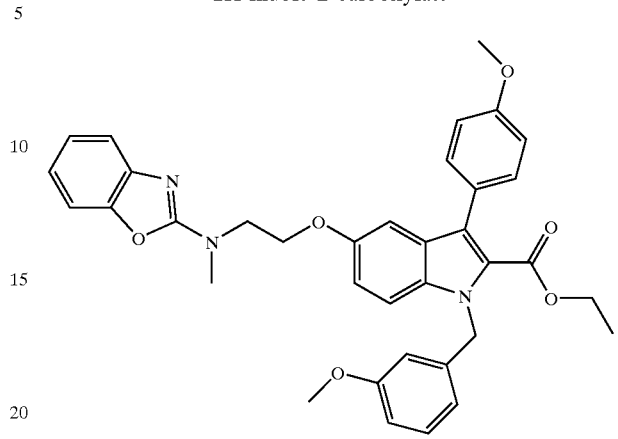

To a solution of Ethyl 1-(3-methoxybenzyl)-3-(4-methoxyphenyl)-5-[2-(methylamino)ethoxy]-1H-indole-2-carboxylate (Example 156, 100 mg, 0.2028 mmol) in N,N-dimethylformamide (1.5 ml) was added diisopropylethylamine (0.09 ml, 0.5167 mmol, 2.5 eq.) and 2-chlorobenzoxazole (0.03 ml, 0.2636 mmol, 1.3 eq.). The reaction mixture was heated at 120° C. for 4 hr. After cooling the reaction was diluted with saturated aqueous sodium bicarbonate and then extracted with ethyl acetate. The combined organic extracts were washed with brine, dried over anhydrous Na2SO4, concentrated in vacuo and purified by flash column (silica gel, dichloromethane to dichloromethane:methanol 95:5). The desired product was obtained as a light yellow oil in 97% yield (119 mg), MS (M+H)=606.3, Rf=0.69 (dichloromethane/methanol 95:5).

The following compounds were prepared according to the method of Example 158:

| Ex. No. | Structure | Yield [%] | MS [M + H+] | Rf | mp [° C.] |
|---|---|---|---|---|---|
| 157 | 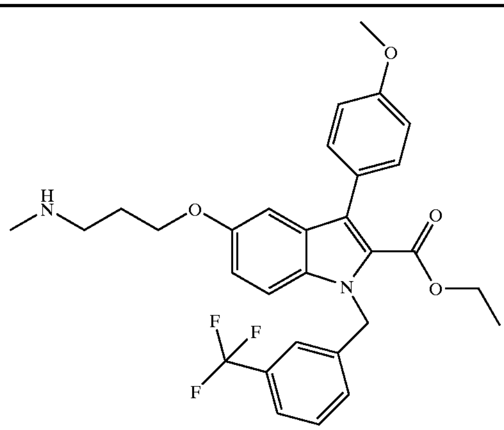 | 67 | 541.2 | 0.34 (ethyl acetate/ (2 M NH₃ in MeOH) 4:1) | |

| Ex. No. | Structure | Yield [%] | MS [M + H⁺] | Rf | mp [° C.] |
|---|---|---|---|---|---|
| 159 | 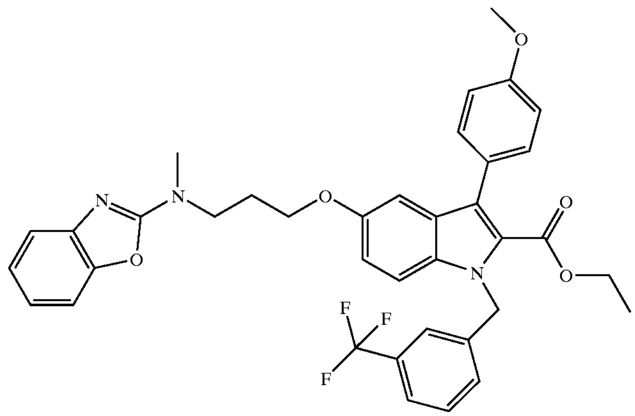 | crude | 658.3 | | |

EXAMPLE 160

Ethyl 5-amino-3-(4-tert-butylphenyl)-1-(3-methoxybenzyl)-1H-indole-2-carboxylate

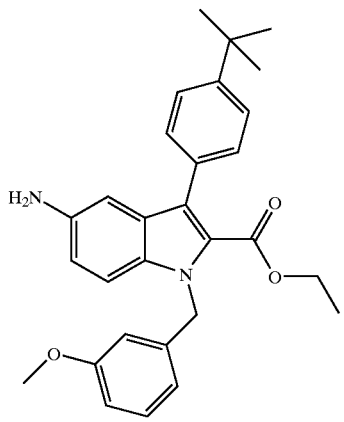

EXAMPLE 161

Ethyl 7-amino-3-(4-methoxyphenyl)-1-[(3-methoxyphenyl)methyl]indole-2-carboxylate

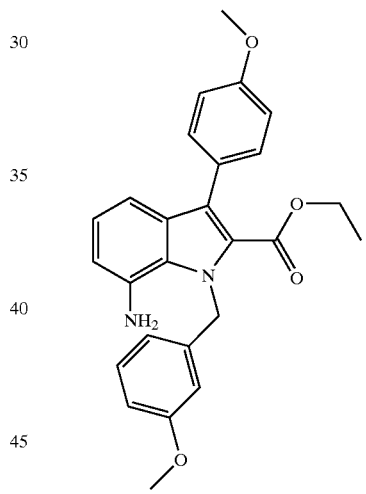

Tin (II) chloride (8.5 g, 45 mmol) was added to a stirred solution of ethyl 3-(4-tert-butylphenyl)-1-(3-methoxybenzyl)-5-nitro-1H-indole-2-carboxylate (Example 28, 4.5 g, 9.3 mmol) in EtOH (24 mL). The mixture was heated (50° C.) until there was a homogenous solution and then concentrated hydrochloric acid (16 mL) was added. The reaction was stirred at 60° C. for 2 h and then cooled. The pH of the solution was adjusted to pH=12 using 1 M aqueous sodium hydroxide and then the product was extracted with ethyl acetate (3×10 mL). The combined organic extracts were dried over anhydrous magnesium sulfate, and concentrated in vacuo to leave 2.8 g (67%) of crude product that was taken to the next reaction without as proceeded to the next step without further purification. Mass spectroscopy gave MH⁺=457.4 (exact mass calc'd for $C_{29}H_{32}N_2O_4$=456.24).

A solution of ethyl 3-(4-methoxyphenyl)-1-[(3-methoxyphenyl)methyl]-7-nitroindole-2-carboxylate (Example 96, 425 mg, 0.99 mmol) in ethyl acetate (15 mL) was added to 10% Pd/C Degussa type (70 mg) and the resulting suspension put under a $H_2$ atmosphere and stirred for 18 h. The reaction was put back under argon, filtered through Celite, and the filtrate concentrated to a dark oil which was purified by flash chromatography on silica in 2:1 hexane:ethyl acetate to yield 401 mg, (100%) of an orange oil. ¹H NMR (300 MHz, DMSO-d₆) δ 7.28–7.22 (m, 2H), 7.19–7.12 (m, 1H), 7.00–6.95 (m, 2H), 6.89–6.83 (m, 1H), 6.80–6.70 M, 2H), 6.67–6.60 (m, 1H), 6.55–6.50 (m, 2H), 5.89 (s, 2H), 4.93 (s, 2H), 4.05 (q, J=7.1 Hz, 2H), 3.78 (s, 3H), 3.63 (s, 3H), 0.94 (t, J=7.1 Hz, 3H); Mass spectroscopy gave MH⁺=431.2 (calc'd exact mass for $C_{26}H_{26}N_2O_4$=430.19); TLF $R_f$=0.40 (2:1 hexane:ethyl acetate).

The following compounds were prepared according to the method of Example 161:

| Ex. No. | Structure | Yield [%] | MS [M + H+] | Rf | mp [° C.] |
|---|---|---|---|---|---|
| 162 | 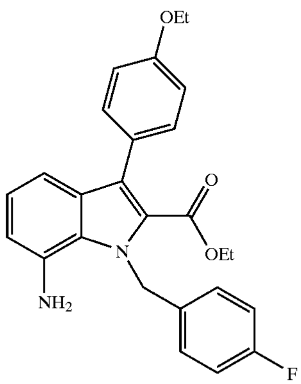 | 84 | 433 | | |
| 163 | 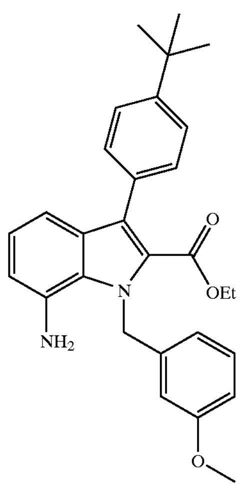 | 85 | 457 | | |
| 164 | 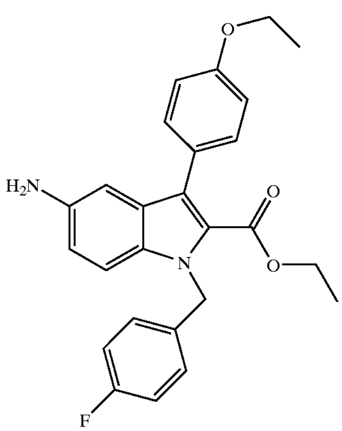 | 63 | 433.4 | 0.34 (Hexane/ethyl acetate 2:1) | |

EXAMPLE 165

Ethyl 3-(4-tert-butylphenyl)-5-[(cyclopropylmethyl)amino]-1-(3-methoxybenzyl)-1H-indole-2-carboxylate

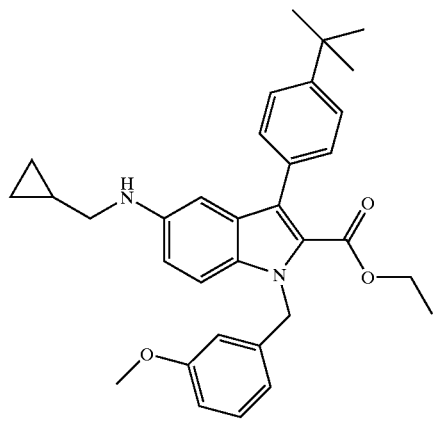

Cyclopropanecarboxaldehyde (168 mg, 2.4 mmol) was added to a stirred mixture of ethyl 5-amino-3-(4-tert-butylphenyl)-1-(3-methoxybenzyl)-1H-indole-2-carboxylate (Example 160, 530 mg, 1.2 mmol) in toluene (12 mL) and molecular sieves (2 g). The reaction was stirred for 16 h and then filtered using toluene to rinse. The filtrate was concentrated in vacuo and the residue was dissolved in methanol (12 mL). Sodium borohydride (15 mg, 1.2 mmol) was added and the reaction was stirred for 2 h. The mixture was diluted with ethyl acetate (50 mL), washed with water and brine, dried over anhydrous magnesium sulfate, and concentrated in vacuo. Flash chromatography of the residue over silica gel using 4:1 hexane/ethyl acetate afforded 480 mg (78%) of desired product. The product had: $^1$H NMR (300 MHz, acetone-D6) δ 7.45–7.48 (m, 2 H), 7.34–7.38 (m, 2 H), 7.31 (d, 1 H), 7.18 (dd, 1 H), 6.87 (dd, 1H), 6.77 (ddd, 1 H), 6.65–6.70 (m, 2 H), 6.62 (d, 1 H), 5.75 (s, 2 H), 4.68 (s, 1 H), 4.08 (q, 2 H), 3.69 (s, 3 H), 2.89 (d, 2 H), 1.37 (s, 9 H), 1.00–1.10 (m, 1 H), 0.93 (t, 3 H), 0.42–0.49 (m, 2 H), 0.16–0.25 (m, 2 H).

The following compounds were prepared according to the method of Example 165:

| Ex. No. | Structure | Yield [%] | MS [M + H$^+$] | Rf | mp [° C.] |
|---|---|---|---|---|---|
| 166 | 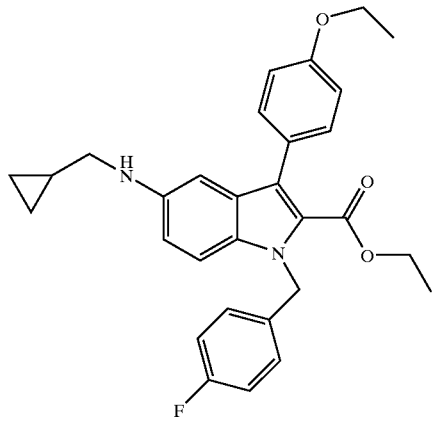 | 72 | | | |

EXAMPLE 167

Methyl 3-(4-tert-butylphenyl)-5-[(cyclopropylcarbonyl)amino]-1-(3-methoxybenzyl)-1H-indole-2-carboxylate

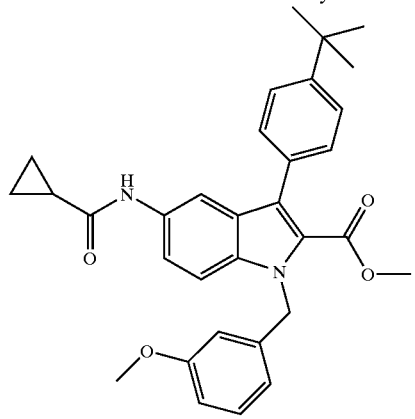

Triethylamine (0.12 mL, 91 mg, 0.90 mmol), dimethylaminopyridine (20 mg, 0.16 mmol), and cyclopropanecarbonyl chloride (82 µL, 94 mg, 0.90 mmol) were added successively to a cooled (0° C.) and stirred solution of methyl 5-amino-3-(4-tert-butylphenyl)-1-(3-methoxybenzyl)-1H-indole-2-carboxylate (Example 160, 140 mg, 0.31 mmol) in dichloromethane (10 mL). The reaction was warmed to rt and stirred for 16 h. The solution was diluted with dichloromethane (50 mL), washed with water and brine, dried over anhydrous magnesium sulfate and concentrated in vacuo. Flash chromatography of the residue over silica gel using 4:1 hexane/ethyl acetate afforded 58 mg (37%) of desired product. The product had: $^1$H NMR (300 MHz, acetone-D$_6$) δ 9.38 (s, 1 H), 8.02 (d, 1 H), 7.37–7.65 (m, 6 H), 7.19 (dd, 1 H), 6.80 (dd, 1 H), 6.6–6.74 (m, 2 H), 5.81 (s, 2 H), 3.73 (s, 3 H), 3.62 (s, 3 H), 1.70–1.80 (m, 1 H), 1.40 (s, 9 H), 0.82–0.90 (m,2H), 0.70–0.78 (m,2H).

EXAMPLE 168 AND 168A

Ethyl 7-(cyclopropylcarbonylamino)-3-(4-methoxyphenyl)-1-[(3-methoxyphenyl)methyl]indole-2-carboxylate (Example 168) and Ethyl 7-[cyclopropyl-N-(cyclopropylcarbonyl)carbonylamino]-3-(4-methoxyphenyl)-1-[(3-methoxyphenyl)methyl]indole-2-carboxylate (Example 168A)

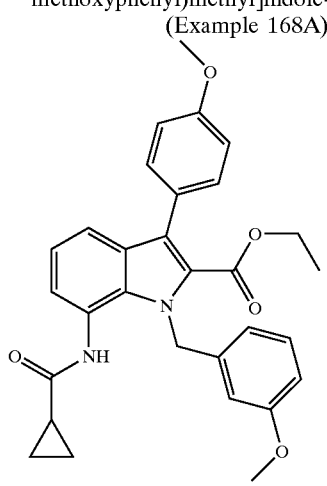

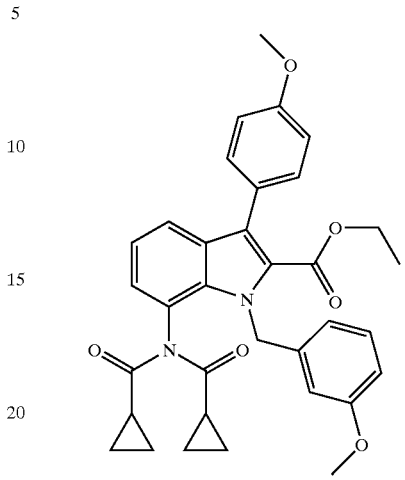

To a solution of ethyl 7-amino-3-(4-methoxyphenyl)-1-[(3-methoxyphenyl)methyl]indole-2-carboxylate (Example 161, 400 mg, 0.93 mmol) in tetrahydrofuran (5 mL) was added triethylamine (0.278 mL, 2.00 mmol) and catalytic dimethylaminopyridine. The solution was stirred while cyclopropanecarbonyl chloride (0.10 mL, 1.1 mmol) was added. After 1 h stirring, the reaction was quenched with 1 M hydrogen chloride and the resulting mixture extracted with ethyl acetate. The combined organic layers were dried over anhydrous magnesium sulfate, adsorbed onto silica, and purified by flash chromatography on silica in a 3:1 to 1:1 hexane:ethyl acetate gradient to yield 170 mg (32%) of the diacylated Example 168A and 190 mg (41%) of the monoacylated Example 168: $^1$H NMR (300 MHz, DMSO-d$_6$) δ 10.04 (s, 1H), 7.39–7.27 (m, 3H), 7.15–6.95 (m, 5H), 6.75–6.70 (m, 1H), 6.40–6.35 (m, 2H), 5.75 (s, 2H), 4.06 (q, J=7.1 Hz, 2H), 3.80 (s, 3H), 3.62 (s, 3H), 1.80–1.70 (m, 1H), 0.94 (t, J=7.1 Hz, 3H), 0.80–0.66 (m, 4H); TLC R$_f$=0.06 (2:1 hexane:ethyl acetate (v/v)). Example 168A: $^1$H NMR (300 MHz, DMSO-d$_6$) □7.58–7.53 (m, 1H), 7.40–7.34 (m, 2H), 7.24–7.11 (m, 3H), 7.07–7.02 (m, 2H), 6.80–6.73 (m, 1H), 6.42–6.33 (m, 2H), 5.63 (s, 2H), 4.03 (q, J=7.1 Hz, 2H), 3.81 (s, 3H), 3.65 (s, 3H), 1.85–1.76 (m, 2H), 0.90 (t, J=7.1 Hz, 3H), 0.84–0.60 (m, 8H); TLC R$_f$=0.40 (2:1 hexane:ethyl acetate (v/v)).

The following compounds were prepared according to the methods of Examples 167–168:

| Ex. No. | Structure | Yield [%] | MS [M + H+] | Rf | mp [° C.] |
|---|---|---|---|---|---|
| 169 | 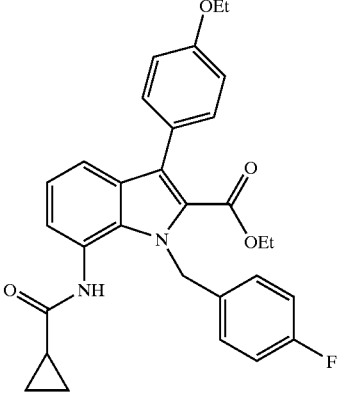 | 100 | 501 | | |
| 170 | 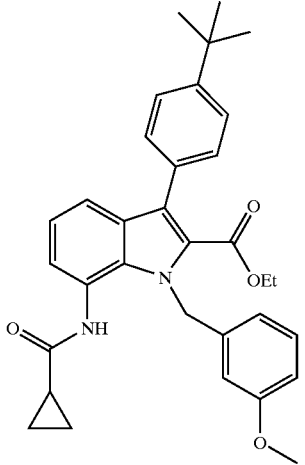 | 39 | | | |
| 171 | 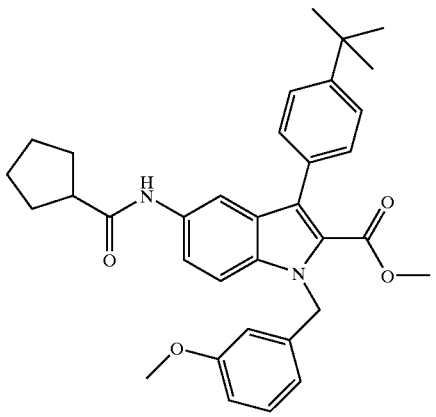 | 25 | | | |

EXAMPLE 172

Ethyl 3-(4-tert-butylphenyl)-5-({[(cyclopropylmethyl)amino]carbonyl}amino)-1-(3-methoxybenzyl)-1H-indole-2-carboxylate

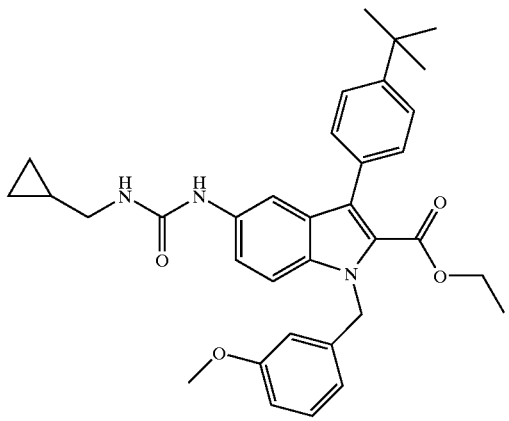

Pyridine (0.18 mL, 174 mg, 2.2 mmol) and phosgene (1.9 M in toluene, 0.66 mL, 1.2 mmol) were added to a cooled (0° C.) and stirred solution of ethyl 5-amino-3-(4-tert-butylphenyl)-1-(3-methoxybenzyl)-1H-indole-2-carboxylate (Example 160, 500 mg, 1.1 mmol) in dichloromethane (10 mL). The reaction was warmed to rt and stirred for 3 h. The solution was concentrated in vacuo leaving crude Example 172. A portion (260 mg, 0.54 mmol) of the intermediate was dissolved in dichloromethane (10 mL) and then (cyclopropylmethyl)amine (0.13 mL, 108 mg, 1.5 mmol) was added. The reaction was stirred at rt for 16 h and then diluted with dichloromethane (100 mL). The solution was washed with water and brine, dried over anhydrous magnesium sulfate, and concentrated in vacuo. Flash chromatography of the residue over silica gel using 3:1 hexane/ethyl acetate gave 160 mg (54%) of the desired product. The product had: $^1$H NMR (300 MHz, acetone-$D_6$) δ 8.08 (d, 1 H), 7.09–7.45 (m, 7 H), 6.60–6.78 (m, 3 H), 6.33 (dd, 1 H), 5.76 (s, 2 H), 3.91 (q, 2 H), 3.68 (s, 3 H), 1.32 (s, 3 H), 0.87–0.96 (m, 1 H), 0.72 (t, 3 H), 0.31–0.41 (m, 2 H), 0.11–0.21 (m, 2 H).

EXAMPLE 173

Ethyl 3-{3-[(cyclopropylamino)carbonylamino]phenyl}-1-[(3-methoxyphenyl)methyl]indole-2-carboxylate

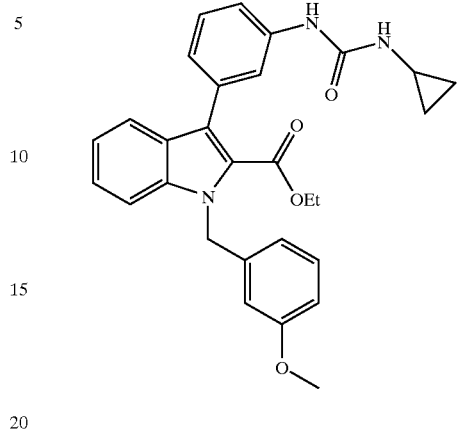

To a 25 mL round-bottomed flask at rt was charged with ethyl 3-(3-aminophenyl)-1-[(3-methoxyphenyl)methyl]indole-2-carboxylate (Example 93, 222 mg, 0.55 mmol) and dichloromethane (1.5 mL). The resulting solution was cooled to 0° C., to which was added pyridine (0.09 mL, 1.1 mmol) and phosgene (20% in toluene, 0.35 mL, 0.66 mmol). The mixture was left stirred at 0° C. for 2 hours and rt for 2 hours before it was concentrated in vacuo. The residue was dissolved in dichloromethane (2 mL) and cyclopropylamine (0.11 mL, 1.65 mmol) was added. The mixture was left at rt for 15 minutes before it was mixed with hydrochloric acid (1 N) and extracted with dichloromethane (10 mL). The organic layer was washed with aqueous sodium bicarbonate, brine, and dried over anhydrous magnesium sulfate. The crude mixture was purified with silica gel flash chromatography using hexane/ethyl acetate (3/1) as the eluant to give ethyl 3-{3-[(cyclopropylamino)carbonylamino]phenyl}-1-[(3-methoxyphenyl)methyl]indole-2-carboxylate (140 mg, 53%): MS (electrospray, MH$^+$) calcd for $C_{29}H_{30}N_3O_4$ 484.2, found 484.1; $^1$H NMR (DMSO-d$^6$) δ 8.36 (s, 1H), 7.52–7.64 (m, 3H), 7.15–7.38 (m, 5H) 6.95 (ddd, J=6.9 Hz, 1H), 6.79 (dd, J=8.1, 1.9 Hz, 1H), 6.65 (dd, 1H), 6.59 (d, J=7.6 Hz, 1H), 6.38 (d, J=2.6 Hz, 1H), 5.77 (s, 2H), 4.10 (q, J=7.1 Hz), 3.68 (s, 3H), 2.50–2.60 (m, 1H), 0.97 (t, J=7.1 Hz), 0.60–0.64 (m, 2H), 0.39–0.41 (m. 2H).

The following compounds were prepared according to the methods of Examples 172–173:

| Ex. No. | Structure | Yield [%] | MS [M + H⁺] | Rf | mp [° C.] |
|---|---|---|---|---|---|
| 174 | 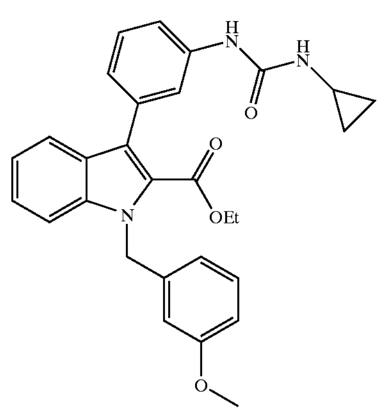 | 53 | 484.1 | | |

-continued

| Ex. No. | Structure | Yield [%] | MS [M + H⁺] | Rf | mp [° C.] |
|---|---|---|---|---|---|
| 175 | 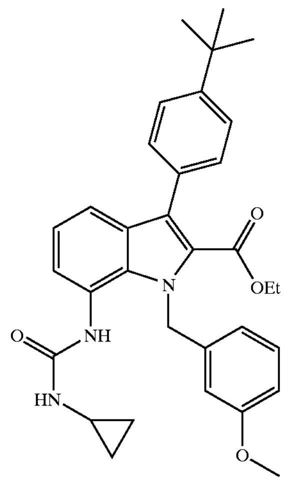 | 21 | | | |

EXAMPLE 176

Methyl 3-(4-tert-butylphenyl)-5-[(cyclopropylcarbonyl)(methyl)amino]-1-(3-methoxybenzyl)-1H-indole-2-carboxylate

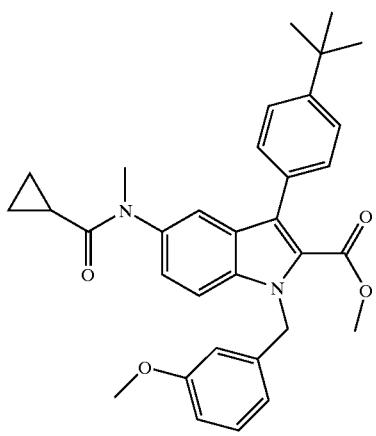

Sodium hydride (192 mg, 0.800 mmol) was added to a cooled (0° C.) and stirred solution of 3-(4-tert-butylphenyl)-5-[(cyclopropylcarbonyl)amino]-1-(3-methoxybenzyl)-1H-indole-2-carboxylic acid (Example 167, 94.5 mg, 0.190 mmol) in tetrahydrofuran (5 mL). The cold bath was removed and stirring was continued for 1 h. Dimethylsulfate (0.75 mL, 101 mg, 0.80 mmol) was added and the reaction was stirred for an additional 2 h. The reaction was quenched with water (50 mL) and then extracted with ethyl acetate (3×30 mL). The combined organic extracts were washed with brine, dried over anhydrous magnesium sulfate and concentrated in vacuo. Flash chromatography of the residue over silica gel using 40% ethyl acetate/hexane afforded 894 mg (90%) of the desired product. The product had: ¹H NMR (300 MHz, CDCl₃) δ 7.38–7.50 (m, 3 H), 7.28–7.36 (m, 3 H), 7.11–7.24 (m, 2 H), 6.59–6.76 (m, 3 H), 5.70 (s, 2 H), 3.90 (s, 3 H), 3.69 (s, 3 H) 3.21 (s, 3 H), 1.34 (s, 9 H), 1.15–1.35 (m, 1 H), 0.87–0.97 (m, 2 H), 0.48–0.58 (m, 2 H); mass spectroscopy gave MH⁺=525.3 (calc'd exact mass for $C_{33}H_{36}N_2O_4$=524.27).

EXAMPLE 177

Methyl 3-[4-(N-cyclopentyl-N-methylcarbamoyl)phenyl]-1-[(3-methoxyphenyl)methyl]indole-2-carboxylate

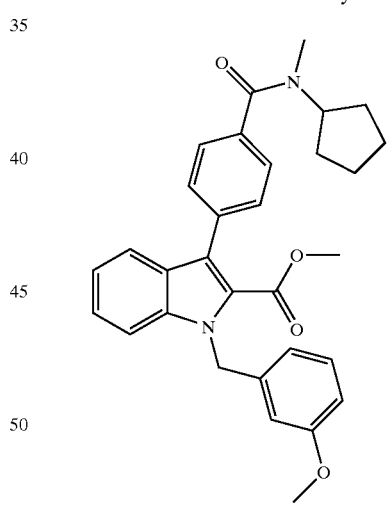

To a solution of 3-[4-(N-cyclopentylcarbamoyl)phenyl]-1-[(3-methoxyphenyl)-methyl]indole-2-carboxylic acid (Example 96, 260 mg, 0.53 mmol) in tetrahydrofuran (5 mL), was added a 1.0 M solution of potassium tert-butoxide in tetrahydrofuran (0.70 mL, 0.70 mmol) and the resulting orange solution was stirred for 5 minutes. Iodomethane (0.10 mL, 1.6 mmol) was added and the reaction was allowed to stir at RT for 18 h. The reaction was quenched with 10% aqueous citric acid and the resulting mixture was extracted with ethyl acetate. The combined organic layers were dried over anhydrous magnesium sulfate, adsorbed onto silica, and purified by flash chromatography on silica in 2:1 hexane:ethyl acetate to yield 113 mg (43%) of a clear oil. ¹H NMR (300 MHz, DMSO-d₆) δ 7.67–7.67 (m, 1H), 7.59–7.53 (m, 1H), 7.51–7.40 (m, 4H), 7.40–7.33 (m, 1H, 7.22–7.14 (m, 2H), 6.82–6.776 (m, 1H), 6.67–6.64 (m, 1H), 6.62–6.57 (m, 1H), 5.78 (s, 2H), 3.67 (s, 3H), 3.61 (s, 3H), 2.86 (s, 3H), 1.83–1.32 (m, 9H); mass spectroscopy gave MH⁺=511.3 (calc'd exact mass for $C_{32}H_{34}N_2O_4$=510.25); TLF $R_f$=0.40 (1:1 hexane:ethyl acetate).

The following compounds were prepared according to the method of Example 177:

| Ex. No. | Structure | Yield [%] | MS [M + H⁺] | Rf | mp [° C.] |
|---|---|---|---|---|---|
| 178 | 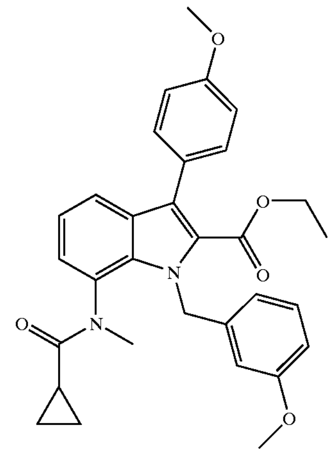 | crude | 513.2 | 0.28 (Hexane/ethyl acetate 2:1) | |
| 179 | 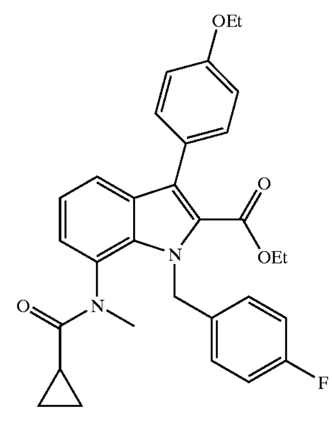 | 87 | | | |
| 180 | 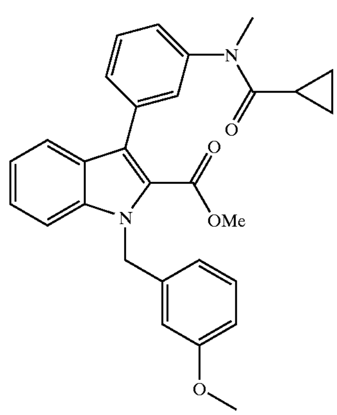 | 89 | | | 469 |

| Ex. No. | Structure | Yield [%] | MS [M + H+] | Rf | mp [° C.] |
|---|---|---|---|---|---|
| 181 | 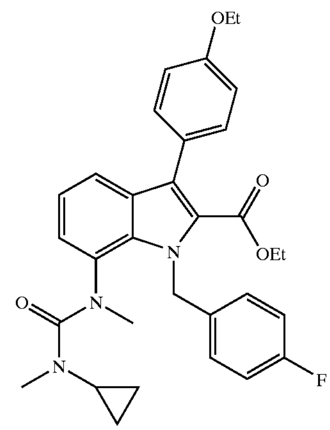 | 87 | | | |

EXAMPLE 182

Ethyl 3-(cyclopropylidenemethyl)-1-[3-(trifluoromethyl)benzyl]-1H-indole-2-carboxylate

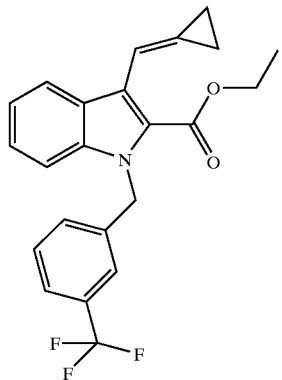

Sodium hydride (60% dispersion in mineral oil, 128 mg, 3.20 mmol) was suspended in anhydrous tetrahydrofuran (10 mL) and cooled to 0° C. Triphenylcyclopropylphosphonium bromide (1.23 g, 3.20 mmol) was added as a solid all at once, and the mixture was allowed to stir at room temperature. Once gas evolution ceased, a tetrahydrofuran solution of ethyl 3-formyl-1-[3-(trifluoromethyl)benzyl]-1H-indole-2-carboxylate (Example 40, 1.0 g, 2.7 mmol) was added, the mixture was stirred for 15 hours, and the resulting mixture was partitioned between water and ethyl acetate. Layers were separated, and the aqueous layer was extracted with ethyl acetate (2×). The combined organic layers were dried over anhydrous magnesium sulfate and concentrated. The resulting crude oil was purified by flash chromatography on silica gel eluted with 5% ethyl acetate/hexane. The title compound was collected as a bright yellow oil (403 mg, 38%). The product had: $^1$H NMR (300 MHz, CDCl$_3$) δ 8.04 (d, 1 H), 7.53 (s, 1 H), 7.41–7.38 (m, 2 H), 7.29–7.20 (m, 3 H), 7.15–7.12 (m, 1 H), 7.05 (d, 1 H), 5.72 (s, 2 H), 4.27 (q, 2 H), 1.50–1.45 (m, 2 H), 1.25 (t, 3 H), 0.83–0.76 (m, 2 H); mass spectroscopy gave MH$^+$=400.2 (calc'd exact mass for C$_{23}$H$_{20}$F$_3$NO$_2$=399.14).

The following compounds were prepared according to the method of Example 182:

| Ex. No. | Structure | Yield [%] | MS [M + H+] | Rf | mp [° C.] |
|---|---|---|---|---|---|
| 183 | 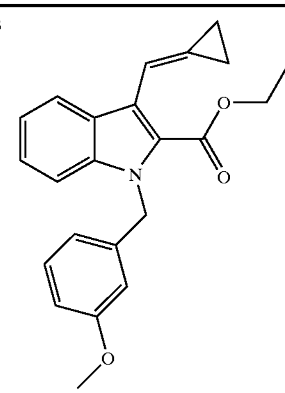 | 43 | 362 | | |

EXAMPLE 184

Ethyl 3-(4-tert-butylphenyl)-5-cyclopentyl-1-(3-methoxybenzyl)-1H-indole-2-carboxylate

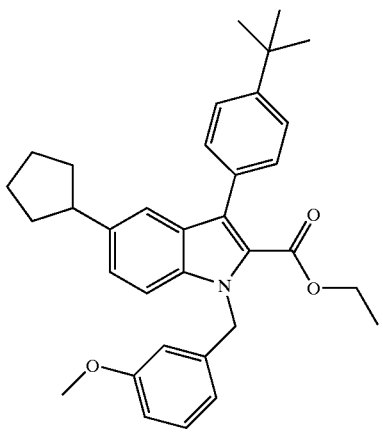

A solution of ethyl 5-(1-cyclopenten-2-yl)-3-[3-(cyclopropylmethoxy)phenyl]-1-(3-methoxybenzyl)-1H-indole-2-carboxylate (Example 128, 225 mg, 0.44 mmol) in ethyl acetate (3 mL) and ETOH (3 mL) was added to a slurry of 10% palladium on charcoal (100 mg) in ethyl acetate (2 mL) and EtOH (2 mL). The reaction was placed under hydrogen (1 atm) and stirred for 16 h. The mixture was filtered through a pad of Celite using ethyl acetate to rinse. Evaporation of the filtrate gave 210 mg (93%) of the product. The product had: $^1$H NMR (300 MHz, acetone-D$_6$) δ 7.37–7.53 (m, 6 H), 7.28 (dd, 1 H), 7.19 (dd, 1 H), 6.67–6.82 (m, 3 H), 5.83 (s, 3 H), 4.08 (q, 2 H), 3.75 (s, 3 H), 3.06 (p, 1 H), 1.99–2.06 (m, 2 H), 1.47–1.83 (m, 6 H), 1.40 (s, 9 H), 0.98 (t, 3 H).

EXAMPLE 185

Ethyl 3-(cyclopropylmethyl)-1-[3-(trifluoromethyl)benzyl]-1H-indole-2-carboxylate

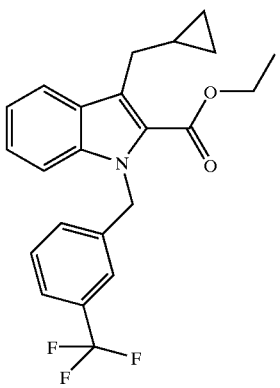

Ethyl 3-(cyclopropylidenemethyl)-1-[3-(trifluoromethyl)benzyl]-1H-indole-2-carboxylate (Example 182, 140 mg, 0.351 mmol) was stirred over Lindlar catalyst (28 mg) in ethanol (15 mL) under 1 atmosphere of hydrogen for 1 hour. The mixture was filtered through Celite with an excess of ethanol. The filtrate was concentrated, and the resulting crude oil was purified by flash chromatography on silica gel eluted with 20% Et$_2$O/hexane. The title compound was collected as a yellow oil (95 mg, 67%). The product had: $^1$H NMR (300 MHz, acetone-d$_6$) δ 7.78 (d, 1 H), 7.56–7.45 (m, 4 H), 7.34–7.32 (m, 1 H), 7.28–7.26 (m, 1 H), 7.16–7.13 (m, 1 H), 5.93 (s, 2 H), 4.32 (q, 2 H), 3.08 (d, 2 H), 1.31 (t, 3 H), 1.13–1.15 (m, 1 H), 0.42–0.38 (m, 2 H), 0.29–0.26 (m, 2 H).

The following compounds were prepared according to the methods of Examples 184–185:

| Ex. No. | Structure | Yield [%] | MS [M + H$^+$] | Rf | mp [° C.] |
|---|---|---|---|---|---|
| 186 | 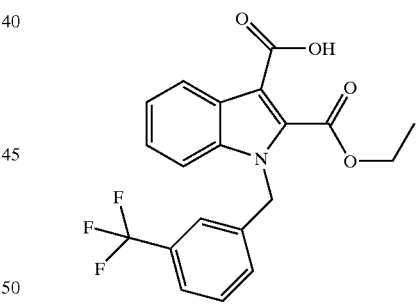 | 55 | | | |

EXAMPLE 187

Ethyl-1-(3-trifluoromethylbenzyl)-1H-indole-2-carboxylate-3-carboxylate

To a solution of ethyl-1-(3-trifluoromethylbenzyl)-1H-indole-2-carboxylate-3-carboxaldehyde (Example 40, 6.0 g, 15.9 mmol) in pH 3.5 phosphate buffer (48 mL) and t-butanol (90 mL) was added 2-methyl-2-butene (30 mL) and sodium chlorate (2.1 g, 1.5 eq.). The reaction was stirred at room temperature for 16 hours and then extracted with dichloromethane (3×200 mL). The combined organic extracts were washed with brine, dried over anhydrous magnesium sulfate, and concentrated in vacuo. Flash chromatography of the residue over silica afforded the desired product as a white solid. The product had: $^1$H NMR (300 MHz, dmso-D$_6$) 8.03 (d, 1 H), 7.5–7.65 (m, 4 H), 7.2–7.39 (m, 3 H), 5.61 (s, 2 H), 4.26 (q, 2 H), 1.15 (t, 3 H).

EXAMPLE 189

Ethyl-1-(3-trifluoromethylbenzyl)-1H-indole-2-carboxylate-3-carbonyl chloride

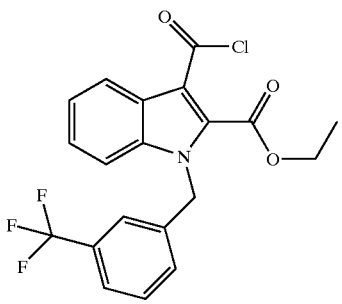

Ethyl-1-(3-trifluoromethylbenzyl)-1H-indole-2-carboxylate-3-carboxylic acid (Example 187, 100 mg, 0.25 mmol) was taken up in dichloromethane (10 mL) with a catalytic amount of DMF, and the mixture was cooled (0° C.) Oxalyl chloride (0.044 mL, 2 eq.) was added, and the reaction was stirred for 1 hour. The mixture was concentrated in vacuo and used directly with no further purification.

EXAMPLE 191
Ethyl-1-(3-trifluoromethylbenzyl)-1H-indole-2-carboxylate-3-carboxylic acid, morpho-line amide

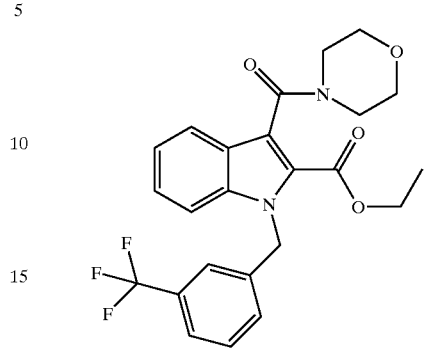

Ethyl-1-(3-trifluoromethylbenzyl)-1H-indole-2-carboxylate-3-carbonyl chloride (Example 189, 0.16 g, 0.4 mmol) was taken up in excess morpholine (0.3 mL) at room temperature. The reaction was stirred for 72 hours, quenched with water, and extracted with diethyl ether (2×25 mL.) The combined organic extracts were dried over sodium sulfate and purified by flash chromatography to yield 0.268 mg (91%) of the desired product. The product had: $^1$H NMR (300 MHz, dmso-$D_6$) δ 7.42–7.75 (m, 5 H), 7.4 (t, 1 H), 7.22 (m, 2 H), 5.95 (s, 2 H), 4.21 (q, 2 H), 3.0–3.8 (broad m, 8 H), 1.1 (t, 3 H)

The following compounds were prepared according to the method of Example 191:

| Ex. No. | Structure | Yield [%] | MS [M + H$^+$] | Rf | mp [° C.] |
|---|---|---|---|---|---|
| 192 | 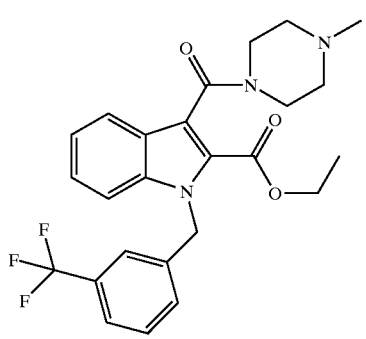 | 86 | | | |

EXAMPLE 193

Ethyl-3-benzoxazol-2-yl-1-(3-trifluoromethylbenzyl)-1H-indole-2-carboxylate

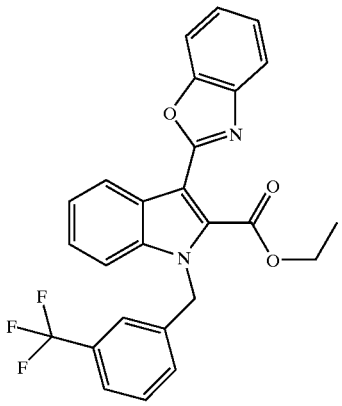

Ethyl-1-(3-trifluoromethylbenzyl)-1H-indole-2-carboxylate-3-carbonyl chloride (Example 189) was prepared as above from the corresponding acid (600 mg, 1.53 mmol.) The crude material was taken up in dichloromethane (50 mL) and cooled to 0° C. Triethylamine (0.85 mL, 4 eq.) was added, followed by 2-aminophenol (0.5 g, 3 eq.), and the reaction mixture was allowed to warm to room temperature. The mixture was quenched with 1 N HCl, and the organic layers were separated and concentrated in vacuo. The crude intermediate was taken up in toluene (20 mL) with p-toluenesulfonic acid (0.73 g) and heated to reflux for 3 hours. The reaction was cooled to room temperature, quenched with water, and extracted with ethyl acetate (3×75 mL.) The organic layers were dried over sodium sulfate and purified by flash chromatography over silica gel to give the desired product (260 mg, 37%.) The product had: $^1$H NMR (300 MHz, dmso-$D_6$) δ 8.3 (d, 1 H), 7.35–7.9 (m, 11 H), 5.81 (s, 2 H), 4.37 (q, 2 H), 1.16 (t, 3 H) Mass spectroscopy gave MH$^+$=437.2 (calc'd exact mass for $C_{24}H_{15}F_3N_2O_3$=436.1).

EXAMPLE 194

Ethyl-3-benzthiazol-2-yl-1-(3-cyclopropylmethoxybenzyl)-1H-indole-2-carboxylate

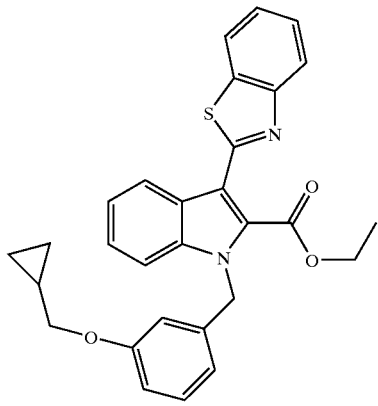

Ethyl-3-benzthiazol-2-yl-1-(3-cyclopropylmethoxybenzyl)-1H-indole-2-carboxaldehyde (Example 41, 0.42 g, 1.1 mmol) was taken up in EtOH (30 mL) at room temperature. 2-aminothiophenol (0.15 g, 1.05 eq.) was added, followed by conc. HCl (0.5 mL), and the reaction mixture was heated to reflux for 24 hours. The mixture was cooled to room temperature, quenched with water and extracted with diethyl ether (3×50 mL.) The organic layers were separated, dried over sodium sulfate, and concentrated in vacuo to give the desired product (0.38 g, 71%) which was taken to the hydrolysis step without further purification.

The following compounds were prepared according to the method of Example 194:

| Ex. No. | Structure | Yield [%] | MS [M + H$^+$] | Rf | mp [° C.] |
|---|---|---|---|---|---|
| 195 | 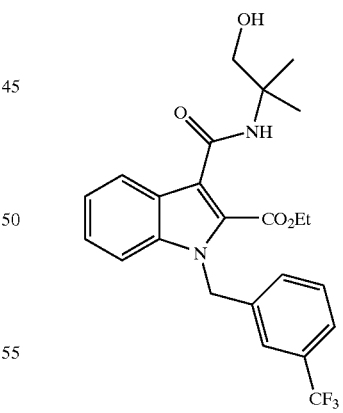 | crude | | | |

EXAMPLE 196

Ethyl 3-{[(2-hydroxy-1,1-dimethylethyl)amino]carbonyl}-1-[3-(trifluoromethyl)benzyl]-1H-indole-2-carboxylate To a 0° C. solution of Example 189 (545 mg, 1.28 mmol) in dichloromethane (8 mL) was added 2-hydroxy-1,1-dimethyl-ethylamine (285 mg, 3.2 mmol). Triethyl amine (0.7 mL, 5.12 mmol) was added in one portion. The mixture was stirred for 15 min. and then allowed to warm to r.t. over 20 min. The reaction was quenched with 1N HCl and the resulting mixture was washed with 1N HCl (2×). The organic layer was dried over anhydrous sodium sulfate, concentrated, and filtered through a short plug of silica gel (elution with 8:92 methanol:dichloromethane). Concentration of the filtrate provide 440 mg (74%) of Example 196. LRMS (+esi) obs'd: 463.1; calc'd 462.2.

EXAMPLE 197

Ethyl 3-(4,4-dimethyl-4,5-dihydro-1,3-oxazol-2-yl)-1-[3-(trifluoromethyl)benzyl)-1H-indole-2-carboxylate

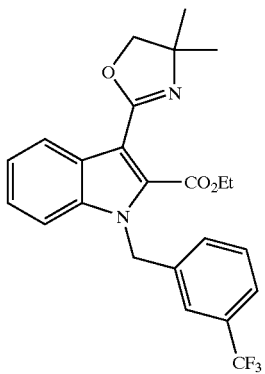

A solution of Example 196 (440 mg, 0.95 mmol) and p-toluenesulfonic acid monohydrate (170 mg, 0.89 mmol) in toluene (6 mL) was refluxed for 1.5 h. The mixture was cooled and washed with water. The organic layer was dried over anhydrous sodium sulfate and concentrated. The remaining material was purified by flash chromatography (silica gel, 10:90 methanol:dichloromethane) to provide 100 mg (24%) of Example 197, which was used in the next step without purification. Rf=0.95 (1/9 methanol/dichloromethane); LRMS (+esi) obs'd: 445.2; calc'd 444.2.

EXAMPLE 198

Ethyl 3-({[1-hydroxymethyl)cyclopentyl]amino}carbonyl)-1-[3-(trifluoromethyl)benzyl]-1H-indole-2-carboxylate

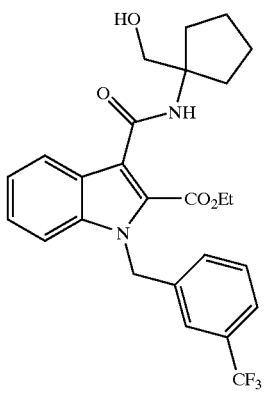

To a 0° C. solution of acid chloride Example 189 (434 mg, 1.02 mmol) in dichloromethane (7 mL) was added cyclo-leucinol (295 mg, 2.55 mmol). Triethyl amine (0.57 mL, 4.08 mmol) was added in one portion. The mixture was stirred for 1 h and was then allowed to warm to r.t. over 40 min. The reaction was diluted with water and the organic layer was washed with 1N HCl, dried over anhydrous sodium sulfate and concentrated to afford 498 mg of Example 198 which was used without further purification. LRMS (+esi) obs'd: 489.1; calc'd 488.2.

EXAMPLE 199

Ethyl 3-(3-oxa-1-azaspiro[4.4]non-1-en-2-yl)-1-[3-(trifluoromethyl)benzyl]-1H-indole-2-carboxylate

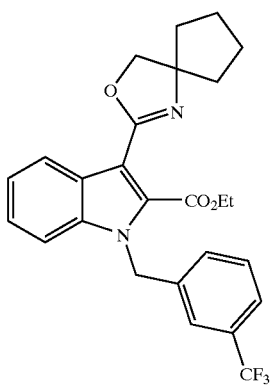

A solution of Example 198 (498 mg, 1.02 mmol) and p-toluenesulfonic acid monohydrate (210 mg, 1.1 mmol) in toluene (7 mL) was refluxed for 2 h. The mixture was cooled and washed with water. The organic layer was dried over anhydrous sodium sulfate and concentrated. Flash chromatography (5:95 methanol:dichloromethane) provided impure Example 199. Rf=0.96 (6/94 methanol/dichloromethane); LRMS (+esi) obs'd: 471.2; calc'd 470.2.

EXAMPLE 200 and 201

Ethyl 3-(4-t-butylphenyl)-5-(cyclopropyl)carbonyl-1H-indole-2-carboxylate

EXAMPLE 200and

Ethyl 3-(4-t-butylphenyl)-7-(cyclopropyl)carbonyl-1H-indole-2-carboxylate

EXAMPLE 201

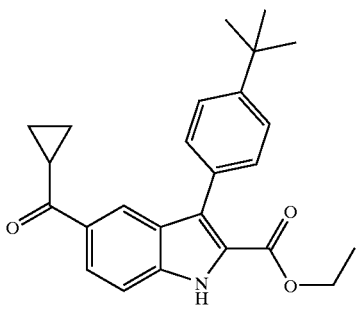

-continued

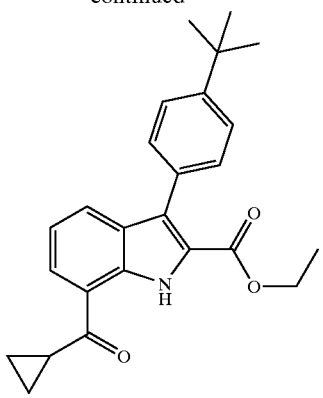

Aluminum chloride (4.07 g, 1.5 eq.) was suspended in dichloromethane (70 mL) and cooled to 0° C. Cyclopropyl carbonyl chloride (3.2 g, 1.5 eq.) was added slowly, and the mixture was stirred for 15 minutes. A solution of ethyl 3-(4-t-butylphenyl)-1H-indole-2-carboxylate (Example 224, 5.16 g, 20.4 mmol) in dichloromethane (20 mL) was added dropwise. The reaction was allowed to warm to room temperature, and was then heated to reflux for 24 hours, cooled to room temperature, quenched with water and diluted with diethyl ether. The organic layers were washed with water and 1N HCl and dried over sodium sulfate, then purified by flash chromatography over silica to give 5.25 g of the 5-acylated Example 200, which had $^1$H NMR (300 MHz, CDCl$_3$) 9.35 (bs, 1H), 8.4 (s, 1 H), 8.03 (d, 1 H), 7.45 (m, 5 H), 4.35 (q, 2 H), 2.72 (m, 1 H), 1.4 (s, 9 H), 0.9–1.4 (m, 9 H) and 1.27 g of the 7-acylated Example 201, which had: $^1$H NMR (300 MHz, CDCl$_3$) 10.9 (bs, 1H), 8.17 (d, 1 H), 7.92 (d, 1 H), 7.45 (m, 5 H), 4.35 (q, 2 H), 2.86 (m, 1 H), 1.4 (s, 9 H), 1.1–1.4 (m, 9 H).

The following compounds were prepared according to the method of Example 200:

EXAMPLE 203

Ethyl 3-(4-methyoxybenzoyl)-1H-indole-2-carboxylate (53354-02)

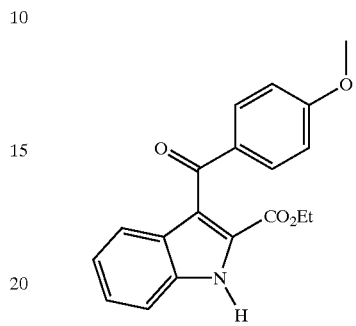

A 0° C. suspension/solution of AlCl$_3$ (693 mg, 5.2 mmol) and 4-methoxybenzyl acid chloride (887 mg, 5.2 mmol) in 1,2 dichloroethane (10 mL) was stirred for 5 min. A solution of indole (0.5 gm, 2.6 mmol) in 1,2-dichloroethane (10 mL) was added dropwise and upon complete addition the mixture was warmed to reflux for 1 h. The mixture was cooled and poured over ice. The aq. layer was extracted with ethyl acetate. The extracts were washed with sat. aq. Na$_2$CO$_3$, dried and concentrated. Purification of the remaining oil by flash chromatography (silica gel, elution with 5:5 ethyl acetate:hexane) afforded 481 mg (57%) of Example 203. Rf=0.48 (1/1 hexane/ethyl acetate); LRMS (+esi) obs'd: 324.1; calc'd 323.1.

| Ex. No. | Structure | Yield [%] | MS [M + H$^+$] | Rf | mp [° C.] |
|---|---|---|---|---|---|
| 202 | 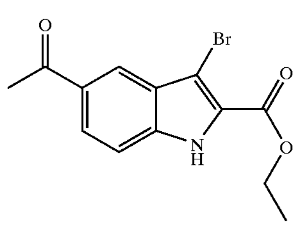 | 25 | | 0.25 (Hexane/ethyl acetate 4:1) | |

EXAMPLE 204

Ethyl 3-(cyclobutylcarbonyl)indole-2-carboxylate

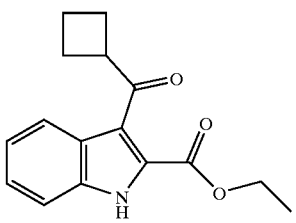

To a 50 mL reaction vial and stir bar was charged with 0.563 g of $FeCl_3$ (5.28 mmoles) followed by addition of 10 ml of dichloromethane. The heterogeneous solution was cooled to 0° C. followed by addition of a 10 mL dichloromethane solution of ethyl indole-2-carboxylate (0.5 g, 2.64 mmoles). The contents were maintained at 0 c for 0.5 hours then poured into 30 mL of ice water and neutralized with $NaHCO_3$ saturated solution. The contents were then extracted with 3×20 mL of dichloromethane and dried over $Na_2SO_4$ and concentrated in vacuo to yield 0.71 g (99.0%) of a white solid (Rf-0.10 in 10% ethyl acetate/hexane). The product had: $^1H$ NMR (300 MHz, acetone-$D_6$); δ 11.4 Hz (s, 1H), 7.93 Hz (dd, 1H), 7.54 Hz (dt, 1H), 7.34 Hz (td, 1H), 7.20 Hz (td, 1H), 4.43 Hz (q, 2H), 2.32 Hz (m, 1H), 2.17 Hz (m, 4H), 1.97 Hz (m, 2H), 1.40 Hz (t, 3H); mass spectroscopy gave $M^+$ of 272.2 (calc'd mass for $C_{16}H_{17}NO_3$ of 271.31).

EXAMPLE 205

Ethyl 3-(cyclobutylmethyl)indole-2-carboxylate

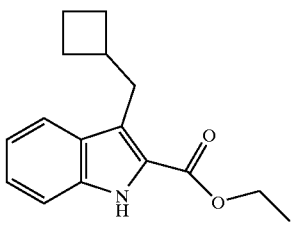

To a dry 50 mL round bottom flask and stir bar was charged with ethyl-3-(cyclobutylcarbonyl)indole-2-carboxylate (Example 204, 0.81 g, 3.0 mmol) followed by addition of TFA (5.6 mL). The contents were stirred and cooled to 0° C. followed by dropwise addition of triethylsilane (1.56 mL, 9.8 mmol) via syringe. The contents of the reaction were maintained at 0° C. for 20 minutes then heated to reflux for 3 hours. The reaction was cooled to room temperature followed by addition of water (20 mL) triturating a solid. The solid was filtered and washed 3×20 mL of water and air dried providing 0.76 g (99.0% yield) of a white solid. The product had a Rf of 0.38 10% ethyl acetate/hexane; $^1H$ NMR (300 MHz, acetone-$D_6$); 10.5 Hz (s, 1H), 7.71 Hz (dd, 1H), 7.46 Hz (dt, 1H) 7.26 Hz (td, 1H), 7.08 Hz (td, 1H) 4.37 Hz (q, 2H), 3.24 Hz (d, 2H), 2.74 Hz (m, 1H 1.93 Hz (m, 2H), 1.80 Hz (m, 4H), 1.39 Hz (t, 3H) mass spectroscopy gave $M^-$ of 256.5 (calc'd mass for $C_{16}H_{19}NO_2$ of 257.33).

EXAMPLE 206

Ethyl (2E)-3-(2-hydroxy-6-nitrophenyl)prop-2-enoate

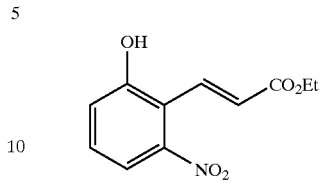

To a thick-walled vessel was charged with 2-bromo-3-nitrophenol (1.16 g, 5.32 mmol), ethyl acrylate (666 mg, 0.72 mmol), tri-(o-tolyl)phosphine (65 mg, 0.21 mmol), palladium acetate (12 mg, 0.05 mmol), and triethylamine(10 mL). The vessel was then sealed and the resulting mixture was heated to 100° C. overnight. In the morning, the vessel was cooled to rt and the mixture was poured into water. The mixture was acidified with hydrochloric acid and extracted with ethyl acetate (2×50 mL). The combined organic layer was washed with water, brine and dried over anhydrous sodium sulfate. The residue was purified with silica gel flash chromatography by using hexane/ethyl acetate (2/1) as the eluant to give ethyl (2E)-3-(2-hydroxy-6-nitrophenyl)prop-2-enoate (883 mg, 70%): $R_f$0.16 (3/1 hexane/ethyl acetate); $^1H$ NMR ($CDCl_3$) δ 7.6(d, J=16.1 Hz, 1H), 7.05–7.23 (m, 3H), 6.71 (dd, J=16.1, 0.8 Hz, 1H), 4.18 (q, J=7.1 Hz, 2H), 1.26 (t, J=7.1 Hz, 2H).

EXAMPLE 207

Ethyl 4-(1,1,2,2-tetramethyl-1-silapropoxy)indole-2-carboxylate

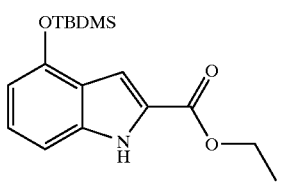

To a round-bottomed flask at rt was charged with ethyl (2E)-3-(2-hydroxy-6-nitrophenyl)prop-2-enoate (Example 206, 260 mg, 1.10 mmol), N,N-dimethylformamide (2 mL), t-butyldimethylsilyl chloride (198 mg, 1.32 mmol), and imidazole (150 mg, 2.20 mmol). The resulting mixture was left stirring at rt for 2 hours before hydrochloric acid was added and the mixture was extracted with diethyl ether (2×20 mL). The combined organic layer was washed with water, brine, and dried over anhydrous sodium sulfate. The concentrated residue was used without further purification. It was mixed with triethyl phosphite (920 mg, 5.50 mmol) and heated to 170° C. for 3 hours before it was cooled to rt and diluted with ethyl acetate. The mixture was washed with water, brine and dried over anhydrous sodium sulfate. The concentrated residue was purified with silica gel flash chromatography by using hexane/ethyl acetate (3/1) as the eluant to give ethyl 4-(1,1,2,2-tetramethyl-1-silapropoxy)indole-2- carboxylate as a white solid (224 mg, 64%): R$_f$ 0.57 (3/1 hexane/ethyl acetate); %): MS (MH$^+$) calcd for C$_{17}$H$_{26}$NO$_3$Si 320.2, found 320.2; $^1$H NMR (DMSO-d$_6$) δ 11.87 (br s, 1H), 6.99–7.15 (m, 3H), 6.47 (dd, J=7.3, 0.6 Hz, 1H), 4.33 (q, J=7.0 Hz, 2H), 1.33 (t, J=7.0 Hz, 3H), 1.01 (s, 9H), 0.22 (s, 6H).

EXAMPLE 208

Ethyl 3-bromo-4-(cyclopropylmethoxy)-1-[(3-methoxyphenyl)methyl]indole-2-carboxylate

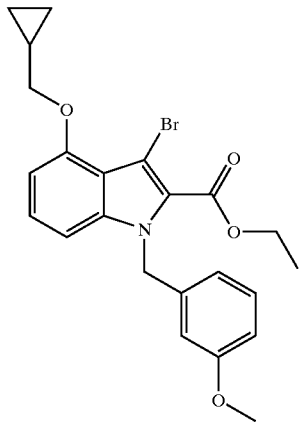

To a round-bottomed flask at rt was charged with ethyl 4-(1,1,2,2-tetramethyl-1-silapropoxy)indole-2-carboxylate (Example 18, 100 mg, 0.19 mmol), tetrabutylammonium fluoride (1M in tetrahydrofuran, 0.29 mL, 0.29 mmol), molecule sieves (3A, 30 mg), and tetrahydrofuran (1 mL). After 0.5 hours at rt, cyclopropylmethyl bromide (52 mg, 0.04 mL, 0.38 mol) was added to the reaction mixture. After 2 hours at rt, the mixture was diluted with water and extracted with ethyl acetate (2×20 mL). The combined organic layer was washed with water, brine and dried over anhydrous sodium sulfate. The concentrated residue was purified with silica gel flash chromatography by using hexane/ethyl acetate (3/1) as the eluant to give ethyl 3-bromo-4-(cyclopropylmethoxy)-1-[(3-methoxyphenyl)methyl]indole-2-carboxylate (90 mg, 100%). The product was used without further purification: MS (MH$^+$) calcd for C$_{23}$H$_{25}$BrNO$_4$ 458.1, found 458.5; $^1$H NMR (DMSO-d$_6$) δ 7.17–7.30 (m, 3H), 6.82 (dd, J=8.2,1.7 Hz, 1H), 6.66 (d, J=6.9 Hz, 1H), 6.59–6.61 (m, 1H), 6.51 (d, J=7.6 Hz, 1H), 5.72 (s, 2H), 4.33 (q, J=7.0 Hz, 2H), 4.02 (d, J=6.4 Hz, 2H), 3.71 (s, 3H), 1.30 (t, J=7.0 Hz, 3H), 0.85–0.95 (m, 1H), 0.59–0.66 (m, 2H), 0.45–0.50 (m, 2H).

EXAMPLE 209

Ethyl 6-(benzyloxy)-1-(phenylsulfonyl)indole-2-carboxylate

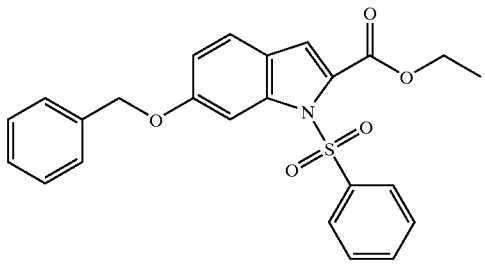

To a dry 100 ml round bottom flask and stir bar attached with a septa and purged with argon was charged with 7.5 mL of tetrahydrofuran and 0.33g (3.25 mmol) of diisopropylamine then cooled to −78° C. To the cooled solution of the amine n-BuLi (2.6M hexane, 1.20 mL, 3.1 mmol) was added dropwise via syringe and allowed to stir for 20 minutes at −78° C. At this time a 7.5 mL tetrahydrofuran solution of 6-(phenylmethoxy)-1-(phenylsulfonyl)indole (Example 57, 1.06 g, 2.95 mmol) was added to the LDA solution via cannula over a 10–15 minute period. The yellow solution was maintained at −78° C. for 1 hour then warmed to 0° C. for ½ hour followed by cooling to −78° C. Once cooled to −78° C. 0.96 g of ethyl chloroformate (8.85 mmol) was rapidly added via syringe. Upon complete addition the contents were warmed to room temperature and stirred for ½ hour then quenched with 20 mL of water then extracted with 3×20 mL of ethyl acetate. The organics were dried over Na$_2$SO$_4$ then concentrated in vacuo. The crude material was purified via SiO$_2$ column chromatography to yield 0.85 g (67% yield) of a white solid. The product had a Rf of 0.15 10% ethyl acetate/hexane; $^1$H NMR (300 MHz, Acetone-D$_6$); 7.90 Hz, (d, 2H), 7.66 Hz, (m, 2H), 7.54 Hz, (m, 4H), 7.40 Hz, (m, 2H), 7.21 Hz, (s, 1H), 7.03 Hz, (dd, 1H), 5.27 Hz, (s, 2H), 4.32 Hz, (q, 2H), 1.32 Hz, (t, 3H).

EXAMPLE 210

Ethyl 6-(benzoyloxy)-1-(phenylsulfonyl)indole carboxylate (dpd-53586-97)

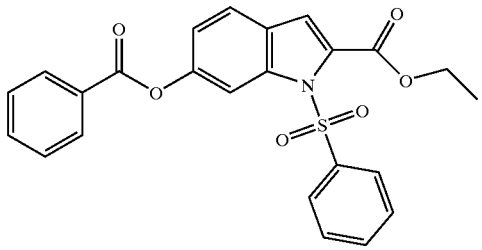

To a dry 100 mL round-bottom flask, stir bar and purged with argon was charged with 5.10 g of ethyl 6-hydroxy-1-(phenylsulfonyl)indole-2-carboxylate (Example 123, 15 mmol) followed by addition of 30 mL of anhydrous tetrahydrofuran and cooled to 0° C. To the rapidly stirring solution was added via syringe 15.2 g of triethylamine (150 mmol)

followed by slow addition of 3.15 g of benzoyl chloride (22.4 mmol) via syringe while maintaining the solution at 0° C. The reaction was warmed to rt and stirred for an additional hour. The reaction was then quenched with 15 mL of 3N HCl then extracted with 3×50 mL of ethyl acetate and dried over Na$_2$SO$_4$ then concentrated in vacuo. The crude material was purified via column chromatography to yield 4.7 g (70.1% yield) of a white solid. The product had a Rf of 0.33 20% ethyl acetate/hexane; $^1$H NMR (300 MHz, Acetone-D$_6$); 8.22 Hz, (d, 2H), 8.11 Hz, (m, 3H), 7.73 Hz, (m, 3H), 7.62 Hz, (t, 4H), 7.34 Hz, (s, 1H), 7.29 Hz, (dd, 1H).

EXAMPLE 211

Ethyl 6-(benzoyloxy)indole-2-carboxylate

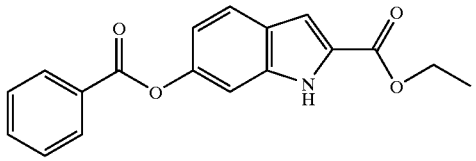

To a dry 100 mL and stir bar was charged with 4.70 g ethyl 6-(benzoyloxy)-1-(phenylsulfonyl)indole carboxylate (Example 210) and dissolved in 12.5 mL of anhydrous tetrahydrofuran then cooled to 0° C. To this rapidly stirring solution was added 35.0 mL 1.0 M tetrahydrofuran solution of potassium tert-butoxide dropwise via syringe. Upon complete addition the contents were warmed to room temperature and stirred an additional ½ hour then quenched with 10 mL of 3N HCl solution followed by addition of 30 mL of water. The reaction was extracted with 3×50 mL of ethyl acetate then dried over Na$_2$SO$_4$ and concentrated in vacuo. The crude material was purified via column chromatography to yield 3.28g (99.0% yield) of an off white solid. The product had a Rf of 0.42 20% ethyl acetate/hexane; $^1$H NMR (300 MHz, Acetone-D$_6$); 8.80 Hz, (s, 1H), 8.02 Hz, (dd, 1H), 7.95 Hz, (dd, 1H), 7.68 Hz, (dd, 1H), 7.58 Hz, (m, 2H), 7.46 Hz, (d, 2H), 7.21 Hz, (d, 1H), 6.87 Hz, (dd, 1H), 4.31 Hz (q, 2H), 1.31 Hz (t, 3H).

The following compounds were prepared according to the method of Example 211:

EXAMPLE 213

Ethyl 3-bromo-6-hydroxy-1-(4-methoxybenzyl)indole-2-carboxylate

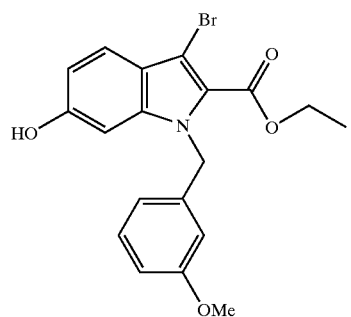

A 0.5 mL ethanol/ 0.5 mL HF solution of 44 mg ethyl 6-(benzoyloxy)-1-(4-methoxybenzyl)indole-2-carboxylate (Example 20, 0.1 mmol) was cooled to 0° C. in a 10 mL round-bottom flask and stir bar. To this stirring solution was added 0.3 mL of NaOEt 1.0 M in ethanol dropwise. The contents were then brought to reflux and maintained for 2 hours. The content were then cooled to room temperature and quenched with water then acidified with 1 N HCl. The reaction contents were then extracted with 3×5 mL of ethyl acetate, dried with Na$_2$SO$_4$ to yield 0.42 mg (95% yield) of an off white solid. The product had a Rf of 0.17 20% ethyl acetate/hexane; $^1$H NMR (300 MHz, Acetone-D$_6$); 8.68 Hz (s, 1H), 7.47 Hz (d, 1H), 7.19 Hz (t, 1H), 6.87 Hz (m, 2H), 6.79 Hz (dd, 1H), 6.67 Hz (s, 1H), 6.62 Hz (dt, 1H), 5.76 Hz (s, 2H), 4.35 Hz (q, 2H), 3.40 Hz (s, 3H), 1.37 Hz (t, 3H).

| Ex. No. | Structure | Yield [%] | MS [M + H$^+$] | Rf | mp [° C.] |
|---|---|---|---|---|---|
| 212 | 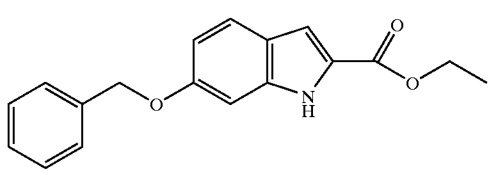 | 28 | | 0.41 (Hexane/ ethyl acetate 4:1) | |

EXAMPLE 214

Ethyl 3-bromo-6-(cyclopropylmethoxy)-1-(3-methoxybenzyl)indole-2-carboxylate

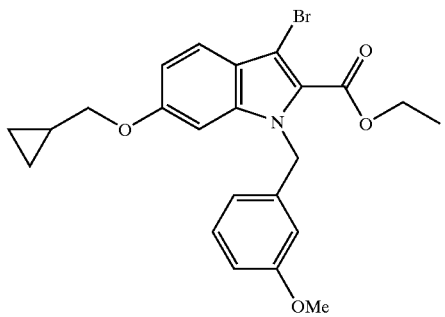

To a dry 5 mL round-bottom flask and stir bar was charged with 3.0 mg of NaH (0.12 mmol) followed by addition of 0.2 mL of DMF and cooled to 0° C. To the heterogeneous solution was added a 0.3 ml 42 mg DMF solution of ethyl 3-bromo-6-hydroxy-1-(4-methoxybenzyl)indole-2-carboxylate (Example 213, 0.1 mmol). The solution was maintained at 0° C. for 20 minutes after which bromomethyl cyclopropane was added via syringe and the reaction contents were warmed to rt. and stirred overnight. The reaction was quenched with water then acidified followed by extraction with ethyl acetate and concentration in vacuo to yield 30.0 mg (61.05 yield) of an off white solid. The product had a Rf of 0.58 20% ethyl acetate/hexane; mass spectroscopy gave M⁺ of 459.6 (calc'd exact mass for $C_{23}H_{24}BrNO_4$= 458.34)

EXAMPLE 215

Ethyl-3-(4-t-butylphenyl)-7-cyclopropylmethyl-1-(3-methoxybenzyl)-1H-indole-2-carboxylate

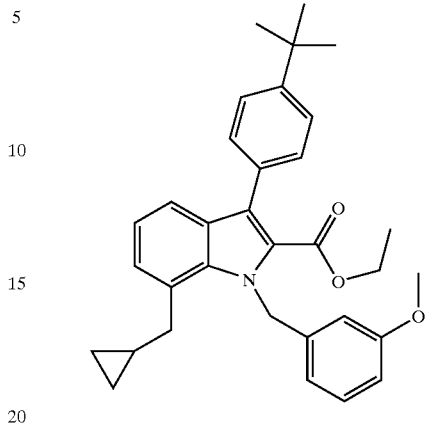

Aluminum chloride (0.24 g, 2 eq.) was suspended in dichloromethane (20 mL) and cooled to 0° C. Borane-t-butylamine complex (0.14 g, 1.8 eq.) was added slowly, and the mixture was stirred for 30 minutes. A solution of ethyl-3-(4-t-butylphenyl)-7-(cyclopropyl)carbonyl-1-(3-methoxybenzyl)-1H-indole-2-carboxylate (Example 201, 0.405 g, 0.9 mmol.) in dichloromethane (5 mL) was added, and the reaction was stirred for two hours. The mixture was quenched with water and diluted with dichloromethane. The organic layer was washed with 1N HCl and saturated sodium bicarbonate, dried over sodium sulfate, then purified by flash chromatography over silica to give 0.26 g (62%.) The desired product had: ¹H NMR (300 MHz, CDCl₃) 7.21–7.4 (m, 5 H), 7.11 (d, 1 H), 7.02 (t, 1 H), 6.95 (t, 1 H), 6.59 (d, 1H), 6.35 (m, 2 H), 5.9 (s, 2 H), 3.9 (q, 2 H), 3.58 (s, 3 H), 2.75 (d, 2 H), 1.26 (s, 9 H), 0.85 (t, 3 H), 0.4 (m, 2 H), 0.02 (m, 2H).

The following compounds were prepared according to the method of Example 215:

| Ex. No. | Structure | Yield [%] | MS [M + H⁺] | Rf | mp [° C.] |
|---------|-----------|-----------|-------------|-----|-----------|
| 216 | 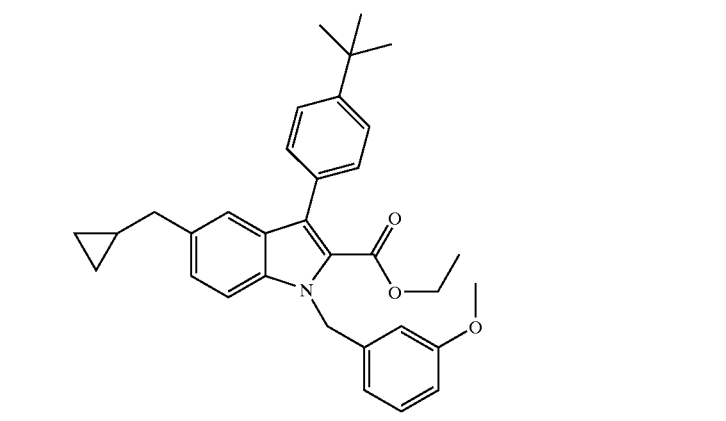 | crude | | | |

EXAMPLE 217

(3-(4-Methoxyphenyl)-1-{[3-(trifluoromethyl)phenyl]methyl}indol-2-yl)methan-1-ol

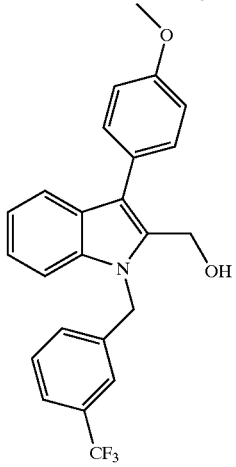

To a stirred solution of ethyl 3-(4-methoxyphenyl)-1-{[3-(trifluoromethyl)phenyl]-methyl}indole-2-carboxylate, prepared by the method described in WO94/14434 (1.20 g, 2.65 mmol), in tetrahydrofuran was added a 2.0 M solution of LiBH4 in tetrahydrofuran (2.65 mL, 5.29 mmol). The resulting mixture was heated to reflux for 18 h. The reaction was cooled to RT and then to 0° C. A 1.0 M solution of LiAlH4 in tetrahydrofuran (4 mL, 4 mmol) was added and the reaction stirred another 2 h. The reaction was quenched by the addition of water then 1.0 M HCl in water. The resulting mixture was extracted with ethyl acetate. The combined organic layers were dried over anhydrous magnesium sulfate and concentrated to a residue. Flash chromatography of the residue on silica in a 2:1 to 1:2 hexane:ethyl acetate gradient yielded 650 mg (60%) of a white solid. $^1$H NMR (300 MHz, DMSO-d$_6$) δ 7.65–7.46 (m, 6H), 7.39–7.34 (m, 1H), 7.32–7.25 (m, 1H), 7.17–7.02 (m, 4H), 5.68 (s, 2H), 5.40 (s, 2H), 4.59 (s, 2H), 3.81 (s, 3H) ppm; $R_f$=0.41 (2:1 hexane:ethyl acetate (v/v)).

EXAMPLE 218

3-(4-Methoxyphenyl)-1-{[3-(trifluoromethyl)phenyl]methyl}indole-2-carbaldehyde

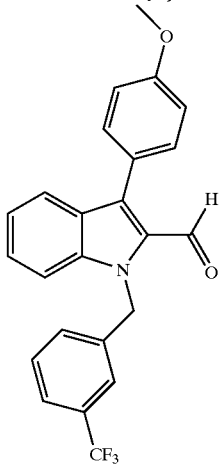

To a solution of (3-(4-methoxyphenyl)-1-{[3-(trifluoromethyl)phenyl]methyl}indol-2-yl)methan-1-ol (Example 217, 600 mg, 1.45 mmol) in dichloromethane (20 mL) was added Dess-Martin Periodinane (1.2 g, 2.9 mmol) and the resulting yellow solution was stirred for 30 min at RT. The reaction was quenched by the addition of saturated aqueous sodium bicarbonate (10 mL) and saturated aqueous sodium thiosulfate (10 mL). The resulting mixture was extracted with ethyl acetate and the combined organic layers were dried over anhydrous magnesium sulfate and concentrated to an orange solid. The solid was washed with Et2O and collected by filtration to yield 257 mg (45%) of a pale yellow solid. $R_f$=0.66 (4:1 hexane:ethyl acetate (v/v)).

EXAMPLE 219

2,2,2-Trifluoro-1-(3-(4-methoxyphenyl)-1-{[3-(trifluoromethyl)phenyl]methyl}indol-2-yl)ethan-1-ol

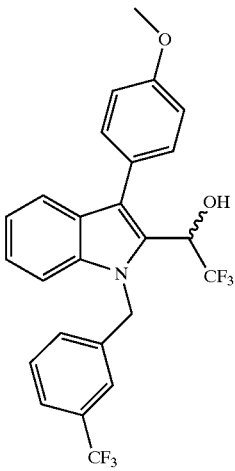

To a solution of 3-(4-methoxyphenyl)-1-{[3-(trifluoromethyl)phenyl]methyl}indole-2-carbaldehyde (Example 218, 200 mg, 0.49 mmol) in tetrahydrofuran (5 mL) was added a 0.5 M solution of TMSCF3 in tetrahydrofuran (4.9 mL, 2.4 mmol). The resulting solution was cooled to 0° C. and a 1.0 M solution of TBAF in tetrahydrofuran (0.10 mL, 0.10 mmol) was added. The mixture was stirred for 10 min at 0° C. and then let warm to RT and quenched by the addition of water. The resulting mixture was extracted with tetrahydrofuran, adsorbed onto silica, and purified by flash chromatography on silica in 4:1 hexane:ethyl acetate (v/v) to yield 49 mg (21%) of an orange solid. $^1$H NMR (300 MHz, DMSO-d$_6$) δ 7.60–7.26 (m, 6H), 7.22–7.01 (m, 6H), 5.81 (s, 2H), 3.83 (s, 3H); mass spectroscopy gave MH$^+$=480.2 (calc'd exact mass for C25H19F3NO2=479.13).

EXAMPLE 220

Ethyl 5-[2-(5-methyl-2-phenyl-1,3-thiazol-4-yl)ethoxy]-1H-indole-2-carboxylate

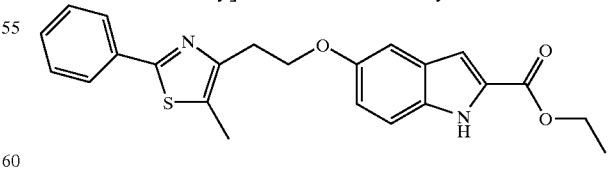

A solution of ethyl 5(hydroxy)-1H-indole-2-carboxylate (991 mg, 4.83 mmol) and 2-(5-methyl-2-phenyl-1,3-thiazol-4-yl)ethanol (1.06 g, 4.83 mmol) in tetrahydrofuran (30 +5 mL rinse) was added to a stirred mixture of triphenylphosphine (1.3 g, 4.9 mmol) and 1,1'-(azodicarbonyl)dipiperidine (1.2 g, 4.9 mmol) in tetrahydrofuran (10 mL).

The reaction was stirred for 48 h and then diluted with ethyl acetate (200 mL). This solution was washed successively with water, 10% hydrochloric acid, and brine, dried over anhydrous magnesium sulfate, and concentrated in vacuo. Flash chromatography of the residue over silica gel using 25% ethyl acetate/hexane gave 1.04 g (53%) of the desired product. The product had: $^1$H NMR (300 MHz, acetone-D$_6$) □ 10.40–10.55 (br s, 1 H), 7.89–7.95 (m, 2 H), 7.38–7.49 (m, 4 H), 7.19 (d, 1 H), 7.06–7.09 (m, 1 H), 6.95 (dd, 1 H), 4.30–4.40 (m, 4 H), 3.20 (t, 2 H), 2.51 (s, 3 H), 1.35 (t, 3 H); mass spectrometry gave MH$_+$=407.1 (calc'd exact mass for C$_{23}$H$_{22}$N$_2$O$_3$S=406.14).

The following compounds were prepared according to the method of Example 220:

118, 237 mg, 0.57 mmol) in acetone (20 mL) was added potassium carbonate (200 mg, 1.45 mmol) and 1,6-dibromohexane (0.079 mL, 0.52 mmol). The resulting mixture was heated to reflux for 48 h, cooled to RT, concentrated and partitioned between ethyl acetate and water. The organic layer was collected and the aqueous layer was extracted with ethyl acetate. The combined organics were dried over anhydrous magnesium sulfate and concentrated to 25 mg (9%) of an oil. Mass spectroscopy gave MH$^+$=500.2 (calc'd exact mass for C$_{31}$H$_{33}$NO$_5$=499.24); TLF R$_f$=0.22 (hexane/ethyl acetate 2:1).

| Ex. No. | Structure | Yield [%] | MS [M + H$^+$] | Rf | mp [° C.] |
|---|---|---|---|---|---|
| 221 | 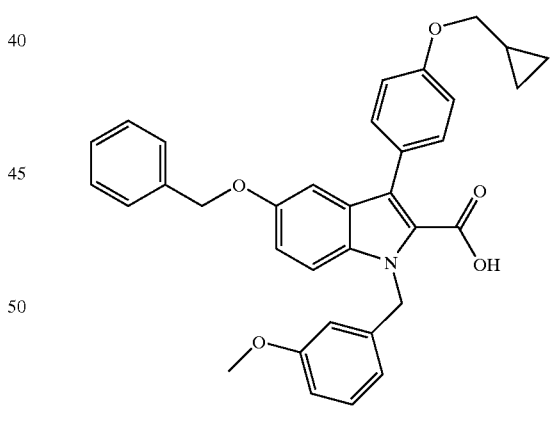 | 36 | 475.3 | 0.1 (Hexane/ ethyl acetate 7:3) | |

EXAMPLE 222

Ethyl 19-aza-19-[(3-methoxyphenyl)methyl]-7,14-dioxatetracyclo-[13.5.2.1<2,6>0.0<18,21>]tricosa-1(20),2,4,6(23),15(22),16,18(21)-heptaene-20-carboxylate

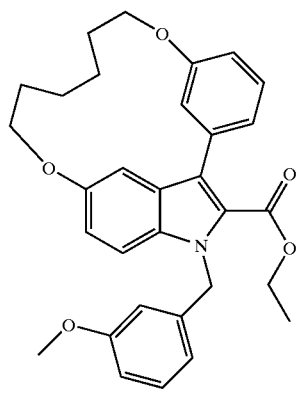

To a solution of ethyl 5-hydroxy-3-(3-hydroxyphenyl)-1-[(3-methoxyphenyl)methyl]indole-2-carboxylate (Example

EXAMPLE 229

5-(Benzyloxy)-3-[4-(cyclopropylmethoxy)phenyl]-1-(3-methoxybenzyl)-1H-indole-2-carboxylic acid 1 M Aqueous sodium hydroxide (1 mL) was added to a stirred solution of ethyl 5-(benzyloxy)-3-[4-(cyclopropylmethoxy)phenyl]-1-(3-methoxybenzyl)-1H-indole-2-carboxylate (Example 61, 100 mg, 0.178 mmol) in methanol (1 mL). The reaction was warmed (50° C.) and stirring was continued for 18 h. After cooling the reaction was diluted with water (20 mL) and then the solution was adjusted to pH=2 using 1 M hydrochloric acid. The product was extracted with ethyl acetate (3×20 mL) and then the combined organic extracts were washed with brine, dried over anhydrous magnesium sulfate, and concentrated in vacuo. Flash chromatography of the residue over silica gel using 50% ethyl acetate/hexane gave 38.4 mg (40%) of the desired product as a pure white solid (mp=185–187° C.). The product had: $^1$H NMR (300 MHz, CDCl$_3$) δ 7.25–7.48 (m, 8 H), 6.89–7.17 (m, 3 H), 6.65–6.78 (m, 2 H), 5.83 (s, 2 H), 5.05 (s, 2 H), 3.84 (d, 2 H), 3.68 (s, 3 H), 1.25–1.35 (m, 1 H), 0.57–0.67 (m, 2 H), 0.31–0.41 (m, 2 H); mass spectroscopy gave MH$^+$=534.1 (calcd exact mass for C$_{34}$H$_{31}$NO$_5$=533.22).

EXAMPLE 230

1-(Cyclopropylmethyl)-3-[(4-methoxyphenyl)methyl]indole-2-carboxylic acid

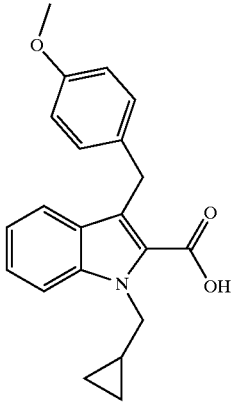

1.0 M Aqueous sodium hydroxide (4 mL), methanol (2 mL), and potassium hydroxide (5 pellets) were added to a stirred solution of Example 42 (181 mg, 0.499 mmol) in tetrahydrofuran (4 mL). The resulting mixture was heated to reflux for 18 h, cooled to RT, and acidified with 1.0 M hydrochloric aced. The resulting mixture was extracted with ethyl acetate and the combined organic extracts were dried over anhydrous magnesium sulfate and concentrated in vacuo to give 122 mg (72%) of a white solid. $^1$H NMR (300 MHz, DMSO-d$_6$) δ 7.65–7.53 (m, 2H), 7.30–7.23 (m, 1H), 7.16–7.11 (m, 2H), 7.07–7.00 (m, 1H), 6.79–6.74 (m, 2H), 4.44 (d, J=7.0 Hz, 2H), 4.35 (s, 2H), 3.66 (s, 3H), 1.25–1.15 (m, 1H), 0.40–0.30 (m, 4H); mass spectroscopy gave MH$^+$= 336.0 (calcd exact mass for C$_{21}$H$_{21}$NO$_3$=335.15), mp=162–163° C.

EXAMPLE 231

3-(Cyclopropylidenemethyl)-1-[3-(trifluoromethyl)benzyl]-1H-indole-2-carboxylic acid

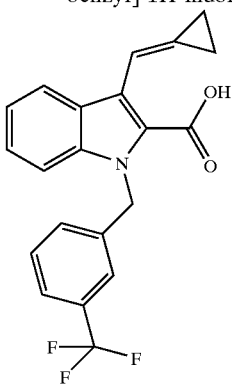

The compound was prepared from ethyl 3-(cyclopropylidenemethyl)-1-[3-(trifluoromethyl)benzyl]-1H-indole-2-carboxylate (Example 182) using the method described in Example 229, except 6N aqueous sodium hydroxide solution was used with tetrahydrofuran as a co-solvent. Flash chromatography of the residue over silica gel using 50% ethyl acetate/hexane gave the title compound (57%) as a pale yellow solid (mp=148–150° C). The product had: $^1$H NMR (300 MHz, acetone-d$_6$) δ 11.70 (s, 1 H), 8.16 (d, 1 H), 7.70 (s, 1 H), 7.56–7.46 (m, 4 H), 7.35–7.27 (m, 2 H), 7.19–7.15 (m, 1 H), 5.98 (s, 2 H), 1.58–1.53 (m, 2 H), 1.33–1.28 (m, 2 H); mass spectroscopy gave MH$^+$=372.1 (calcd exact mass for C$_{21}$H$_{16}$F$_3$NH$_2$=371.11).

EXAMPLE 232

3-(Benzothien-2-yl)-1-[3-(trifluoromethyl)benzyl]-indole-2-carboxylic acid

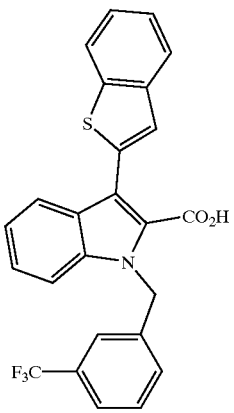

A mixture of 3 N aq. potassium hydroxide (0.85 mL), Example 62 (100 mg, 0.210 mmol), tetrahydrofuran (0.75 mL) and ethanol (0.75 mL) was refluxed for 2 h. The resulting mixture was diluted with ethyl acetate and acidified with 2 N hydrochloric acid. The organic layer was separated, dried over anhydrous sodium sulfate and concentrated to afford 67 mg (71%) of product as a white solid. Rf=0.40 (9/1 dichloromethane/methanol); LRMS (+esi) obs'd: 452.0; calcd 451.1, m.p. 243–246° C.

The following compounds were prepared according to the methods of Examples 229, 230, 232 or 232:

| Ex. No. | Structure | Yield [%] | MS [M + H⁺] | Rf (TLC) | mp [° C.] |
|---|---|---|---|---|---|
| 233 | 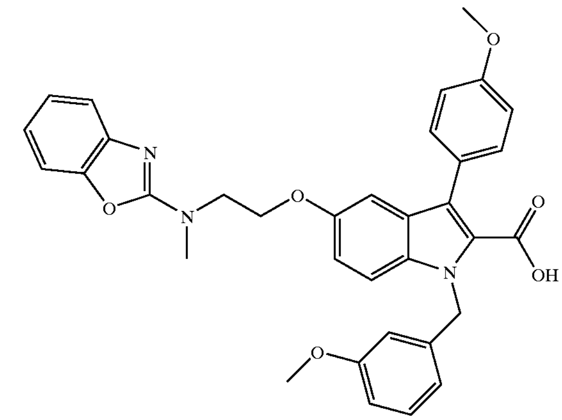 | 95 | 578.2 | 0.26 (CH₂Cl₂/ methanol 95:5) | |
| 234 | 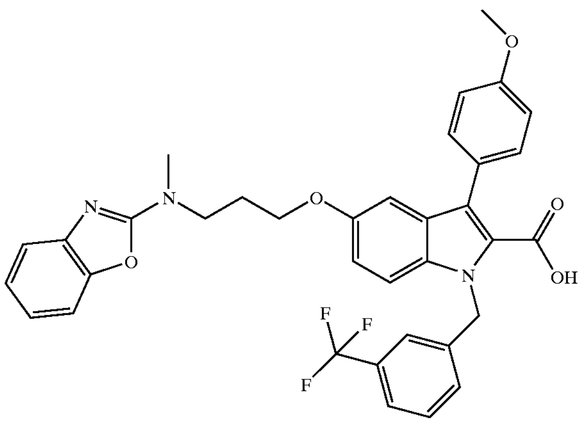 | 55 | 630.3 | 0.71 (ethyl acetate) | |
| 235 | 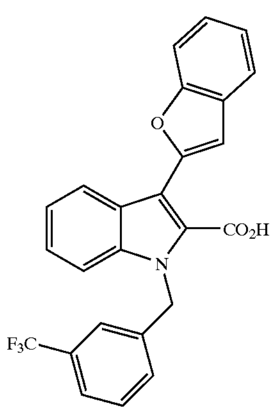 | 33 | 436.0 | 0.39 (CH₂Cl₂/ methanol 9:1) | 211– 214 |

-continued

| Ex. No. | Structure | Yield [%] | MS [M + H⁺] | Rf (TLC) | mp [° C.] |
|---|---|---|---|---|---|
| 236 | 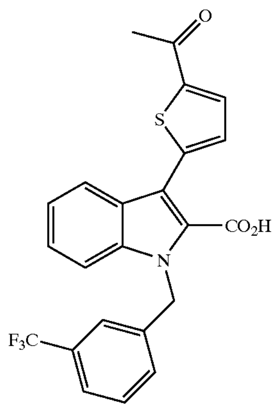 | 76 | 444.1 | 0.22 (CH$_2$Cl$_2$/methanol 9:1) | 212–214 |
| 237 | 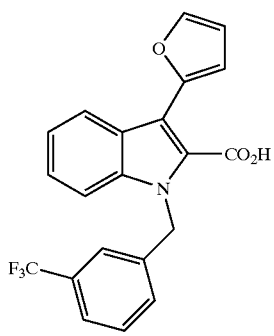 | 81 | 386.1 | 0.34 (CH$_2$Cl$_2$/methanol 9:1) | 172–173 |
| 238 | 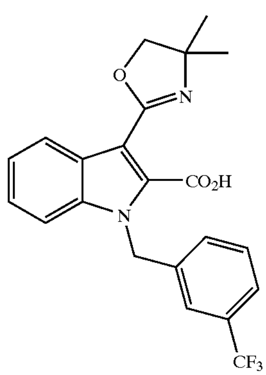 | 20 (2 steps) | 417.2 | 0.32 (CH$_2$Cl$_2$/methanol 9:1) | |
| 239 | 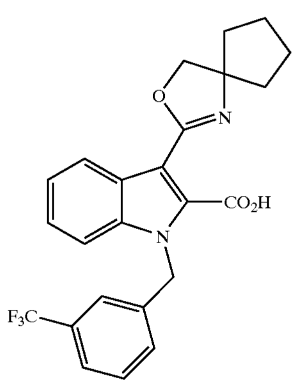 | 7 (3 steps) | 443.2 | 0.38 (CH$_2$Cl$_2$/methanol 9:1) | |

-continued

| Ex. No. | Structure | Yield [%] | MS [M + H⁺] | Rf (TLC) | mp [° C.] |
|---|---|---|---|---|---|
| 240 | 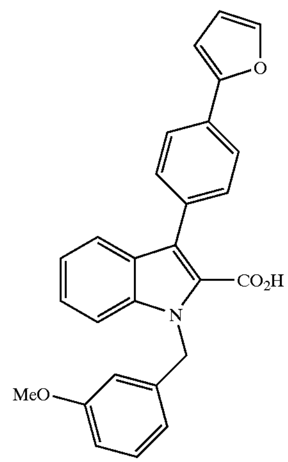 | 57 | 424.1 | 0.20 CH₂Cl₂/methanol 95:5) | 190–192 |
| 241 | 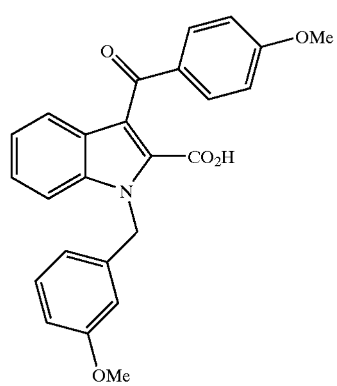 | 65 | 416.1 | 0.24 (CH₂Cl₂/methanol 9:1) | 68–69 |
| 242 | 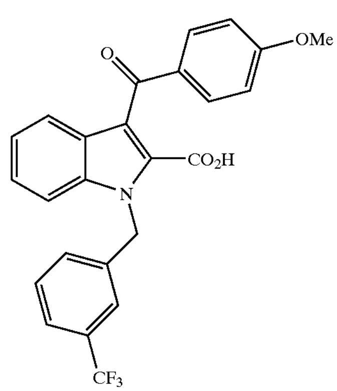 | 77 | 454.0 | 0.29 (CH₂Cl₂/methanol 9:1) | 215–216 |

-continued

| Ex. No. | Structure | Yield [%] | MS [M + H⁺] | Rf (TLC) | mp [° C.] |
|---|---|---|---|---|---|
| 243 | 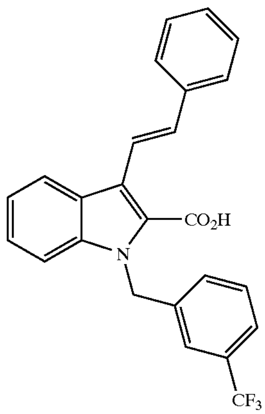 | 2 | 420.4 (−FIMS) | 0.42 (CH₂Cl₂/methanol 9:1) | 183–185 |
| 244 | 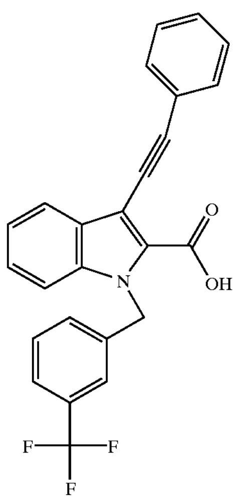 | 47 | 419 (M+) | 0.39 (CH₂Cl₂/methanol 9:1) | 165–167 |
| 245 | 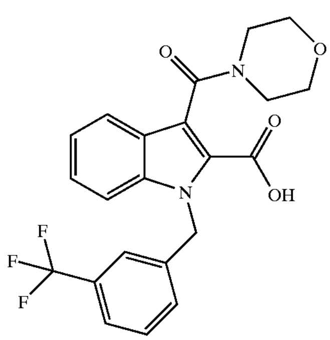 | 28 | | | |

-continued
| Ex. No. | Structure | Yield [%] | MS [M + H⁺] | Rf (TLC) | mp [° C.] |
|---|---|---|---|---|---|
| 246 | 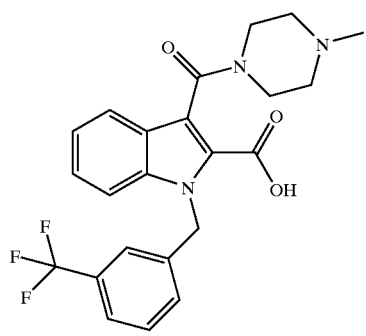 | 11 | 446 | | |
| 247 | 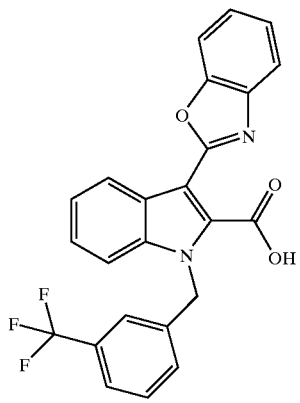 | 54 | 437 | | |
| 248 | 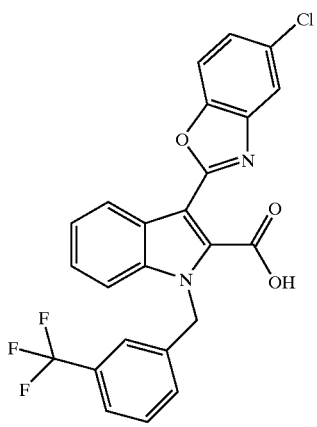 | 32 | 471 | | |

| Ex. No. | Structure | Yield [%] | MS [M + H⁺] | Rf (TLC) | mp [° C.] |
|---|---|---|---|---|---|
| 249 | 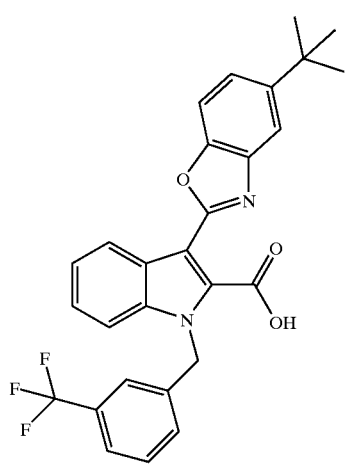 | 48 | 493 | | |
| 250 | 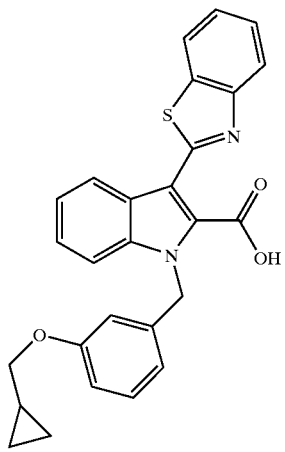 | 34 | n.d. | | |
| 251 | 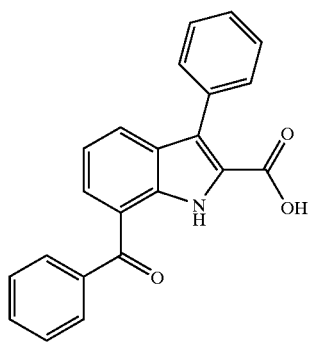 | 72 | 342 | | |

-continued
| Ex. No. | Structure | Yield [%] | MS [M + H+] | Rf (TLC) | mp [° C.] |
|---|---|---|---|---|---|
| 252 | 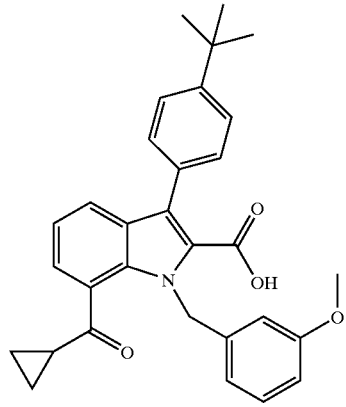 | 79 | | | |
| 253 | 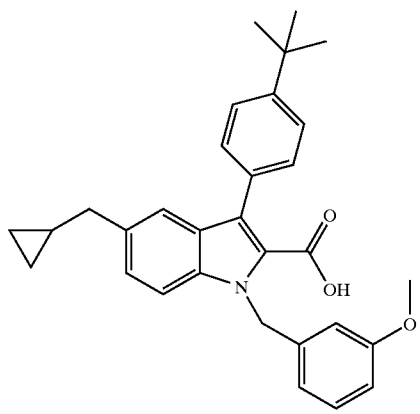 | 93 | | | |
| 254 | 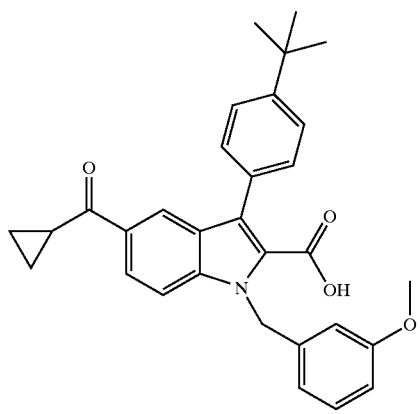 | 88 | | | |

-continued
| Ex. No. | Structure | Yield [%] | MS [M + H+] | Rf (TLC) | mp [° C.] |
|---|---|---|---|---|---|
| 255 | 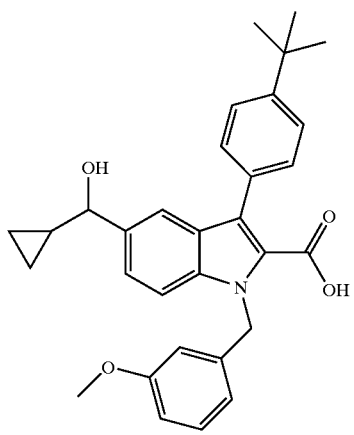 | 19 | | | |
| 256 | 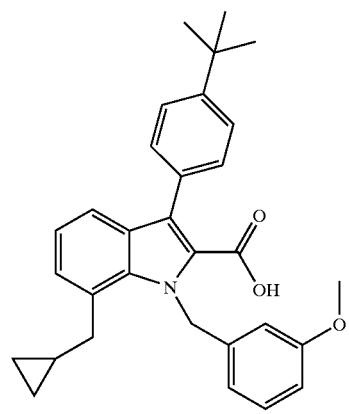 | 51 | | | |
| 257 | 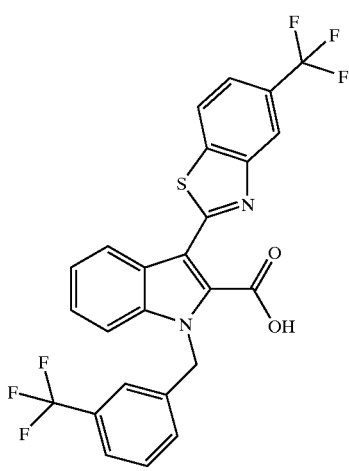 | 23 | 521 | | |

-continued
| Ex. No. | Structure | Yield [%] | MS [M + H⁺] | Rf (TLC) | mp [° C.] |
|---|---|---|---|---|---|
| 258 | 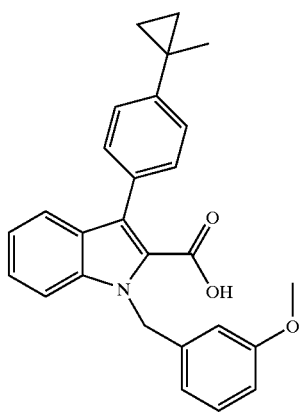 | 25 | 412 | | |
| 259 | 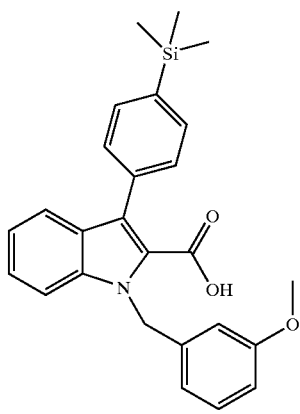 | 35 | 402 | | |
| 260 | 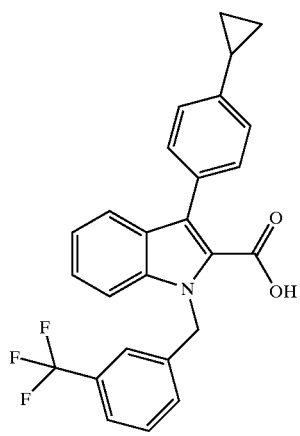 | 90 | 436 | | |

-continued
| Ex. No. | Structure | Yield [%] | MS [M + H+] | Rf (TLC) | mp [° C.] |
|---|---|---|---|---|---|
| 261 | 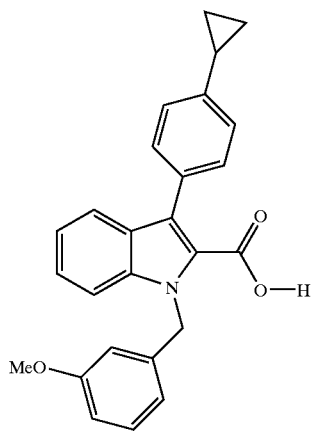 | 92 | 398 | | |
| 262 | 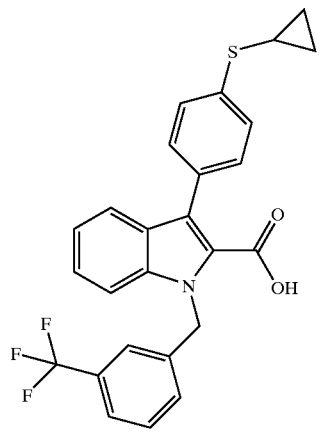 | 96 | 468 | | |
| 263 | 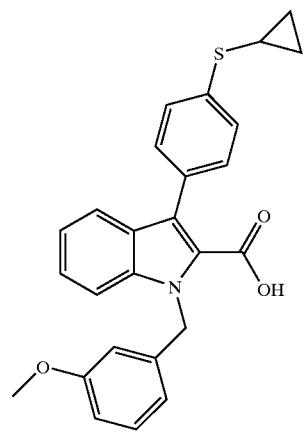 | 93 | 430 | | |

-continued

| Ex. No. | Structure | Yield [%] | MS [M + H+] | Rf (TLC) | mp [° C.] |
|---|---|---|---|---|---|
| 264 | 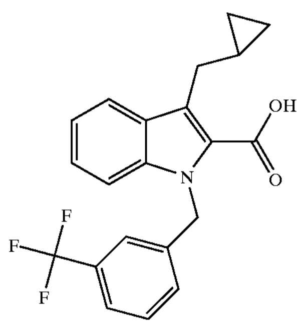 | 65 | 374.4 | 0.25 (Hexane/ Et₂O 80:20) | 174–175 |
| 265 | 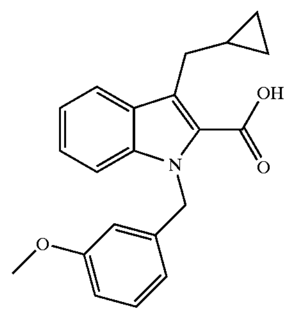 | 70 | 336.2 | 0.10 (Hexane/ ethyl acetate 90:10) | 165–167 |
| 266 | 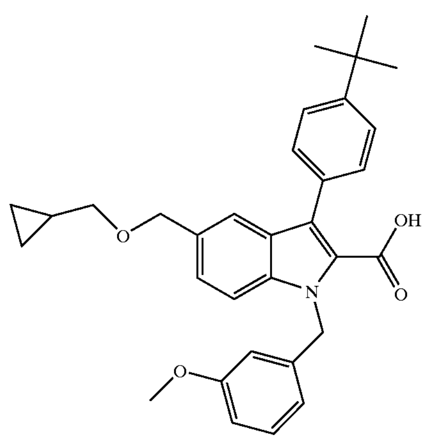 | 69 | 498.6 | 0.10 (45:45:10 hexane/ ethyl acetate/ methanol) | 79–80 |
| 267 | 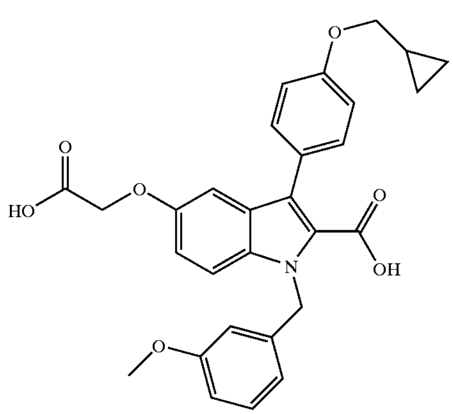 | 9 | 502 | | |

-continued

| Ex. No. | Structure | Yield [%] | MS [M + H⁺] | Rf (TLC) | mp [° C.] |
|---|---|---|---|---|---|
| 268 | 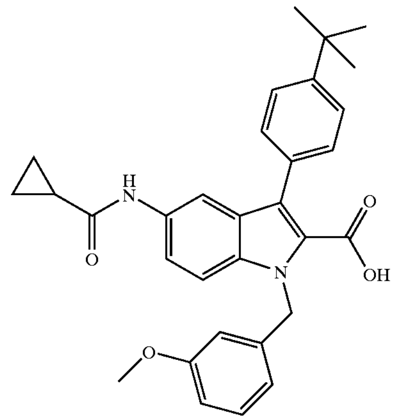 | 38 | 497.3 | | 194–196 |
| 269 | 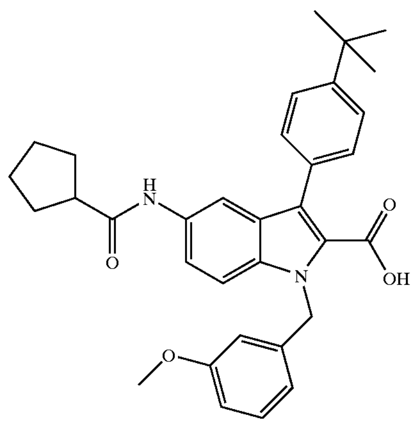 | 64 | 525.3 | | 154–156 |
| 270 | 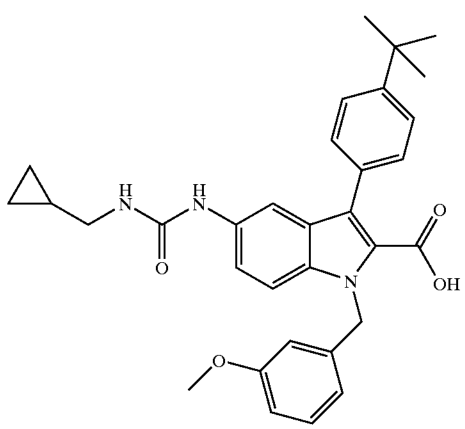 | 46 | 526.3 | | 141–142 |

-continued

| Ex. No. | Structure | Yield [%] | MS [M + H⁺] | Rf (TLC) | mp [° C.] |
|---|---|---|---|---|---|
| 271 | 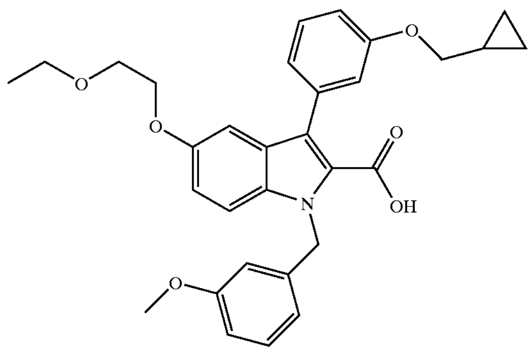 | 91 | 516.2 | 0.15 (2:1 hexane-ethyl acetate) | |
| 272 | 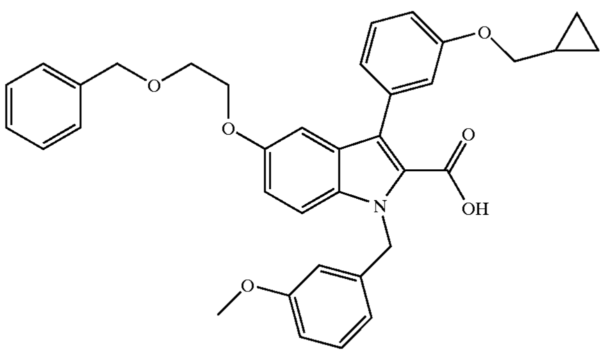 | 65 | 578.2 | 0.15 (2:1 hexane-ethyl acetate) | |
| 273 | 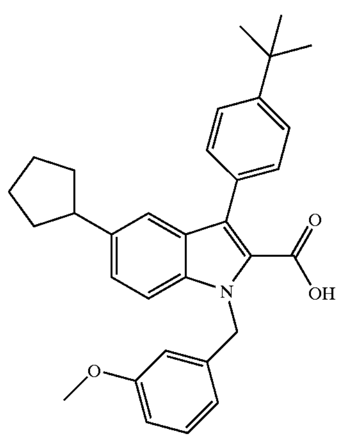 | 56 | 482.2 | | 192–193 |
| 274 | 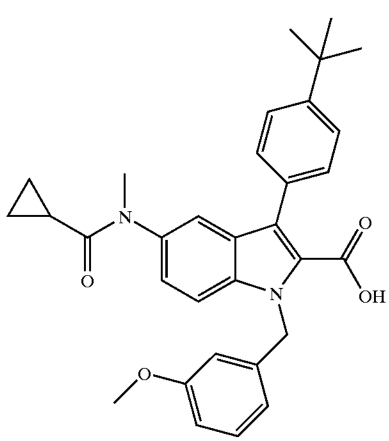 | 90 | 511.3 | | 219–222 |

-continued
| Ex. No. | Structure | Yield [%] | MS [M + H⁺] | Rf (TLC) | mp [° C.] |
|---|---|---|---|---|---|
| 275 | 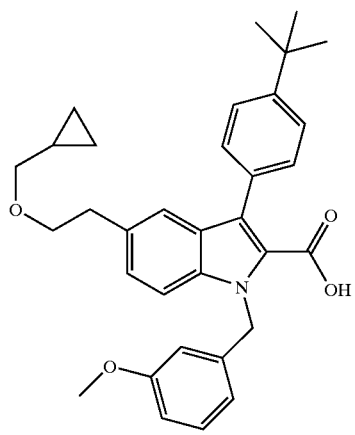 | 75 | 512.2 | | |
| 276 | 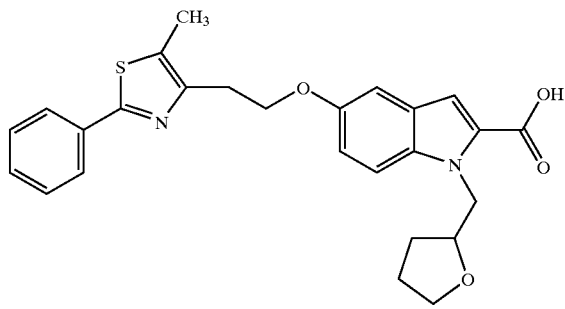 | 66 | 463.2 | | |
| 277 | 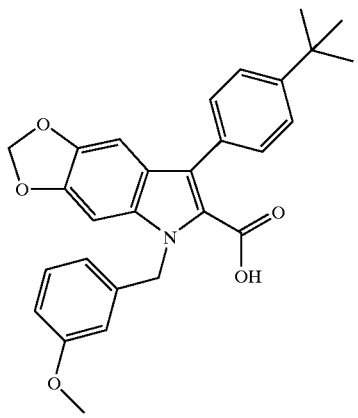 | 42 | 458.1 | 0.5 (2.5% methanol/ CH2Cl2 | 179.1– 179.7 |

-continued

| Ex. No. | Structure | Yield [%] | MS [M + H⁺] | Rf (TLC) | mp [° C.] |
|---|---|---|---|---|---|
| 278 | 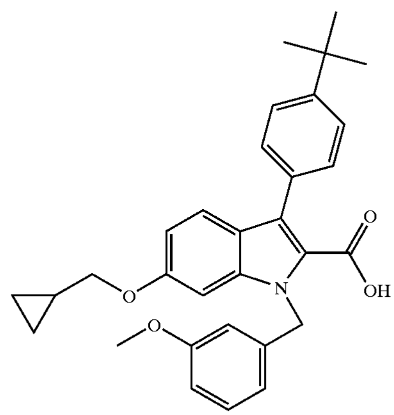 | 99 | 386.5 [M − H⁺] | | |
| 279 | 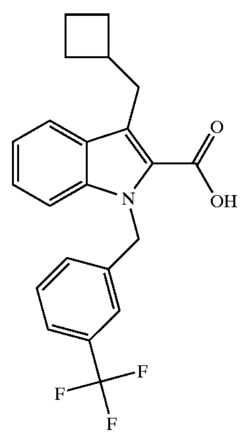 | 45 | 484.2 | 0.13 (20% ethyl acetate/ hexane) | |
| 280 | 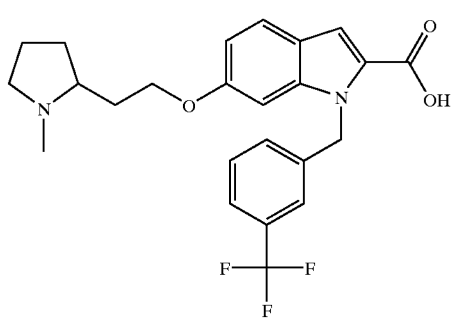 | 44 | 447.3 | 0.29 (5% methanol/ $CH_2Cl_2$) | |

-continued

| Ex. No. | Structure | Yield [%] | MS [M + H⁺] | Rf (TLC) | mp [° C.] |
|---|---|---|---|---|---|
| 281 | 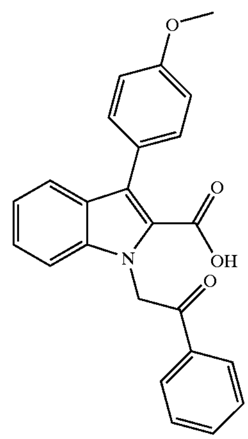 | 85 | 386 | | |
| 282 | 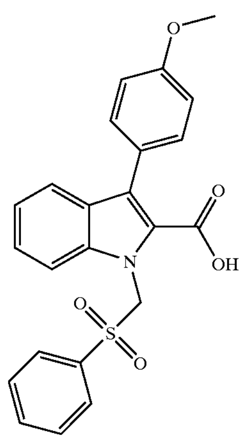 | 100 | | | 166–168 |
| 283 | 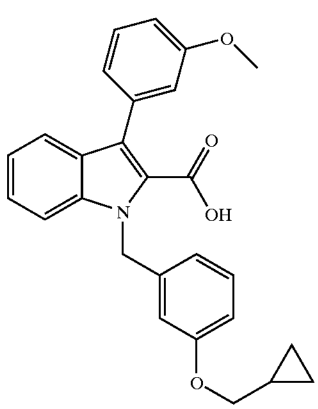 | 59 | 428 | | |

-continued
| Ex. No. | Structure | Yield [%] | MS [M + H⁺] | Rf (TLC) | mp [° C.] |
|---|---|---|---|---|---|
| 284 | 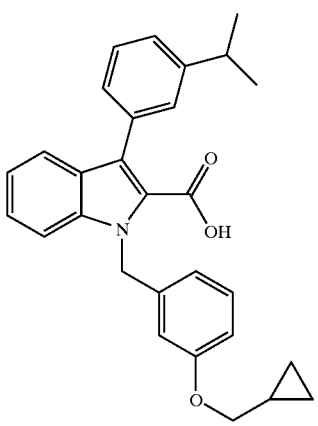 | 78 | 440 | | 204 |
| 285 | 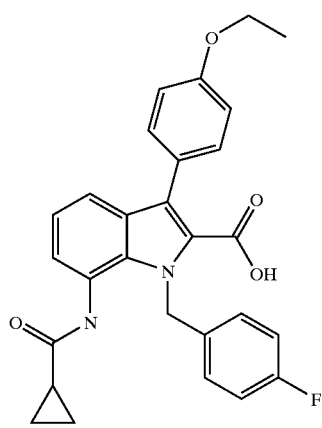 | 88 | 473 | | 250 |
| 286 | 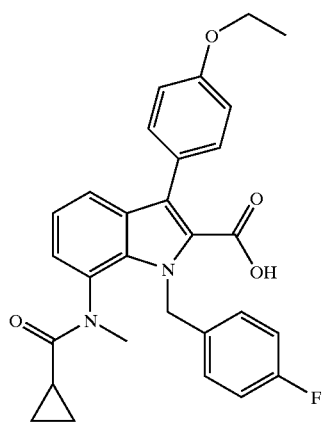 | 77 | 487 | | 128 |

-continued
| Ex. No. | Structure | Yield [%] | MS [M + H+] | Rf (TLC) | mp [° C.] |
|---|---|---|---|---|---|
| 287 | 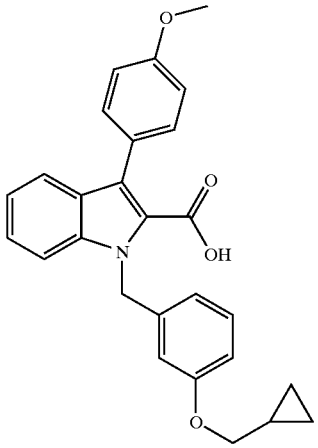 | 76 | 428 | | 168 |
| 288 | 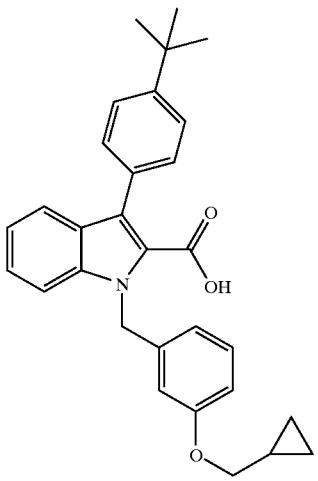 | 82 | 454 | | 120 |
| 289 | 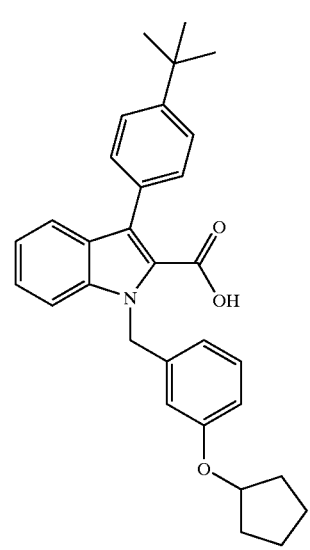 | 70 | 468 | | 159 |

-continued

| Ex. No. | Structure | Yield [%] | MS [M + H⁺] | Rf (TLC) | mp [° C.] |
|---|---|---|---|---|---|
| 290 | 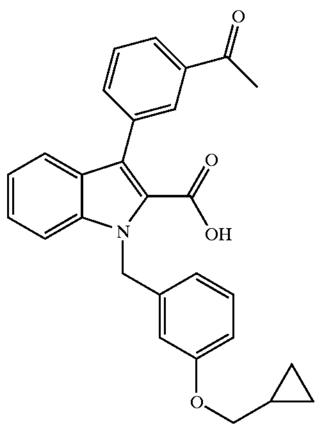 | 74 | 440 | | 103 |
| 291 | 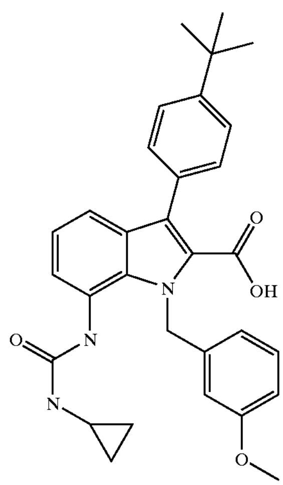 | 50 | 512 | | 168 (dec.) |
| 292 | 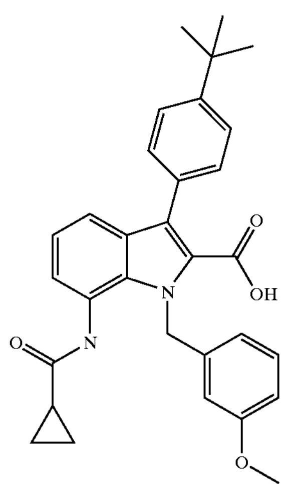 | 95 | 497 | | 151 |

-continued

| Ex. No. | Structure | Yield [%] | MS [M + H⁺] | Rf (TLC) | mp [° C.] |
|---|---|---|---|---|---|
| 293 | 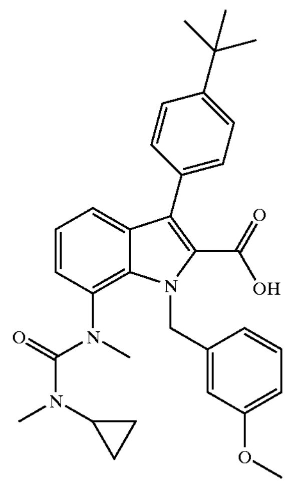 | 66 | 540 | | 112–115 (dec.) |
| 294 | 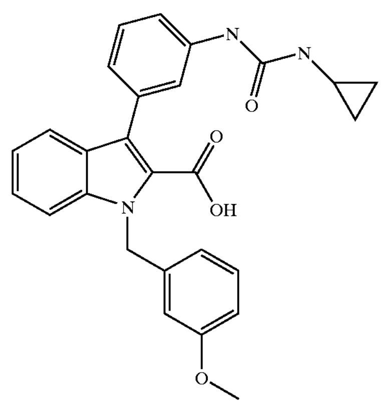 | 45 | 456 | | 110 (dec.) |
| 295 | 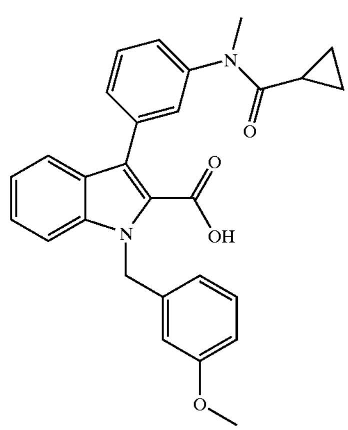 | 71 | 455 | | 200 |

-continued
| Ex. No. | Structure | Yield [%] | MS [M + H⁺] | Rf (TLC) | mp [° C.] |
|---|---|---|---|---|---|
| 296 | 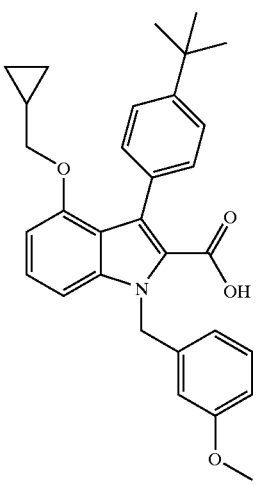 | 75 | 484 | | 162 |
| 297 | 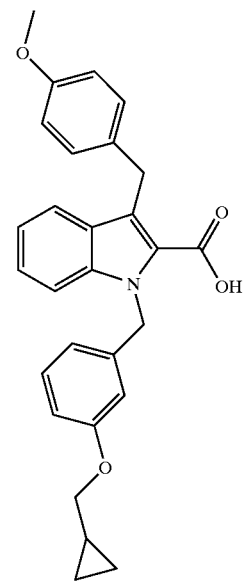 | 86 | 442 | | 168–170 |
| 298 | 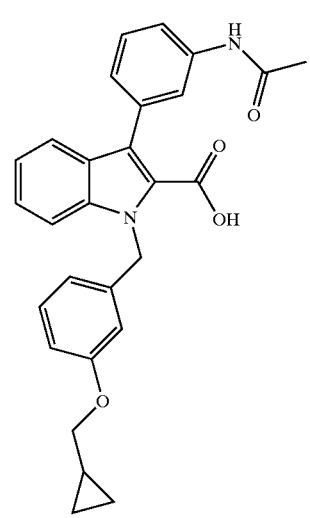 | 20 | 455.0 | | 122–123 |

-continued

| Ex. No. | Structure | Yield [%] | MS [M + H⁺] | Rf (TLC) | mp [° C.] |
|---|---|---|---|---|---|
| 299 | 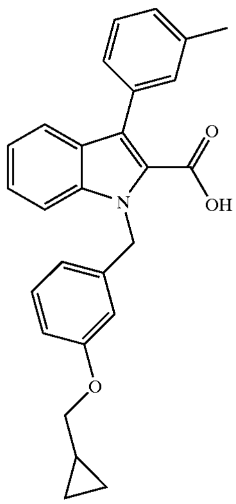 | 79 | 412.1 | | 58–60 |
| 300 | 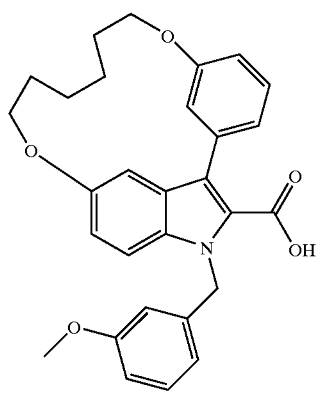 | 50 | 472.2 | | 79–80 |
| 301 | 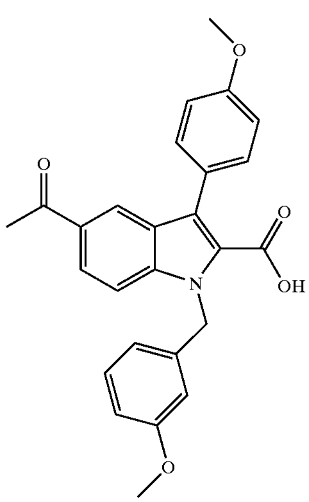 | 87 | 430.2 | 0.29 (ethyl acetate) | 190d |

-continued

| Ex. No. | Structure | Yield [%] | MS [M + H+] | Rf (TLC) | mp [° C.] |
|---|---|---|---|---|---|
| 302 | 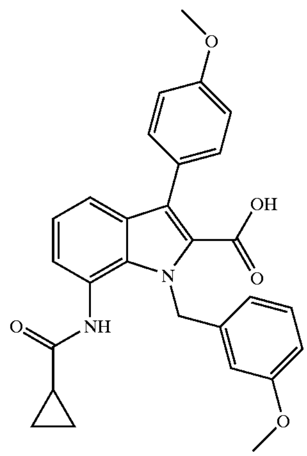 | 76 | 471.0 | | 210d |
| 303 | 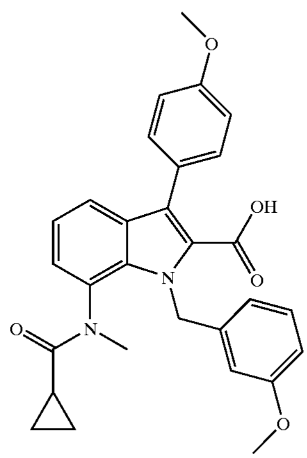 | 63 | 485.1 | | 98d |
| 304 | 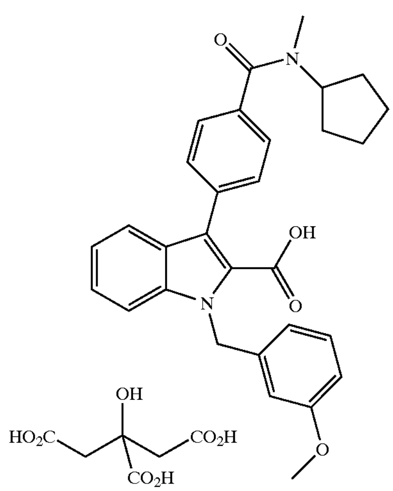 | 89 | 483.3 | | 169d |

EXAMPLE 305

3-[4-(Cyclopropylmethoxy)phenyl]-1-(3-methoxybenzyl)-1H-indole-2-carboxylic acid

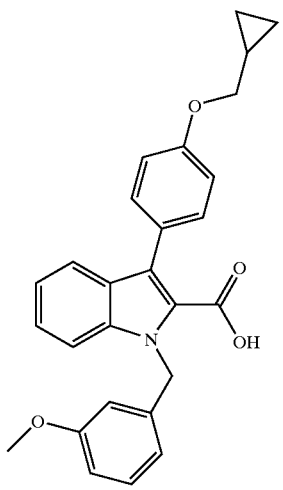

Ethyl 3-[4-hydroxyphenyl]-1-(3-methoxybenzyl)-1H-indole-2-carboxylate (Example 121, 21 mg, 0.05 mmol), bromomethylcyclopropane (14 mg, 0.10 mmol), potassium carbonate (21 mg, 0.15 mmol), and potassium iodide (catalytic amount) were heated (90° C.) in DMF (0.8 mL) for 15 hrs. The solvent was then removed under reduced pressure and the residue was dissolved in dichloromethane (2 mL). The mixture was filtered and then preparative thin layer chromatography of the filtrate (ethyl acetate:hexane= 1:3) afforded the desired intermnediate (31%).

Ethanol (300 μL) was added to the intermediate (7 mg). A 2 N solution of potassium hydroxide in ethanol/water (1:1, 200 μL) was added and the mixture was heated (60° C.) for 2 hrs. The mixture was cooled to rt and put into an ice bath. 2 N hydrochloric acid (210 μL) was added and a white precipitate formed. The solvent was removed under reduced pressure and the residue was dissolved in 2 mL of dichloromethane. The mixture was filtered and then preparative thin layer chromatography of the filtrate (ethyl acetate:methanol=95:5) gave 4 mg (61%) of desired product. $^1$H NMR (300 MHz, CDCl$_3$) δ 6.65–7.60 (m, 12 H), 5.75 (s, 2 H), 3.84 (d, 2 H), 3.68 (s, 3 H), 1.25 (m, 1 H), 0.65 (m, 2 H), 0.40 (m, 2 H); mass spectroscopy (negative ion mode) gave [M−H]$^-$=426.2 (RT=4.73, calcd exact mass for $C_{27}H_{25}NO_4$=427.18).

The following compounds were prepared according to the method of Example 305:

| Ex. No. | Structure | Yield [%] | MS [M + H$^+$] | RT (TLC) | mp [° C.] |
|---|---|---|---|---|---|
| 306 | 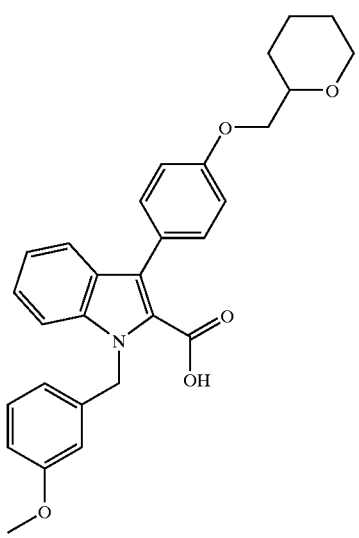 | 31 | 472.2 | 4.49 | |

-continued

| Ex. No. | Structure | Yield [%] | MS [M + H⁺] | RT (TLC) | mp [° C.] |
|---|---|---|---|---|---|
| 307 | 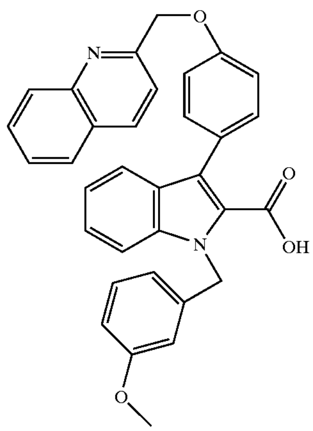 | 24 | 515.2 | 4.14 | |
| 308 | 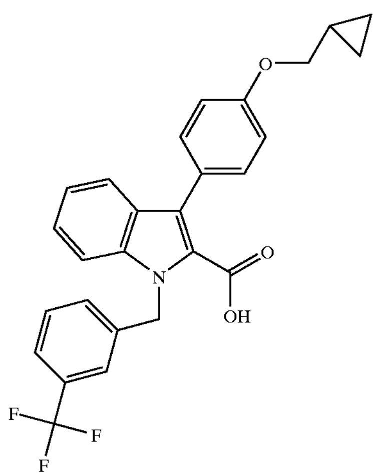 | 35 | 466.0 | 5.01 | |
| 310 | 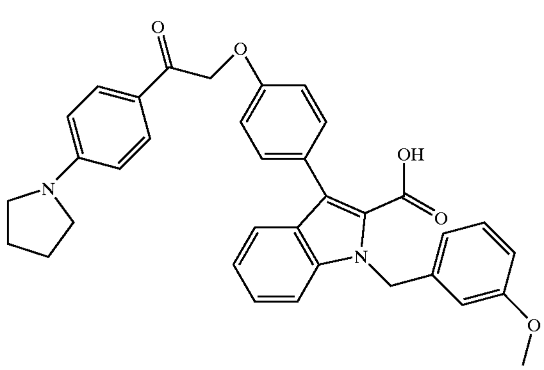 | 19 | 561.2 | 4.06 | |

-continued
| Ex. No. | Structure | Yield [%] | MS [M + H+] | RT (TLC) | mp [° C.] |
|---|---|---|---|---|---|
| 311 | 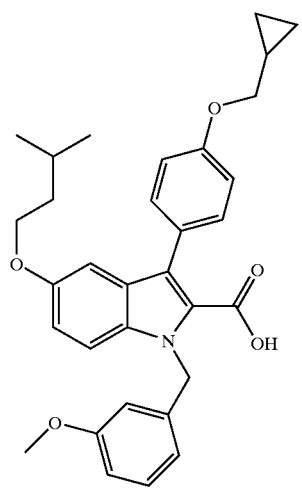 | 35 | 542.2 | 4.97 | |
| 312 | 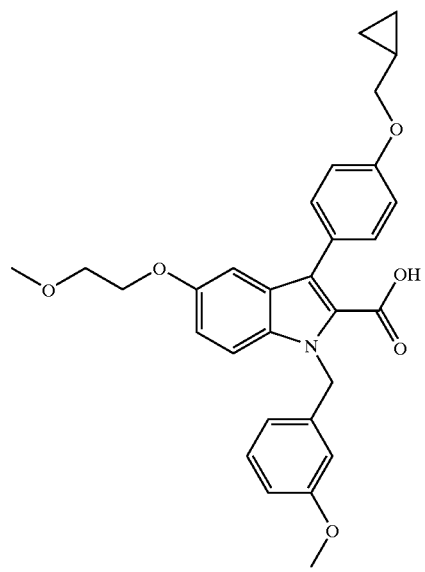 | 32 | 500.2 | 3.40 | |

-continued
| Ex. No. | Structure | Yield [%] | MS [M + H+] | RT (TLC) | mp [° C.] |
|---|---|---|---|---|---|
| 313 | 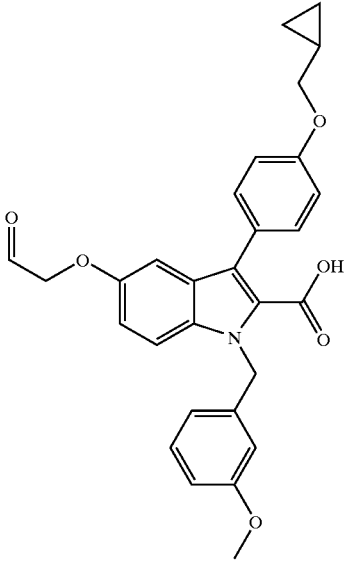 | 15 | 484.2 | 3.41 | |
| 314 | 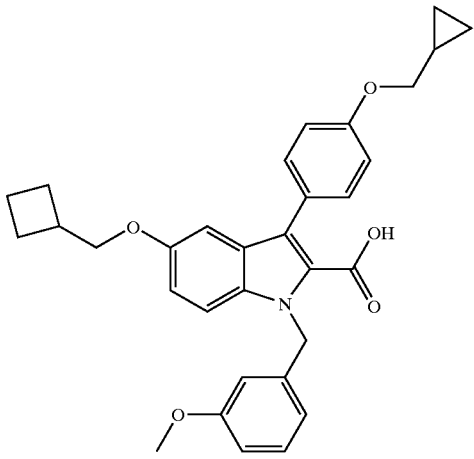 | 41 | 510.2 | 3.88 | |
| 315 | 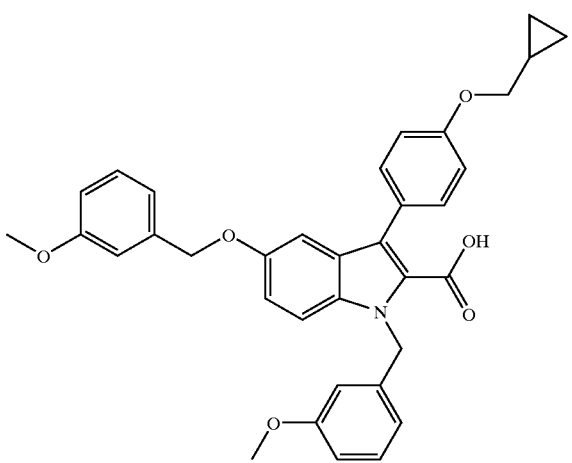 | 38 | 562.2 | 3.76 | |

-continued
| Ex. No. | Structure | Yield [%] | MS [M + H⁺] | RT (TLC) | mp [° C.] |
|---|---|---|---|---|---|
| 316 | 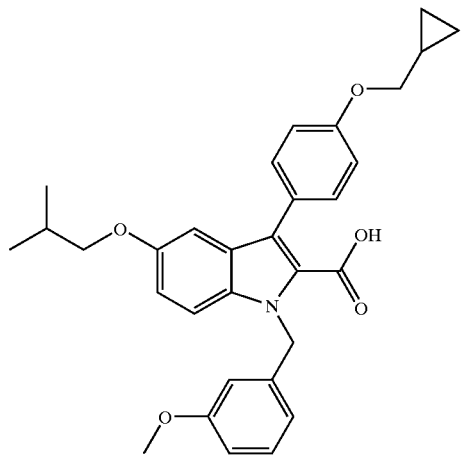 | 32 | 498.2 | 3.85 | |
| 317 | 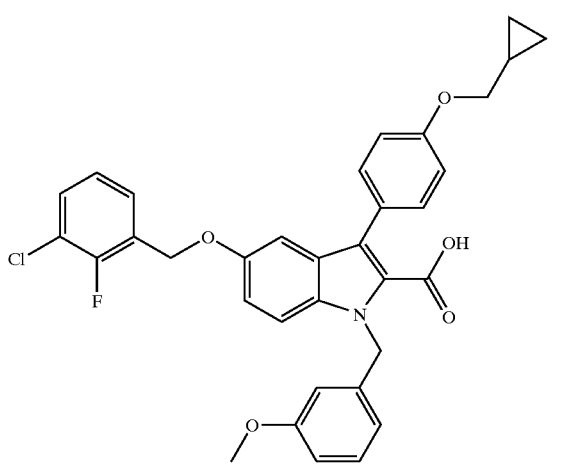 | 40 | 584.2 | 3.90 | |
| 318 | 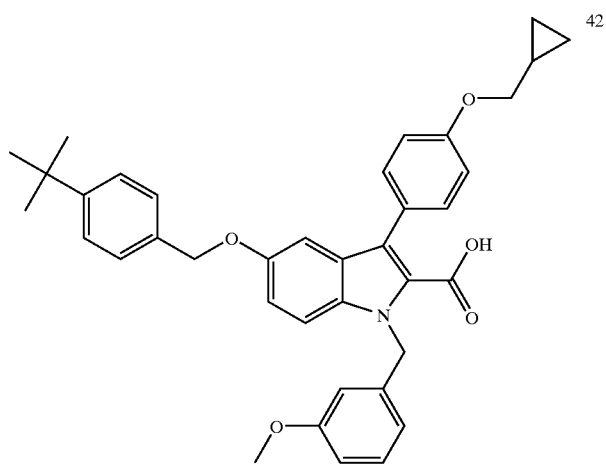 | 42 | 588.3 | 4.14 | |

-continued

| Ex. No. | Structure | Yield [%] | MS [M + H⁺] | RT (TLC) | mp [° C.] |
|---|---|---|---|---|---|
| 319 | 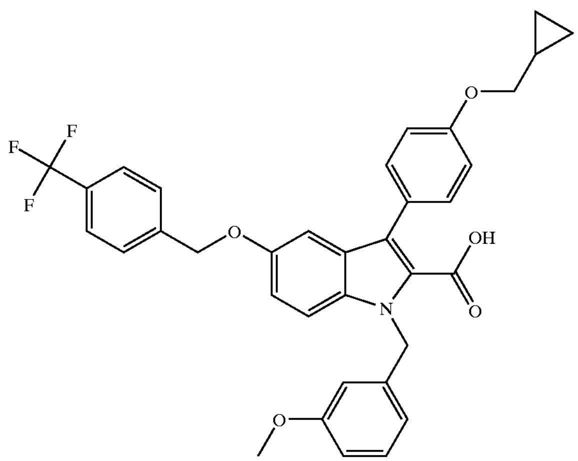 | 37 | 600.3 | 3.94 | |
| 320 | 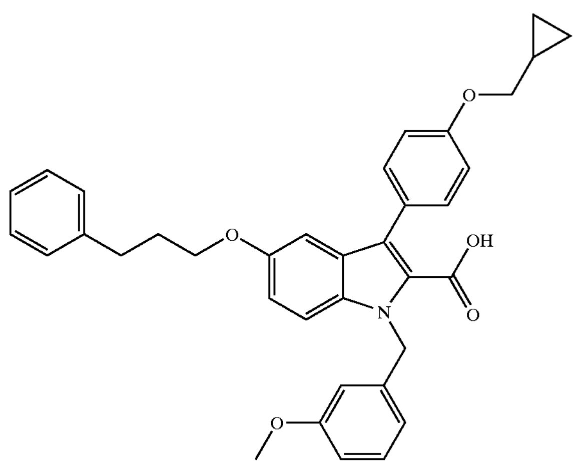 | 33 | 560.2 | 3.97 | |
| 321 | 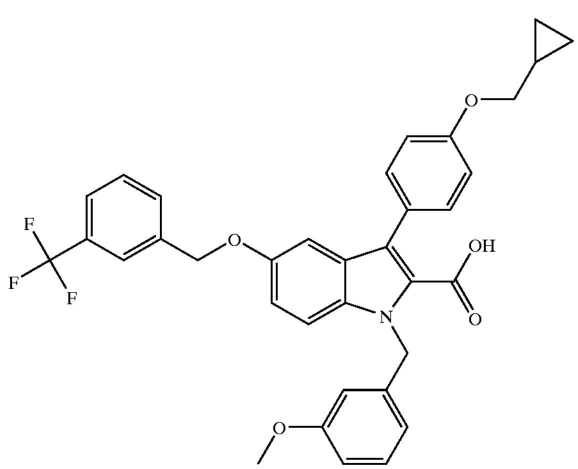 | 34 | 600.2 | 3.93 | |

| Ex. No. | Structure | Yield [%] | MS [M + H⁺] | RT (TLC) | mp [° C.] |
|---|---|---|---|---|---|
| 322 | 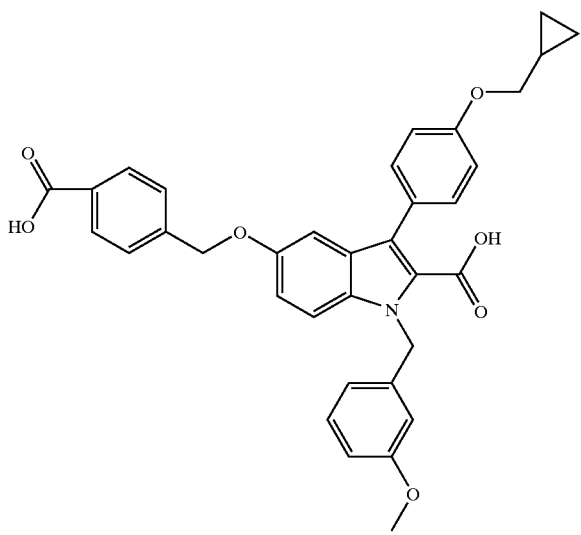 | 19 | 576.2 | 3.29 | |

EXAMPLE 323

3-[4-(N-cyclopropylcarbamoyl)phenyl]-1-[(3-methoxyphenyl)methyl]indole-2-carboxylic acid

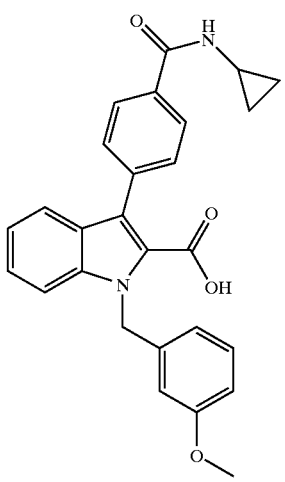

To a 25 mL round-bottomed flask at rt was charged with 4-{2-(ethoxycarbonyl)-1-[(3-methoxyphenyl)methyl]indol-3-yl}benzoic acid (Example 98, 270 mg, 0.63 mmol), tetrahydrofuran (2 mL) and one drop of N,N-dimethylformamide. Oxalyl chloride (240 mg, 0.16 mL, 1.89 mmol) was added to the above mixture dropwise. After 1 hour, the reaction mixture was concentrated and re-dissolved in tetrahydrofuran (2 mL) and cyclopropylamine (359 mg, 6.3 mmol) was added. After 10 minutes at rt, aqueous sodium hydroxide (3 N) was added to the reaction mixture and enough methanol was added to make the mixture one phase. The resulting solution was refluxed for 1 hour before it was cooled to rt and acidified with hydrochloric acid (1N) and extracted with ethyl acetate (25 mL). The organic layer was washed with water, brine and dried over anydrous sodium sulfate. The solution was concentrated in vacuo to give a white solid which was triturated with diethyl ether to provide 3-[4-(N-cyclopropylcarbamoyl)phenyl]-1-[(3-methoxyphenyl)methyl]indole-2-carboxylic acid as a white solid (142 mg, 51%): mp 237° C.; MS (electrospray, MH⁺) calcd for $C_{27}H_{25}N_2O_4$ 441, found 441; $^1$H NMR (DMSO-d$^6$) δ 13.1 (br s, 1H), 8.48 (d, J=4.0 Hz, 1H), 7.88 (d, J=8.3 Hz, 2H), 7.62 (d, J=8.4 Hz, 1H), 7.50 (d, J=8.6 Hz, 2H), 7.46 (d, J=8.1 Hz, 1H), 7.30–7.37 (m, 1H), 7.12–7.22 (m, 2H), 6.79 (dd, J=8.2, 2.5 Hz, 1H), 6.69 (dd, 1H), 6.62 (d, J=7.6 Hz, 1H), 5.83 (s, 2H), 3.68 (s, 3H), 2.85–2.89 (m, 1H), 0.56–0.64 (m, 2H), 0.65–0.75 (m, 2H).

The following compounds were prepared according to the method of Example 323.

| Ex. No. | Structure | Yield [%] | MS [M + H+] | Rf (TLC) | mp [° C.] |
|---|---|---|---|---|---|
| 324 | 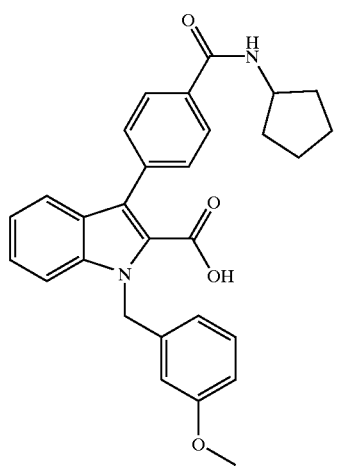 | 82 | 469 | | 230 |
| 325 | 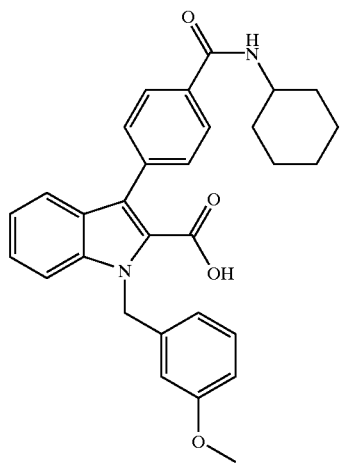 | 30 | 483 | | 245 |
| 326 | 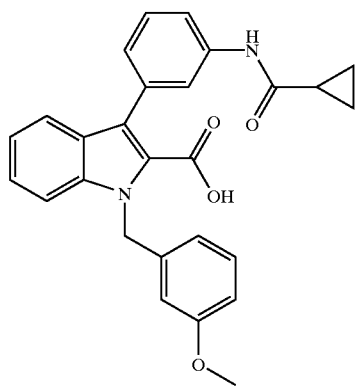 | 41 | 441 | | |

-continued
| Ex. No. | Structure | Yield [%] | MS [M + H+] | Rf (TLC) | mp [° C.] |
|---|---|---|---|---|---|
| 327 | 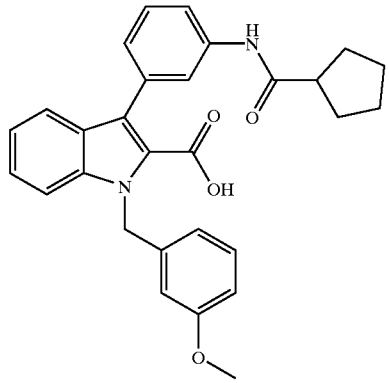 | 97 | 469 | | 133 (dec.) |
| 328 | 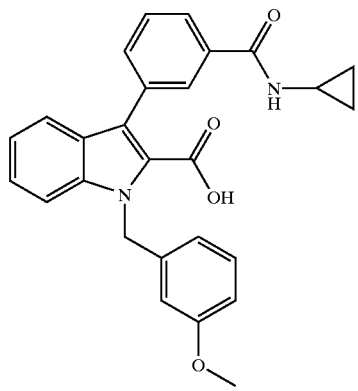 | 86 | 441 | | 204 |
| 329 | 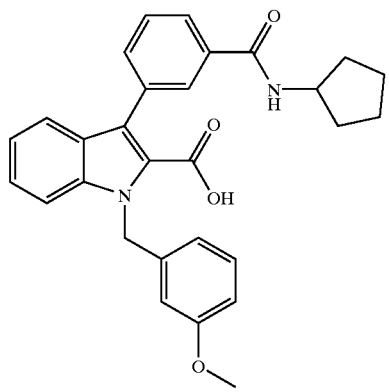 | 82 | 469 | | 108 |

EXAMPLE 330

3-[4-(Cyclopropylmethoxy)phenyl]-5-ethoxy-1-(3-methoxybenzyl)-1H-indole-2-carboxylic acid

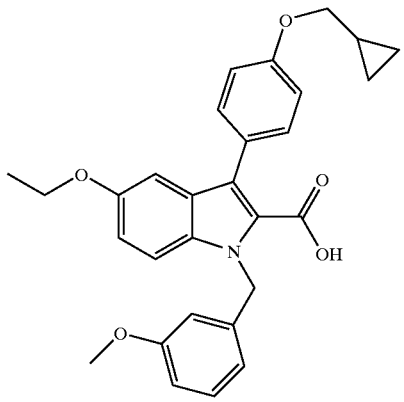

Water (5 uL) was added to a cooled (0° C.) and stirred suspension of potassium t-butoxide (90 mg, 0.80 mmol) in ethyl ether (5 mL). The slurry was stirred for 5 min and then a solution of ethyl 3-[4-(cyclopropylmethoxy)phenyl]-5-ethoxy-1-(3-methoxybenzyl)-1H-indole-2-carboxylate (Example 144, 52 mg, 0.10 mmoL) in ethyl ether (2+1 mL rinse) was added. The mixture was warmed to rt and stirred for 16 h. The solution was adjusted to pH=7 with 1 M hydrochloric acid and diluted with ethyl acetate (50 mL). This mixture was washed with water and brine, dried over anhydrous magnesium sulfate, and concentrated in vacuo. The residue was purified by preparative TLC, using 1:1 ethyl acetate/hexane as the eluent, to afford 7.0 mg (14%) of desired product. The product had: $^1$H NMR (300 MHz, acetone-$D_6$) δ 7.45–7.37 (m, 3 H), 7.18 (t, 1 H), 6.99–6.91 (m, 4 H), 6.77 (dd, 1 H), 6.70 (m, 2 H), 5.85 (d, 2 H), 3.99–3.86 (m, 4 H), 3.69 (s, 3 H), 1.36–1.28 (m, 4 H), 0.63–0.59 (m, 2 H), 0.39–0.37 (m, 2 H); mass spectroscopy gave MH$^+$=472.2 (calcd exact mass for $C_{29}H_{29}NO_5$= 471.20).

The following compounds were prepared according to the method of Example 330:

| Ex. No. | Structure | Yield [%] | MS [M + H$^+$] | Rf (tlc) | mp [° C.] |
|---|---|---|---|---|---|
| 331 | 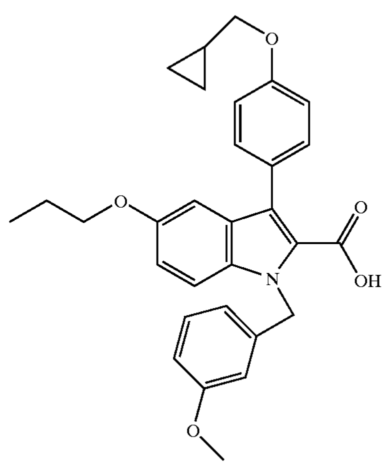 | 30 | 486.2 | 0.52 (2:1 hexane-ethyl acetate) | |
| 332 | 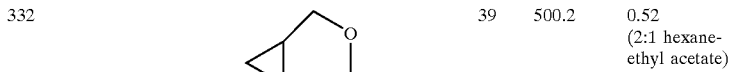 | 39 | 500.2 | 0.52 (2:1 hexane-ethyl acetate) | |

-continued

| Ex. No. | Structure | Yield [%] | MS [M + H⁺] | Rf (tlc) | mp [° C.] |
|---|---|---|---|---|---|
| 333 | 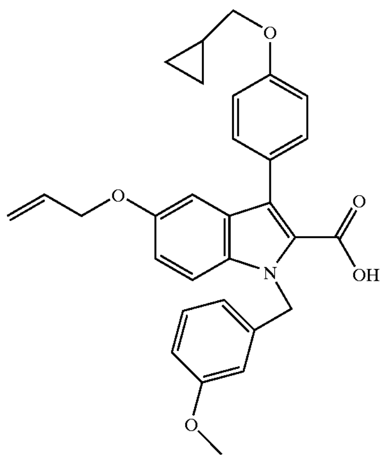 | 51 | 484.2 | 0.52 (2:1 hexane-ethyl acetate) | |
| 334 | 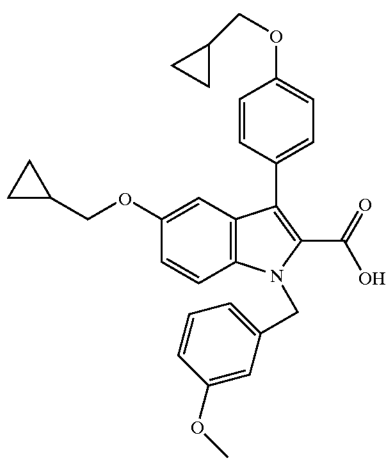 | 29 | 498.2 | 0.52 (2:1 hexane-ethyl acetate) | |
| 335 | 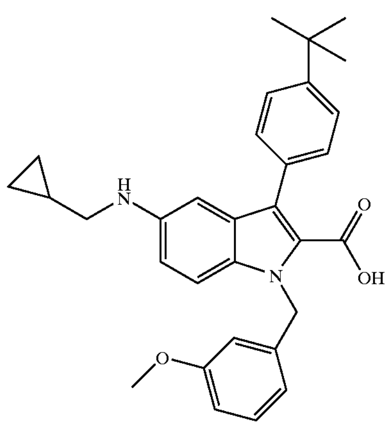 | 55 | 483.3 | | 180–181 |

| Ex. No. | Structure | Yield [%] | MS [M + H⁺] | Rf (tlc) | mp [° C.] |
|---|---|---|---|---|---|
| 336 | 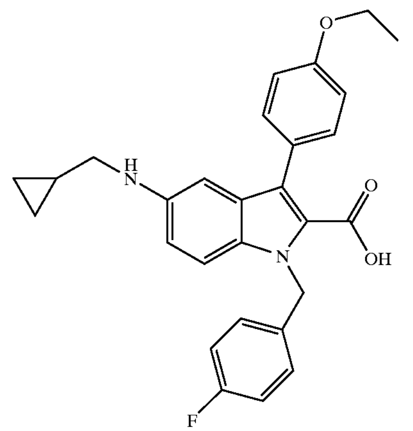 | 48 | 516.2 | 0.17 (2:1 hexane-ethyl acetate) | |

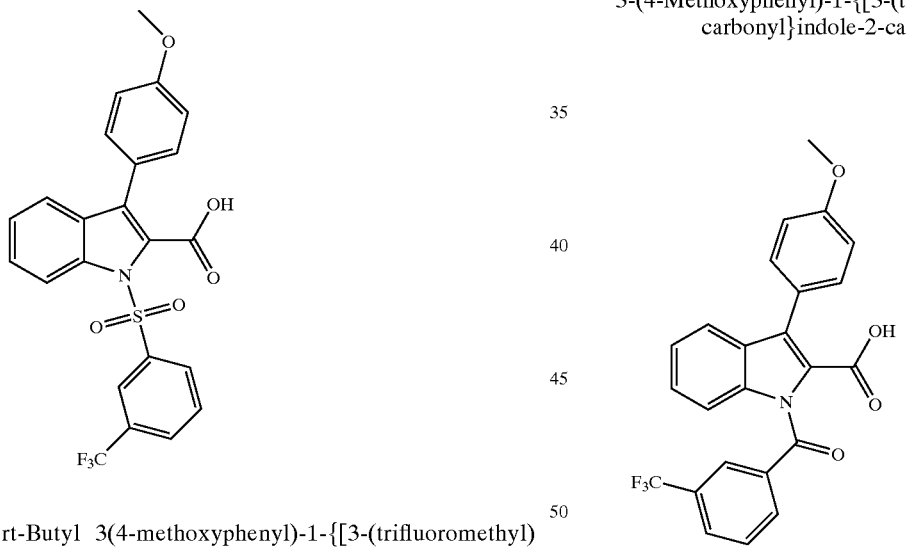

EXAMPLE 337

3-(4-Methoxyphenyl)-1-{[3-(trifluoromethyl)phenyl]sulfonyl}indole-2-carboxylic acid tert-Butyl 3(4-methoxyphenyl)-1-{[3-(trifluoromethyl)phenyl]sulfonyl}indole-2-carboxylate (Example 27, 45 mg, 0.085 mmol) was dissolved in trifluoroacetic acid (0.4 mL). The resulting mixture was allowed to stir for 5 minutes. The reaction mixture was treated with a saturated aqueous sodium bicarbonate solution and then extracted with ethyl acetate (3×4 mL). The combined organic extracts were dried over anhydrous magnesium sulfate and concentrated in vacuo to afford 3-(4-methoxyphenyl)-1-{[3-(trifluoromethyl)phenyl]sulfonyl}indole-2-carboxylic acid as an oil (17 mg, 42%): ¹H (acetone-d₆) δ 3.70 (s, 3 H), 6.85–6.89 (m, 2 H), 7.20–7.34 (m, 2 H), 7.47 (dd, J=0.6, 8.1 Hz, 1 H), 7.60–7.68 (m, 3 H), 7.83 (br d, 1 H), 8.06 (d, J=8.2 Hz, 1 H), 8.63 (m, 2 H); mass spectroscopy HPLC ES MS m/z (rel abundance) 476 ((M+H)⁺, 48%).

EXAMPLE 338

3-(4-Methoxyphenyl)-1-{[3-(trifluoromethyl)phenyl]carbonyl}indole-2-carboxylic Acid tert-Butyl 3-(4-methoxyphenyl)-1-{[3-(trifluoromethyl)phenyl]carbonyl}indole-2-carboxylate (Example 226, 32 mg, 0.065 mmol) was converted using the method described above for Example 230 afford 3-(4-methoxyphenyl)-1-{[3-(trifluoromethyl)phenyl]carbonyl}indole-2-carboxylic acid as an oil (2 mg, 7%): ¹H NMR (acetone-d₆) 3.84 (s, 1 H), 7.04–7.05 (m, 2 H), 7.32–7.33 (m, 1 H), 7.50–7.52 (m, 4 H), 7.84–7.87 (m, 1 H), 7.99–8.06 (m, 1 H), 8.14–8.19 (m, 1 H), 8.42–8.47 (m, 2 H).

EXAMPLE 339

3-[3-(Cyclopropylmethoxy)phenyl]-1-[(4-fluorophenyl)methyl]indole-2-carboxylic Acid

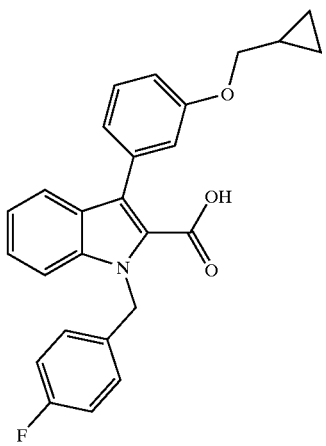

Formic acid (4 mL) was added dropwise to a stirred solution of tert-Butyl 3-[3-(cyclopropylmethoxy)phenyl]-1-[(4-fluorophenyl)methyl]indole-2-carboxylate (Example 72, 431 mg, 0.91 mmol) in dichloromethane (1.0 mL). The reaction was stirred at room temperature for 8 h, then concentrated in vacuo. The resulting solids were placed on a pad of silica gel and purified by chromatography (gradient from 30% ethyl acetate/hexane to 100% ethyl acetate) to afford 3-[3-(cyclopropylmethoxy)phenyl]-1-[(4-fluorophenyl)methyl]indole-2-carboxylic acid (324 mg, 85%): mp=200–202° C., $^1$H NMR acetone-$d_6$) 0.32–0.37 (m, 2 H), 0.55–0.61 (m, 2 H), 1.21–1.31 (m, 1 H), 3.86 (d, J=7.0 Hz, 2 H), 5.90 (s, 2 H), 6.89–6.93 (m, 1 H), 7.00–7.08 (m, 4 H), 7.11–7.16 (m, 2 H), 7.18–7.24 (m, 2 H), 7.30–7.36 (m, 2 H), 7.52–7.58 (m, 2 H), 11.28 (br s, 1 H); mass spectroscopy gave MH$^+$=416 (60%).

The following compounds were prepared in according to the method of Example 339:

| Ex. No. | Structure | Yield [%] | MS [M + H$^+$] | Rf (TLC) | mp [° C.] |
|---|---|---|---|---|---|
| 340 | 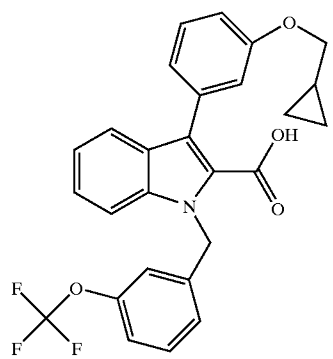 | 77 | 482 | | glass |
| 341 | 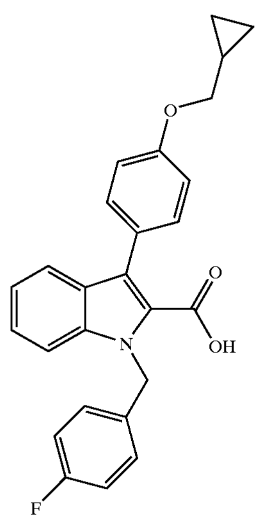 | 86 | 416 | | 197–198 |

-continued

| Ex. No. | Structure | Yield [%] | MS [M + H+] | Rf (TLC) | mp [° C.] |
|---|---|---|---|---|---|
| 342 | 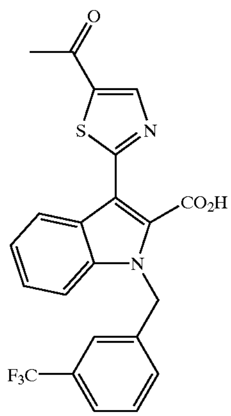 | 52 (over 2 steps) | 445.2 | 0.50 (methanol/ CH$_2$Cl$_2$ 1:9) | |
| 343 | 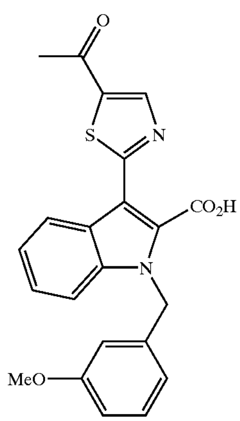 | 47 (2 steps) | 407.2 | | 218 (dec.) |
| 344 | 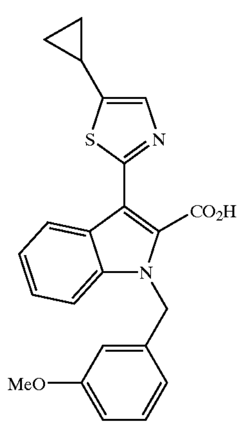 | 5 | 405.2 | 0.42 (methanol/ CH$_2$Cl$_2$ 1:9) | |

| Ex. No. | Structure | Yield [%] | MS [M + H+] | Rf (TLC) | mp [° C.] |
|---|---|---|---|---|---|
| 345 | 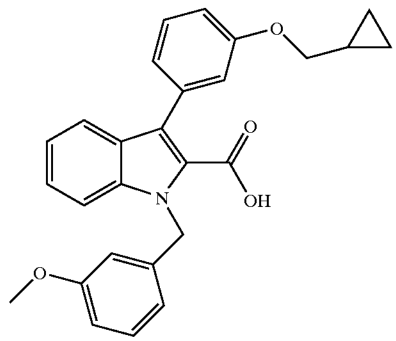 | 76 | 428.1 | | 147–148 |
| 346 | 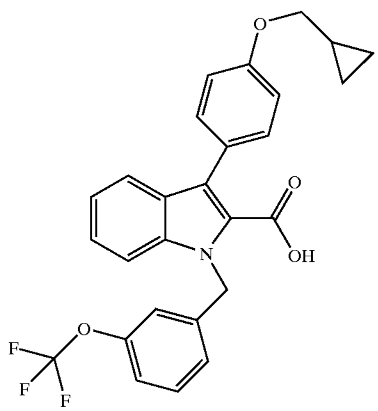 | 82 | 482.2 | | 204–205 |

EXAMPLE 347

5-[(Cyclopropylmethoxy)methyl]-3-(4-ethoxyphenyl)-1-(4-fluorobenzyl)-1H-indole-2-carboxylic acid

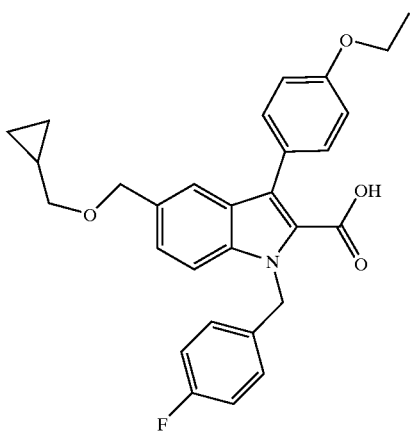

Sodium hydride (60% dispersion in mineral oil, 64 mg, 1.60 mmol) was added in portions to a cooled (0° C.) and stirred solution of ethyl 3-(4-ethoxyphenyl)-1-(4-fluorobenzyl)-5-(hydroxymethyl)-1H-indole-2-carboxylate (Example 141, 480 mg, 1.073 mmol) in tetrahydrofuran (10 mL). The mixture was allowed to warm to room temperature over a period of 1 hour. Cyclopropylmethylbromide (216 mg, 1.60 mmol) was added, and the mixture was stirred for 18 hours. The reaction was partitioned between water and ethyl acetate. The aqueous layer was extracted with ethyl acetate (2x). The combined organic extracts were washed with brine, dried over anhydrous magnesium sulfate, and concentrated in vacuo. The resulting crude oil was purified by flash chromatography on silica gel eluted on a gradient from 100% hexane to 50% ethyl acetate/hexane. The title compound was obtained as a white solid (50 mg, 10%) with a mp=171–173° C. The product had: $^1$H NMR (300 MHz, acetone-$d_6$) δ 7.52 (d, 1 H), 7.48–7.47 (m, 1 H), 7.42–7.38 (m, 2 H), 7.34–7.33 (m, 1 H), 7.22–7.18 (m, 2 H), 7.06–6.98 (m, 4 H), 5.89 (s, 2 H), 4.53 (s, 2 H), 4.10 (q, 2 H), 3.27 (d, 2 H), 1.40 (t, 3 H), 1.13–1.01 (m, 1 H), 0.47–0.42 (m, 2 H), 0.25–0.22 (m, 2 H); mass spectroscopy gave MH$^+$=474.2 (calcd exact mass for $C_{29}H_{28}FNO_4$=473.20).

EXAMPLE 348

5-[2-(Cyclopropylmethoxy)ethyl]-3-(4-ethoxyphenyl)-1-(4-fluorobenzyl)-1H-indole-2-carboxylic acid

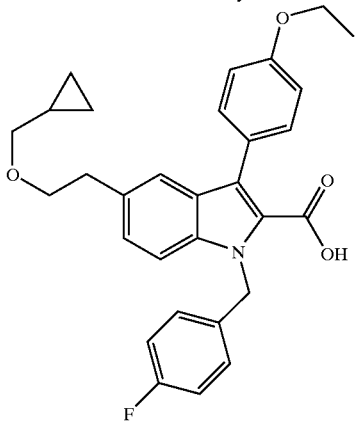

A solution of ethyl 3-(4-ethoxyphenyl)-1-(4-fluorobenzyl)-5-(2-hydroxyethyl)-1H-indole-2-carboxylate (Example 133, 275 mg, 0.596 mmol) in tetrahydrofuran (8+2 mL rinse) was added slowly (5 min) to a cooled suspension of sodium hydride (72 mg, 3.0 mmol) in tetrahydrofuran (2 mL). The reaction was stirred for 1 h and then (bromomethyl)cyclopropane (0.29 mmol, 400 mg, 3.0 mmol) was added. The cold bath was removed and the solution was stirred for 18 h. The reaction was quenched by pouring onto ice water (100 mL) and then the solution was adjusted to pH=7 using 1 M hydrochloric acid. The product was extracted with ethyl acetate (3×70 mL) and then the combined organic extracts were washed with brine, dried over anhydrous magnesium sulfate and concentrated in vacuo. Flash chromatography of the residue over silica gel using 50% ethyl acetate/hexane gave 154 mg (53%) of product. The product had: $^1$H NMR (300 MHz, acetone-D$_6$) δ 7.32–7.50 (m, 4 H), 7.18–7.30 (m, 3 H), 6.97–7.10 (m, 4 H), 5.87 (s, 2 H), 4.09 (q, 2 H), 3.59 (t, 2 H), 3.22 (d, 2 H), 2.88 (t, 2 H), 1.40 (t, 3 H), 0.85–0.10 (m, 1 H), 0.38–0.48 (m, 2 H), 0.13–0.23 (m, 2 H); mass spectroscopy gave MH$^+$=488.0 (exact mass calcd for C$_{30}$H$_{30}$FNO$_4$=487.22).

EXAMPLE 349

1-((1E)-2-Phenylvinyl)-3-(4-methoxyphenyl)indole-2-carboxylate

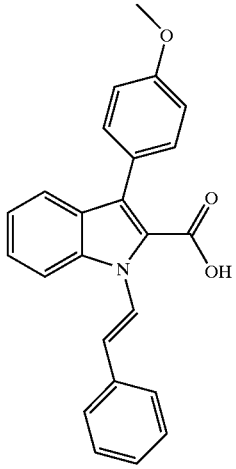

A 60% suspension of sodium hydride in mineral oil (75 mg, 1.85 mmol) was stirred in DMF (5 mL). To this suspension was added ethyl 3-(4-methoxyphenyl)indole-2-carboxylate (Example 105, 500 mg, 1.65 mmol). The resulting mixture was stirred for 30 min at RT before (R)-styrene oxide was added. The resulting mixture was then heated to 120° C. for 18 h. The reaction was cooled to RT, diluted with water, and washed with ethyl acetate. The aqueous layer was collected, acidified with hydrochloric acid, and the resulting suspended solid collected by filtration to yield 311 mg (51%) of a solid. $^1$H NMR (300 MHz, DMSO-d$_6$) δ 13.00 (s, 1H), 8.02 (d, J=14.9 Hz, 1H), 7.87–7.82 (m, 1H), 7.63–7.56 (m, 2H), 7.52–7.36 (m, 6H), 7.36–7.25 (m, 2H), 7.07–7.00 (m, 2H), 6.91 (d, J=14.9 Hz, 1H), 3.81 (s, 3H).

EXAMPLE 350

Sodium 3-[4-(cyclopropylsulfanyl)phenyl]-1-[3-(trifluoromethyl)benzyl]-1H-indole-2-carboxylate

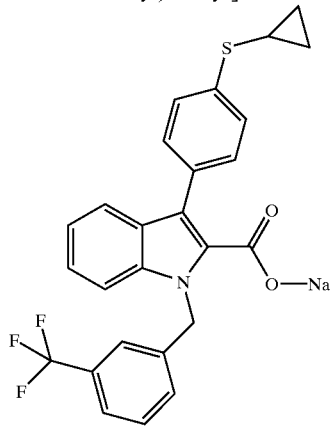

To a slurry of sodium hydride (10.8 mg, 0.428 mmol) in 5 ml tetrahydrofuran, was added a solution of 3-(4-Cyclopropylthiophenyl)-1-{[3-(trifluoromethyl)phenyl]methyl}indole-2-carb-oxylic acid (Example 77, 100 mg, 0.214 mmol) in tetrahydrofuran (5 mL). The reaction mixture was stirred at rt for 30 min and filtered to give a 210 mg (100%) of product. $^1$H NMR (DMSO-D$_6$, δ=2.48): 7.78 (s, 1H), 7.46–7.61 (m, 6 H), 7.29–7.35 (m, 3H), 6.95–7.05 (m, 2H), 5.71(s, 2H), 2.47–2.49 (m, 1H), 1.04–1.15 (m, 2H), and 0.58–0.63 (m, 2H).

EXAMPLE 351

Sodium 3-(4-tert-butylphenyl)-5-[2-(cyclopropylmethoxy)ethyl]-1-(3-methoxybenzyl)-1H-indole-2-carboxylate

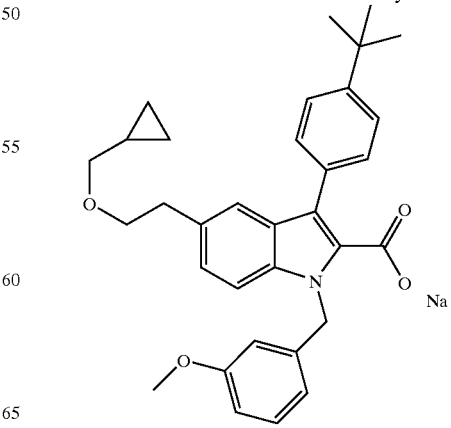

Sodium hydride (6.8 mg, 0.28 mmol) was added to a cooled (0° C.) and stirred solution of 3-(4-tert-butylphenyl)-5-[2-(cyclopropylmethoxy)ethyl]-1-(3-methoxybenzyl)-1H-indole-2-carboxylic acid (Example 275, 145 mg, 0.283 mmol) in tetrahydrofuran (10 mL). The cold bath was removed and the mixture was stirred 2 h. Concentration in vacuo left 148 mg (98%) of the desired product. The product had: $^1$H NMR (300 MHz, acetone-D$_6$) δ 7.63 (d, 2 H), 7.47 (s, 1 H), 7.34 (d, 2 H), 7.18 (d, 1 H), 7.09(dd, 1 H), 6.96 (dd, 1 H), 6.91 (s, 1 H), 6.85 (d, 1 H), 6.69 (dd, 1 H), 5.75 (s, 2 H), 3.66 (s, 3 H), 3.56 (t, 2 H), 3.22 (d, 2 H), 2.84 (t, 2 H), 1.32 (s, 9 H), 0.89–1.05 (m, 1 H), 0.35–0.45 (m, 2 H), 0.07–0.17 (m, 2 H); mass spectroscopy gave M+2H$^+$–Na= 512.2 (calcd exact mass for C$_{33}$H$_{36}$NNaO$_4$=533.25).

EXAMPLE 352

Potassium 3-(4-cyclopropylthiophenyl)-1-{[3-(trifluoromethyl)-phenyl]methyl}indole-2-carboxylate

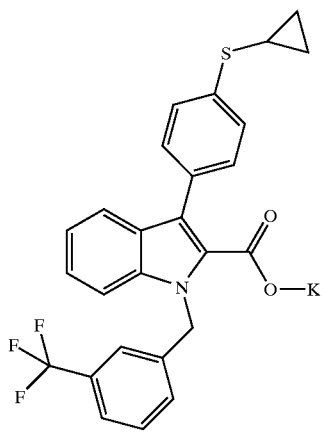

A solution of 10% potassium hydroxide in methanol:water (1:9, 30 mL) was added to a stirred solution of ethyl 3-(4-cyclopropylthiophenyl)-1-{[3-(trifluoromethyl)-phenyl]methyl}indole-2-carboxylate (Example 262.5 g, 3 mmol) in tetrahydrofuran (3 mL). The reaction was warmed to 50° C. and stirred 18 h. After cooling, the reaction mixture was filtered to leave 50 mg of potassium 3-(4-cyclopropylthiophenyl)-1-{[3-(trifluoromethyl)-phenyl]methyl}indole-2-carboxylate. $^1$H NMR (DMSO-D$_6$) δ 7.80 (s, 1 H), 7.69–7.60 (m, 11 H), 5.69 (s, 2 H), 2.27–2.31 (m, 1 H), 1.04–1.10 (m, 2 H), and 0.58–0.63 (m, 2 H).

EXAMPLE 353

3–[4-(Cyclopropylsulfonyl)phenyl]-1-{[3-(trifluoromethyl)phenyl]methyl}indole-2-carb-oxylic acid

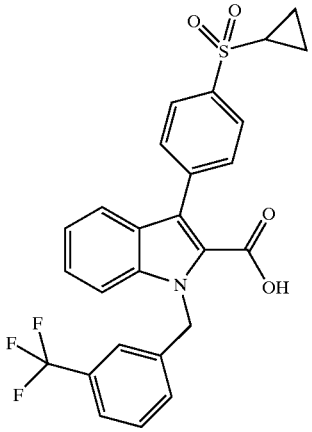

To a solution of 3-(4-Cyclopropylthiophenyl)-1-{[3-(trifluoromethyl)phenyl]methyl}indole-2-carb-oxylic acid (Example 262) 100 mg, 0.214 mmol) in 10 mL CHCl$_3$, m-CPBA (162 mg, 0.47 mmol) was added at –10° C. The reaction was stirred for 2 h and then warmed to rt. The reaction was diluted with dichloromethane and washed with water and brine. The organic layer was dried over anhydrous sodium sulfate and concentrated in vacuo. Flash chromatography of the residue over silica gel using ethyl acetate/hexane gave 70 mg (65%) of product. $^1$H NMR (DMSO-D$_6$) δ 13.22 (br s, 1H), 7.93 (d, J=8.7 Hz, 2H), 7.14–7.12 (m, 10 H), 5.94 (s, 2H), 2.89–2.93 (m, 1H), and 1.06–1.16 (m, 4H). MS [M–H]=498 (HPLC/MS).

EXAMPLE 354

3-(4-tert-Butylphenyl)-5-[(cyclopropylmethyl)amino]-1-(3-methoxybenzyl)-1H-indole-2-carboxylic acid hydrochloride

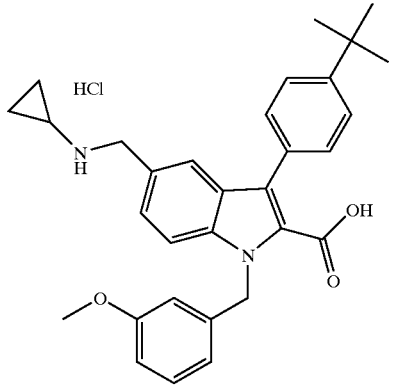

Ethyl 3(4-tert-butylphenyl)-5-[(cyclopropylmethyl)amino]-1-(3-methoxybenzyl)-1H-indole-2-carboxylate (Example 165, 420 mg, 0.84 mmol) was reacted using the method described for Example 237. After hydrolysis the solution was adjusted to pH=1 using 1 M hydrochloric acid. The resulting precipitate was collected by filtration, using ethyl ether to wash, to afford 250 mg, (59%) of product. The product had: $^1$H NMR (300 MHz, CD$_3$OD) δ 7.71 (d, 1 H), 7.39–7.59 (m, 6 H), 7.16 (dd, 1 H), 6.72–6.80 (m, 1 H), 6.61–6.69 (m, 2 H), 5.84 (s, 2 H), 4.36 (s, 2 H), 3.71 (s, 3 H), 2.68–2.80 (m, 1 H), 1.41 (s, 9 H), 1.15–1.25 (m, 1 H), 0.80–0.96 (m, 4 H); mass spectroscopy gave MH$^+$–HCl= 483.3 (calcd exact mass for C$_{31}$H$_{34}$N$_2$O$_3$=482.26).

EXAMPLE 355

5-[(Cyclopropylmethyl)amino]-3-(4-ethoxyphenyl)-1-(4-fluorobenzyl)-1H-indole-2-carboxylic acid hydrochloride

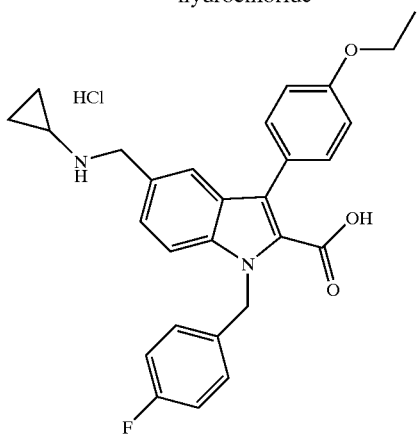

Ethyl 5-[(cyclopropylmethyl)amino]-3-(4-ethoxyphenyl)-1-(4-fluorobenzyl)-1H-indole-2-carboxylate (Example 166, 470 mg, 0.97 mmol) was converted to 430 mg (90%) of product using the method described for Example 238. The product had: $^1$H NMR (300 MHz, CD$_3$OD) δ 7.70 (d, 1 H), 0.87 (d, 1 H), 7.34–7.44 (m, 3 H), 7.07–7.16 (m, 2 H), 6.92–7.03 (m, 4 H), 5.82 (s, 2 H), 4.35 (s, 2 H), 4.08 (q, 2 H), 2.68–2.77 (m 1 H), 1.41 (t, 3 H), 1.34–1.43 (m, 1 H), 0.83–0.94 (m, 4 H).

EXAMPLE 356

(3-(4-Methoxyphenyl)-1-{[3-(trifluoromethyl)phenyl]methyl}indol-2-yl)-N-(phenylsulfonyl)carboxamide

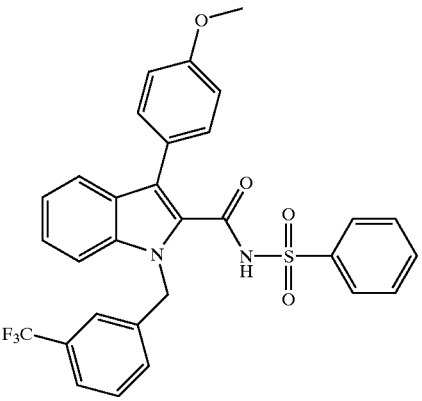

Benzenesulfonamide (155 mg, 1.0 mmol), 1-(3-dimethylaminopropyl)-3-ethyl-carbodiimide hydrochloride (96 mg, 0.50 mmol), and 4-(dimethylamino)pyridine (20 mg, 0.16 mmol) were added to a stirred solution of 3-(4-methoxyphenyl)-1-{[3-(trifluoromethyl)phenyl]methyl}indole-2-carboxylic acid (Lit: WO94/14434, 213 mg, 0.50 mmol in dichloromethane (5 mL). The resulting mixture was stirred for 18 h and then quenched with hydrochloric acid (1N). The mixture was extracted with ethyl acetate (2×20 mL) and the combined organic extracts was washed with brine, dried over anhydrous sodium sulfate, and concentrated in vacuo. The residue was purified with silica gel flash chromatography using hexane/ethyl acetate (2/1) as the eluant to give a white solid. It was further purified by trituration with diethyl ether to afford (3-(4-methoxyphenyl)-1-{[3-(trifluoromethyl)phenyl]methyl}indol-2-yl)-N-(phenylsulfonyl) carboxamide as a white solid (220 mg, 78%): mp>250° C.; MS (electrospray, MH$^+$) calcd for C$_{30}$H$_{24}$F$_3$N$_2$O$_4$S 565.1, found 565.0; $^1$H NMR (DMSO-d$_6$) δ 7.51–8.31 (m, 17 H), 7.03 (br s, 1H), 6.17 (s, 2H), 4.36 (s, 3H).

The following compounds were prepared according to the method of Example 356:

| Ex. No. | Structure | Yield [%] | MS [M + H$^+$] | Rf (TLC) | mp [° C.] |
|---|---|---|---|---|---|
| 357 | 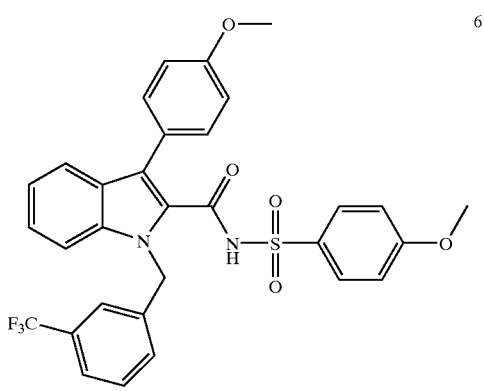 | 66 | 595 | | |

| Ex. No. | Structure | Yield [%] | MS [M + H⁺] | Rf (TLC) | mp [° C.] |
|---|---|---|---|---|---|
| 358 | 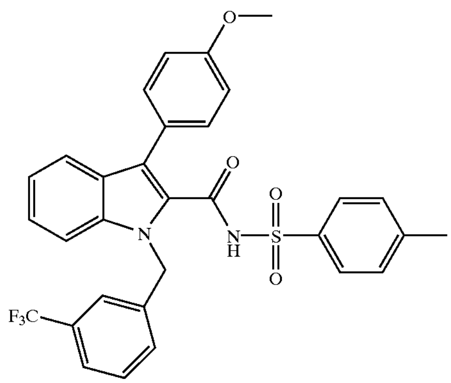 | 33 | 579 | | 162 |
| 359 | 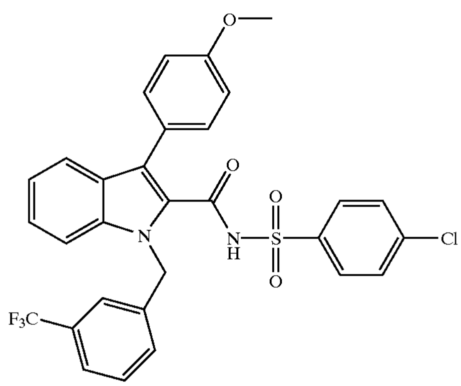 | 16 | 599 | | 166 |

EXAMPLE 360

2,2,2-Trifluoro-1-{3-(4-methoxyphenyl)-1-[3-(trifluoromethyl)benzyl]-1H-indol-2-yl}ethanone

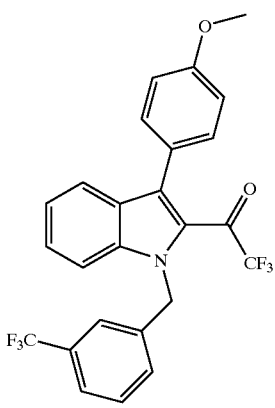

Dess-Martin reagent (39 mg, 0.09 mmol) was added to a stirred solution of 2,2,2-trifluoro-1-(3-(4-methoxphenyl)-1-{[3-(trifluoromethyl)phenyl]methyl}indol-2-yl)ethan-1-ol (Example 219, 40 mg, 0.08 mmol) in dichloromethane (2 mL). The resulting solution was stirred for 2 hours, more oxidant was added, and then the mixture was left stirring for 18 h. The reaction was quenched with a mixed aqueous solution of saturated sodium bicarbonate and saturated sodium thio sulfate (1:1, 10 mL), and the mixture was extracted with ethyl acetate (2×10 mL). The combined organic extracts were washed with water, and brine, dried over anhydrous magnesium sulfate, and concentrated in vacuo. Silica gel flash chromatography using hexane/ethyl acetate (4/1) as the eluant gave 2,2,2-trifluoro-1-(3-(4-methoxyphenyl)-1-{[3-(trifluoromethyl)phenyl]methyl}indol-2-yl)ethan-1-one as an orange oil (27 mg, 70%): $^1$H NMR (300 MHz, DMSO-$d_6$) δ 7.76 (d, 1H), 7.47–7.62 (m, 4H), 7.20–7.45 (m, 5H), 7.05 (d, 2H), 5.76 (s, 2H); MS (MH⁺) calcd for $C_{25}H_{18}F_6NO_2$: 478., found: 478.

Biological Protocol

The activity of a given compound in binding to PPAR-γ can be assayed routinely according to procedures known in the art. See, e.g., Nichols, et al., *Anal. Biochem.*, 257 (2), (1998), 112–119, 114; Brown, et al., *Chem. & Bio.*, 4 (12), (1997) 909–918. The PPAR-γ binding assay described below was used to determine the PPAR-γ binding activities of the compounds of the invention.

Compounds were tested for their ability to bind to PPARγ using a spin plate assay (gel filtration binding assay). The PPARγ ligand binding domain (LBD) (amino acids 195–475) was expressed in *Escherichia coli* as polyHis-tagged fusion proteins and purified by means of an epitope tag. The LBD (210 ng per well) was then incubated in 96-well microtiter plates for two hours at room temperature with a constant concentration of radioligand (8rM per well) ([$^3$H]BRL 49653) and four concentrations (1 nM, 10 nM, 100 nM and 1 μM) of test compound. Each compound was tested in triplicate. Fifty-micloliter aliquots of each well were loaded into each well of an equilibrated 96-well gel filtration plate (Edge Biosystems 31909) and placed on top of a pre-labeled Wallac plate (1450–515). The plates were centrifuged (Beckman GS-6R) at 2500 rpm for 5 minutes, 170 μl Scitisafe® scintillation fluid (Fisher) was added to each well, the plates were sealed, and after 1 hour, were counted in a Wallac MicroBeta counter. The amount of nonspecific binding, as assessed by control wells containing 10 μM of the corresponding unlabeled ligand, was subtracted from each data point. For each compound tested, the data was averaged and plots of ligand concentration versus CPM of radioligand bound were constructed. Apparent $IC_{50}$ values were estimated from nonlinear least-squares fit of the data assuming simple competitive binding.

The compounds of the invention were found to inhibit [$^3$H]BRL 49653 binding at PPAR-γ with an $IC_{50}$ of 10 μM or less. $IC_{50}$ ranges of compounds of the present invention in the PPAR-γ Binding Assay are given in the table below.

Activity of Exemplified Compounds

| $IC_{50}$ between 10 nM and 10 μM | $IC_{50}$ between 100 pM and 9.99 nM |
| --- | --- |
| 230 | 231 |
| 233 | 232 |
| 238 | 234 |
| 239 | 235 |
| 241 | 236 |
| 242 | 237 |
| 245 | 240 |
| 246 | 243 |
| 247 | 244 |
| 248 | 249 |
| 251 | 250 |
| 252 | 253 |
| 254 | 257 |
| 255 | 258 |
| 256 | 259 |
| 267 | 260 |
| 269 | 261 |
| 270 | 262 |
| 274 | 263 |
| 276 | 264 |
| 278 | 265 |
| 279 | 266 |
| 280 | 268 |
| 281 | 271 |
| 282 | 272 |
| 286 | 273 |
| 291 | 275 |
| 292 | 277 |
| 293 | 283 |
| 294 | 284 |
| 295 | 287 |
| 296 | 288 |
| 298 | 289 |
| 300 | 290 |
| 301 | 297 |
| 302 | 299 |
| 303 | 304 |
| 306 | 305 |
| 310 | 307 |
| 318 | 308 |
| 319 | 311 |
| 322 | 312 |
| 323 | 313 |
| 324 | 314 |
| 325 | 315 |
| 326 | 316 |
| 327 | 317 |
| 328 | 320 |
| 329 | 321 |
| 333 | 330 |
| 337 | 331 |
| 338 | 332 |
| 355 | 334 |
| 358 | 335 |

-continued

Activity of Exemplified Compounds

| $IC_{50}$ between 10 nM and 10 μM | $IC_{50}$ between 100 pM and 9.99 nM |
| --- | --- |
| 360 | 336 |
| | 339 |
| | 340 |
| | 341 |
| | 342 |
| | 343 |
| | 344 |
| | 345 |
| | 346 |
| | 347 |
| | 348 |
| | 349 |
| | 350 |
| | 351 |
| | 352 |
| | 353 |
| | 354 |
| | 356 |
| | 357 |
| | 359 |

The entire disclosures of all applications, patents and publications cited above are hereby incorporated by reference.

The invention may be embodied in other specific forms without departing from the spirit or essential characteristics thereof. The foregoing examples are included by way of illustration only. Accordingly, the scope of the invention is limited only by the scope of the appended claims.

What is claimed is:

1. A compound selected from the group consisting of

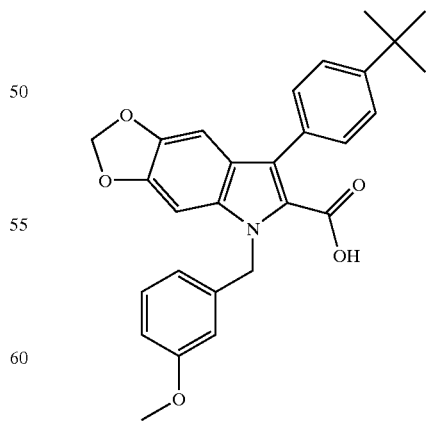

and pharmaceutically acceptable salts thereof.

2. A compound selected from the group consisting of
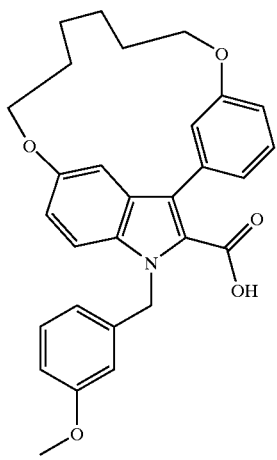
and pharmaceutically acceptable salts thereof.
3. A compound selected from the group consisting of
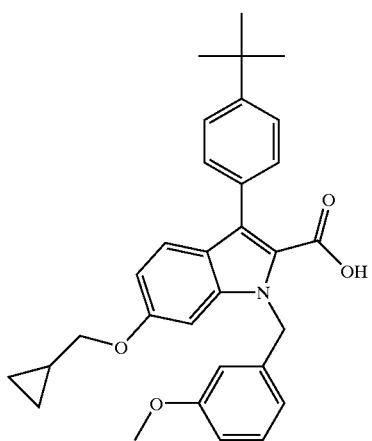
and pharmaceutically acceptable salts thereof.
4. A compound selected from the group consisting of
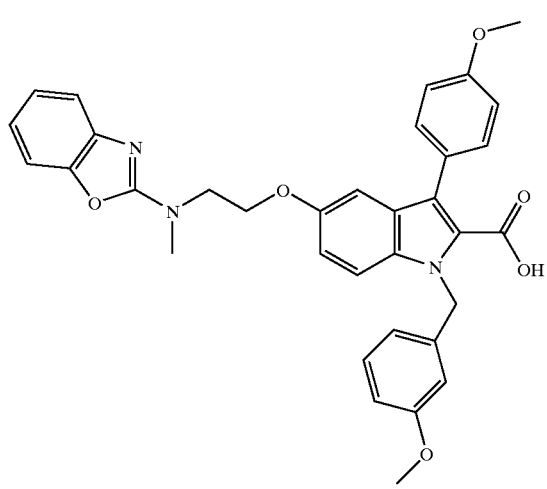
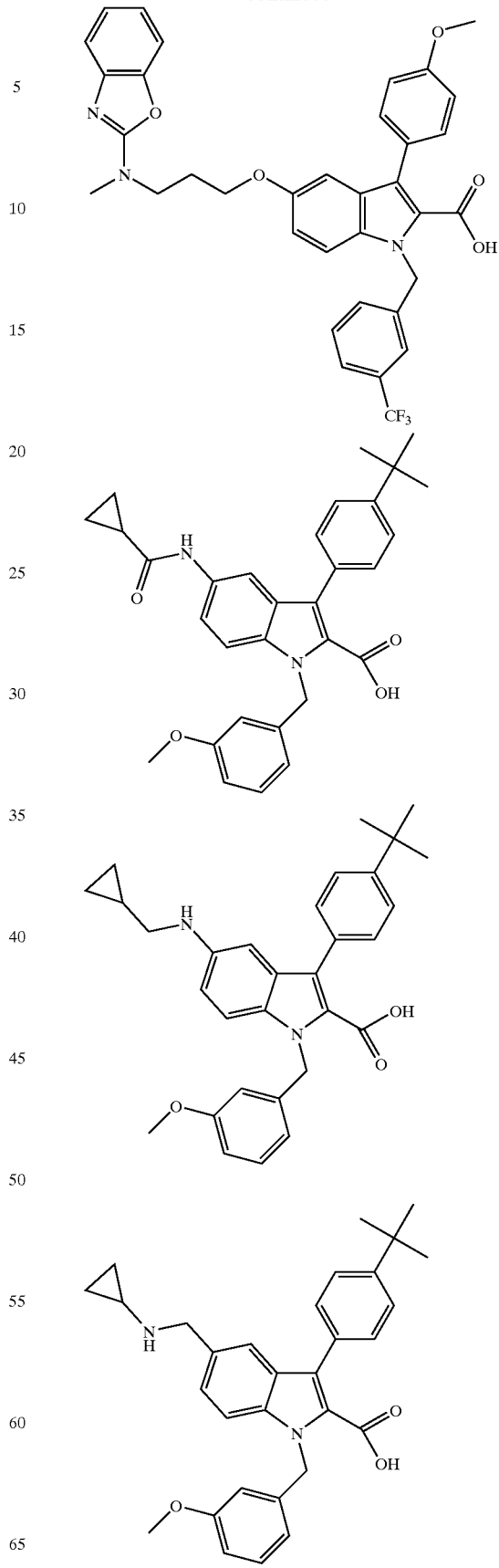

271
-continued
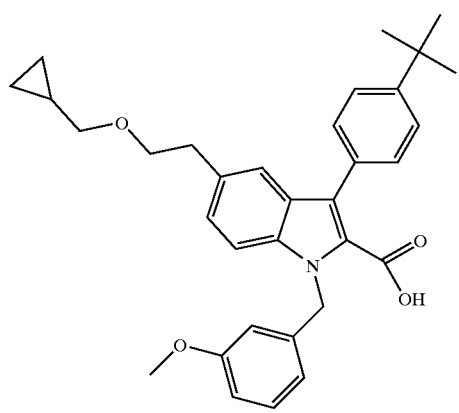
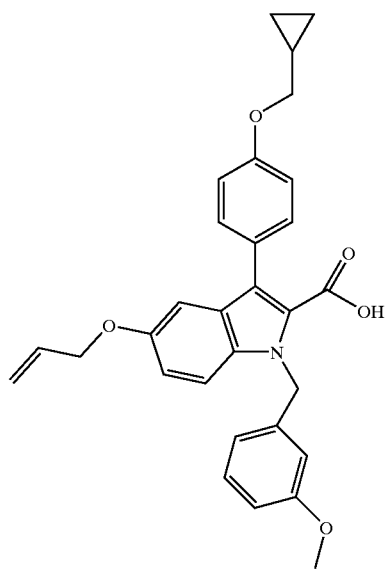
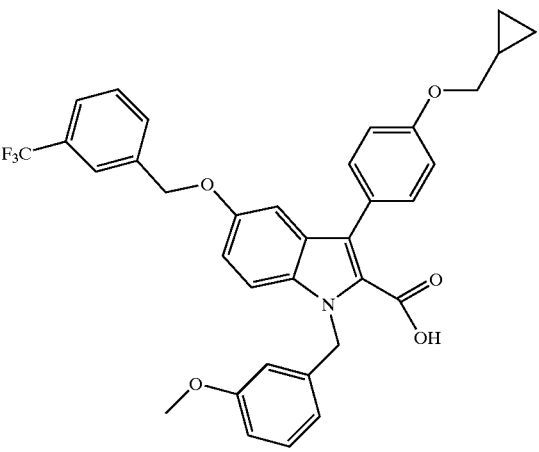
272
-continued
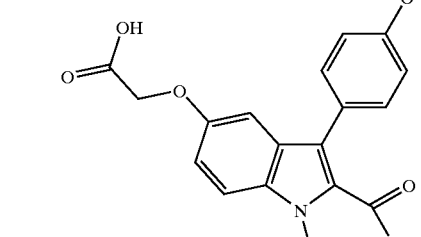
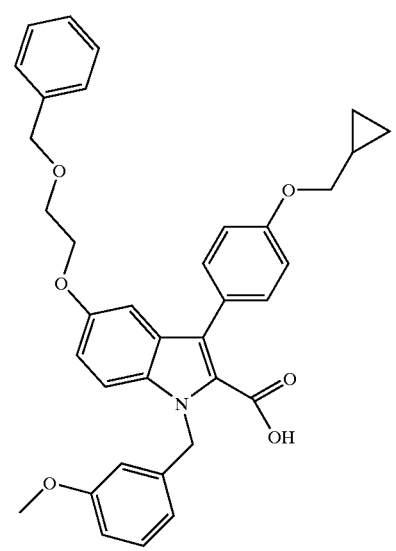
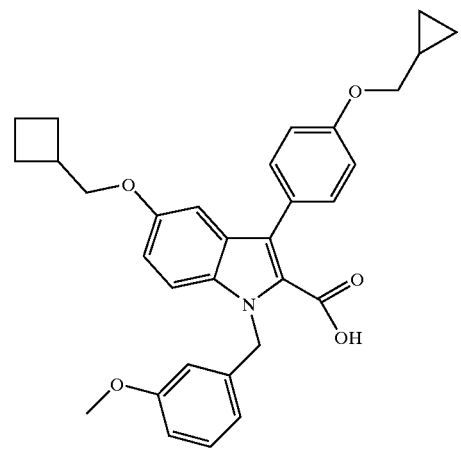

273
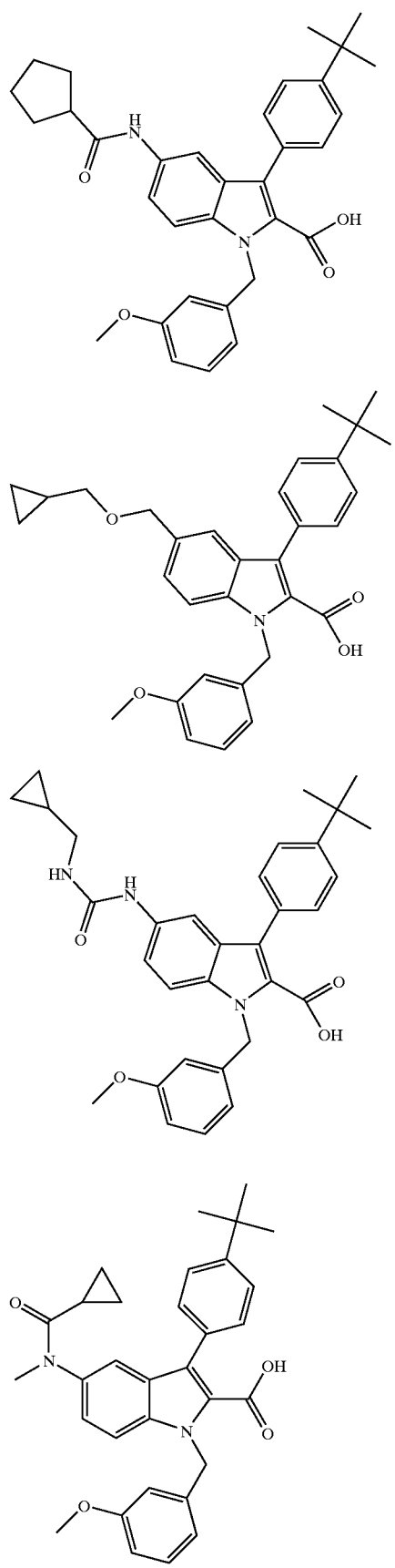
274
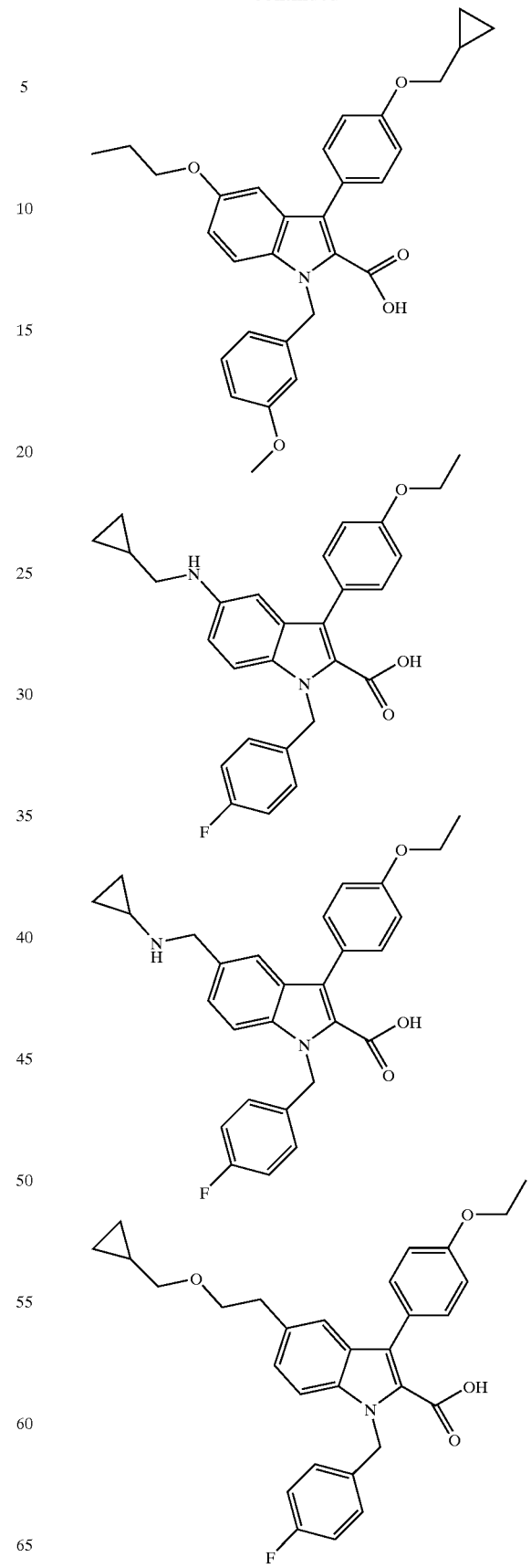

275
-continued
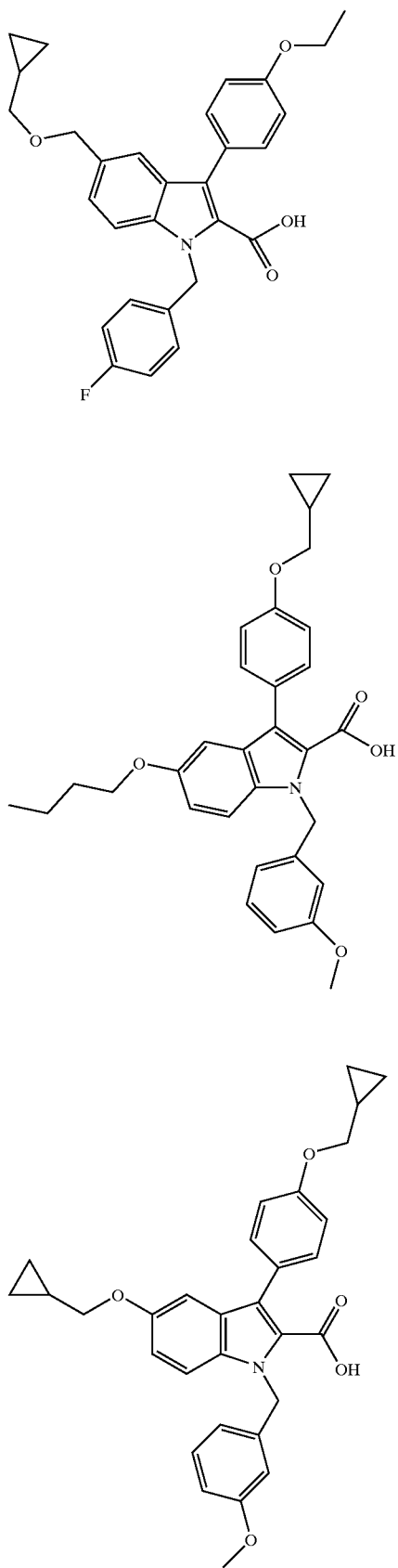
276
-continued
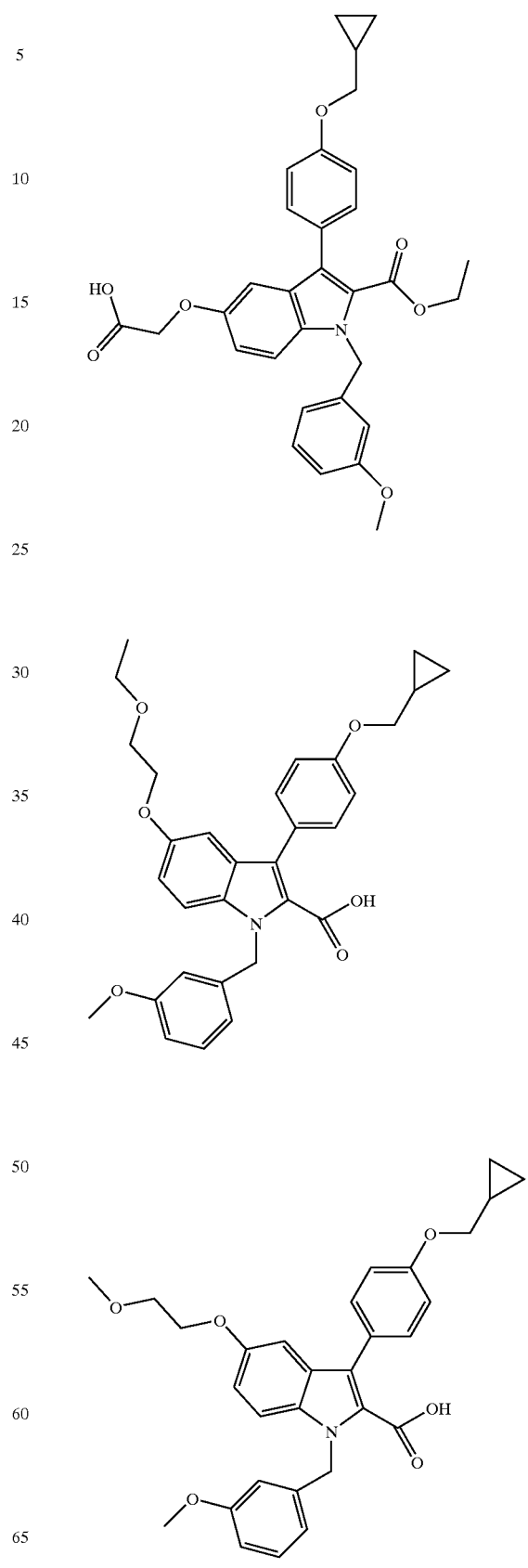

277
-continued
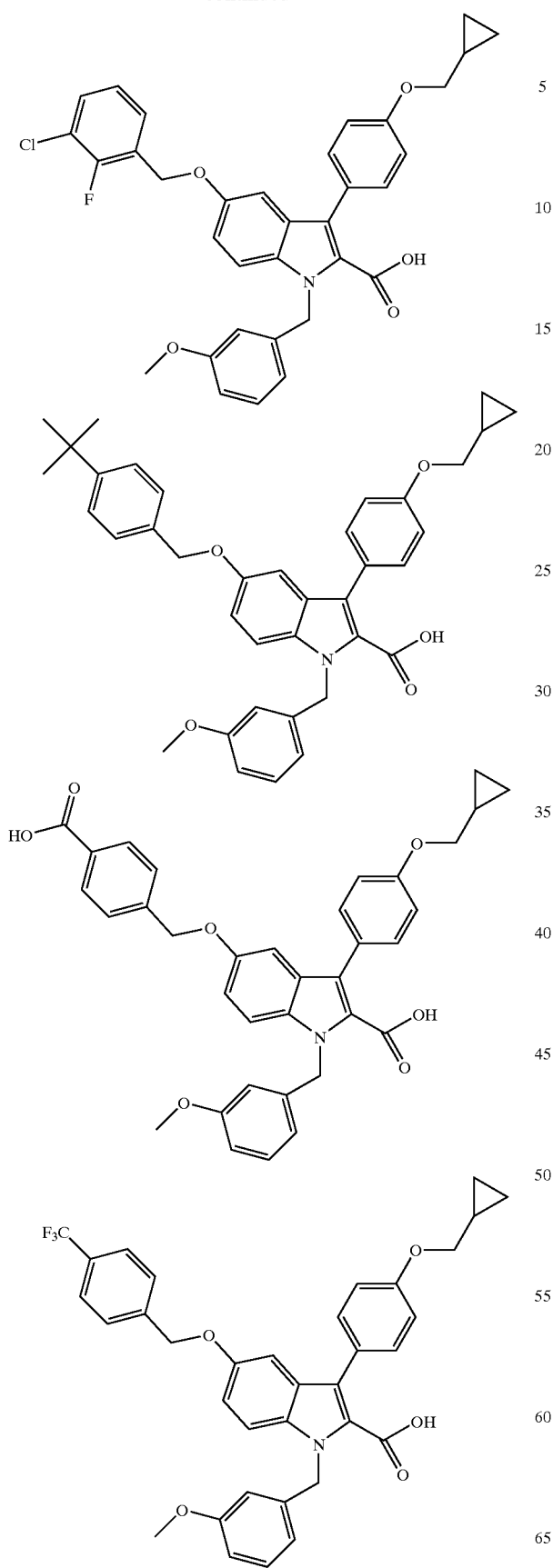
278
-continued
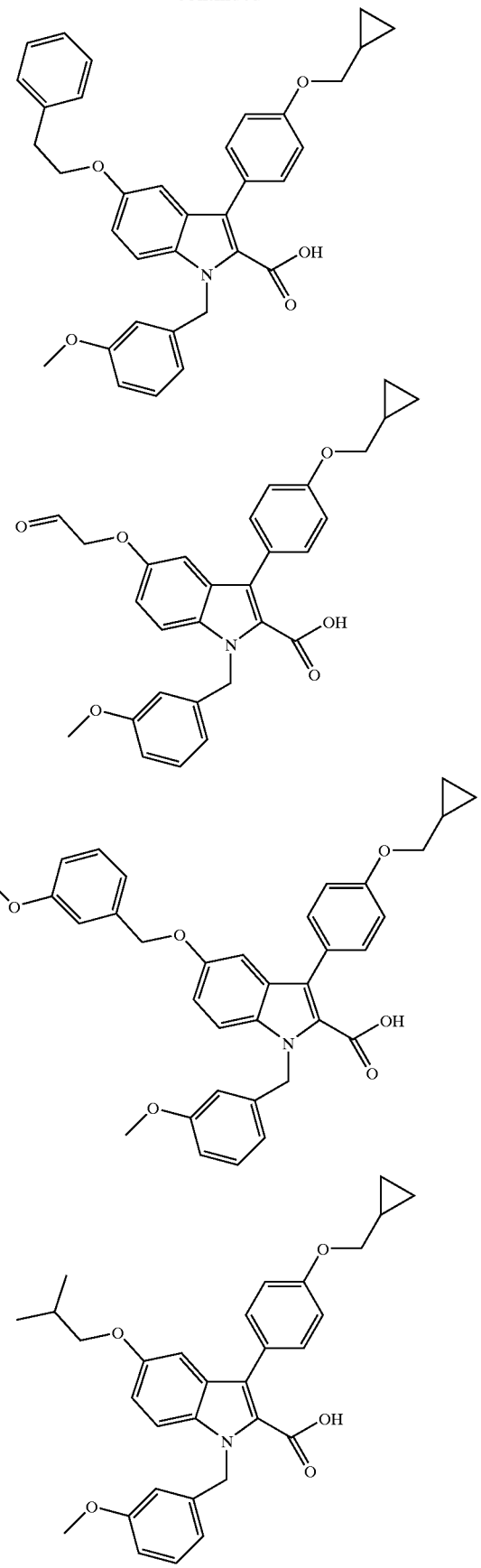

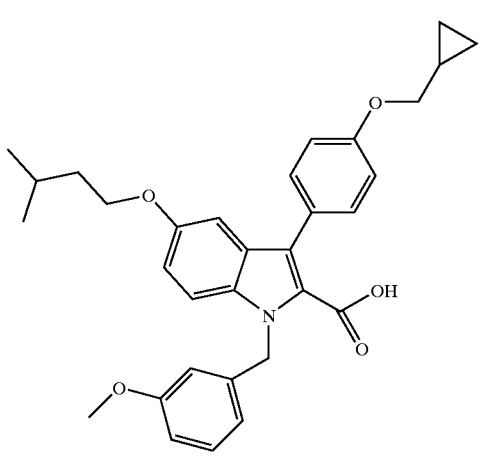
and pharmaceutically acceptable salts thereof.
5. A compound selected from the group consisting of
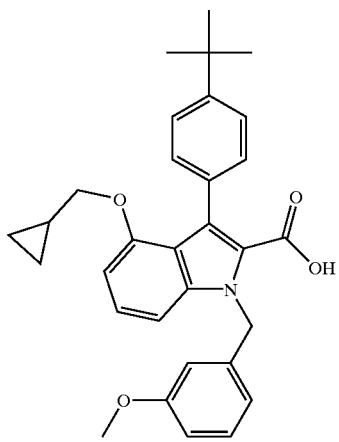
and pharmaceutically acceptable salts thereof.
6. A compound selected from the group consisting of
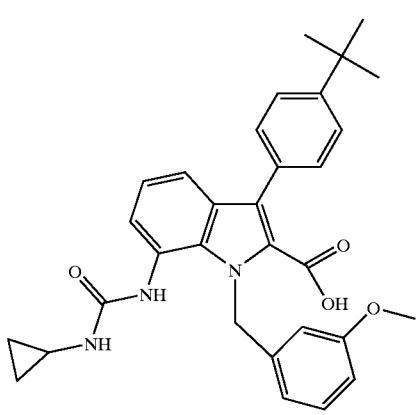
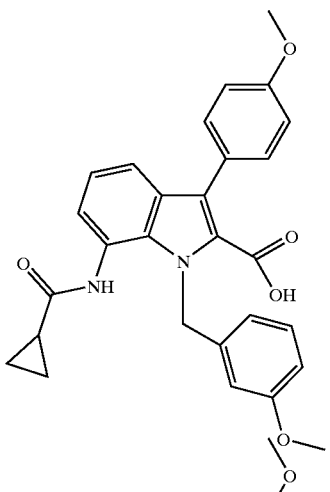
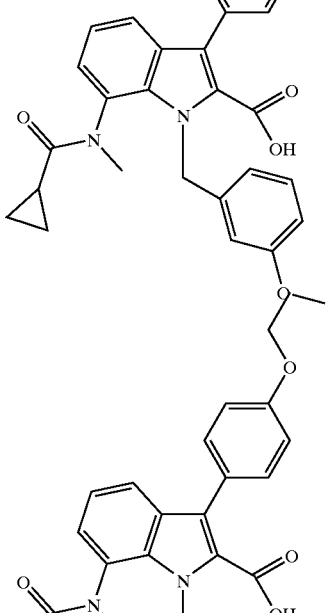
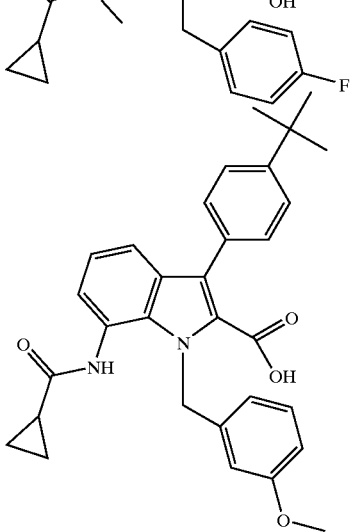

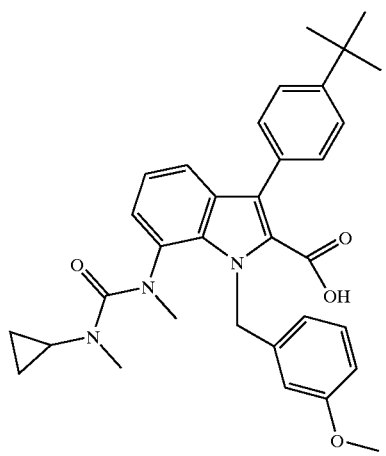
and pharmaceutically acceptable salts thereof.
7. A compound selected from:
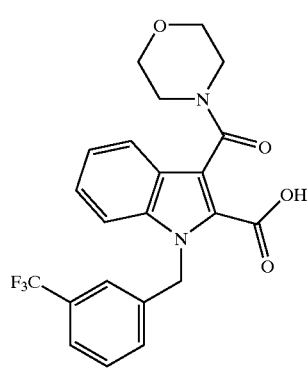 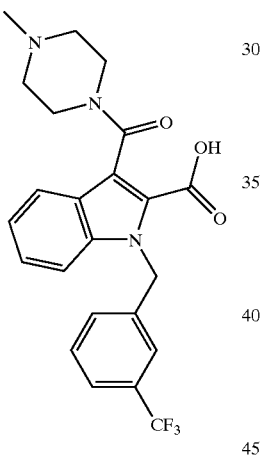
and pharmaceutically acceptable salts thereof.
8. A compound selected from the group consisting of:
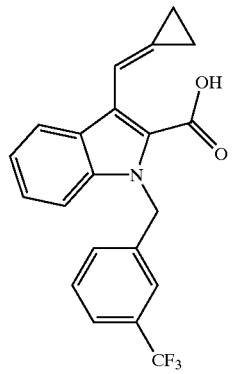 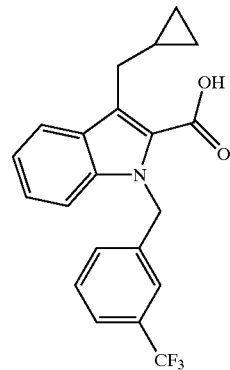
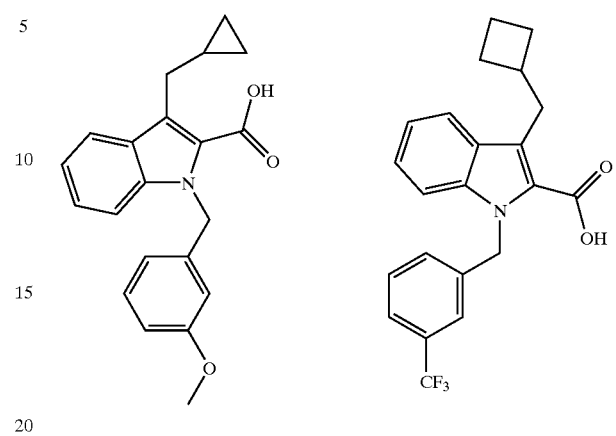
and pharmaceutically acceptable salts thereof.
9. A compound selected from:
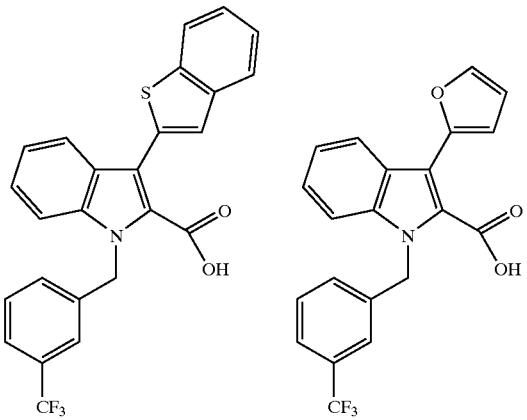
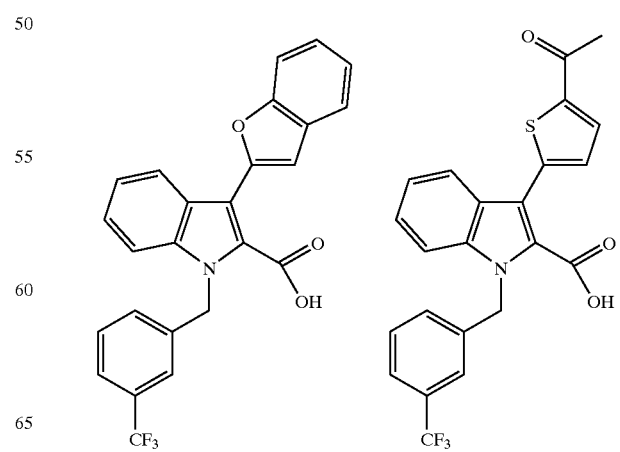

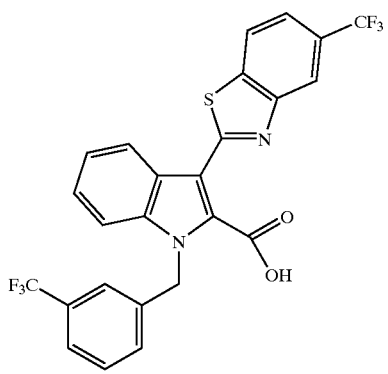
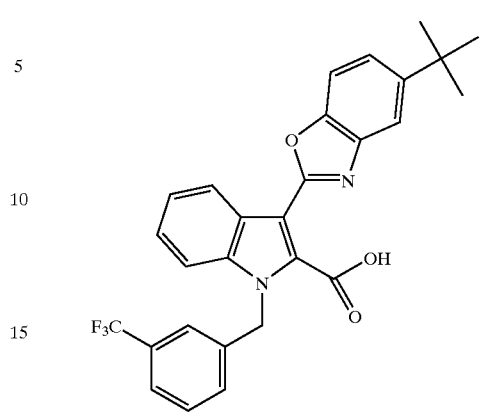
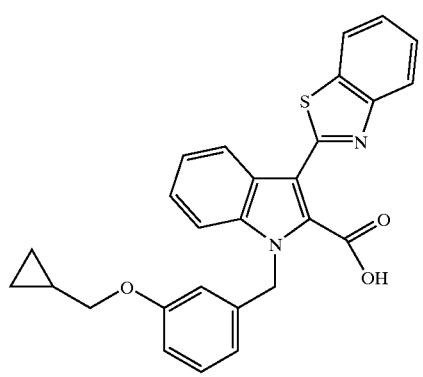
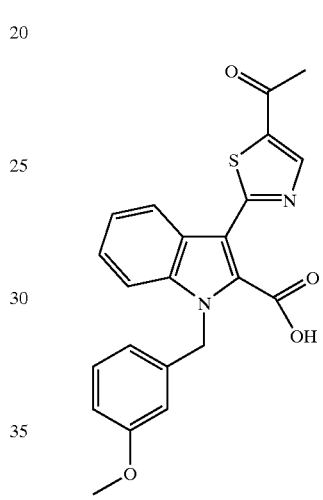
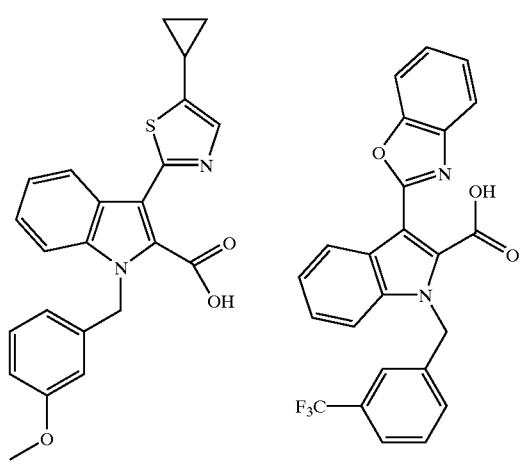
and pharmaceutically acceptable salts thereof.
10. A compound selected from:
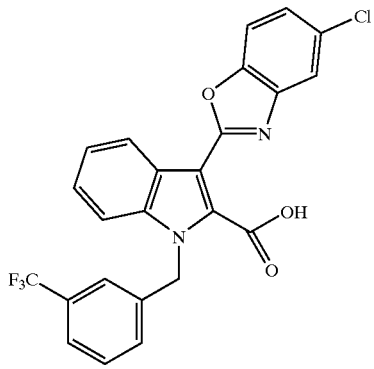
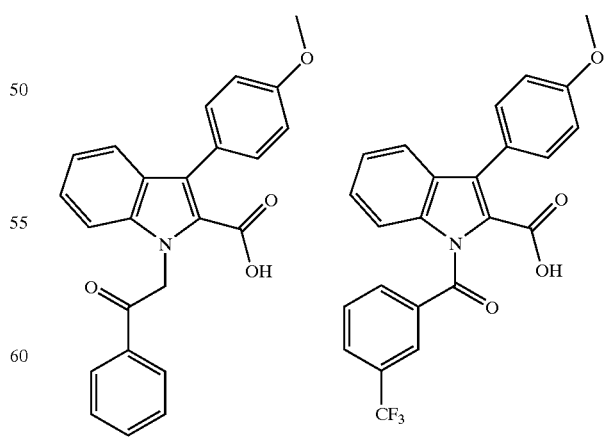
and pharmaceutically acceptable salts thereof.

11. A compound selected from:
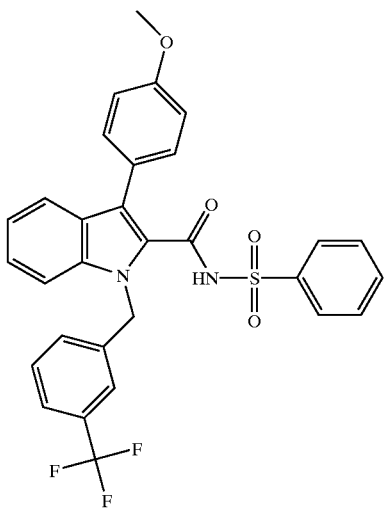
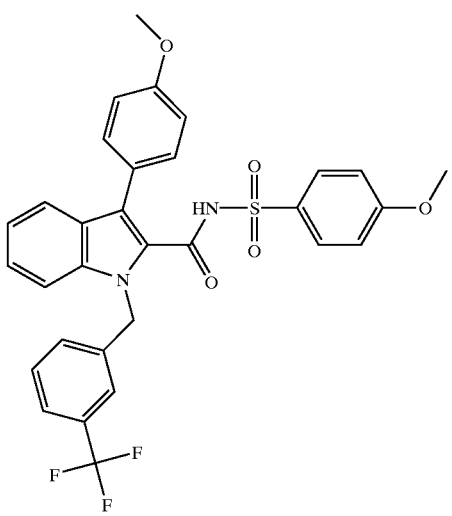
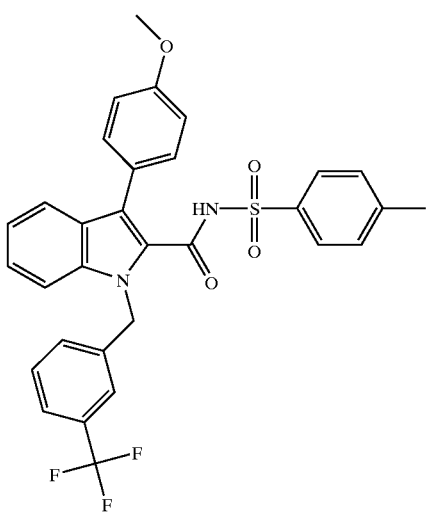
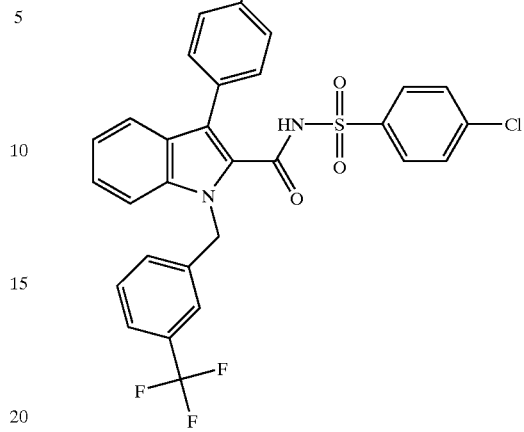
and pharmaceutically acceptable salts thereof.
12. A compound selected from:
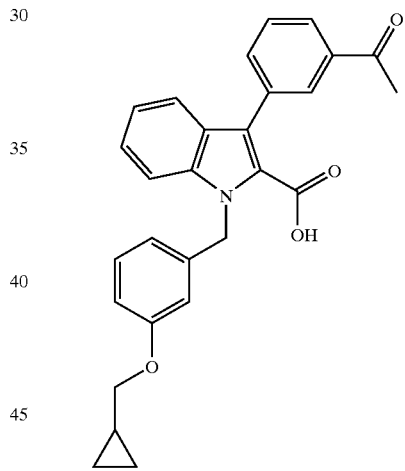
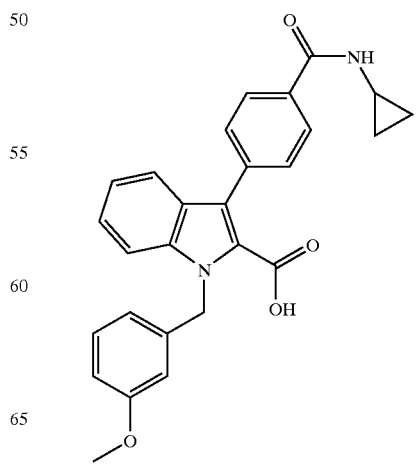

287
-continued
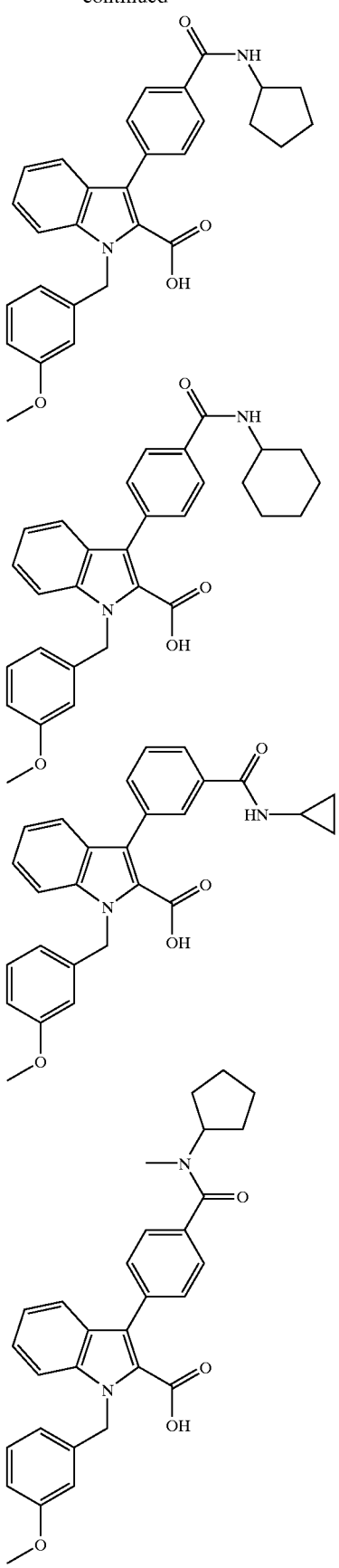
288
-continued
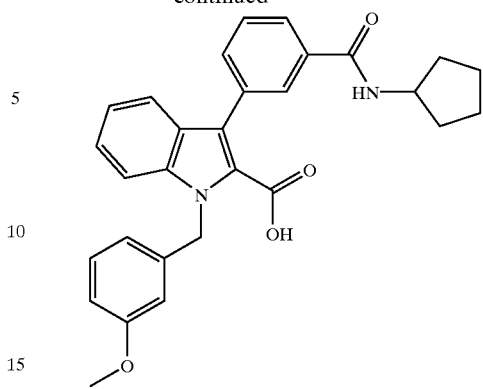
and pharmaceutically acceptable salts thereof.
13. A compound selected from:
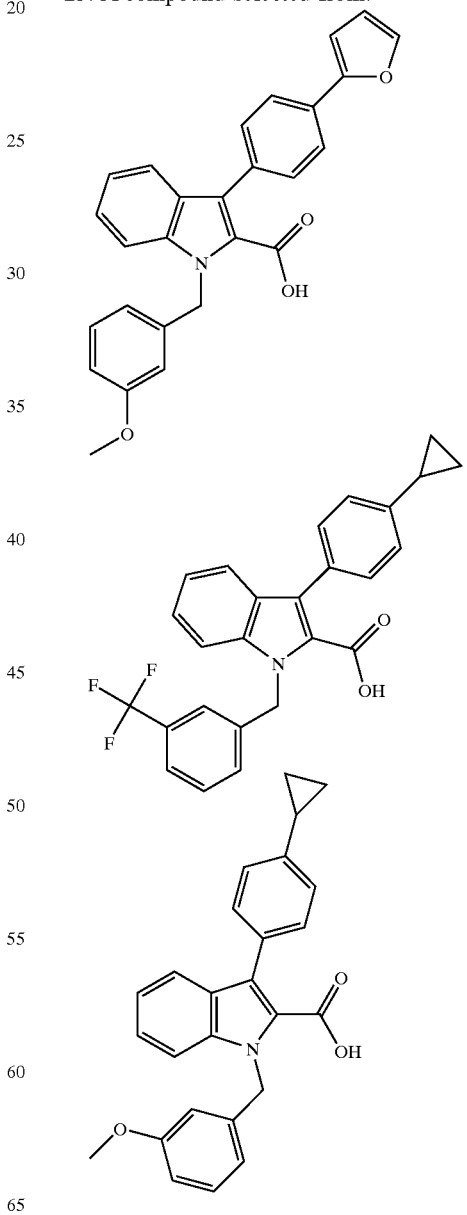
and pharmaceutically acceptable salts thereof.

14. A compound selected from:
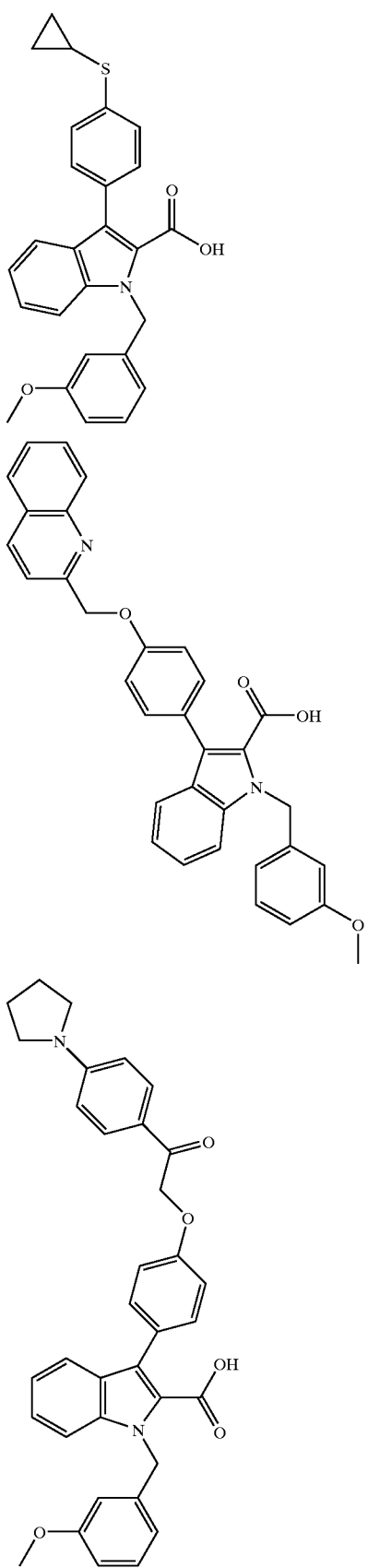
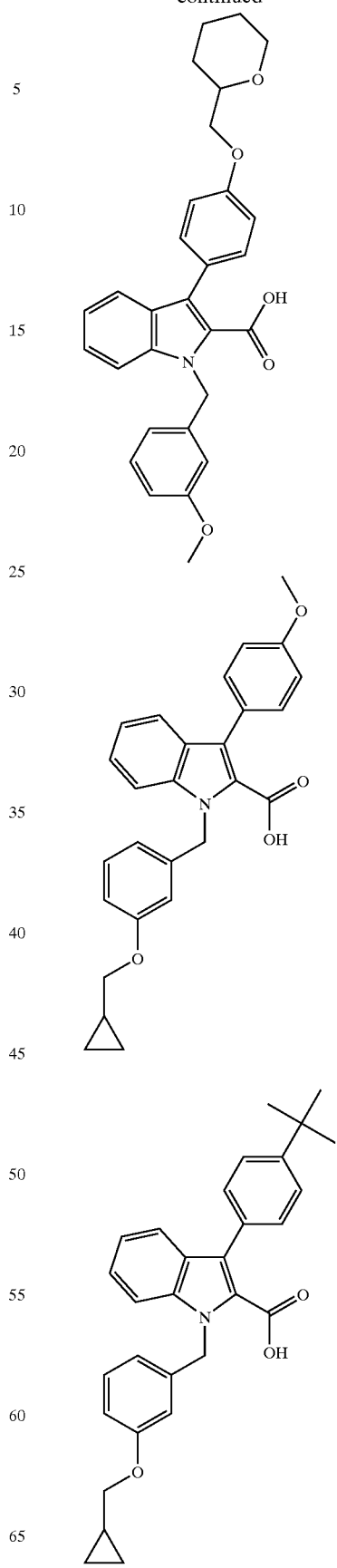

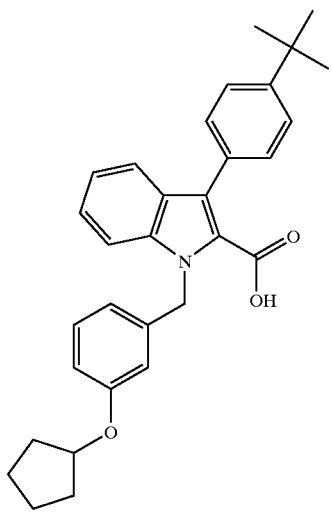
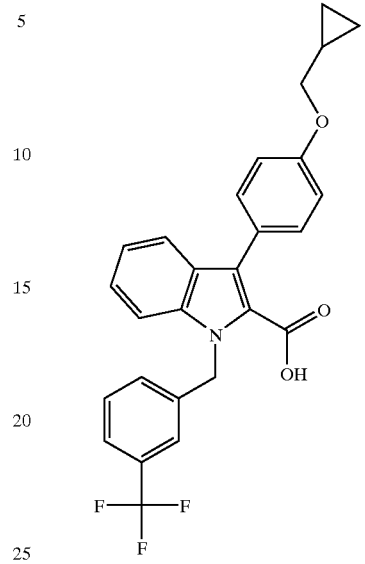
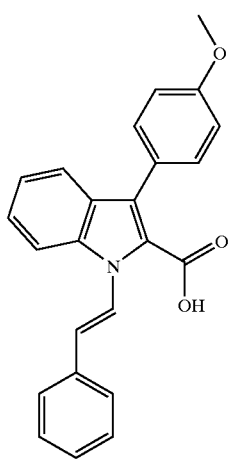
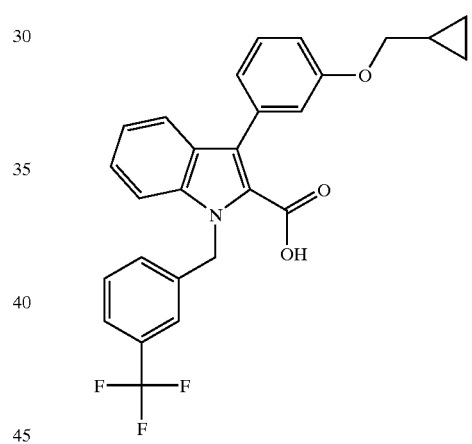
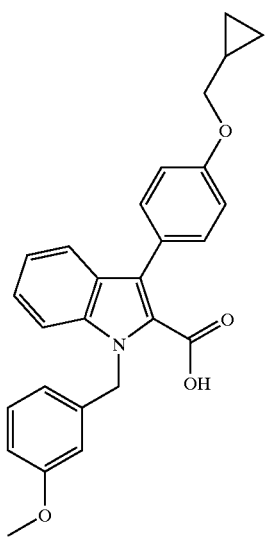
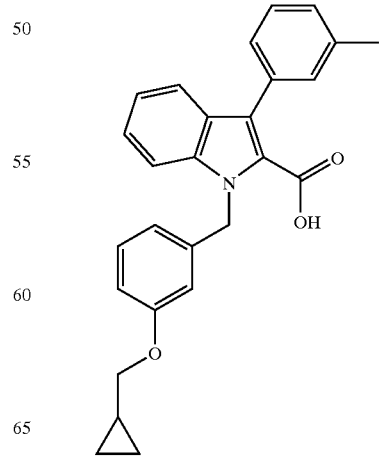

293
-continued
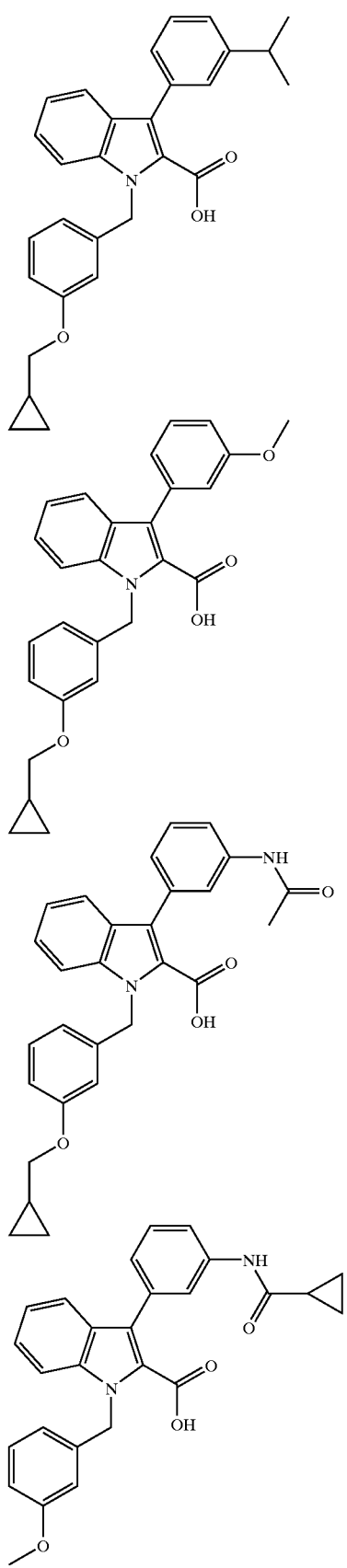
294
-continued
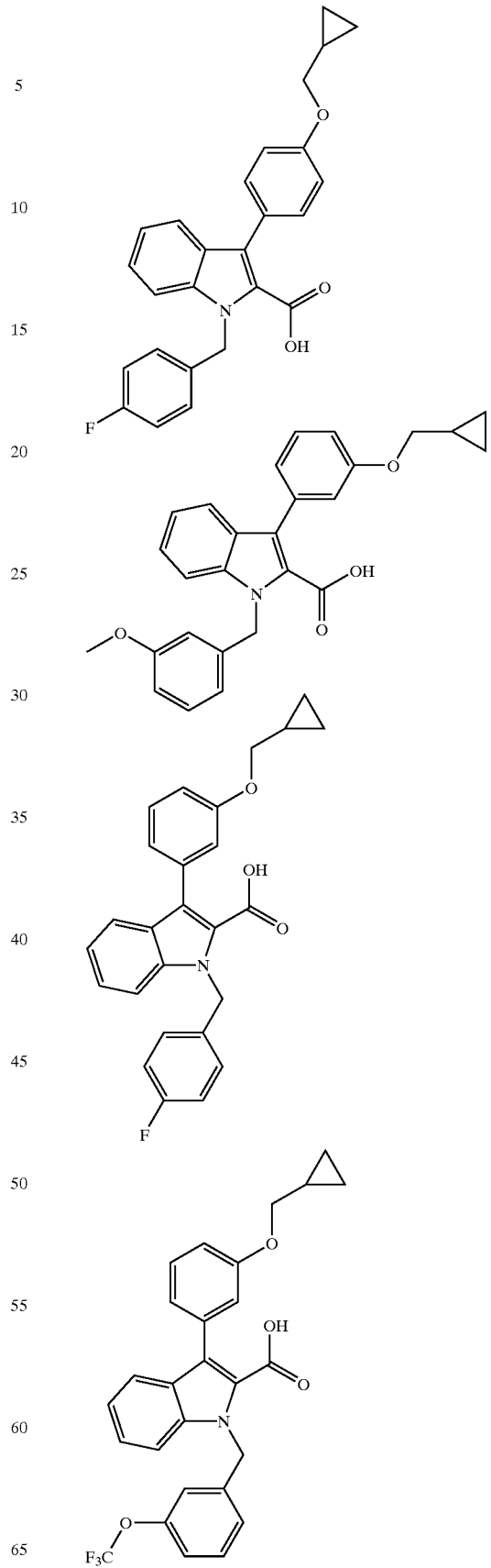

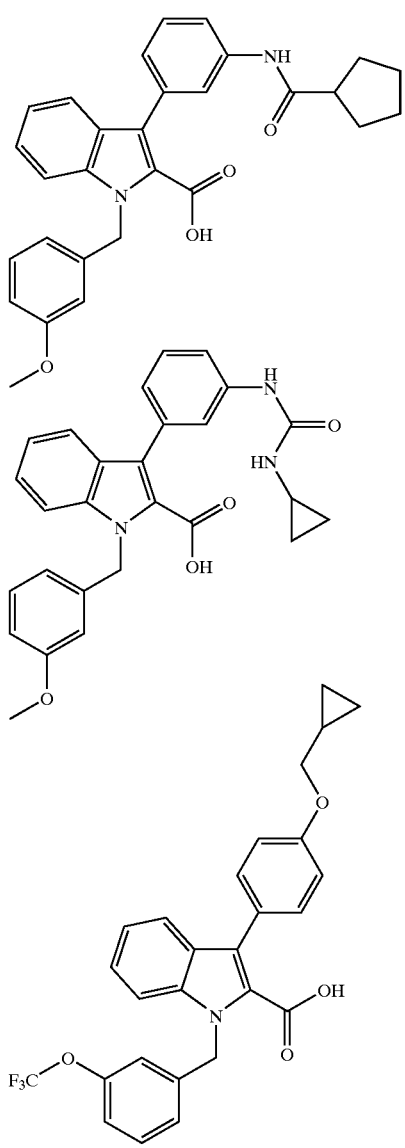
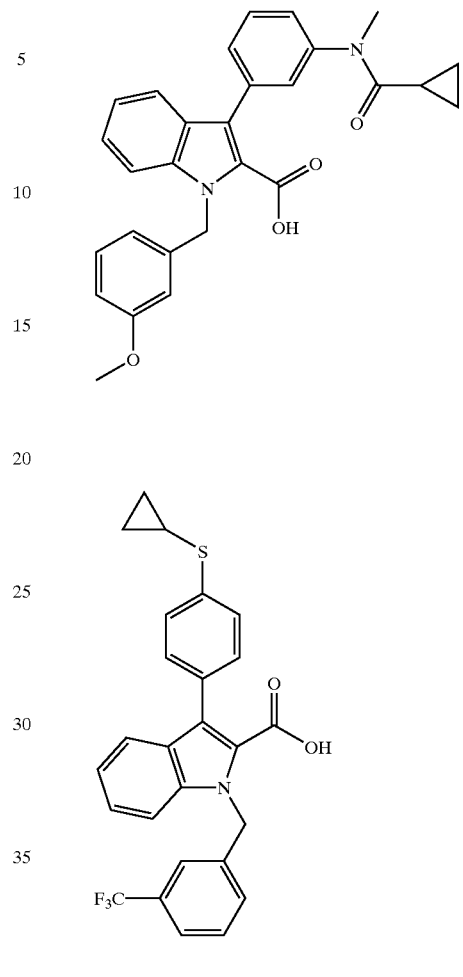
and pharmaceutically acceptable salts thereof.
* * * * *